US011014873B2

(12) United States Patent
Miller et al.

(10) Patent No.: US 11,014,873 B2
(45) Date of Patent: May 25, 2021

(54) ANTI-FIBROTIC COMPOUNDS

(71) Applicant: Certa Therapeutics Pty Ltd, Melbourne (AU)

(72) Inventors: Thomas Miller, Wakefield, MA (US); Nikolaos Papaioannou, Newton, MA (US)

(73) Assignee: CERTA THERAPEUTICS PTY LTD., Melbourne (AU)

( * ) Notice: Subject to any disclaimer, the term of this patent is extended or adjusted under 35 U.S.C. 154(b) by 0 days.

(21) Appl. No.: 16/483,341

(22) PCT Filed: Jan. 31, 2018

(86) PCT No.: PCT/US2018/016272
§ 371 (c)(1),
(2) Date: Aug. 2, 2019

(87) PCT Pub. No.: WO2018/144620
PCT Pub. Date: Aug. 9, 2018

(65) Prior Publication Data
US 2020/0055814 A1    Feb. 20, 2020

Related U.S. Application Data

(60) Provisional application No. 62/454,358, filed on Feb. 3, 2017.

(51) Int. Cl.
| | |
|---|---|
| *C07C 235/38* | (2006.01) |
| *C07D 241/42* | (2006.01) |
| *C07D 265/36* | (2006.01) |
| *C07C 255/60* | (2006.01) |
| *C07D 213/06* | (2006.01) |
| *C07D 215/08* | (2006.01) |
| *C07D 231/56* | (2006.01) |
| *C07D 233/58* | (2006.01) |
| *C07D 249/08* | (2006.01) |
| *C07D 257/04* | (2006.01) |
| *C07D 265/34* | (2006.01) |
| *C07D 271/10* | (2006.01) |
| *C07D 305/08* | (2006.01) |
| *C07D 307/06* | (2006.01) |

(52) U.S. Cl.
CPC .......... *C07C 235/38* (2013.01); *C07C 255/60* (2013.01); *C07D 213/06* (2013.01); *C07D 215/08* (2013.01); *C07D 231/56* (2013.01); *C07D 233/58* (2013.01); *C07D 241/42* (2013.01); *C07D 249/08* (2013.01); *C07D 257/04* (2013.01); *C07D 265/34* (2013.01); *C07D 271/10* (2013.01); *C07D 305/08* (2013.01); *C07D 307/06* (2013.01)

(58) Field of Classification Search
CPC .... C07C 235/38; C07D 241/42; C07D 265/36
See application file for complete search history.

(56) References Cited

U.S. PATENT DOCUMENTS

| | | |
|---|---|---|
| 3,940,422 A | 2/1976 | Harita et al. |
| 4,026,896 A | 5/1977 | Harita et al. |
| 4,587,356 A | 5/1986 | Lizuka et al. |
| 4,769,384 A | 9/1988 | Kise et al. |
| 5,026,705 A | 6/1991 | Pricher et al. |
| 5,244,893 A | 9/1993 | Elbe et al. |
| 5,248,825 A | 9/1993 | Dinerstein et al. |
| 5,356,620 A | 10/1994 | Yamamoto et al. |
| 5,622,977 A | 4/1997 | Warrellow et al. |
| 5,663,414 A | 9/1997 | Oinuma et al. |
| 6,114,383 A | 9/2000 | Isaji et al. |
| 6,127,392 A | 10/2000 | Lennox et al. |
| 6,239,177 B1 | 5/2001 | Mori et al. |
| 6,407,139 B1 | 6/2002 | Isaji |
| 6,646,009 B2 | 11/2003 | Premkumar Reddy et al. |
| 7,094,801 B2 | 8/2006 | Sikorski et al. |
| 7,250,444 B2 | 7/2007 | Kennedy et al. |
| 7,351,719 B2 | 4/2008 | Stenkamp et al. |
| 7,592,373 B2 | 9/2009 | Lehmann-Lintz et al. |
| 8,106,051 B2 | 1/2012 | Yamamori et al. |
| 8,624,056 B2 | 1/2014 | Kelly et al. |
| 8,765,812 B2 | 7/2014 | Williams et al. |
| 9,062,076 B2 | 6/2015 | Williams et al. |
| 9,561,201 B2 | 2/2017 | Williams et al. |
| 9,839,640 B2 | 12/2017 | Kelly et al. |
| 9,951,087 B2 | 4/2018 | Williams et al. |

(Continued)

FOREIGN PATENT DOCUMENTS

| | | |
|---|---|---|
| AU | 2007271734 A1 | 1/2008 |
| AU | 2008341010 A1 | 7/2009 |
| CA | 2246418 | 8/1997 |
| CA | 2 656 851 A1 | 1/2008 |
| CA | 2 709 937 A1 | 7/2009 |
| CN | 101423503 A | 5/2009 |
| CN | 101445469 A | 6/2009 |
| DE | 2 402 398 A1 | 8/1974 |
| EP | 0 193 013 A2 | 9/1986 |
| EP | 0 816 329 A1 | 1/1998 |
| EP | 0 894 496 A1 | 2/1999 |
| EP | 0 937 722 A1 | 8/1999 |

(Continued)

OTHER PUBLICATIONS

International Search Report and Written Opinion dated Apr. 20, 2018, in connection with PCT/US2018/016272.

(Continued)

*Primary Examiner* — Karen Cheng
(74) *Attorney, Agent, or Firm* — Wolf, Greenfield & Sacks, P.C.

(57) ABSTRACT

Provided herein are anti-fibrotic compounds, in particular those of Formula (I), that inhibit the TGF-beta signaling pathway. Also provided are pharmaceutical compositions comprising the anti-fibrotic compounds, and methods of treating diseases or conditions associated with fibrosis, inflammation, and benign or malignant neoplastic diseases in a subject by administering a compound or composition described herein. (Formula (I))

16 Claims, 9 Drawing Sheets

(56) References Cited

U.S. PATENT DOCUMENTS

| | | |
|---|---|---|
| 2002/0099089 A1 | 7/2002 | Hauel et al. |
| 2004/0077646 A1 | 4/2004 | Bamberg et al. |
| 2006/0014807 A1 | 1/2006 | Lin |
| 2006/0030543 A1 | 2/2006 | Malecha et al. |
| 2006/0089413 A1 | 4/2006 | Schmaus et al. |
| 2006/0128725 A1 | 6/2006 | Guzi et al. |
| 2006/0148834 A1 | 7/2006 | Xu et al. |
| 2006/0293379 A1 | 12/2006 | Lagu et al. |
| 2007/0060646 A1 | 3/2007 | Gericke et al. |
| 2007/0191378 A1 | 8/2007 | Campbell et al. |
| 2007/0281969 A1 | 12/2007 | Colletti et al. |
| 2007/0286892 A1 | 12/2007 | Herzberg et al. |
| 2007/0299101 A1 | 12/2007 | Colletti et al. |
| 2008/0008660 A1 | 1/2008 | Rabenhorst et al. |
| 2008/0032983 A1 | 2/2008 | Gericke et al. |
| 2008/0103204 A1 | 5/2008 | Weller et al. |
| 2009/0012031 A1 | 1/2009 | Chinnaiyan et al. |
| 2009/0042987 A1 | 2/2009 | Selley |
| 2009/0197957 A1 | 8/2009 | Selley et al. |
| 2009/0226537 A1 | 9/2009 | Schmaus et al. |
| 2009/0253656 A1 | 10/2009 | Yamazaki et al. |
| 2010/0130497 A1 | 5/2010 | Williams et al. |
| 2010/0158905 A1 | 6/2010 | Pearlman et al. |
| 2011/0112187 A1 | 5/2011 | Schneider et al. |
| 2011/0195977 A1 | 8/2011 | Fancelli et al. |
| 2012/0270863 A1 | 10/2012 | Williams et al. |
| 2013/0338151 A9 | 12/2013 | Williams et al. |
| 2014/0357628 A1 | 12/2014 | Williams et al. |
| 2015/0266893 A1 | 9/2015 | Williams et al. |
| 2018/0117049 A1 | 5/2018 | Kelly et al. |
| 2018/0117050 A1 | 5/2018 | Kelly et al. |
| 2018/0117051 A1 | 5/2018 | Kelly et al. |

FOREIGN PATENT DOCUMENTS

| | | |
|---|---|---|
| EP | 1101758 A1 | 5/2001 |
| EP | 1 460 067 A1 | 9/2004 |
| EP | 1 864 972 A1 | 12/2007 |
| EP | 1972624 A1 | 9/2008 |
| EP | 2 185 150 B1 | 3/2012 |
| EP | 2 035 369 B1 | 6/2014 |
| GB | 2 372 986 A | 9/2002 |
| JP | S50-135047 A | 10/1975 |
| JP | S50-140413 A | 11/1975 |
| JP | S51-001440 A | 8/1976 |
| JP | S52-83428 A | 7/1977 |
| JP | S54-132544 A | 10/1979 |
| JP | S55-076852 A | 6/1980 |
| JP | S57-038759 A | 3/1982 |
| JP | S60-019754 A | 1/1985 |
| JP | S60-152454 A | 8/1985 |
| JP | S62-005966 A | 1/1987 |
| JP | S63-295543 A | 12/1988 |
| JP | S64-016755 A | 1/1989 |
| JP | H01-287066 A | 11/1989 |
| JP | H05-178852 A | 7/1993 |
| JP | H08-113567 A | 5/1996 |
| JP | H08-337523 A | 12/1996 |
| JP | H10-259129 A | 9/1998 |
| JP | H10-510513 A | 10/1998 |
| JP | H10-306024 A | 11/1998 |
| JP | H10-330254 A | 12/1998 |
| JP | H11-506753 A | 6/1999 |
| JP | 2003-507329 A | 2/2003 |
| JP | 2003-119132 A | 4/2003 |
| JP | 2004-075614 A | 3/2004 |
| JP | 2004-143134 A | 5/2004 |
| JP | 2004-531513 A | 10/2004 |
| JP | 2005-523251 A | 8/2005 |
| JP | 2006-512328 A | 4/2006 |
| JP | 2006-298893 A | 11/2006 |
| JP | 2006-528646 A | 12/2006 |
| JP | 2007-506676 A | 3/2007 |
| JP | 2007-509037 A | 4/2007 |
| JP | 2008-501804 A | 1/2008 |
| JP | 2008-504241 A | 2/2008 |
| JP | 2008-274246 A | 11/2008 |
| JP | 2009-511487 A | 3/2009 |
| JP | 2009-541363 A | 11/2009 |
| JP | 2011-506490 A | 3/2011 |
| JP | 2013-508306 A | 3/2013 |
| MX | 2010 006787 A | 10/2010 |
| WO | WO 96/11917 A1 | 4/1996 |
| WO | WO 96/39391 A1 | 12/1996 |
| WO | WO 97/37650 A1 | 3/1997 |
| WO | WO 1997/29744 A1 | 8/1997 |
| WO | WO 98/11438 A1 | 3/1998 |
| WO | WO 98/35668 A1 | 8/1998 |
| WO | WO 00/37455 A1 | 6/2000 |
| WO | WO 00/73283 A1 | 12/2000 |
| WO | WO 01/12189 A1 | 2/2001 |
| WO | WO 01/74810 A2 | 10/2001 |
| WO | WO 02/30894 A2 | 4/2002 |
| WO | WO 02/055454 A2 | 7/2002 |
| WO | WO 02/059108 A1 | 8/2002 |
| WO | WO 02/066454 A | 8/2002 |
| WO | WO 02/080926 A | 10/2002 |
| WO | WO 2003/049702 A2 | 6/2003 |
| WO | WO 03/059913 A1 | 7/2003 |
| WO | WO 2004/022525 A1 | 3/2004 |
| WO | WO 2004/047833 A2 | 6/2004 |
| WO | WO 2004/096757 A1 | 11/2004 |
| WO | WO 2005/004863 A1 | 1/2005 |
| WO | WO 2005/010009 A2 | 1/2005 |
| WO | WO 2005/030704 A1 | 4/2005 |
| WO | WO 2005/030705 A1 | 4/2005 |
| WO | WO 2005/123077 A2 | 12/2005 |
| WO | WO 2006/014012 A2 | 2/2006 |
| WO | WO 2006/053390 A1 | 5/2006 |
| WO | WO 2006/073126 A1 | 7/2006 |
| WO | WO 2006/087393 A2 | 8/2006 |
| WO | WO 2006/094235 A1 | 9/2006 |
| WO | WO 2006/102645 A1 | 9/2006 |
| WO | WO 2006/106778 A | 10/2006 |
| WO | WO 2006/117602 A2 | 11/2006 |
| WO | WO 2006/134120 A1 | 12/2006 |
| WO | WO 2007/015744 A1 | 2/2007 |
| WO | WO 2007/073503 A2 | 6/2007 |
| WO | WO 2007/118137 A1 | 10/2007 |
| WO | WO 2008/003141 A1 | 1/2008 |
| WO | WO 2008/003378 A1 | 1/2008 |
| WO | WO 2008/051047 A1 | 5/2008 |
| WO | WO 2008/057862 A2 | 5/2008 |
| WO | WO 2008/058037 A1 | 5/2008 |
| WO | WO 2008/073461 A2 | 6/2008 |
| WO | WO 2008/079906 A1 | 7/2008 |
| WO | WO 2008/109238 A1 | 9/2008 |
| WO | WO 2008/124153 A1 | 10/2008 |
| WO | WO 2008/156573 A1 | 12/2008 |
| WO | WO 2009/006577 A2 | 1/2009 |
| WO | WO 2009/035818 A1 | 3/2009 |
| WO | WO 2009/057811 A2 | 5/2009 |
| WO | WO 2009/065028 A2 | 5/2009 |
| WO | WO 2009/068557 A1 | 6/2009 |
| WO | WO 2009/079011 A1 | 6/2009 |
| WO | WO 2009/079692 A1 | 7/2009 |
| WO | WO 2009/082347 A1 | 7/2009 |
| WO | WO 2009/092284 A1 | 7/2009 |
| WO | WO 2010/027875 A2 | 3/2010 |
| WO | WO 2010/103130 A2 | 9/2010 |
| WO | WO 2010/144959 A1 | 12/2010 |
| WO | WO 2011/047432 A1 | 4/2011 |

OTHER PUBLICATIONS

Fancelli et al., Cinnamic anilides as new mitochondrial permeability transition pore inhibitors endowed with ischemia-reperfusion injury protective effect in vivo. J Med Chem. Jun. 26, 2014;57(12):5333-47. doi: 10.1021/jm500547c. Epub Jun. 11, 2014.

Fu et al., Synthesis, structure and structure-activity relationship analysis of caffeic acid amides as potential antimicrobials. Eur J Med Chem. Jun. 2010;45(6):2638-43. doi:10.1016/j.ejmech.2010.01.066. Epub Feb. 6, 2010.

(56) References Cited

OTHER PUBLICATIONS

He et al., Discovering potent inhibitors against the beta-hydroxyacyl-acyl carrier protein dehydratase (FabZ) of Helicobacter pylori: structure-based design, synthesis, bioassay, and crystal structure determination. J Med Chem. Apr. 23, 2009;52(8):2465-81. doi: 10.1021/jm8015602. PubMed PMID: 19309082.
Hung et al., Evaluation of caffeic acid amide analogues as anti-platelet aggregation and anti-oxidative agents. Bioorg Med Chem. Mar. 1, 2005;13(5):1791-7.
Supplementary European Search Report for Application No. EP 07763756.9, dated Jan. 19, 2011.
European Search Report for Application No. EP 14173039.0, dated Oct. 7, 2014.
Search Report and Written Opinion for Application No. SG 200900016-7, dated Oct. 14, 2010.
Supplementary Search Report for Application No. SG 200900016-7, dated Mar. 26, 2012.
International Search Report and Written Opinion for Application No. PCT/AU2007/000934, dated Aug. 16, 2007.
International Preliminary Report on Patentability for Application No. PCT/AU2007/000934, dated Jan. 6, 2009.
Supplementary European Search Report for Application No. EP 08865709.3, dated Jan. 19, 2011.
Extended European Search Report for Application No. EP 16156167.5, dated Jun. 1, 2016.
International Search Report and Written Opinion for Application No. PCT/AU2008/001868, dated Feb. 26, 2009.
International Preliminary Report on Patentability for Application No. PCT/AU2008/001868, dated Mar. 25, 2010.
Extended European Search Report for Application No. EP 10824314, dated Mar. 19, 2013.
International Search Report and Written Opinion for Application No. PCT/AU2010/001398, dated Mar. 7, 2011.
International Preliminary Report on Patentability for Application No. PCT/AU2010/001398, dated May 3, 2012.
Partial European Search Report for Application No. EP 15169791.9, dated Sep. 11, 2015.
Extended European Search Report for Application No. EP 15169791.9, dated Jan. 20, 2016.
Search Report and Written Opinion for Application. No. SG201202623-3, dated Aug. 20, 2013.
Extended European Search Report for European Application No. 18207689.3 dated Feb. 12, 2019.
[No Author Listed], Analogue. Merriam-Webster Online Dictionary. http://www.merriam-webster.com/dictionary/analogue [Last accessed Dec. 11, 2010].
[No Author Listed], Derivative. Merriam-Webster Online Dictionary. http://www.merriam-webster.com/dictionary/derivative [Last accessed Dec. 5, 2010].
[No Author Listed], Cancer Drug Design and Discovery. Neidle, Stephen, ed. Elsevier Academic Press. 2008;427.
[No Author Listed], Expert Scientific Group On Phase One Clinical Trials Final Report. Nov. 30, 2006;C1:C35-8.
Ahluwalia et al., CCLXXX.—The condensation of aromatic aldehydes with malonanilic acid and its derivatives. J Chem Soc. 1931;2059-62.
Ali et al., Synthesis and Antimicrobial Activities of Some Novel Quinoxalinone Derivatives. Molecules. 2000;5(6):864-73.
Anari et al., Bridging cheminformatic metabolite predictions and tandem mass spectrometry. DDT. 2005; 10:711-7.
Azizian et al., A Rapid and Highly Efficient One-Pot Methodology for Preparation of Alkyl Oxindolideneacetates. Lett Org Chem. 2006;3:56-7.
Bain et al., Synthesis of 2-Substituted-4H-3,1-benzoxazin-4-ones. J Chem Soc. 1968;C:1593-97.
Bakhite et al., Synthesis, reactions and biological activity of some new thieno[2,3-f]-1,3-benzodioxoles. Pharmazie. Jul. 1999;54(7):491-8.
Bang et al., Facile Total Synthesis of Benzo[b]furan Natural Product XH-14. Synth Commun. 2009;39:506-15.
Byun et al., Aminostyrylbenzofuran derivatives as potent inhibitors for Abeta fibril formation. Bioorg Med Chem Lett. Oct. 15, 2008;18(20):5591-3. doi: 10.1016/j.bmcl.2008.08.111. Epub Sep. 3, 2008.
Castro et al., Synthesis and cytotoxic evaluation of C-9 oxidized podophyllotoxin derivatives. Bio Med Chem. Jan. 2007;15(4);1670-8.
Chemical Abstracts Accession No. 1987:4861. JP 61-91168 A. May 9, 1986.
Chemical Abstracts Accession No. 1994:244706. JP 5-320133 A. Dec. 3, 1993.
Chemical Abstracts Accession No. 1999:182701. JP 11-72913 A. Mar. 16, 1999.
Chemical Abstracts Accession No. 1999:420913. JP 11-180952 A. Jul. 6, 1999.
Chemical Abstracts Accession No. 1999:631099. JP 11-269068 A. Oct. 5, 1999.
Chemical Abstracts Accession No. 2004:198513. JP 2004-75614 A. Mar. 11, 2004.
Chemical Abstracts Accession No. 2009:875995. US 2009-0163545 A1. Jun. 25, 2009.
Cheng et al., Synthesis of propenamides with anti-malarial activities and 3D-QSAR study. Acta Pharma Sinica. 2003; 38(7):505-10. Abstract only.
Collins, Oat Phenolics: Avenanthramides, Novel Substituted N-Cinnamoylanthranilate Alkaloids from Oat Groats and Hulls. Agric Food Chem. 1989;37:60-6.
Database Caplus [Online]; Chemical Abstracts Service, Columbus, Ohio, CAS Registry File RN 1991:101904, STN Entry Date: 1991.
Database Caplus [Online]; Chemical Abstracts Service, Columbus, Ohio, CAS Registry File RN 1991:42719, STN Entry Date: 1990.
Database Caplus [Online]; Chemical Abstracts Service, Columbus, Ohio, CAS Registry File RN 1995:436368, STN Entry Date: 1995.
Database Registry [Online]; Chemical Abstracts Service, Columbus, Ohio, CAS Registry File RN 1004255-12-2, STN Entry Date: Feb. 18, 2008.
Database Registry [Online]; Chemical Abstracts Service, Columbus, Ohio, CAS Registry File RN 1013293-13-4, STN Entry Date: Apr. 10, 2008.
Database Registry [Online]; Chemical Abstracts Service, Columbus, Ohio, CAS Registry File RN 1025584-02-4, STN Entry Date: Jun. 5, 2008.
Database Registry [Online]; Chemical Abstracts Service, Columbus, Ohio, CAS Registry File RN 1025810-34-7, STN Entry Date: Jun. 5, 2008.
Database Registry [Online]; Chemical Abstracts Service, Columbus, Ohio, CAS Registry File RN 317327-64-3, STN Entry Date: Jan. 26, 2001.
Database Registry [Online]; Chemical Abstracts Service, Columbus, Ohio, CAS Registry File RN 340996-04-5, STN Entry Date: Jun. 14, 2001.
Database Registry [Online]; Chemical Abstracts Service, Columbus, Ohio, CAS Registry File RN 457607-17-9, STN Entry Date: Oct. 1, 2002.
Database Registry [Online]; Chemical Abstracts Service, Columbus, Ohio, CAS Registry File RN 462069-64-3, STN Entry Date: Oct. 17, 2002.
Database Registry [Online]; Chemical Abstracts Service, Columbus, Ohio, CAS Registry File RN 577770-02-6, STN Entry Date: Sep. 2, 2003.
Database Registry [Online]; Chemical Abstracts Service, Columbus, Ohio, CAS Registry File RN 622349-10-4, STN Entry Date: Dec. 1, 2003.
Database Registry [Online]; Chemical Abstracts Service, Columbus, Ohio, CAS Registry File RN 785773-47-9, STN Entry Date: Nov. 22, 2004.
Einhorn et al., Mild and Convenient One Pot Synthesis of N-Hydroxyimides from N-Unsubstituted Imides. Synth Comm. 2001;31(5):741-8.
El-Ahmad et al., Sur le mécanisme de la réaction de meth-cohn-tarnowski de préparation des thiocoumarines. J Heterocyclic Chem. May/Jun. 1988;25(3):711-4.

(56) References Cited

OTHER PUBLICATIONS

Fura, Role of pharmacologically active metabolites in drug discovery and development. DDT. 2006;11:133-42.
Gao Xinmin, "Brief talk about diabetic eye diseases", Scientific and Technical Documentation Press, Section 41, pp. 25-26, Jul. 2002.
Gazit et al., Tyrphostins, 2, Heterocyclic and α-Substituted Benzlidenemalononnitrile Tyrphostins as Potent Inhibitors of EGF Receptor and ErbB2/neu Tyrosine Kinases. J Med Chem. 1991;34(17):1896-907.
Guay et al., Discovery of L-791,943: a potent, selective, non emetic and orally active phosphodiesterase-4 inhibitor. Bioorg Med Chem Lett. Jun. 3, 2002;12(11):1457-61.
Gura, Systems for Identifying New Drugs Are Often Faulty. Science. Nov. 7, 1997;278(5340): 1041-2.
Hajra et al., Lewis acid catalyzed intramolecular halo-arylation of tethered alkenes using N-halosuccinimide (NXS) as the halogen source; a general method for the synthesis of chromanones, chromans, quinolones, tetrahydroquinolines and tetralins. Tetrahedron Lett. 2005;46(49):8599-603.
Hiroi et al., Anti-tumor Effect of N-[3,4-dimethoxycinnamoyl]-anthranilic Acid (tranilast) on Experimental Pancreatic Cancer. J Nippon Med Sch. 2002;69(3): 224-34.
Hocher et al., Inhibition of left ventricular fibrosis by tranilast in rats with renovascular hypertension. J Hypertens. Apr. 2002;20(4):745-51.
Ikeda et al., Inhibitory effect of tranilast on activation and transforming growth factor beta 1 expression in cultured rat stellate cells. Biochem Biophys Res Commun. Oct. 14, 1996;227(2):322-7.
Isaji et al., Selective Inhibition of Collagen Accumulation by N-(3,4-Dimethoxycinnamoyl)Anthranilic Acid (N-5') In Granulation Tissue. Biochem Pharmacol. 1987; 36(4):469-74.
Isaji et al., Tranilast inhibits the proliferation, chemotaxis and tube formation of human microvascular endothelial cells in vitro and angiogenesis in vivo. Br J Pharmacol. Nov. 1997;122(6):1061-6.
Isaji et al., Tranilast: a new application in the cardiovascular field as an antiproliferative drug. Cardiovasc Drug Rev. 1998;16(3):288-99.
Ishihara et al., Induction of hydroxyanthranilate hydrocinnamoyl transferase activity by oligo-n-acethylchitooligosaccharides in oats. Phytochem. 1998;47(6):969-74.
Jackson et al., Synthesis of 2,3-Dimethoxy-7-methyl-7,12-dihydro-6H-[1]-benzofuro-[2,3-c]-[1]-benzazepin-6,12-dione. Molecules. 2002;7(3):353-362.
Jeschke et al., alpha-fluorinated ethers as "exotic" entity in medicinal chemistry. Mini Rev Med Chem. Oct. 2007;7(10):1027-34.
Kamb, What's wrong with our cancer models? Nature Rev Drug Disc. Feb. 2005;4:161-5.
Kelly et al., Tranilast attenuates structural and functional aspects of renal injury in the remnant kidney model. J Am Soc Nephrol. Oct. 2004;15(10):2619-29.
Leaf, Why are we losing the war on cancer (and how to win it). Health Administrator. 2005; XVII(1):172-83.
Lozano et al., Cytotoxic anionic tribomo platinum (II) complexes containing benzothiazole and benzoxazole donors: synthesis, characterization, and structure-activity correlation. Inorganica Chimica Acta. 1998;271:137-44.
Luo et al., Principles of Cancer Therapy: Oncogene and Non-oncogene Addiction. Cell. 2009;136: 823-37.
Martin et al., Tranilast attenuates cardiac matrix deposition in experimental diabetes: role of transforming growth factor-beta. Cardiovasc Res. Feb. 15, 2005;65(3):694-701.
Messiah et al., Synthesis of Some Benzoxazin-4-ones, Qinazolin-4-ones & Related Products. Indian J Chem. 1975;13:326-8.
Mifsud et al., Intervention with Tranilast Attenuates Renal Pathology and Albuminuria in Advanced Experimental Diabetic Nephropathy. Nephron Physiol. 2003;95:83-91.
Miyazawa et al., Inhibition of PDGF- and TGF-beta 1-induced collagen synthesis, migration and proliferation by tranilast in vascular smooth muscle cells from spontaneously hypertensive rats. Atherosclerosis. Dec. 1995;118(2):213-21.
Muiesan, Left ventricular hypertrophy: a new approach for fibrosis inhibition. J Hypertens. 2002;20(4):611-3.
Nedderman, Metabolites in Safety Testing: Metabolite Identification Strategies in Discovery and Development. Biopharm. Drug Dispos. 2009;30:152-62.
Ogawa et al., Dry eye as a major complication associated with chronic graft-versus-host disease after hematopoietic stem cell transplantation. Cornea. Oct. 2003;22(7 Suppl):S19-27. Abstract only.
Ogita et al., Synthesis and structure-activity relationship of diarylamide derivatives as selective inhibitors of the proliferation of human coronary artery smooth muscle cells. Bioorg Med Chem Lett. 2001;11(4):549-51.
Okazaki et al., Metabolism of avenanthramide phytoalexins in oats. Plant J. 2004;39:560-57.
Patani et al., Bioisosterism: a rational approach in drug design. Chem Rev. 1996;96:3147-76.
Rani et al., Isoxazolinyl derivatives of anthranilic acid as anti inflammatory agents. Indian J Chem. Section B: Organic and Medicinal Chemistry, Council of Scientific and Industrial Research. 2003;42:1729-33.
Sato et al., A Novel Class of in Vivo Active Anticancer Agents: Achiralseco-Amino- and seco-Hydroxcyclopropylbenz[e]indolone (seco-CBI) Analogues of the Duocarmycins and CC-1065. J Med Chem. 2005;48(11):3903-18.
Shigeki et al., Treatment of keloid and hypertrophic scars by iontophoretic transdermal delivery of tranilast. Scand J Plast Reconstr Surg Hand Surg. Jun. 1997;31(2):151-8.
STN File Registry; CAS Registry No. 463307-21-3. Oct. 21, 2002.
STN File Registry; CAS Registry No. 475190-68-2. Dec. 5, 2002.
STN File Registry; CAS Registry No. 572907-40-5. Aug. 25, 2003.
STN File Registry; CAS Registry No. 850701-35-8. May 19, 2005.
STN File Registry; CAS Registry No. 875398-18-8. Feb. 27, 2006.
STN File Registry; CAS Registry No. 891611-78-2. Jul. 10, 2006.
STN File Registry; CAS Registry No. 900671-62-7. Aug. 11, 2006.
STN File Registry; CAS Registry No. 903317-85-1. Aug. 22, 2006.
STN File Registry; CAS Registry No. 926525-60-2. Mar. 15, 2007.
STN File Registry; CAS Registry No. 926872-74-4. Mar. 18, 2007.
STN File Registry; CAS Registry No. 930720-96-0. Apr. 18, 2007.
STN File Registry; CAS Registry No. 931079-11-7. Apr. 20, 2007.
STN File Registry; CAS Registry No. 938782-52-6. Jun. 25, 2007.
Taniguchi et al., Treatment of linear localized scleroderma with the anti-allergic drug, tranilast. Clin Exp Dermatol. Sep. 1994;19(5):391-3.
Tao et al., [Effects of 1-(3-fluorophenyl)-5-methyl-2-(1H)-pyridone on renal fibroblast in rats]. Zhong Nan Da Xue Xue Bao Yi Xue Ban. Apr. 2004;29(2):139-41. Chinese.
Yamada et al., Tranilast, a selective inhibitor of collagen synthesis in human skin fibroblasts. J Biochem. Oct. 1994;116(4):892-7.
U.S. Appl. No. 14/317,602, filed Feb. 4, 2010, Williams et al.
U.S. Appl. No. 13/503,160, filed Jul. 9, 2012, Williams et al.
U.S. Appl. No. 14/730,753, filed Jun. 4, 2015, Williams et al.
EP 07763756.9, Jan. 19, 2011, Supplementary European Search Report.
EP 14173039.0, Oct. 7, 2014, European Search Report.
SG 200900016-7, Oct. 14, 2010, Search Report and Written Opinion.
SG 200900016-7, Mar. 25, 2012, Supplementary Search Report.
PCT/AU2007/000934, Aug. 16, 2007, International Search Report and Written Opinion.
PCT/AU2007/000934, Jan. 6, 2009, International Preliminary Report on Patentability.
EP 08865709.3, Jan. 19, 2011, Supplementary European Search Report.
EP 16156167.5, Jun. 1, 2016, Extended European Search Report.
PCT/AU2008/001868, Feb. 26, 2009, International Search Report and Written Opinion.
PCT/AU2008/001868, Mar. 26, 2010, International Preliminary Report on Patentability.
EP 10824314, Mar. 19, 2013, Extended European Search Report.
PCT/AU2010/001398, Mar. 7, 2011, International Search Report and Written Opinion.

(56) References Cited

OTHER PUBLICATIONS

PCT/AU2010/001398, May 3, 2012, International Preliminary Report on Patentability.
EP 15169791.9, Sep. 11, 2015, Partial European Search Report.
EP 15169791.9, Jan. 20, 2016, Extended European Search Report.
EP 18207689.3, Feb. 12, 2019, Extended European Search Report.
PCT/US2018/016272, Apr. 20, 2018, International Search Report and Written Opinion.

ANTI-FIBROTIC COMPOUNDS

CROSS-REFERENCE TO RELATED APPLICATIONS

The present application is a National Stage filing under 35 U.S.C. 371 of International Patent Application No. PCT/US2018/016272, filed Jan. 31, 2018, which claims priority under 35 U.S.C. § 119(e) to U.S. Provisional Patent Application Ser. No. 62/454,358, filed Feb. 3, 2017. Each of which is incorporated herein by reference in its entirety.

FIELD OF THE INVENTION

The present invention relates generally to compounds that inhibit fibrosis, and use of the compounds in the treatment of medical disorders, in particular conditions associated with tissue fibrosis.

BACKGROUND OF THE INVENTION

Tranilast (n-[3,4-dimethoxycinnamoyl] anthranilic acid) is an anti-fibrotic agent approved in Japan for the treatment of fibrotic skin disorders such as keloids and scleroderma. Although the precise mechanisms and mode of action are not completely understood, its ability to inhibit ERK phosphorylation, a major intermediate in the TGF-β signalling pathway, may underlie its antifibrotic effects, with known actions of tranilast including the inhibition of TGF-β-induced extracellular matrix production in a range of cell types. Tranilast has also been shown to attenuate TGF-β-induced collagen synthesis in cardiac fibroblasts using an experimental model of diabetic cardiac disease.

Fibrosis is a common response to a range of tissue insults that may lead to organ dysfunction. Diseases that are characterized by such pathological fibrosis include hepatic cirrhosis, pulmonary interstitial fibrosis, glomerulonephritis, heart failure (ischaemic and non-ischaemic), diabetic nephropathy, scleroderma, excessive scar tissue post surgery or device insertion, progressive kidney disease, glomerulonephritis, hypertension, heart failure due to ischaemic heart disease, valvular heart disease or hypertensive heart disease and hypertrophic scars. In addition, the elaboration of pathological matrix also has a role in fibroproliferative tumor progression and metastasis.

Diabetic subjects have a two- to five-fold increase risk of developing heart failure. In addition to ischaemic heart disease, heart failure in diabetes is also associated with a cardiomyopathy, independent of coronary artery disease. This so-called "diabetic cardiomyopathy" is characterised histologically by myocardial fibrosis with reduced myocardial elasticity, impaired contractility and overt cardiac dysfunction. Accordingly, strategies that reduce the pathological accumulation of extracellular matrix have been advocated as potential therapies for the treatment and prevention of heart failure in both diabetic and nondiabetic states.

Current treatment of chronic heart failure focuses on the modulation of the neurohormonal activation that typically develops in response to the evolving functional abnormalities. However, despite such therapy, frequently used in combination, cardiac dysfunction continues to progress in the majority of patients. Given the importance of pathological fibrosis in adverse cardiac remodelling, a potential role of antifibrotic agents has been suggested. Studies conducted over more than a decade have consistently indicated a major role for the prosclerotic growth factor, transforming growth factor-β (TGF-β) in organ fibrosis and dysfunction, such that blockade of its expression and action represent an important therapeutic target.

Tranilast has also been shown to reduce inflammation in allergic diseases, such as allergic rhinitis and bronchial asthma, etc., and have anti-proliferative activity.

However, it has recently been shown that genetic factors in certain patients, specifically a Gilbert's syndrome UGT1A1 variant, confers susceptibility to tranilast-induced hyperbilirubinemia. Such hyperbilirubinemia may be associated with tranilast itself or the formation, in vivo, of the following tranilast metabolite,

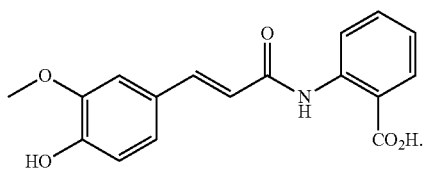 [SMILES: COc1cc(/C=C/C(=O)Nc2ccccc2C(=O)O)ccc1O]

An ongoing need exists to identify and provide drugs with potential anti-fibrotic, anti-inflammatory, and anti-proliferative or anti-neoplastic activity for the treatment or prevention of diseases associated with fibrosis, diseases characterized by inflammation and neoplastic disease (both benign and malignant), and as alternatives/adjuncts to tranilast.

SUMMARY OF THE INVENTION

In one aspect, provided are compounds of Formula I:

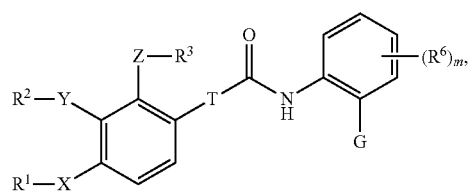

or pharmaceutically acceptable salts, co-crystals, tautomers, stereoisomers, solvates, hydrates, polymorphs, isotopically enriched derivatives, or prodrugs thereof, wherein:

T is

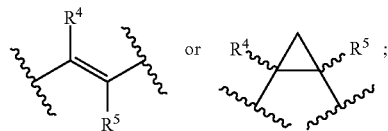

X is O, $NR^{10}$, —$NR^{10}C(O)$—, or a bond;
Y is O, $NR^{10}$, —$C(O)NR^{10}$—, or a bond;
Z is O, $NR^{10}$, or a bond;
$R^1$ and $R^2$ are independently hydrogen, alkyl, heteroalkyl, alkenyl, alkynyl, cycloalkyl, cycloalkylalkyl, arylalkyl, heteroarylalkyl, heterocyclyl, or heterocyclylalkyl, wherein $R^1$ and $R^2$ are each optionally substituted with 1-3 independent substituents $R^8$;
or $R^1$ and $R^2$ together with the atoms to which they are attached form a heterocyclyl ring;
$R^3$ is hydrogen, heteroalkyl, alkyl, alkenyl, alkynyl, cycloalkyl, cycloalkylalkyl, arylalkyl, heteroarylalkyl, heterocyclyl, or heterocyclylalkyl, wherein $R^3$ is optionally substituted with 1-3 independent substituents $R^8$;

$R^4$ and $R^5$ are hydrogen;

each occurrence of $R^6$ is, independently, halogen, cyano, alkyl, alkenyl, alkynyl, haloalkyl, hydroxyl, alkoxy, aryl, heteroaryl, heterocyclyl, $NR^aR^b$, or $-S(O)_2R^c$;

G is $C(O)R^7$ or hydrogen;

$R^7$ is OH or $NHR^9$;

m is 0, 1, or 2;

each occurrence of $R^8$ is, independently, alkyl, alkynyl, hydroxyl, alkoxy, carboxyl, oxo, aryl, heteroaryl, heterocyclyl, $-NR^aR^b$, $-S(O)_2R^c$, or $-CO_2R^d$;

$R^9$ is heteroaryl, heterocyclyl, or $-S(O)_2R^c$, wherein $R^9$ is optionally substituted with 1-3 independent substituents $R^8$;

$R^{10}$ is hydrogen or alkyl optionally substituted with 1-3 independent substituents $R^8$; and each occurrence of $R^a$, $R^b$, $R^c$, and $R^d$ is, independently, hydrogen, acyl, alkyl, alkenyl, alkynyl, heteroalkyl, cycloalkyl, heterocyclylalkyl, aryl, heteroaryl, heterocyclyl, $C(O)OC_{1-6}$ alkyl, $C(O)C_{1-6}$ alkyl, or $R^a$ and $R^b$ together with the atoms to which they are attached form a heterocyclyl ring;

provided that when G is hydrogen, then m is not 0;

provided that when G is $C(O)R^7$, $R^7$ is OH, and $-Z-R^3$ is H, then at least one of $-X-R^1$ and $-Y-R^2$ is $-O$-heterocyclyl or heterocyclyl, or $R^1$ and $R^2$ together with the atoms to which they are attached form a heterocyclyl ring;

provided that when $-X-R^1$ is H, then neither $-Y-R^2$ nor $-Z-R^3$ are hydrogen;

provided that when $-Y-R^2$ is H, then neither $-X-R^1$ nor $-Z-R^3$ are hydrogen; and provided that when $-Z-R^3$ is H, then neither $-X-R^1$ nor $-Y-R^2$ are hydrogen.

Exemplary compounds of Formula I include, but are not limited to:

(E)-N-(2-fluorophenyl)-3-(3-methoxy-4-(prop-2-yn-1-yloxy)phenyl)acrylamide (1);
(E)-3-(3-methoxy-4-(prop-2-yn-1-yloxy)phenyl)-N-(2-(5-methyl-1H-1,2,4-triazol-3-yl)phenyl)acrylamide (2);
(E)-N-(2-chlorophenyl)-3-(3-methoxy-4-(prop-2-yn-1-yloxy)phenyl)acrylamide (3);
(E)-N-(2-bromophenyl)-3-(3-methoxy-4-(prop-2-yn-1-yloxy)phenyl)acrylamide (4);
(E)-3-(3-methoxy-4-(prop-2-yn-1-yloxy)phenyl)-N-(o-tolyl)acrylamide (5);
(E)-N-(2-cyanophenyl)-3-(3-methoxy-4-(prop-2-yn-1-yloxy)phenyl)acrylamide (6);
(E)-N-(3,4-dichlorophenyl)-3-(3-methoxy-4-(prop-2-yn-1-yloxy)phenyl)acrylamide (7);
(E)-N-(2-(2H-tetrazol-5-yl)phenyl)-3-(3-methoxy-4-(prop-2-yn-1-yloxy)phenyl)acrylamide (16);
(E)-N-(2-(1,2,4-oxadiazol-3-yl)phenyl)-3-(3-methoxy-4-(prop-2-yn-1-yloxy)phenyl)acrylamide (17);
(E)-3-(3-methoxy-4-(prop-2-yn-1-yloxy)phenyl)-N-(2-(5-methyl-1,2,4-oxadiazol-3-yl)phenyl)-acrylamide (18);
(E)-3-(3-methoxy-4-(prop-2-yn-1-yloxy)phenyl)-N-(2-(5-oxo-4,5-dihydro-1,2,4-oxadiazol-3-yl)phenyl)acrylamide (19);
(E)-N-(2-(1,2,4-oxadiazol-5-yl)phenyl)-3-(3-methoxy-4-(prop-2-yn-1-yloxy)phenyl)acrylamide (20);
(E)-N-(2-(1,3,4-oxadiazol-2-yl)phenyl)-3-(3-methoxy-4-(prop-2-yn-1-yloxy)phenyl)acrylamide (21);
(E)-3-(3-methoxy-4-(prop-2-yn-1-yloxy)phenyl)-N-(2-(1-methyl-1H-pyrazol-4-yl)phenyl)-acrylamide (22);
(E)-3-(3-methoxy-4-(prop-2-yn-1-yloxy)phenyl)-N-(2-(3-methyl-1H-1,2,4-triazol-1-yl)phenyl)acryl-amide (23);
(E)-N-(2-(1H-pyrazol-4-yl)phenyl)-3-(3-methoxy-4-(prop-2-yn-1-yloxy)phenyl)acrylamide (24);
(E)-N-(2-(1H-imidazol-4-yl)phenyl)-3-(3-methoxy-4-(prop-2-yn-1-yloxy)phenyl)acrylamide (25);
(E)-3-(3-methoxy-4-(prop-2-yn-1-yloxy)phenyl)-N-(2-(1-methyl-1H-imidazol-4-yl)phenyl)acrylamide (26);
(E)-2-(3-(3-methoxy-4-(prop-2-yn-1-yloxy)phenyl)acrylamido)-N-(methylsulfonyl)benzamide (27);
(E)-3-(3-methoxy-4-(prop-2-yn-1-yloxy)phenyl)-N-(2-(3-methyl-1,2,4-oxadiazol-5-yl)phenyl)acryl-amide (28);
(E)-3-(3-methoxy-4-(prop-2-yn-1-yloxy)phenyl)-N-(2-(5-methyl-1,3,4-oxadiazol-2-yl)phenyl)-acrylamide (29);
(E)-2-(3-(3-methoxy-4-(prop-2-yn-1-yloxy)phenyl)acrylamido)-N-(2H-tetrazol-5-yl)benzamide (31);
(E)-2-(3-(3-methoxy-4-(prop-2-yn-1-yloxy)phenyl)acrylamido)-N-(1-methylpiperidin-4-yl)benzamide (36);
(E)-2-(3-(3-methoxy-4-(prop-2-yn-1-yloxy)phenyl)acrylamido)-N-(oxetan-3-yl)benzamide (38);
(E)-2-(3-(3-methoxy-4-(prop-2-yn-1-yloxy)phenyl)acrylamido)-N-(pyridin-4-yl)benzamide (44);
(E)-2-(3-(3-methoxy-4-(prop-2-yn-1-yloxy)phenyl)acrylamido)-N-(1-methyl-1H-pyrazol-4-yl)benzamide (47);
(E)-2-(3-(3-methoxy-4-(prop-2-yn-1-yloxy)phenyl)acrylamido)-N-(1-methyl-1H-pyrazol-3-yl)benzamide (48);
(E)-2-(3-(3-methoxy-4-(prop-2-yn-1-yloxy)phenyl)acrylamido)-N-(piperidin-4-yl)benzamide (49);
(E)-2-(3-(3-methoxy-4-((1-methylpyrrolidin-3-yl)oxy)phenyl)acrylamido)benzoic acid (51);
(E)-N-(3-cyanophenyl)-3-[2-[2-(dimethylamino)ethoxy]-3-methoxy-4-prop-2-ynoxy-phenyl]prop-2-enamide (76);
((E)-N-(2-cyanophenyl)-3-(2-(2-(dimethylamino)ethoxy)-3-methoxy-4-(prop-2-yn-1-yloxy)phenyl)acrylamide (77);
(E)-2-(3-(2-(2-(dimethylamino)ethoxy)-3-methoxy-4-(prop-2-yn-1-yloxy)phenyl)acrylamido)-benzoic acid (78);
(E)-N-(2-cyanophenyl)-3-[3-methoxy-2-(1-methylazetidin-3-yl)oxy-4-prop-2-ynoxy-phenyl]prop-2-enamide (79);
2-[[(E)-3-(3-methoxy-4-prop-2-ynoxy-2-pyrrolidin-3-yloxyphenyl)prop-2-enoyl]amino]benzoic acid (80);
(E)-N-(2-cyanophenyl)-3-[3-methoxy-2-(1-methylpyrrolidin-3-yl)oxy-4-prop-2-ynoxy-phenyl]prop-2-enamide (81);
(E)-N-(2-cyanophenyl)-3-(3-methoxy-4-prop-2-ynoxy-2-pyrrolidin-3-yloxy-phenyl)prop-2-enamide (82);
2-[[(E)-3-[3-methoxy-2-(4-piperidyloxy)-4-prop-2-ynoxy-phenyl]prop-2-enoyl]amino]benzoic acid (83);
2-[[(E)-3-[3-methoxy-2-(2-morpholinoethoxy)-4-prop-2-ynoxy-phenyl]prop-2-enoyl]amino]benzoic acid (84);
(E)-N-(2-cyanophenyl)-3-[3-methoxy-2-(2-morpholinoethoxy)-4-prop-2-ynoxy-phenyl]prop-2-enamide (85);
2-[[(E)-3-[2-[3-(dimethylamino)propoxy]-3-methoxy-4-prop-2-ynoxy-phenyl]prop-2-enoyl]amino]benzoic acid (86);
(E)-N-(2-cyanophenyl)-3-[2-[3-(dimethylamino)propoxy]-3-methoxy-4-prop-2-ynoxy-phenyl]prop-2-enamide (87);
(E)-N-(2-cyanophenyl)-3-[3-methoxy-2-(4-piperidyloxy)-4-prop-2-ynoxy-phenyl]prop-2-enamide (88);
(E)-N-(2-cyanophenyl)-3-[3-methoxy-2-[(1-methyl-4-piperidyl)oxy]-4-prop-2-ynoxy-phenyl]prop-2-enamide (89);
2-[[(E)-3-[4-(cyclopropylmethoxy)-2-[2-(dimethylamino)ethoxy]-3-methoxy-phenyl]prop-2-enoyl]amino]benzoic acid (90);
(E)-N-(3-cyanophenyl)-3-(2-(2-(dimethylamino)ethoxy)-3-methoxyphenyl)acrylamide (91);

(E)-N-(2-cyanophenyl)-3-(2-(2-(dimethylamino)ethoxy)-3-methoxyphenyl)acrylamide (92);
(E)-N-(3-cyanophenyl)-3-(2-(2-(dimethylamino)ethoxy)-4-methoxyphenyl)acrylamide (93);
(E)-N-(2-cyanophenyl)-3-[2-[2-(dimethylamino)ethoxy]-4-methoxy-phenyl]prop-2-enamide (94);
(E)-2-(3-(3,4-dimethoxy-2-(prop-2-yn-1-yloxy)phenyl)acrylamido)benzoic acid (95);
(E)-2-(3-(3,4-dimethoxy-2-(pyridin-3-ylmethoxy)phenyl)acrylamido)benzoic acid (96);
(E)-2-(3-(3-methoxy-4-(4-methylpiperazin-1-yl)phenyl)acrylamido)benzoic acid (97);
(E)-2-(3-(3-methoxy-4-(1,2,3,6-tetrahydropyridin-4-yl)phenyl)acrylamido)benzoic acid (98);
(E)-2-(3-(3-methoxy-4-(1-methyl-1,2,3,6-tetrahydropyridin-4-yl)phenyl)acrylamido)benzoic acid (99);
(E)-2-(3-(4-methoxy-3-morpholinophenyl)acrylamido)benzoic acid (101);
(E)-2-(3-(3-methoxy-4-morpholinophenyl)acrylamido)benzoic acid (103);
(E)-2-(3-(4-methoxy-3-(1-methyl-1,2,3,6-tetrahydropyridin-4-yl)phenyl)acrylamido)benzoic acid (104);
2-[[(E)-3-(4-methyl-2,3-dihydro-1,4-benzoxazin-6-yl)prop-2-enoyl]amino]benzoic acid (107);
(E)-N-(2-(1,2,4-oxadiazol-5-yl)phenyl)-3-(3-methoxy-4-(prop-2-yn-1-yloxy)phenyl)acrylamide (108);
(E)-2-(3-(4-methyl-3-oxo-3,4-dihydro-2H-benzo[b][1,4]oxazin-7-yl)acrylamido)benzoic acid (109);
(E)-2-(3-(4-methyl-3,4-dihydro-2H-benzo[b][1,4]oxazin-7-yl)acrylamido)benzoic acid (110);
(E)-2-(3-(3-oxo-3,4-dihydro-2H-benzo[b][1,4]oxazin-6-yl)acrylamido)benzoic acid (111);
(E)-2-(3-(4-methyl-3-oxo-3,4-dihydro-2H-benzo[b][1,4]oxazin-6-yl)acrylamido)benzoic acid (112);
(E)-3-(3-ethyl-4-(prop-2-yn-1-yloxy)phenyl)-N-(2-(3-methyl-1H-1,2,4-triazol-1-yl)phenyl)-acrylamide (114);
(E)-2-(3-(2-(2-(dimethylamino)ethoxy)-3,4-dimethoxyphenyl)acrylamido)benzoic acid (116);
(E)-4-chloro-2-(3-(2-(2-(dimethylamino)ethoxy)-3,4-dimethoxyphenyl)acrylamido)benzoic acid (117);
(E)-N-(4-fluorophenyl)-3-(3-methoxy-4-(1,2,3,6-tetrahydropyridin-4-yl)phenyl)acrylamide (120);
N-(4-cyanophenyl)-2-(3-methoxy-4-(1,2,3,6-tetrahydropyridin-4-yl)phenyl)cyclopropane carboxamide (121);
2-(2-(2-(dimethylamino)ethoxy)-3,4-dimethoxyphenyl)-N-(4-fluorophenyl)cyclopropane-1-carboxamide (122);
(E)-3-(3-ethyl-4-(prop-2-yn-1-yloxy)phenyl)-N-(2-fluorophenyl)acrylamide (123);
(E)-N-(4-cyanophenyl)-3-(3-ethyl-4-(prop-2-yn-1-yloxy)phenyl)acrylamide (124);
(E)-3-(3-ethyl-4-(prop-2-yn-1-yloxy)phenyl)-N-(4-fluorophenyl)acrylamide (125);
(E)-3-(2-(2-(dimethylamino)ethoxy)-3,4-dimethoxyphenyl)-N-(2-fluorophenyl)acrylamide (127);
(E)-3-(2-(2-(dimethylamino)ethoxy)-3,4-dimethoxyphenyl)-N-(4-fluorophenyl)acrylamide (128);
(E)-N-(4-cyanophenyl)-3-(2-(2-(dimethylamino)ethoxy)-3,4-dimethoxyphenyl)acrylamide (129);
(E)-2-(3-(4-methyl-3,4-dihydro-2H-benzo[b][1,4]oxazin-7-yl)acrylamido)benzoic acid (130);
(E)-N-(4-cyanophenyl)-3-(3-methoxy-4-((1-methylpyrrolidin-3-yl)oxy)phenyl)acrylamide (131);
(E)-N-(4-fluorophenyl)-3-(3-methoxy-4-((1-methylpyrrolidin-3-yl)oxy)phenyl)acrylamide (132);
N-(4-fluorophenyl)-2-(3-methoxy-4-(prop-2-yn-1-yloxy)phenyl)cyclopropanecarboxamide (133);
N-(4-cyanophenyl)-2-(3-methoxy-4-(prop-2-yn-1-yloxy)phenyl)cyclopropanecarboxamide (135);
N-(4-fluorophenyl)-2-(3-methoxy-4-((1-methylpyrrolidin-3-yl)oxy)phenyl)cyclopropane-1-carboxamide (136);
N-(4-cyanophenyl)-2-(3-methoxy-4-((1-methylpyrrolidin-3-yl)oxy)phenyl)cyclopropane-1-carboxamide (137);
N-(2-fluorophenyl)-2-(3-methoxy-4-((1-methylpyrrolidin-3-yl)oxy)phenyl)cyclopropane carboxamide (138);
(E)-N-(4-cyanophenyl)-3-(3-methoxy-4-(1,2,3,6-tetrahydropyridin-4-yl)phenyl)acrylamide (139);
(E)-3-(3-methoxy-4-(1,2,3,6-tetrahydropyridin-4-yl)phenyl)-N-(2-(3-methyl-1H-1,2,4-triazol-1-yl)phenyl)acrylamide (140);
(E)-N-(2-fluorophenyl)-3-(3-methoxy-4-(1,2,3,6-tetrahydropyridin-4-yl)phenyl)acrylamide (141);
N-(4-fluorophenyl)-2-(3-methoxy-4-(1,2,3,6-tetrahydropyridin-4-yl)phenyl)cyclopropane carboxamide (143);
2-(3-methoxy-4-(1,2,3,6-tetrahydropyridin-4-yl)phenyl)-N-(2-(3-methyl-1H-1,2,4-triazol-1-yl)phenyl)cyclopropanecarboxamide (144);
N-(2-fluorophenyl)-2-(3-methoxy-4-(1,2,3,6-tetrahydropyridin-4-yl)phenyl)cyclopropane carboxamide (145);
(E)-N-(3-chlorophenyl)-3-(3-methoxy-4-(oxetan-3-ylmethoxy)phenyl)acrylamide (147);
N-(3-chlorophenyl)-2-(3-methoxy-4-(oxetan-3-ylmethoxy)phenyl)cyclopropane-1-carboxamide (148);
N-(4-chlorophenyl)-2-(4-methoxy-3-((1-methyl-1H-pyrazol-4-yl)methoxy)phenyl)cyclopropane-1-carboxamide (149);
(E)-N-(3-chlorophenyl)-3-(4-methoxy-3-morpholinophenyl)acrylamide (151);
(E)-N-(2-chlorophenyl)-3-(3-methoxy-4-(oxetan-3-ylmethoxy)phenyl)acrylamide (152);
(E)-N-(4-chlorophenyl)-3-(3-methoxy-4-(oxetan-3-ylmethoxy)phenyl)acrylamide (153);
N-(4-chlorophenyl)-2-(3-methoxy-4-(oxetan-3-ylmethoxy)phenyl)cyclopropane-1-carboxamide (154);
N-(2-chlorophenyl)-2-(3-methoxy-4-(oxetan-3-ylmethoxy)phenyl)cyclopropane-1-carboxamide (155);
N-(3-chlorophenyl)-2-(4-methoxy-3-((1-methyl-1H-pyrazol-4-yl)methoxy)phenyl)cyclopropane-1-carboxamide (156);
N-(2-chlorophenyl)-2-(4-methoxy-3-((1-methyl-1H-pyrazol-4-yl)methoxy)phenyl)cyclopropane-1-carboxamide (157);
2-(4-methoxy-3-((1-methyl-1H-pyrazol-4-yl)methoxy)phenyl)-N-(3-(methylsulfonyl)phenyl) cyclopropane-1-carboxamide (158);
(E)-N-(2-chlorophenyl)-3-(4-methoxy-3-((1-methyl-1H-pyrazol-4-yl)methoxy)phenyl)acrylamide (159);
(E)-N-(3-chlorophenyl)-3-(4-methoxy-3-((1-methyl-1H-pyrazol-4-yl)methoxy)phenyl)acrylamide (160); and pharmaceutically acceptable salts thereof.

In another aspect, provided are the following compounds:
(E)-3-(3-methoxy-4-(prop-2-yn-1-yloxy)phenyl)-N-phenylacrylamide (8);
methyl (E)-1-(3-(3-methoxy-4-(prop-2-yn-1-yloxy)phenyl)acryloyl)-1,2,3,4-tetrahydroquinoline-4-carboxylate (9)
(E)-1-(3,4-dihydroquinolin-1(2H)-yl)-3-(3-methoxy-4-(prop-2-yn-1-yloxy)phenyl)prop-2-en-1-one (10);
(E)-1-(3,4-dihydroquinoxalin-1(2H)-yl)-3-(3-methoxy-4-(prop-2-yn-1-yloxy)phenyl)prop-2-en-1-one (11);
(E)-1-(2,3-dihydro-4H-benzo[b][1,4]oxazin-4-yl)-3-(3-methoxy-4-(prop-2-yn-1-yloxy)phenyl)prop-2-en-1-one (12);
(E)-N-((trans)-2-aminocyclohexyl)-3-(3-methoxy-4-(prop-2-yn-1-yloxy)phenyl)acrylamide (13);

(E)-1-(4-hydroxy-3,4-dihydroquinolin-1(2H)-yl)-3-(3-methoxy-4-(prop-2-yn-1-yloxy)phenyl)prop-2-en-1-one (14);

(E)-1-(3-hydroxy-1H-indazol-1-yl)-3-(3-methoxy-4-(prop-2-yn-1-yloxy)phenyl)prop-2-en-1-one (15);

(E)-N-(2-(dimethylamino)ethyl)-2-(3-(3-methoxy-4-(prop-2-yn lyloxy) phenyl) acrylamido) benzamide (30);

(E)-N-(3-(dimethylamino)propyl)-2-(3-(3-methoxy-4-(prop-2-yn-1-yloxy)phenyl)acrylamido) benzamide (32);

(E)-2-(3-(3-methoxy-4-(prop-2-yn-1-yloxy)phenyl)acrylamido)-N-(2-methoxyethyl)benzamide (33);

(E)-2-(3-(3-methoxy-4-(prop-2-yn-1-yloxy)phenyl)acrylamido)-N-(2-(4-methylpiperazin-1-yl)ethyl)benzamide (34);

(E)-2-(3-(3-methoxy-4-(prop-2-yn-1-yloxy)phenyl)acrylamido)-N-(2-morpholino ethyl)benzamide (35);

(E)-2-(3-(3-methoxy-4-(prop-2-yn-1-yloxy)phenyl)acrylamido)-N-((1-methylpiperidin-4-yl)methyl)benzamide (37);

(E)-2-(3-(3-methoxy-4-(prop-2-yn-1-yloxy)phenyl)acrylamido)-N-((tetrahydrofuran-3-yl)methyl)benzamide (39);

(E)-2-(3-(3-methoxy-4-(prop-2-yn-1-yloxy)phenyl)acrylamido)-N-((1-methyl-1H-imidazol-5-yl)methyl)benzamide (40);

(E)-2-(3-(3-methoxy-4-(prop-2-yn-1-yloxy)phenyl)acrylamido)-N-(pyridin-2-ylmethyl)benzamide (41);

(E)-2-(3-(3-methoxy-4-(prop-2-yn-1-yloxy)phenyl)acrylamido)-N-(2-(pyridin-2-yl)ethyl)benzamide (42);

(E)-2-(3-(3-methoxy-4-(prop-2-yn-1-yloxy)phenyl)acrylamido)-N-(pyridin-3-ylmethyl)benzamide (43);

(E)-2-(3-(3-methoxy-4-(prop-2-yn-1-yloxy)phenyl)acrylamido)-N-(pyridin-4-ylmethyl)benzamide (45);

(E)-2-(3-(3-methoxy-4-(prop-2-yn-1-yloxy)phenyl)acrylamido)-N-(2-(pyridin-4-yl)ethyl)benzamide (46);

(E)-2-(3-(3-methoxy-4-(piperidin-4-ylmethoxy)phenyl)acrylamido)benzoic acid (50);

(E)-2-(3-(4-((3,5-dimethylisoxazol-4-yl)methoxy)-3-methoxyphenyl)acrylamido)benzoic acid (52);

(E)-2-(3-(3-methoxy-4-((1-methyl-1H-pyrazol-4-yl)methoxy)phenyl)acrylamido)benzoic acid (53);

(E)-2-(3-(3-methoxy-4-(oxetan-3-ylmethoxy)phenyl)acrylamido)benzoic acid (54);

(E)-2-(3-(3-methoxy-4-(pyridin-2-ylmethoxy)phenyl)acrylamido)benzoic acid (55);

(E)-2-(3-(3-methoxy-4-(2-(pyridin-2-yl)ethoxy)phenyl)acrylamido)benzoic acid (56);

(E)-2-(3-(3-methoxy-4-(2-(pyridin-3-yl)ethoxy)phenyl)acrylamido)benzoic acid (57);

(E)-2-(3-(3-methoxy-4-(pyridin-4-ylmethoxy)phenyl)acrylamido)benzoic acid (58);

(E)-2-(3-(3-methoxy-4-(2-(pyridin-4-yl)ethoxy)phenyl)acrylamido)benzoic acid (59);

(E)-2-(3-(3-methoxy-4-((1-methyl-1H-pyrazol-5-yl)methoxy)phenyl)acrylamido)benzoic acid (60);

(E)-2-(3-(4-methoxy-3-(2-methoxyethoxy)phenyl)acrylamido)benzoic acid (61);

(E)-2-(3-(4-methoxy-3-(2-(pyridin-2-yl)ethoxy)phenyl)acrylamido)benzoic acid (62);

(E)-2-(3-(4-methoxy-3-(pyridin-3-ylmethoxy)phenyl)acrylamido)benzoic acid (63);

(E)-2-(3-(4-methoxy-3-(2-(pyridin-3-yl)ethoxy)phenyl)acrylamido)benzoic acid (64);

(E)-2-(3-(4-methoxy-3-(2-(pyridin-4-yl)ethoxy)phenyl)acrylamido)benzoic acid (65);

(E)-2-(3-(4-methoxy-3-((1-methyl-1H-pyrazol-4-yl)methoxy)phenyl)acrylamido)benzoic acid (66);

(E)-2-(3-(4-methoxy-3-((1-methyl-1H-pyrazol-5-yl)methoxy)phenyl)acrylamido)benzoic acid (67);

(E)-2-(3-(3-methoxy-4-((4-methylpiperazin-1-yl)methyl)phenyl)acrylamido)benzoic acid (68);

(E)-2-(3-(3-methoxy-4-(morpholinomethyl)phenyl)acrylamido)benzoic acid (69);

(E)-2-(3-(4-methoxy-3-(((1-methylpiperidin-4-yl)oxy)methyl)phenyl)acrylamido)benzoic acid (70)

(E)-2-(3-(4-methoxy-3-((prop-2-yn-1-yloxy)methyl)phenyl)acrylamido)benzoic acid (71);

(E)-2-(3-(3-methoxy-4-((prop-2-yn-1-yloxy)methyl)phenyl)acrylamido)benzoic acid (72);

(E)-2-(3-(4-methoxy-3-(methoxymethyl)phenyl)acrylamido)benzoic acid (73);

(E)-2-(3-(4-methoxy-3-((prop-2-yn-1-ylamino)methyl)phenyl)acrylamido)benzoic acid (74);

(E)-2-(3-(3-methoxy-4-((prop-2-yn-1-ylamino)methyl)phenyl)acrylamido)benzoic acid (75);

(E)-2-(3-(4-ethyl-3-methoxyphenyl)acrylamido)benzoic acid (100);

2-[[(E)-3-[4-(cyclopropylmethyl)-3-methoxyphenyl]prop-2-enoyl]amino]benzoic acid (102);

(E)-2-(3-(3-ethyl-4-methoxyphenyl)acrylamido)benzoic acid (105);

(E)-2-(3-(3-(cyclopropylmethyl)-4-methoxyphenyl)acrylamido)benzoic acid (106);

(E)-1-(2H-benzo[b][1,4]oxazin-4(3H)-yl)-3-(3-ethyl-4-(prop-2-yn-1-yloxy)phenyl)prop-2-en-1-one (113);

(E)-1-(2H-benzo[b][1,4]oxazin-4(3H)-yl)-3-(2-(2-(dimethylamino)ethoxy)-3,4-dimethoxyphenyl)-prop-2-en-1-one (115);

(E)-1-(2H-benzo[b][1,4]oxazin-4(3H)-yl)-3-(3-methoxy-4-((1-methylpyrrolidin-3-yl)oxy)phenyl)prop-2-en-1-one (118); (2H-benzo[b][1,4]oxazin-4(3H)-yl)(2-(3-methoxy-4-(prop-2-yn-1-yloxy) phenyl) cyclopropyl) methanone (119);

(E)-3-(3-ethyl-4-(prop-2-yn-1-yloxy)phenyl)-1-(3-hydroxy-1H-indazol-1-yl)prop-2-en-1-one (126);

(3-hydroxy-1H-indazol-1-yl)(2-(3-methoxy-4-(prop-2-yn-1-yloxy)phenyl)cyclopropyl) methanone (134);

(E)-1-(3-hydroxy-1H-indazol-1-yl)-3-(3-methoxy-4-(1,2,3,6-tetrahydropyridin-4-yl)phenyl)prop-2-en-1-one (142);

(3-hydroxy-1H-indazol-1-yl)(2-(3-methoxy-4-(1,2,3,6-tetrahydropyridin-4-yl)phenyl) cyclopropyl)methanone (146);

(E)-3-(4-methoxy-3-((1-methyl-1H-pyrazol-4-yl)methoxy)phenyl)-N-(pyridin-3-yl)acrylamide (150); and pharmaceutically acceptable salts thereof.

In another aspect, provided are pharmaceutical compositions comprising any compound of the present disclosure (e.g., compound of Formula I, 2-[[(E)-3-[4-(cyclopropylmethyl)-3-methoxyphenyl]prop-2-enoyl]amino]benzoic acid)) or a pharmaceutically acceptable salt thereof, and a pharmaceutically acceptable excipient.

In another aspect, provided are methods of disease or condition associated with fibrosis in a subject in need thereof, the method comprising administering any compound of the present disclosure (e.g., compound of Formula I, 2-[[(E)-3-[4-(cyclopropylmethyl)-3-methoxyphenyl]prop-2-enoyl]amino]benzoic acid)) or a pharmaceutically acceptable salt thereof, or a pharmaceutical composition comprising any compound of the present disclosure (e.g., compound of Formula I, 2-[[(E)-3-[4-(cyclopropylmethyl)-3-methoxyphenyl]prop-2-enoyl]amino]benzoic acid)) or pharmaceutically acceptable salt thereof, to the subject. In certain embodiments, the disease or condition associated with fibrosis is selected from the group consisting of fibrotic skin disorders, lung disease, heart disease, kidney disease, and cirrhosis of the liver. In certain embodiments, the disease or condition associated with fibrosis is kidney disease. In certain embodiments, the kidney disease is progressive kidney disease, glomerulonephritis, diabetic kidney disease, diabetic nephropathy, systemic lupus, primary glomerulonephritis, membranous nephropathy, focal segmental glomerulosclerosis, membranoproliferative glomerulonephritis, diffuse proliferative glomerulonephritis, membranous focal segmental glomerulosclerosis, secondary glomerulonephritis, or ischemic nephropathy. In certain embodiments, the disease or condition associated with fibrosis is focal segmental glomerulosclerosis.

In another aspect, provided are kits comprising any compound of the present disclosure (e.g., compound of Formula I, 2-[[(E)-3-[4-(cyclopropylmethyl)-3-methoxyphenyl]prop-2-enoyl]amino]benzoic acid)) or a pharmaceutically acceptable salt thereof, or a pharmaceutical composition comprising any compound of the present disclosure (e.g., compound of Formula I, 2-[[(E)-3-[4-(cyclopropylmethyl)-3-methoxyphenyl]prop-2-enoyl]amino]benzoic acid)) or pharmaceutically acceptable salt thereof. In certain embodiments, the kits further comprise instructions for administration (e.g., human administration).

The details of certain embodiments of the invention are set forth in the Detailed Description of Certain Embodiments, as described below. Other features, objects, and advantages of the invention will be apparent from the Definitions, Examples, Figures, and Claims.

DEFINITIONS

Chemical Definitions

Figure 1:
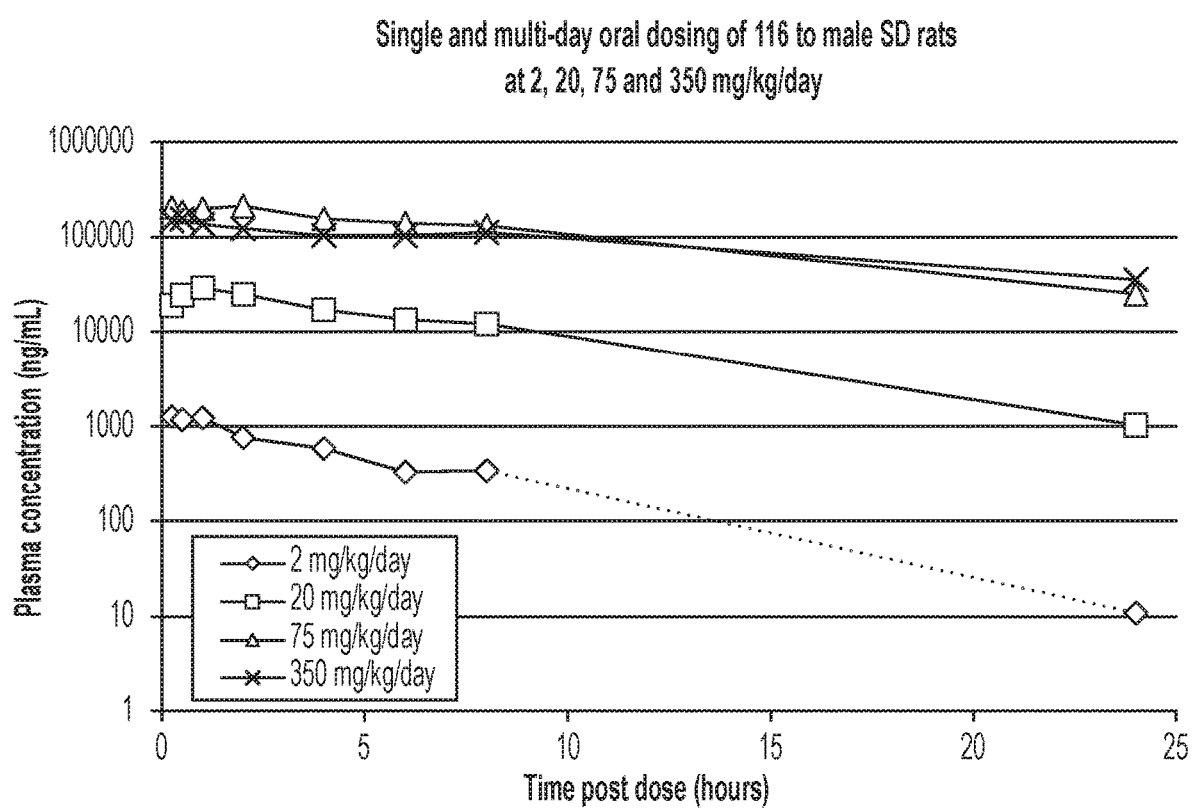
FIG. 1 shows a pharmacokinetic profile plot (plasma concentration vs. time) after administration of 2 mg/kg, 20 mg/kg, 75 mg/kg, and 350 mg/kg of 116 to male SD rats.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March, March's Advanced Organic Chemistry, 5$^{th}$ Edition, John Wiley & Sons, Inc., New York, 2001; Larock, Comprehensive Organic Transformations, VCH Publishers, Inc., New York, 1989; and Carruthers, Some Modern Methods of Organic Synthesis, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ⁓ is a single bond where the stereochemistry of the moieties immediately attached thereto is not specified, --- is absent or a single bond, and === or ≡≡≡ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("hetero$C_{1-20}$ alkyl"). In some embodiments, a heteroalkyl group is a saturated group having 1 to 18 carbon atoms and 1 or more heteroatoms within the parent chain ("hetero$C_{1-18}$ alkyl"). In some embodiments, a heteroalkyl group is a saturated group having 1 to 16 carbon atoms and 1 or more heteroatoms within the parent chain ("hetero$C_{1-16}$ alkyl"). In some embodiments, a heteroalkyl group is a saturated group having 1 to 14 carbon atoms and 1 or more heteroatoms within the parent chain ("hetero$C_{1-14}$ alkyl"). In some embodiments, a heteroalkyl group is a saturated group having 1 to 12 carbon atoms and 1 or more heteroatoms within the parent chain ("hetero$C_{1-12}$ alkyl"). In some embodiments, a heteroalkyl group is a saturated group having 1 to 10 carbon atoms and 1 or more heteroatoms within the parent chain ("hetero$C_{1-10}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, the heteroalkyl group defined herein is a partially unsaturated group having 1 or more heteroatoms within the parent chain and at least one unsaturated carbon, such as a carbonyl group. For example, a heteroalkyl group may comprise an amide or ester functionality in its parent chain such that one or more carbon atoms are unsaturated carbonyl groups. Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-20}$ alkyl. In certain embodiments, the heteroalkyl group is an unsubstituted hetero$C_{1-10}$ alkyl. In certain embodiments, the heteroalkyl group is a substituted hetero$C_{1-20}$ alkyl. In certain embodiments, the heteroalkyl group is an unsubstituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$ or

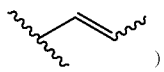)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

"Carbocyclylalkyl" is a subset of "alkyl" and refers to an alkyl group substituted by an carbocyclyl group, wherein the point of attachment is on the alkyl moiety.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

"Cycloalkylalkyl" is a subset of "alkyl" and refers to an alkyl group substituted by an cycloalkyl group, wherein the point of attachment is on the alkyl moiety.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

"Heterocyclylalkyl" is a subset of "alkyl" and refers to an alkyl group substituted by an heterocyclyl group, wherein the point of attachment is on the alkyl moiety.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Arylalkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

"Heteroaryalkyl" is a subset of "alkyl" and refers to an alkyl group substituted by a heteroaryl group, wherein the point of attachment is on the alkyl moiety.

The term "silyl" refers to the group —Si($R^{aa}$)$_3$, wherein $R^{aa}$ is as defined herein.

The term "boronyl" refers to boranes, boronic acids, boronic esters, borinic acids, and borinic esters, e.g., boronyl groups of the formula —B($R^{aa}$)$_2$, —B($OR^{cc}$)$_2$, and —B$R^{aa}$ ($OR^{cc}$), wherein $R^{aa}$ and $R^{cc}$ are as defined herein.

The term "phosphino" refers to the group —P($R^{cc}$)$_3$, wherein $R^{cc}$ is as defined herein. An exemplary phosphino group is triphenylphosphine.

The term "phosphono" refers to the group —O(P=O)($OR^{cc}$)$R^{aa}$, wherein $R^{aa}$ and $R^{cc}$ are as defined herein.

The term "phosphoramido" refers to the group —O(P=O)(N($R^{bb}$)$_2$)$_2$, wherein each $R^{bb}$ is as defined herein.

The term "stannyl" refers to the group —Sn($R^{cc}$)$_3$, wherein $R^{cc}$ is as defined herein.

The term "germyl" refers to the group —Ge($R^{cc}$)$_3$, wherein $R^{cc}$ is as defined herein.

The term "arsenyl" refers to the group —As($R^{cc}$)$_3$, wherein $R^{cc}$ is as defined herein.

The term "oxo" refers to the group =O, and the term "thiooxo" refers to the group =S.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —O$R^{aa}$, —ON($R^{bb}$)$_2$, —OC(=O)S$R^{aa}$, —OC(=O)$R^{aa}$, —OCO$_2R^{aa}$, —OC(=O)N($R^{bb}$)$_2$, —OC(=N$R^{bb}$)$R^{aa}$, —OC(=N$R^{bb}$)O$R^{aa}$, —OC(=N$R^{bb}$)N($R^{bb}$)$_2$, —OS(=O)$R^{aa}$, —OSO$_2R^{aa}$, —OSi($R^{aa}$)$_3$, —OP($R^{cc}$)$_2$, —OP($R^{cc}$)$_3^+X^-$, —OP(O$R^{cc}$)$_2$, —OP(O$R^{cc}$)$_3^+X^-$, —OP(=O)($R^{aa}$)$_2$, —OP(=O)(O$R^{cc}$)$_2$, and —OP(=O)(N($R^{bb}$)$_2$)$_2$, wherein $X^-$, $R^{aa}$, $R^{bb}$, and $R^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —NHCO$_2R^{aa}$, —NHC(=O)N($R^{bb}$)$_2$, —NHC(=N$R^{bb}$)N($R^{bb}$)$_2$, —NHSO$_2R^{aa}$, —NHP(=O)(O$R^{cc}$)$_2$, and —NHP(=O)(N($R^{bb}$)$_2$)$_2$, wherein $R^{aa}$, $R^{bb}$ and $R^{cc}$ are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —N$R^{bb}$C(=O)$R^{aa}$, —N$R^{bb}$CO$_2R^{aa}$, —N$R^{bb}$C(=O)N($R^{bb}$)$_2$, —N$R^{bb}$C(=N$R^{bb}$)N($R^{bb}$)$_2$, —N$R^{bb}$SO$_2R^{aa}$, —N$R^{bb}$P(=O)(O$R^{cc}$)$_2$, and —N$R^{bb}$P(=O)(N($R^{bb}$)$_2$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+X^-$, wherein $R^{bb}$ and $X^-$ are as defined herein.

The term "sulfonyl" refers to a group selected from —SO$_2$N($R^{bb}$)$_2$, —SO$_2R^{aa}$, and —SO$_2$O$R^{aa}$, wherein $R^{aa}$ and $R^{bb}$ are as defined herein.

The term "sulfinyl" refers to the group —S(=O)$R^{aa}$, wherein $R^{aa}$ is as defined herein.

The term "acyl" refers to a group having the general formula —C(=O)$R^{X1}$, —C(=O)O$R^{X1}$, —C(=O)—O—C(=O)$R^{X1}$, —C(=O)S$R^{X1}$, —C(=O)N($R^{X1}$)$_2$, —C(=S)$R^{X1}$, —C(=S)N($R^{X1}$)$_2$, —C(=S)O($R^{X1}$), —C(=S)S($R^{X1}$), —C(=N$R^{X1}$)$R^{X1}$, —C(=N$R^{X1}$)O$R^{X1}$, —C(=N$R^{X1}$)S$R^{X1}$, and —C(=N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxyi, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is sp$^2$ hybridized, and is substituted with an oxygen, nitrogen or sulfur atom, e.g., a group selected from ketones (e.g., —C(=O)$R^{aa}$), carboxylic acids (e.g., —CO$_2$H), aldehydes (—CHO), esters (e.g., —CO$_2R^{aa}$, —C(=O)S$R^{aa}$, —C(=S)S$R^{aa}$), amides (e.g., —C(=O)N($R^{bb}$)$_2$, —C(=O)N$R^{bb}$SO$_2R^{aa}$, —C(=S)N($R^{bb}$)$_2$), and imines (e.g., —C(=N$R^{bb}$)$R^{aa}$, —C(=N$R^{bb}$)O$R^{aa}$, —C(=N$R^{bb}$)N($R^{bb}$)$_2$), wherein $R^{aa}$ and $R^{bb}$ are as defined herein.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_3$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; each instance of R$^{aa}$ is, independently, selected from $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion; each instance of R$^{cc}$ is, independently, selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(=NH)NH(C$_{1-6}$ alkyl), —OC(=NH)NH$_2$, —NHC(=NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$(C$_{1-6}$ alkyl), —SO$_2$O(C$_{1-6}$ alkyl), —OSO$_2$(C$_{1-6}$ alkyl), —SO(C$_{1-6}$ alkyl), —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{a}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $-S(=O)_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3^+X^-$, $-P(OR^{cc})_2$, $-P(OR^{cc})_3^+X^-$, $-P(=O)(R^{aa})_2$, $-P(=O)(OR^{cc})_2$, and $-P(=O)(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, o-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3rd edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $F^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5\text{-}(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "leaving group" is given its ordinary meaning in the art of synthetic organic chemistry and refers to an atom or a group capable of being displaced by a nucleophile. See, for example, Smith, *March's Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, -OTs), methanesulfonate (mesylate, -OMs), p-bromobenzenesulfonyloxy (brosylate, -OBs), $-OS(=O)_2(CF_2)_3CF_3$ (nonaflate, -ONf), or trifluoromethanesulfonate (triflate, -OTf). In some cases, the leaving group is a brosylate, such as p-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. Further exemplary leaving groups include, but are not limited to, halo (e.g., chloro, bromo, iodo) and activated substituted hydroxyl groups (e.g., $-OC(=O)SR^{aa}$, $-OC(=O)R^{aa}$, $-OCO_2R^{aa}$, $-OC(=O)N(R^{bb})_2$, $-OC(=NR^{bb})R^{aa}$, $-OC(=NR^{bb})OR^{aa}$, $-OC(=NR^{bb})N(R^{bb})_2$, $-OS(=O)R^{aa}$, $-OSO_2R^{aa}$, $-OP(R^{cc})_2$, $-OP(R^{cc})_3$, $-OP(=O)_2R^{aa}$, $-OP(=O)(R^{aa})_2$, $-OP(=O)(OR^{cc})_2$, $-OP(=O)_2N(R^{bb})_2$, and $-OP(=O)(NR^{bb})_2$, wherein $R^{aa}$, $R^{bb}$, and $R^{cc}$ are as defined herein).

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and claims. The invention is not intended to be limited in any manner by the above exemplary listing of substituents.

Other Definitions

The following definitions are more general terms used throughout the present application.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.2$H_2O$) and hexahydrates (R.6$H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_{1-8}$alkyl, $C_{2-8}$ alkenyl, $C_{2-8}$ alkynyl, aryl, $C_{7-12}$ substituted aryl, and $C_{7-12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "target tissue" refers to any biological tissue of a subject (including a group of cells, a body part, or an organ) or a part thereof, including blood and/or lymph vessels, which is the object to which a compound, particle, and/or composition of the invention is delivered. A target tissue may be an abnormal or unhealthy tissue, which may need to be treated. A target tissue may also be a normal or healthy tissue that is under a higher than normal risk of becoming abnormal or unhealthy, which may need to be prevented. In certain embodiments, the target tissue is the liver. In certain embodiments, the target tissue is the lung. A "non-target tissue" is any biological tissue of a subject (including a group of cells, a body part, or an organ) or a part thereof, including blood and/or lymph vessels, which is not a target tissue.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces, or avoids symptoms, signs, or causes of the condition, and/or enhances the therapeutic efficacy of another therapeutic agent. In certain embodiments, a therapeutically effective amount is an amount sufficient for fibrosis inhibition. In certain embodiments, a therapeutically effective amount is an amount sufficient for treating diseases associated with fibrosis. In certain embodiments, a therapeutically effective amount is an amount sufficient for fibrosis inhibition and treating diseases associated with fibrosis.

A "prophylactically effective amount" of a compound described herein is an amount sufficient to prevent a condition, or one or more signs or symptoms associated with the condition, or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for fibrosis inhibition. In certain embodiments, a prophylactically effective amount is an amount sufficient for treating diseases associated with fibrosis. In certain embodiments, a prophylactically effective amount is an amount sufficient for fibrosis inhibition and treating diseases associated with fibrosis.

As used herein, the term "inhibit" or "inhibition" in the context of the TGF-β signalling pathway, for example, refers to a reduction in the activity of TGF-β or another enzyme in the TGF-β signalling pathway (e.g., ERK), a reduction in the activity of TGF-β induced proline incorporation in cells, and/or a reduction in the activity of TGF-β induced extracellular matrix production. In some embodiments, the term refers to a reduction of the level of enzyme activity (e.g., TGF-β activity), a reduction in the activity of TGF-β induced proline incorporation in cells, and/or a reduction in the activity of TGF-β induced extracellular matrix production, to a level that is statistically significantly lower than an initial level, which may, for example, be a baseline level of enzyme activity. In some embodiments, the term refers to a reduction of the level of enzyme activity (e.g., TGF-β activity), a reduction in the activity of TGF-β induced proline incorporation in cells, and/or a reduction in the activity of TGF-β induced extracellular matrix production, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

The term "benign or malignant neoplastic disease" as used herein refers to any growth or tumour caused by abnormal and uncontrolled cell division. In certain embodiments, the malignant neoplastic disease may be cancer.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematological cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrim's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphomal-leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemiallymphoma as described above; and multiple myeloma, heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "immunotherapy" refers to a therapeutic agent that promotes the treatment of disease by inducing, enhancing, or suppressing an immune response. Immunotherapies designed to elicit or amplify an immune response are classified as activation immunotherapies, while immunotherapies that reduce or suppress are classified as suppression immunotherapies. Immunotherapies are typically, but not always, biotherapeutic agents. Numerous immunotherapies are used to treat cancer. These include, but are not limited to, monoclonal antibodies, adoptive cell transfer, cytokines, chemokines, vaccines, and small molecule inhibitors.

The term "small molecule" or "small molecule therapeutic" refers to molecules, whether naturally occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "therapeutic agent" refers to any substance having therapeutic properties that produce a desired, usually beneficial, effect. For example, therapeutic agents may treat, ameliorate, and/or prevent disease. Therapeutic agents, as disclosed herein, may be biologics or small molecule therapeutics.

The term "chemotherapeutic agent" refers to a therapeutic agent known to be of use in chemotherapy for cancer.

The term "kidney disease", as used herein, may refer to a disorder of at least one kidney in a subject that compromises the function of the kidney. The kidney disease may result from a primary pathology of the kidney (e.g., injury to the glomerulus or tubule), or another organ (e.g., pancreas) which adversely affects the ability of the kidney to perform biological functions. A kidney disease in the human can be the direct or indirect effect of disease. Examples of a kidney disease as a result or consequence of an indirect effect on the kidneys is kidney disease as a consequence of diabetes or systemic lupus. A kidney disease may be the result or a consequence of any change, damage, or trauma to the glomerulus, tubules or interstitial tissue in either the renal cortex or renal medulla of the kidney.

The term "kidney disease", as used herein, may refer to a progressive kidney disease that over time (e.g., days, weeks, months, years) leads to a loss of renal function.

The kidney disease may include, but is not limited to, a progressive glomerular kidney disease including, without limitation, diabetic nephropathy (e.g., as a consequence of Type I or Type II diabetes or systemic lupus), primary glomerulonephritis (e.g., membranous nephropathy, focal segmental glomerulosclerosis, membranoproliferative glomerulonephritis, diffuse proliferative glomerulonephritis, membranous focal segmental glomerulosclerosis) or secondary glomerulonephritis (e.g., diabetic nephropathy, ischemic nephropathy).

The term "renal function", as used herein, refers to a physiological property of the kidney, such as the ability to retain protein thereby preventing proteinuria. Renal function can be assessed using methods known in the art such as determining one or more of glomerular filtration rate (e.g., creatinine clearance), excretion of protein in urine, blood urea nitrogen, and serum or plasma creatinine.

A progressive kidney disease treated by the compositions and methods described herein includes any kidney disease that can, ultimately, lead to end-stage renal disease. A progressive kidney disease that can be treated by the compositions and methods of the invention can be, for example, associated with endogenous iron deposit in the kidney (e.g., glomerulus, tubules).

"Diabetic cardiomyopathy" refers to any one or more cardiac pathology and/or dysfunction in a subject, which is a complication of either Type I or Type II diabetes in the subject. The diabetes may be symptomatic or asymptomatic. Cardiac pathology which is characteristic of diabetic cardiomyopathy includes myocellular hypertrophy, myocardial fibrosis, and in some cases left ventricular hypertrophy. The pathologies which are contemplated arise independently from complications arising from coronary artery disease, although both diabetic complications and coronary artery complications may be present in the same subject. Diastolic dysfunction, such as an impairment in early diastolic filling, a prolongation of isovolumetric relaxation and increased atrial filling is also characteristic of diabetic cardiomyopathy, and may be identified using Doppler methods such as Doppler 2-dimensional echocardiography (for example Redford M M et al., "Burden of systolic and diastolic dysfunction in the community". JAMA (2003) 289:194-203) or radionuclide imaging for early or mild dysfunction and by standard echocardiograph testing for more severe dysfunction.

"Cardiac fibrosis" refers to the formation of fibrous tissue, including cellular and extracellular components, in the lining and muscle of the heart. If present in sufficient quantities, the fibrous tissue will result in a decrease in the contractility and/or relaxation of one or more regions of the heart, resulting in functional deficit in cardiac output.

DETAILED DESCRIPTION OF CERTAIN EMBODIMENTS

Provided herein are anti-fibrotic compounds. The compounds may inhibit fibrosis. The compounds may inhibit the TGF-β signalling pathway. The compounds may inhibit TGF-β, or another enzyme in the TGF-β signalling pathway (e.g., ERK). The compounds may inhibit TGF-3 induced proline incorporation in cells. The compounds may inhibit TGF-β induced extracellular matrix production. The compounds may inhibit collage biosynthesis. In one aspect, the disclosure provides compounds of Formula I, and pharmaceutically acceptable salts, solvates, hydrates, polymorphs, co-crystals, tautomers, stereoisomers, isotopically labeled derivatives, prodrugs, and pharmaceutical compositions thereof. In another aspect, the disclosure provides 2-[[(E)-3-[4-(cyclopropylmethyl)-3-methoxyphenyl]prop-2-enoyl]amino]benzoic acid, and pharmaceutically acceptable salts, solvates, hydrates, polymorphs, co-crystals, tautomers, stereoisomers, isotopically labeled derivatives, prodrugs, and pharmaceutical compositions thereof. The compounds are useful for the treatment and/or prevention of diseases or conditions associated with fibrosis (e.g., kidney disease, cardiac disease), inflammation, and/or a benign or malignant neoplastic disease in a subject in need thereof.

Compounds

The compounds described herein interact with the TGF-3 signalling pathway. As described herein, the therapeutic effect may be a result of inhibition of TGF-3 or another enzyme in the TGF-3 signalling pathway (e.g., ERK). A compound may be provided for use in any composition, kit, or method described herein as a pharmaceutically acceptable salt, co-crystal, tautomer, stereoisomer, solvate, hydrate, polymorph, isotopically enriched derivative, or prodrug thereof.

In one aspect, disclosed is a compound of Formula I:

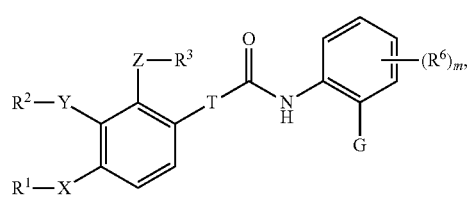

or a pharmaceutically acceptable salt thereof; wherein
T is

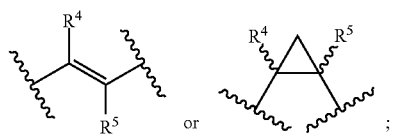

X is O, $NR^{10}$, $-NR^{10}C(O)-$, or a bond;
Y is O, $NR^{10}$, $-C(O)NR^{10}-$, or a bond;
Z is O, $NR^{10}$, or a bond;
$R^1$ and $R^2$ are independently hydrogen, alkyl, heteroalkyl, alkenyl, alkynyl, cycloalkyl, cycloalkylalkyl, arylalkyl, heteroarylalkyl, heterocyclyl, or heterocyclylalkyl, wherein $R^1$ and $R^2$ are each optionally substituted with 1-3 independent substituents $R^8$;

or $R^1$ and $R^2$ together with the atoms to which they are attached form a heterocyclyl ring;
$R^3$ is hydrogen, alkyl, heteroalkyl, alkenyl, alkynyl, cycloalkyl, cycloalkylalkyl, arylalkyl, heteroarylalkyl, heterocyclyl, or heterocyclylalkyl, wherein $R^3$ is optionally substituted with 1-3 independent substituents $R^8$;
$R^4$ and $R^5$ are hydrogen; each occurrence of $R^6$ is, independently, halogen, cyano, alkyl, alkenyl, alkynyl, haloalkyl, hydroxyl, alkoxy, aryl, heteroaryl, heterocyclyl, $NR^aR^b$, or $-S(O)_2R^c$;
G is $C(O)R^7$ or hydrogen;
$R^7$ is OH or $NHR^9$;
m is 0, 1, or 2;
each occurrence of $R^8$ is, independently, alkyl, alkynyl, hydroxyl, alkoxy, carboxyl, oxo, aryl, heteroaryl, heterocyclyl, $-NR^aR^b$, $-S(O)_2R^c$, or $-CO_2R^d$;
$R^9$ is heteroaryl, heterocyclyl, or $-S(O)_2R^c$, wherein $R^9$ is optionally substituted with 1-3 independent substituents $R^8$;
$R^{10}$ is hydrogen or alkyl optionally substituted with 1-3 independent substituents $R^8$; and
each occurrence of $R^a$, $R^b$, $R^c$, and $R^d$ is, independently, hydrogen, acyl, alkyl, alkenyl, alkynyl, heteroalkyl, cycloalkyl, heterocyclylalkyl, aryl, heteroaryl, heterocyclyl, C(O)OC$_{1-6}$ alkyl, C(O)C$_{1-6}$ alkyl, or $R^a$ and $R^b$ together with the atoms to which they are attached form a heterocyclyl ring;
provided that when G is hydrogen, then m is not 0;
provided that when G is $C(O)R^7$, $R^7$ is OH, and $-Z-R^3$ is H, then at least one of $-X-R^1$ and $-Y-R^2$ is $-O$-heterocyclyl or heterocyclyl, or $R^1$ and $R^2$ together with the atoms to which they are attached form a heterocyclyl ring;
provided that when $-X-R^1$ is H, then neither $-Y-R^2$ nor $-Z-R^3$ are hydrogen;
provided that when $-Y-R^2$ is H, then neither $-X-R^1$ nor $-Z-R^3$ are hydrogen; and
provided that when $-Z-R^3$ is H, then neither $-X-R^1$ nor $-Y-R^2$ are hydrogen.

In certain embodiments,
T is

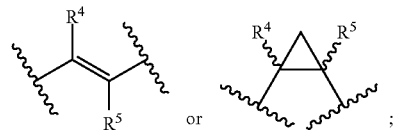

X is O, $NR^{10}$, $-NR^{10}C(O)-$, or a bond;
Y is O, $NR^{10}$, $-C(O)NR^{10}-$, or a bond;
Z is O, $NR^{10}$, or a bond;
$R^1$ and $R^2$ are independently hydrogen, alkyl, heteroalkyl, alkenyl, alkynyl, cycloalkyl, cycloalkylalkyl, arylalkyl, heteroarylalkyl, heterocyclyl, or heterocyclylalkyl, wherein $R^1$ and $R^2$ are each optionally substituted with 1-3 independent substituents $R^8$;
or $R^1$ and $R^2$ together with the atoms to which they are attached form a heterocyclyl ring;
$R^3$ is hydrogen, alkyl, heteroalkyl, alkenyl, alkynyl, cycloalkyl, cycloalkylalkyl, arylalkyl, heteroarylalkyl, heterocyclyl, or heterocyclylalkyl, wherein $R^3$ is optionally substituted with 1-3 independent substituents $R^8$;
$R^4$ and $R^5$ are hydrogen;
each occurrence of $R^6$ is, independently, halogen, cyano, alkyl, alkenyl, alkynyl, haloalkyl, hydroxyl, alkoxy, aryl, heteroaryl, heterocyclyl, $NR^aR^b$, or $-S(O)_2R^c$;

G is C(O)R$^7$ or hydrogen;
R$^7$ is OH or NHR$^9$;
m is 0 or 1;
each occurrence of R$^8$ is, independently, alkyl, alkynyl, hydroxyl, alkoxy, carboxyl, oxo, aryl, heteroaryl, heterocyclyl, —NR$^a$R$^b$, —S(O)$_2$R$^c$, or —CO$_2$R$^d$;
R$^9$ is heteroaryl, heterocyclyl, or —S(O)$_2$R$^c$, wherein R$^9$ is optionally substituted with 1-3 independent substituents R$^8$;
R$^{10}$ is hydrogen or alkyl optionally substituted with 1-3 independent substituents R$^8$; and
each occurrence of R$^a$, R$^b$, R$^c$, and R$^d$ is, independently, hydrogen, acyl, alkyl, alkenyl, alkynyl, heteroalkyl, cycloalkyl, heterocyclylalkyl, aryl, heteroaryl, heterocyclyl, C(O)OC$_{1-6}$ alkyl, C(O)C$_{1-6}$ alkyl, or R$^a$ and R$^b$ together with the atoms to which they are attached form a heterocyclyl ring;
provided that when G is hydrogen, then m is not 0;
provided that when G is C(O)R$^7$, R$^7$ is OH, and —Z—R$^3$ is H, then at least one of —X—R$^1$ and —Y—R$^2$ is —O-heterocyclyl or heterocyclyl, or R$^1$ and R$^2$ together with the atoms to which they are attached form a heterocyclyl ring;
provided that when —X—R$^1$ is H, then neither —Y—R$^2$ nor —Z—R$^3$ are hydrogen;
provided that when —Y—R$^2$ is H, then neither —X—R$^1$ nor —Z—R$^3$ are hydrogen; and
provided that when —Z—R$^3$ is H, then neither —X—R$^1$ nor —Y—R$^2$ are hydrogen.

In certain embodiments, T is

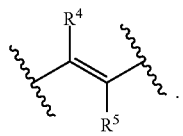

In certain embodiments, T is

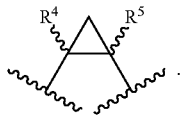

In certain embodiments, X is O, NR$^{10}$, or a bond. In certain embodiments, X is O or a bond. In certain embodiments, X is O. In certain embodiments, X is a bond. In certain embodiments, Y is NR$^{10}$. In certain embodiments, X is —NR$^{10}$C(O)—.

In certain embodiments, Y is O, NR$^{10}$, or a bond. In certain embodiments, Y is O or a bond. In certain embodiments, Y is O. In certain embodiments, Y is a bond. In certain embodiments, Y is NR$^{10}$. In certain embodiments, Y is —NR$^{10}$C(O)—.

In certain embodiments, Z is O or a bond. In certain embodiments, Z is O. In certain embodiments, Z is a bond. In certain embodiments, Z is NR$^{10}$.

In certain embodiments, R$^1$ is hydrogen, alkyl, heteroalkyl, alkenyl, alkynyl, cycloalkyl, cycloalkylalkyl, arylalkyl, heteroarylalkyl, heterocyclyl, or heterocyclylalkyl, wherein R$^1$ is optionally substituted with 1-3 independent substituents R$^8$.

In certain embodiments, R$^1$ is alkyl, alkynyl, cycloalkylalkyl, heteroarylalkyl, heterocyclyl, or heterocyclylalkyl, wherein R$^1$ is optionally substituted with 1-3 independent substituents R$^8$.

In certain embodiments, R$^1$ is alkyl, alkynyl, cycloalkylalkyl, heterocyclyl, or heterocyclylalkyl, wherein R$^1$ is optionally substituted with an alkyl group.

In certain embodiments, R$^1$ is alkyl. In certain embodiments, R$^1$ is C$_{1-4}$ alkyl. In certain embodiments, R$^1$ is alkynyl. In certain embodiments, R$^1$ is C$_{2-4}$ alkynyl. In certain embodiments, R$^1$ is cycloalkylalkyl. In certain embodiments, R$^1$ is cyclopropylmethyl. In certain embodiments, R$^1$ is heterocyclyl optionally substituted with an alkyl group. In certain embodiments, R$^1$ is pyrrolidinyl, tetrahydropyridinyl, morpholinyl, or piperazinyl, optionally substituted with an alkyl group. In certain embodiments, R$^1$ is heterocyclylalkyl optionally substituted with an alkyl group. In certain embodiments, R$^1$ is oxetanylmethyl.

In certain embodiments, R$^2$ is hydrogen, alkyl, heteroalkyl, alkenyl, alkynyl, cycloalkyl, cycloalkylalkyl, arylalkyl, heteroarylalkyl, heterocyclyl, or heterocyclylalkyl, wherein R$^2$ is optionally substituted with 1-3 independent substituents R$^8$.

In certain embodiments, R$^2$ is alkyl, alkynyl, heteroarylalkyl, heterocyclyl, heteroarylalkyl, or heterocyclylalkyl, wherein R$^2$ is optionally substituted with 1-3 independent substituents R$^8$.

In certain embodiments, R$^2$ is alkyl, alkynyl, heterocyclyl, heteroarylalkyl, or heterocyclylalkyl, wherein R$^2$ is optionally substituted with an alkyl group.

In certain embodiments, R$^2$ is alkyl or heteroarylalkyl optionally substituted with an alkyl group.

In certain embodiments, R$^2$ is alkyl. In certain embodiments, R$^2$ is C$_{1-4}$ alkyl. In certain embodiments, R$^2$ is alkynyl. In certain embodiments, R$^2$ is C$_{2-4}$ alkynyl. In certain embodiments, R$^2$ is heterocyclyl optionally substituted with an alkyl group. In certain embodiments, R$^2$ is morpholinyl or tetrahydopyridinyl, optionally substituted with an alkyl group. In certain embodiments, R$^2$ is heterocyclylalkyl optionally substituted with an alkyl group. In certain embodiments, R$^2$ is heteroarylalkyl optionally substituted with one or two alkyl groups. In certain embodiments, R$^2$ is pyrazolylmethyl optionally substituted with one or two alkyl groups.

In certain embodiments, R$^1$ and R$^2$ together with the atoms to which they are attached form a heterocyclyl ring.

In certain embodiments, R$^3$ is hydrogen, heteroalkyl, alkyl, alkynyl, heteroarylalkyl, heterocyclyl, or heterocyclylalkyl, wherein R$^3$ is optionally substituted with 1-3 independent substituents R$^8$.

In certain embodiments, R$^3$ is hydrogen, alkyl, alkynyl, heteroarylalkyl, heterocyclyl, or heterocyclylalkyl, wherein R$^3$ is optionally substituted with —NR$^a$R$^b$ or alkyl.

In certain embodiments, R$^3$ is alkyl optionally substituted with —NR$^a$R$^b$. In certain embodiments, R$^3$ is alkyl optionally substituted with —N(Me)$_2$. In certain embodiments, R$^3$ is C$_{1-4}$ alkyl optionally substituted with —N(Me)$_2$. In certain embodiments, R$^3$ is alkynyl. In certain embodiments, R$^3$ is C$_{2-4}$ alkynyl. In certain embodiments, R$^3$ is heteroarylalkyl. In certain embodiments, R$^3$ is pyridinylmethyl. In certain embodiments, R$^3$ is heterocyclyl. In certain embodiments, R$^3$ is pyrrolidinyl, piperidinyl, or azetidinyl. In certain embodiments, R$^3$ is heterocyclylalkyl. In certain embodiments, R$^3$ is morpholinylethyl or morpholinylmethyl.

In certain embodiments, each occurrence of R$^6$ is, independently, halogen, cyano, alkyl, heteroaryl, heterocyclyl, or —S(O)$_2$R$^c$. In certain embodiments, each occurrence of R$^6$ is halogen. In certain embodiments, each occurrence of R$^6$ is F, Cl, Br, or I. In certain embodiments, each occurrence of R$^6$ is F, Cl, or Br. In certain embodiments, each occurrence of R$^6$ is F. In certain embodiments, each occurrence of R$^6$ is Cl. In certain embodiments, each occurrence of $R^6$ is Br. In certain embodiments, each occurrence of $R^6$ is cyano. In certain embodiments, each occurrence of $R^6$ is alkyl. In certain embodiments, each occurrence of $R^6$ is $C_{1-4}$ alkyl. In certain embodiments, each occurrence of $R^6$ is methyl. In certain embodiments, each occurrence of $R^6$ is heteroaryl. In certain embodiments, each occurrence of $R^6$ is triazolyl, tetrazolyl, oxadiazolyl, pyrazolyl, or imidazolyl. In certain embodiments, each occurrence of $R^6$ is heterocyclyl. In certain embodiments, each occurrence of $R^6$ is dihydrooxadiazolyl or oxodihydrooxadiazolyl. In certain embodiments, each occurrence of $R^6$ is $-S(O)_2R^c$. In certain embodiments, each occurrence of $R^6$ is $-S(O)_2Me$.

In certain embodiments, G is $C(O)R^7$. In certain embodiments, G is hydrogen.

In certain embodiments, $R^7$ is OH. In certain embodiments, $R^7$ is $NHR^9$.

In certain embodiments, m is 0 or 1. In certain embodiments, m is 0 or 2. In certain embodiments, m is 1 or 2. In certain embodiments, m is 0. In certain embodiments, m is 1. In certain embodiments, m is 2.

In certain embodiments, $R^9$ is heteroaryl, heterocyclyl, or $-S(O)_2R^c$. In certain embodiments, $R^9$ is heteroaryl optionally substituted with up to two alkyl groups. In certain embodiments, $R^9$ is tetrazolyl, pyridinyl, pyrazolyl, imidazolyl, or triazolyl, each of which is optionally substituted with up to two alkyl groups. In certain embodiments, $R^9$ is heterocyclyl optionally substituted with up to two alkyl groups. In certain embodiments, $R^9$ is oxetanyl or piperidinyl, each of which is optionally substituted with up to two alkyl groups. In certain embodiments, $R^9$ is $-S(O)_2R^c$. In certain embodiments, $R^9$ is $-S(O)_2Me$.

In certain embodiments, $R^{10}$ is hydrogen or alkyl. In certain embodiments, $R^{10}$ is hydrogen. In certain embodiments, $R^{10}$ is $C_{1-4}$ alkyl. In certain embodiments, $R^{10}$ is methyl.

In certain embodiments, the compound of Formula I is of Formula I-a:

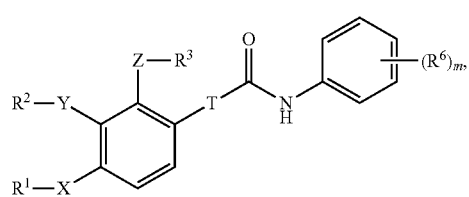

I-a or a pharmaceutically acceptable salt thereof.

In certain embodiments, the compound of Formula I is of Formula I-b or Formula I-c:

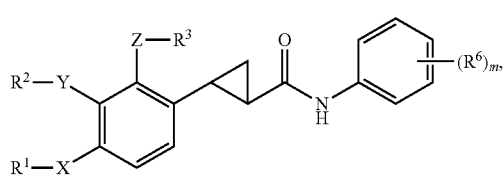

I-b

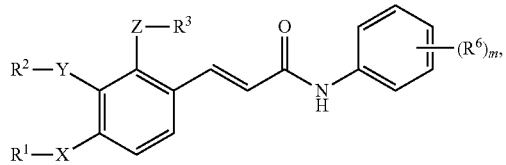

I-c or a pharmaceutically acceptable salt thereof.

In certain embodiments, X is O or a bond; Y is O or a bond; Z is O or a bond; $R^1$ and $R^2$ are independently hydrogen, alkyl, alkynyl, cycloalkylalkyl, heteroarylalkyl, heterocyclyl, or heterocyclylalkyl, wherein $R^1$ and $R^2$ are each optionally substituted with 1 or 2 independent substituents $R^8$; or $R^1$ and $R^2$ together with the atoms to which they are attached form a heterocyclyl ring; $R^3$ is hydrogen, alkyl, alkynyl, heteroarylalkyl, heterocyclyl, or heterocyclylalkyl, wherein $R^3$ is optionally substituted with 1 or 2 independent substituents $R^8$; each occurrence of $R^6$ is, independently, halogen, cyano, alkyl, heteroaryl, heterocyclyl, or $-S(O)_2R^c$; m is 1 or 2; each occurrence of $R^8$ is, independently, alkyl or $NR^aR^b$; and each occurrence of $R^a$, $R^b$, and $R^c$ is, independently, hydrogen, alkyl, heteroalkyl, cycloalkyl, heterocycloalkyl, aryl, heteroaryl, and heterocyclyl.

In certain embodiments, X is O. In certain embodiments, X is a bond.

In certain embodiments, Y is O. In certain embodiments, Y is a bond.

In certain embodiments, Z is O. In certain embodiments, Z is a bond.

In certain embodiments, $R^1$ is hydrogen, alkyl, alkynyl, cycloalkylalkyl, heteroarylalkyl, heterocyclyl, or heterocyclylalkyl, wherein $R^1$ is optionally substituted with 1 or 2 independent substituents $R^8$.

In certain embodiments, $R^1$ is alkyl, alkynyl, cycloalkylalkyl, heterocyclyl, or heterocyclylalkyl, wherein $R^1$ is optionally substituted with 1 or 2 independent substituents $R^8$.

In certain embodiments, $R^1$ is alkyl, alkynyl, cycloalkylalkyl, heterocyclyl, or heterocyclylalkyl, wherein $R^1$ is optionally substituted with an alkyl group.

In certain embodiments, $R^1$ is alkyl. In certain embodiments, $R^1$ is $C_{1-4}$ alkyl. In certain embodiments, $R^1$ is alkynyl. In certain embodiments, $R^1$ is $C_{2-4}$ alkynyl. In certain embodiments, $R^1$ is cycloalkylalkyl. In certain embodiments, $R^1$ is cyclopropylmethyl. In certain embodiments, $R^1$ is heterocyclyl optionally substituted with an alkyl group. In certain embodiments, $R^1$ is pyrrolidinyl, tetrahydropyridinyl, morpholinyl, or piperazinyl, optionally substituted with an alkyl group. In certain embodiments, $R^1$ is heterocyclylalkyl optionally substituted with an alkyl group. In certain embodiments, $R^1$ is oxetanylmethyl.

In certain embodiments, $R^2$ is hydrogen, alkyl, alkynyl, cycloalkylalkyl, heteroarylalkyl, heterocyclyl, or heterocyclylalkyl, wherein $R^2$ is optionally substituted with 1 or 2 independent substituents $R^8$.

In certain embodiments, $R^2$ is alkyl, alkynyl, heteroarylalkyl, heterocyclyl, or heterocyclylalkyl, wherein $R^2$ is optionally substituted with 1 or 2 independent substituents $R^8$.

In certain embodiments, $R^2$ is alkyl, alkynyl, heterocyclyl, heteroarylalkyl, or heterocyclylalkyl, wherein $R^2$ is optionally substituted with an alkyl group.

In certain embodiments, $R^2$ is alkyl or heteroarylalkyl optionally substituted with an alkyl group.

In certain embodiments, $R^2$ is alkyl. In certain embodiments, $R^2$ is $C_{1-4}$ alkyl. In certain embodiments, $R^2$ is alkynyl. In certain embodiments, $R^2$ is $C_{2-4}$ alkynyl. In certain embodiments, $R^2$ is heterocyclyl optionally substituted with an alkyl group. In certain embodiments, $R^2$ is morpholinyl or tetrahydopyridinyl, optionally substituted with an alkyl group. In certain embodiments, $R^2$ is heterocyclylalkyl optionally substituted with an alkyl group. In certain embodiments, $R^2$ is heteroarylalkyl optionally substituted with one or two alkyl groups. In certain embodiments, $R^2$ is pyrazolylmethyl optionally substituted with one or two alkyl groups.

In certain embodiments, $R^1$ and $R^2$ together with the atoms to which they are attached form a heterocyclyl ring.

In certain embodiments, $R^3$ is hydrogen, alkyl, alkynyl, heteroarylalkyl, heterocyclyl, or heterocyclylalkyl, wherein $R^3$ is optionally substituted with 1 or 2 independent substituents $R^8$.

In certain embodiments, $R^3$ is hydrogen, alkyl, alkynyl, heteroarylalkyl, heterocyclyl, or heterocyclylalkyl, wherein $R^3$ is optionally substituted with $-NR^aR^b$ or alkyl.

In certain embodiments, $R^3$ is alkyl optionally substituted with $-NR^aR^b$. In certain embodiments, $R^3$ is alkyl optionally substituted with $-N(Me)_2$. In certain embodiments, $R^3$ is $C_{1-4}$ alkyl optionally substituted with $-N(Me)_2$. In certain embodiments, $R^3$ is alkynyl. In certain embodiments, $R^3$ is $C_{2-4}$ alkynyl. In certain embodiments, $R^3$ is heteroarylalkyl. In certain embodiments, $R^3$ is pyridinylmethyl. In certain embodiments, $R^3$ is heterocyclyl. In certain embodiments, $R^3$ is pyrrolidinyl, piperidinyl, or azetidinyl. In certain embodiments, $R^3$ is heterocyclylalkyl. In certain embodiments, $R^3$ is morpholinylethyl or morpholinylmethyl.

In certain embodiments, each occurrence of $R^6$ is, independently, halogen, cyano, alkyl, heteroaryl, heterocyclyl, or $-S(O)_2R^c$. In certain embodiments, each occurrence of $R^6$ is halogen. In certain embodiments, each occurrence of $R^6$ is F, Cl, Br, or I. In certain embodiments, each occurrence of $R^6$ is F, Cl, or Br. In certain embodiments, each occurrence of $R^6$ is F. In certain embodiments, each occurrence of $R^6$ is Cl. In certain embodiments, each occurrence of $R^6$ is Br. In certain embodiments, each occurrence of $R^6$ is cyano. In certain embodiments, each occurrence of $R^6$ is alkyl. In certain embodiments, each occurrence of $R^6$ is $C_{1-4}$ alkyl. In certain embodiments, each occurrence of $R^6$ is methyl. In certain embodiments, each occurrence of $R^6$ is heteroaryl. In certain embodiments, each occurrence of $R^6$ is triazolyl, tetrazolyl, oxadiazolyl, pyrazolyl, or imidazolyl. In certain embodiments, each occurrence of $R^6$ is heterocyclyl. In certain embodiments, each occurrence of $R^6$ is dihydrooxadiazolyl or oxodihydrooxadiazolyl. In certain embodiments, each occurrence of $R^6$ is $-S(O)_2R^c$. In certain embodiments, each occurrence of $R^6$ is $-S(O)_2Me$.

In certain embodiments, m is 1. In certain embodiments, m is 2.

In certain embodiments, the compound of Formula I-b is of Formula I-b-1:

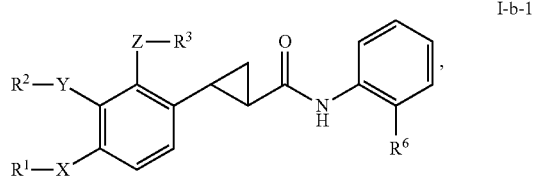

or a pharmaceutically acceptable salt thereof.

In certain embodiments, $R^6$ is F, Cl, Br, or cyano. In certain embodiments, $R^6$ is F, Cl, or cyano. In certain embodiments, $R^6$ is F or cyano. In certain embodiments, $R^6$ is F. In certain embodiments, $R^6$ is cyano.

In certain embodiments, the compound of Formula I-c is of Formula I-c-1:

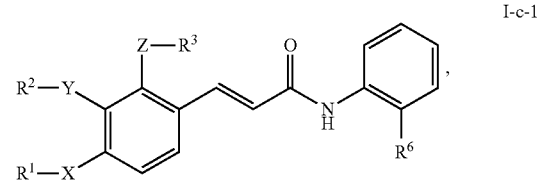

or a pharmaceutically acceptable salt thereof.

In certain embodiments, $R^6$ is F, Cl, Br, or cyano. In certain embodiments, $R^6$ is F, Cl, or cyano. In certain embodiments, $R^6$ is F or cyano. In certain embodiments, $R^6$ is F. In certain embodiments, $R^6$ is cyano.

In certain embodiments, the compound of Formula I is of Formula I-d or Formula I-e:

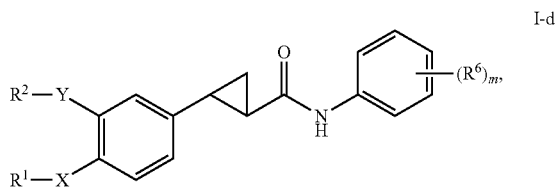

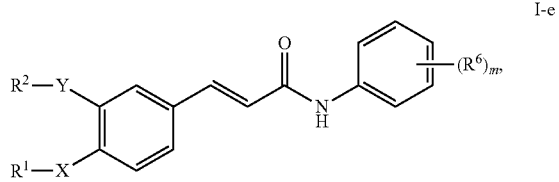

or a pharmaceutically acceptable salt thereof.

In certain embodiments, X is O or a bond; Y is O or a bond; provided that at least one of X and Y is O; $R^1$ and $R^2$ are independently, alkyl, alkynyl, heteroarylalkyl, heterocyclyl, or heterocyclylalkyl, wherein said heteroarylalkyl, heterocyclyl, and heterocyclylalkyl are optionally substituted with 1 or 2 independent alkyl groups; each occurrence of $R^6$ is, independently, halogen, cyano, alkyl, heteroaryl, heterocyclyl, or $-S(O)_2R^c$; m is 1 or 2; and each occurrence of $R^c$ is alkyl.

In certain embodiments, X is O. In certain embodiments, X is a bond.

In certain embodiments, Y is O. In certain embodiments, Y is a bond.

In certain embodiments, $R^1$ is alkyl, alkynyl, heteroarylalkyl, heterocyclyl, or heterocyclylalkyl, wherein said heteroarylalkyl, heterocyclyl, and heterocyclylalkyl are optionally substituted with 1 or 2 independent alkyl groups.

In certain embodiments, $R^1$ is alkyl. In certain embodiments, $R^1$ is $C_{1-4}$ alkyl. In certain embodiments, $R^1$ is alkynyl. In certain embodiments, $R^1$ is $C_{2-4}$ alkynyl. In certain embodiments, $R^1$ is heterocyclyl optionally substituted with an alkyl group. In certain embodiments, $R^1$ is pyrrolidinyl, tetrahydropyridinyl, morpholinyl, or piperazinyl, optionally substituted with an alkyl group. In certain embodiments, $R^1$ is heterocyclylalkyl optionally substituted with an alkyl group. In certain embodiments, $R^1$ is oxetanylmethyl.

In certain embodiments, $R^2$ is alkyl, alkynyl, heteroarylalkyl, heterocyclyl, or heterocyclylalkyl, wherein $R^2$ is optionally substituted with 1-3 independent substituents $R^8$.

In certain embodiments, $R^2$ is alkyl, alkynyl, heteroarylalkyl, heterocyclyl, heteroarylalkyl, or heterocyclylalkyl, wherein said heteroarylalkyl, heterocyclyl, and heterocyclylalkyl are optionally substituted with 1 or 2 independent alkyl groups.

In certain embodiments, $R^2$ is alkyl or heteroarylalkyl optionally substituted with an alkyl group.

In certain embodiments, $R^2$ is alkyl. In certain embodiments, $R^2$ is $C_{1-4}$ alkyl. In certain embodiments, $R^2$ is alkynyl. In certain embodiments, $R^2$ is $C_{2-4}$ alkynyl. In certain embodiments, $R^2$ is heterocyclyl optionally substituted with an alkyl group. In certain embodiments, $R^2$ is morpholinyl or tetrahydopyridinyl, optionally substituted with an alkyl group. In certain embodiments, $R^2$ is heterocyclylalkyl optionally substituted with an alkyl group. In certain embodiments, $R^2$ is heteroarylalkyl optionally substituted with one or two alkyl groups. In certain embodiments, $R^2$ is pyrazolylmethyl optionally substituted with one or two alkyl groups.

In certain embodiments, $R^1$ and $R^2$ together with the atoms to which they are attached form a heterocyclyl ring.

In certain embodiments, each occurrence of $R^6$ is, independently, halogen, cyano, alkyl, heteroaryl, heterocyclyl, or $-S(O)_2R^c$. In certain embodiments, each occurrence of $R^6$ is halogen. In certain embodiments, each occurrence of $R^6$ is F, Cl, Br, or I. In certain embodiments, each occurrence of $R^6$ is F, Cl, or Br. In certain embodiments, each occurrence of $R^6$ is F. In certain embodiments, each occurrence of $R^6$ is Cl. In certain embodiments, each occurrence of $R^6$ is Br. In certain embodiments, each occurrence of $R^6$ is cyano. In certain embodiments, each occurrence of $R^6$ is alkyl. In certain embodiments, each occurrence of $R^6$ is $C_{1-4}$ alkyl. In certain embodiments, each occurrence of $R^6$ is methyl. In certain embodiments, each occurrence of $R^6$ is heteroaryl. In certain embodiments, each occurrence of $R^6$ is triazolyl, tetrazolyl, oxadiazolyl, pyrazolyl, or imidazolyl. In certain embodiments, each occurrence of $R^6$ is heterocyclyl. In certain embodiments, each occurrence of $R^6$ is dihydrooxadiazolyl or oxodihydrooxadiazolyl. In certain embodiments, each occurrence of $R^6$ is $-S(O)_2R^c$. In certain embodiments, each occurrence of $R^6$ is $-S(O)_2Me$.

In certain embodiments, m is 1. In certain embodiments, m is 2.

In certain embodiments, the compound of Formula I-d is of Formula I-d-1:

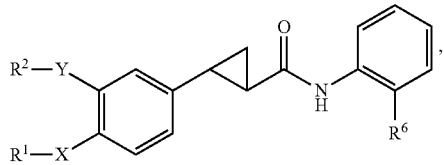

I-d-1 or a pharmaceutically acceptable salt thereof.

In certain embodiments, $R^6$ is F, Cl, Br, or cyano. In certain embodiments, $R^6$ is F, Cl, or cyano. In certain embodiments, $R^6$ is F or cyano. In certain embodiments, $R^6$ is F. In certain embodiments, $R^6$ is cyano.

In certain embodiments, the compound of Formula I-e is of Formula I-e-1:

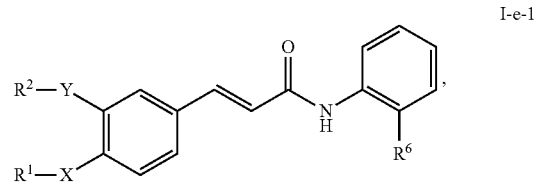

I-e-1 or a pharmaceutically acceptable salt thereof.

In certain embodiments, $R^6$ is F, Cl, Br, or cyano. In certain embodiments, $R^6$ is F, Cl, or cyano. In certain embodiments, $R^6$ is F or cyano. In certain embodiments, $R^6$ is F. In certain embodiments, $R^6$ is cyano.

In certain embodiments, the compound of Formula I is of Formula I-f:

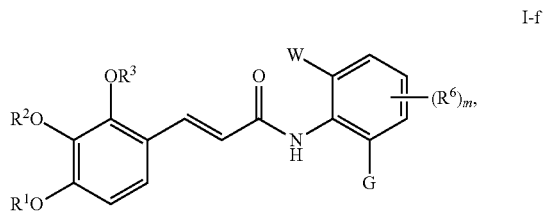

I-f or a pharmaceutically acceptable salt thereof; wherein
G is $CO_2H$ or hydrogen;
W is CN or hydrogen;
m is 0 or 1;
provided that when G is $CO_2H$, then W is hydrogen; and when W is CN, then G is hydrogen; and
provided that when G and W are both hydrogen, then m is 1.

In certain embodiments, $R^1$ and $R^2$ are independently alkyl, alkenyl, alkynyl, cycloalkyl, cycloalkylalkyl, arylalkyl, heteroarylalkyl, heterocyclyl, or heterocyclylalkyl, wherein $R^1$ and $R^2$ are each optionally substituted with 1-3 independent substituents $R^8$; or $R^1$ and $R^2$ together with the atoms to which they are attached form a heterocyclyl ring; $R^3$ is alkyl, alkenyl, alkynyl, cycloalkyl, cycloalkylalkyl, arylalkyl, heteroarylalkyl, heterocyclyl, or heterocyclylalkyl, wherein $R^3$ is optionally substituted with 1-3 independent substituents $R^8$; $R^6$ is halogen, cyano, alkyl, haloalkyl, hydroxyl, alkoxy, carboxyl, aryl, heteroaryl, heterocyclyl, $-(CH_2)_nC(O)NR^aR^b$, $-S(O)_2R^c$, or $NR^aR^b$; m is 0 or 1; q is 0 or 1; n is 0 or 1; and m+n+q is 1 or 2; provided that when n is 1, then q is 0; and when q is 1, then n is 0.

In certain embodiments, $R^1$ is alkyl, alkenyl, alkynyl, cycloalkyl, cycloalkylalkyl, arylalkyl, heteroarylalkyl, heterocyclyl, or heterocyclylalkyl, wherein $R^1$ is optionally substituted with 1-3 independent substituents $R^8$.

In certain embodiments, $R^1$ is alkyl, alkynyl, cycloalkylalkyl, heteroarylalkyl, heterocyclyl, or heterocyclylalkyl, wherein $R^1$ is optionally substituted with 1-3 independent substituents $R^8$.

In certain embodiments, $R^1$ is alkyl, alkynyl, cycloalkylalkyl, heterocyclyl, or heterocyclylalkyl, wherein $R^1$ is optionally substituted with an alkyl group.

In certain embodiments, $R^1$ is alkyl. In certain embodiments, $R^1$ is $C_{1-4}$ alkyl. In certain embodiments, $R^1$ is alkynyl. In certain embodiments, $R^1$ is $C_{2-4}$ alkynyl. In certain embodiments, $R^1$ is cycloalkylalkyl. In certain embodiments, $R^1$ is cyclopropylmethyl. In certain embodiments, $R^1$ is heterocyclyl optionally substituted with an alkyl group. In certain embodiments, $R^1$ is pyrrolidinyl, tetrahydropyridinyl, morpholinyl, or piperazinyl, optionally substituted with an alkyl group. In certain embodiments, $R^1$ is heterocyclylalkyl optionally substituted with an alkyl group. In certain embodiments, $R^1$ is oxetanylmethyl.

In certain embodiments, $R^2$ is alkyl, alkenyl, alkynyl, cycloalkyl, cycloalkylalkyl, arylalkyl, heteroarylalkyl, heterocyclyl, or heterocyclylalkyl, wherein $R^1$ and $R^2$ are each optionally substituted with 1-3 independent substituents $R^8$.

In certain embodiments, $R^2$ is alkyl, alkynyl, heteroarylalkyl, heterocyclyl, heteroarylalkyl, or heterocyclylalkyl, wherein $R^2$ is optionally substituted with 1-3 independent substituents $R^8$.

In certain embodiments, $R^2$ is alkyl, alkynyl, heterocyclyl, heteroarylalkyl, or heterocyclylalkyl, wherein $R^2$ is optionally substituted with an alkyl group.

In certain embodiments, $R^2$ is alkyl or heteroarylalkyl optionally substituted with an alkyl group.

In certain embodiments, $R^2$ is alkyl. In certain embodiments, $R^2$ is $C_{1-4}$ alkyl. In certain embodiments, $R^2$ is alkynyl. In certain embodiments, $R^2$ is $C_{2-4}$ alkynyl. In certain embodiments, $R^2$ is heterocyclyl optionally substituted with an alkyl group. In certain embodiments, $R^2$ is morpholinyl or tetrahydopyridinyl, optionally substituted with an alkyl group. In certain embodiments, $R^2$ is heterocyclylalkyl optionally substituted with an alkyl group. In certain embodiments, $R^2$ is heteroarylalkyl optionally substituted with one or two alkyl groups. In certain embodiments, $R^2$ is pyrazolylmethyl optionally substituted with one or two alkyl groups.

In certain embodiments, $R^1$ and $R^2$ together with the atoms to which they are attached form a heterocyclyl ring.

In certain embodiments, $R^1$ and $R^2$ are independently alkyl, alkynyl, or cycloalkylalkyl. In certain embodiments, $R^1$ and $R^2$ are alkyl. In certain embodiments, $R^1$ and $R^2$ are $C_{1-4}$ alkyl.

In certain embodiments, $R^3$ is alkyl, alkenyl, alkynyl, cycloalkyl, cycloalkylalkyl, arylalkyl, heteroarylalkyl, heterocyclyl, or heterocyclylalkyl, wherein $R^3$ is optionally substituted with 1-3 independent substituents $R^8$.

In certain embodiments, $R^3$ is alkyl, heteroalkyl, heterocyclyl, heteroarylalkyl, or heterocyclylalkyl, wherein $R^3$ is optionally substituted with 1-3 independent substituents $R^8$.

In certain embodiments, $R^3$ is hydrogen, alkyl, alkynyl, heteroarylalkyl, heterocyclyl, or heterocyclylalkyl, wherein $R^3$ is optionally substituted with $-NR^aR^b$ or alkyl.

In certain embodiments, $R^3$ is alkyl substituted with $NR^aR^b$, heterocyclyl substituted with alkyl, unsubstituted heterocyclyl, unsubstituted heteroarylalkyl, or unsubstituted heterocyclylalkyl.

In certain embodiments, $R^3$ is $C_{1-4}$ alkyl substituted with $NR^aR^b$; wherein each occurrence of $R^a$ and $R^b$ is alkyl.

In certain embodiments, $R^3$ is alkyl optionally substituted with $-NR^aR^b$. In certain embodiments, $R^3$ is alkyl optionally substituted with $-N(Me)_2$. In certain embodiments, $R^3$ is $C_{1-4}$ alkyl optionally substituted with $-N(Me)_2$. In certain embodiments, $R^3$ is alkynyl. In certain embodiments, $R^3$ is $C_{2-4}$ alkynyl. In certain embodiments, $R^3$ is heteroarylalkyl. In certain embodiments, $R^3$ is pyridinylmethyl. In certain embodiments, $R^3$ is heterocyclyl. In certain embodiments, $R^3$ is pyrrolidinyl, piperidinyl, or azetidinyl. In certain embodiments, $R^3$ is heterocyclylalkyl. In certain embodiments, $R^3$ is morpholinylethyl or morpholinylmethyl.

In certain embodiments, each occurrence of $R^6$ is, independently, halogen, cyano, alkyl, heteroaryl, heterocyclyl, or $-S(O)_2R^c$. In certain embodiments, each occurrence of $R^6$ is halogen. In certain embodiments, each occurrence of $R^6$ is F, Cl, Br, or I. In certain embodiments, each occurrence of $R^6$ is F, Cl, or Br. In certain embodiments, each occurrence of $R^6$ is F. In certain embodiments, each occurrence of $R^6$ is Cl. In certain embodiments, each occurrence of $R^6$ is Br. In certain embodiments, each occurrence of $R^6$ is cyano. In certain embodiments, each occurrence of $R^6$ is alkyl. In certain embodiments, each occurrence of $R^6$ is $C_{1-4}$ alkyl. In certain embodiments, each occurrence of $R^6$ is methyl. In certain embodiments, each occurrence of $R^6$ is heteroaryl. In certain embodiments, each occurrence of $R^6$ is triazolyl, tetrazolyl, oxadiazolyl, pyrazolyl, or imidazolyl. In certain embodiments, each occurrence of $R^6$ is heterocyclyl. In certain embodiments, each occurrence of $R^6$ is dihydrooxadiazolyl or oxodihydrooxadiazolyl. In certain embodiments, each occurrence of $R^6$ is $-S(O)_2R^c$. In certain embodiments, each occurrence of $R^6$ is $-S(O)_2Me$.

In certain embodiments, G is $CO_2H$. In certain embodiments, G is hydrogen.

In certain embodiments, W is CN. In certain embodiments, W is hydrogen.

In certain embodiments, m is 0. In certain embodiments, m is 1.

In certain embodiments, the compound of Formula I is of Formula I-g:

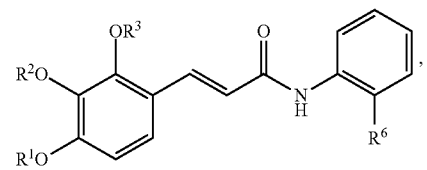

or a pharmaceutically acceptable salt thereof.

In certain embodiments, $R^6$ is F, Cl, Br, or cyano. In certain embodiments, $R^6$ is F, Cl, or cyano. In certain embodiments, $R^6$ is F or cyano. In certain embodiments, $R^6$ is F. In certain embodiments, $R^6$ is cyano.

In certain embodiments, the compound of Formula I is a compound of Formula I-h:

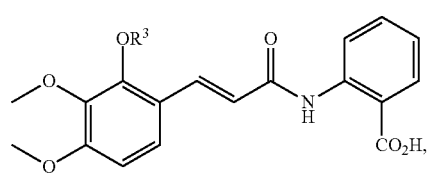

or a pharmaceutically acceptable salt thereof.

In certain embodiments, $R^3$ is hydrogen, alkyl, alkynyl, heteroarylalkyl, heterocyclyl, or heterocyclylalkyl, wherein $R^3$ is optionally substituted with 1-3 independent substituents $R^8$.

In certain embodiments, $R^3$ is hydrogen, alkyl, alkynyl, heteroarylalkyl, heterocyclyl, or heterocyclylalkyl, wherein $R^3$ is optionally substituted with $-NR^aR^b$ or alkyl.

In certain embodiments, $R^3$ is alkyl optionally substituted with $-NR^aR^b$. In certain embodiments, $R^3$ is $C_{1-4}$ alkyl substituted with $NR^aR^b$; wherein each occurrence of $R^a$ and $R^b$ is alkyl. In certain embodiments, $R^3$ is alkyl optionally substituted with —N(Me)$_2$. In certain embodiments, $R^3$ is $C_{1-4}$ alkyl optionally substituted with —N(Me)$_2$. In certain embodiments, $R^3$ is ethyl substituted with $NR^aR^b$; wherein each occurrence of $R^a$ and $R^b$ is $C_{1-4}$ alkyl. In certain embodiments, $R^3$ is ethyl substituted with $NR^aR^b$; wherein each occurrence of $R^a$ and $R^b$ is methyl, ethyl, or propyl. In certain embodiments, $R^3$ is ethyl substituted with $NR^aR^b$; wherein each occurrence of $R^a$ and $R^b$ is methyl. In certain embodiments, $R^3$ is alkynyl. In certain embodiments, $R^3$ is $C_{2-4}$ alkynyl. In certain embodiments, $R^3$ is heteroarylalkyl. In certain embodiments, $R^3$ is pyridinylmethyl. In certain embodiments, $R^3$ is heterocyclyl. In certain embodiments, $R^3$ is pyrrolidinyl, piperidinyl, or azetidinyl. In certain embodiments, $R^3$ is heterocyclylalkyl. In certain embodiments, $R^3$ is morpholinylethyl or morpholinylmethyl.

In certain embodiments, the compound of Formula I is a compound of the formula:

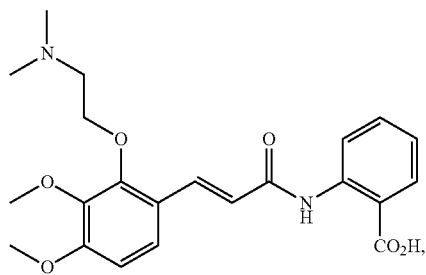 [SMILES: COc1ccc(/C=C/C(=O)Nc2ccccc2C(=O)O)c(OCCN(C)C)c1OC]

or a pharmaceutically acceptable salt thereof.

In certain embodiments, the compound of Formula I is a compound of the formula I-i:

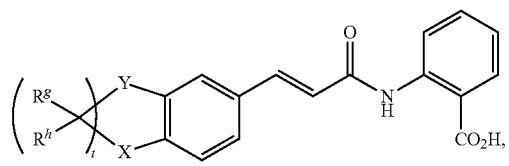

I-i or a pharmaceutically acceptable salt thereof.

In certain embodiments, X is O, $NR^{10}$, —$NR^{10}C(O)$—, or $CR^{11a}R^{11b}$; Y is O, $NR^{10}$, —$C(O)NR^{10}$—, or $CR^{11a}R^{11b}$; provided that at least one of X and Y is not $CR^{11a}R^{11b}$; each occurrence of $R^g$ and $R^h$ is, independently, hydrogen, alkyl, or alkynyl, or $R^g$ and $R^h$ together with the carbon atom to which they are attached form a carbonyl; t is 1, 2, or 3; each occurrence of $R^{10}$ is, independently, hydrogen or alkyl, wherein $R^{10}$ is optionally substituted with 1-3 independent substituents $R^8$; each occurrence of $R^{11a}$ and $R^{11b}$ is, independently, alkyl, alkynyl, cycloalkyl, cycloalkylalkyl, wherein each $R^{11a}$ and $R^{11b}$ are optionally substituted with 1-3 independent substituents $R^8$; each occurrence of $R^8$ is, independently, alkyl, alkynyl, hydroxyl, alkoxy, carboxyl, oxo, aryl, heteroaryl, heterocyclyl, $NR^aR^b$, —$S(O)_2R^c$, or —$CO_2R^d$; and each occurrence of $R^a$, $R^b$, $R^c$, and $R^d$ is, independently, hydrogen, acyl, alkyl, alkenyl, alkynyl, heteroalkyl, cycloalkyl, heterocyclylalkyl, aryl, heteroaryl, heterocyclyl, $C(O)OC_{1-6}$ alkyl, $C(O)C_{1-6}$ alkyl, or $R^a$ and $R^b$ together with the atoms to which they are attached form a heterocyclyl ring.

In certain embodiments, X is O or $NR^{10}$. In certain embodiments, X is O or $NR^{10}$; and $R^{10}$ is hydrogen or alkyl. In certain embodiments, X is O. In certain embodiments, X is $NR^{10}$. In certain embodiments, X is $NR^{10}$; and $R^{10}$ is alkyl. In certain embodiments, X is $NR^{10}$; and $R^{10}$ is $C_{1-4}$ alkyl. In certain embodiments, X is $NR^{10}$; and $R^{10}$ is methyl.

In certain embodiments, Y is O or $NR^{10}$. In certain embodiments, Y is O or $NR^{10}$; and $R^{10}$ is hydrogen or alkyl. In certain embodiments, Y is O. In certain embodiments, Y is $NR^{10}$. In certain embodiments, Y is $NR^{10}$; and $R^{10}$ is alkyl. In certain embodiments, Y is $NR^{10}$; and $R^{10}$ is $C_{1-4}$ alkyl. In certain embodiments, Y is $NR^{10}$; and $R^{10}$ is methyl.

In certain embodiments, X is O or $NR^{10}$; and Y is O or $NR^{10}$. In certain embodiments, X is O or $NR^{10}$; Y is O or $NR^{10}$; and $R^{10}$ is hydrogen or alkyl. In certain embodiments, X is O or $NR^{10}$; Y is O or $NR^{10}$; and $R^{10}$ is hydrogen or $C_{1-4}$ alkyl. In certain embodiments, X is O or $NR^{10}$; Y is O or $NR^{10}$; and $R^5$ is $C_{1-4}$ alkyl. In certain embodiments, X is O or $NR^{10}$; Y is O or $NR^{10}$; and $R^{10}$ is methyl, ethyl, propyl, or butyl. In certain embodiments, X is O; Y is $NR^{10}$; and $R^{10}$ is $C_{1-4}$ alkyl. In certain embodiments, X is O; Y is $NR^{10}$; and $R^{10}$ is methyl, ethyl, propyl, or butyl. In certain embodiments, X is O; Y is $NR^{10}$; and $R^{10}$ is methyl.

In certain embodiments, $R^g$ is hydrogen or alkyl. In certain embodiments, $R^g$ is hydrogen or $C_{1-4}$ alkyl. In certain embodiments, $R^g$ is hydrogen, halogen, or $C_{1-2}$ alkyl. In certain embodiments, $R^g$ is hydrogen.

In certain embodiments, $R^h$ is hydrogen or alkyl. In certain embodiments, $R^h$ is hydrogen or $C_{1-4}$ alkyl. In certain embodiments, $R^h$ is hydrogen or $C_{1-2}$ alkyl. In certain embodiments, $R^h$ is hydrogen.

In certain embodiments, each occurrence of $R^g$ and $R^h$ is, independently, hydrogen or alkyl. In certain embodiments, each occurrence of $R^g$ and $R^h$ is, independently, hydrogen or $C_{1-4}$ alkyl. In certain embodiments, each occurrence of $R^g$ and $R^h$ is, independently, hydrogen, halogen, or $C_{1-2}$ alkyl. In certain embodiments, each occurrence of $R^g$ and $R^h$ is hydrogen. In certain embodiments, $R^g$ and $R^h$ together with the carbon atom to which they are attached form a carbonyl.

In certain embodiments, t is 1, 2, or 3. In certain embodiments, t is 1 or 2. In certain embodiments, t is 1. In certain embodiments, t is 2. In certain embodiments, t is 3.

In certain embodiments, the compound of Formula I is a compound of Formula I-j:

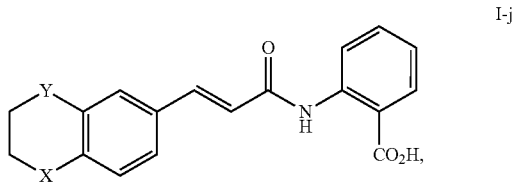

I-j or a pharmaceutically acceptable salt thereof, wherein:

In certain embodiments, X is O, $NR^{10}$, or $CR^{11a}R^{11b}$; Y is O, $NR^{10}$, or $CR^{11a}R^{11b}$; provided that at least one of X and Y is not $CR^{11a}R^{11b}$; each occurrence of $R^{10}$ is, independently, hydrogen or alkyl, wherein $R^{10}$ is optionally substituted with 1-3 independent substituents $R^8$; each occurrence of $R^{11a}$ and $R^{11b}$ is, independently, alkyl, alkynyl, cycloalkyl, cycloalkylalkyl, wherein each $R^{11a}$ and $R^{11b}$ are optionally substituted with 1-3 independent substituents $R^8$; each occurrence of $R^8$ is, independently, alkyl, alkynyl, hydroxyl, alkoxy, carboxyl, oxo, aryl, heteroaryl, heterocyclyl, $NR^aR^b$, —$S(O)_2R^c$, or —$CO_2R^d$; and each occurrence of $R^a$, $R^b$, $R^c$, and $R^d$ is, independently, hydrogen, acyl, alkyl, alkenyl, alkynyl, heteroalkyl, cycloalkyl, heterocyclylalkyl, aryl, heteroaryl, heterocyclyl, C(O)OC$_{1-6}$ alkyl, C(O)C$_{1-6}$ alkyl, or $R^a$ and $R^b$ together with the atoms to which they are attached form a heterocyclyl ring.

In certain embodiments, X is O or NR$^{10}$. In certain embodiments, X is O or NR$^{10}$; and R$^{10}$ is hydrogen or alkyl. In certain embodiments, X is O. In certain embodiments, X is NR$^{10}$. In certain embodiments, X is NR$^{10}$; and R$^{10}$ is alkyl. In certain embodiments, X is NR$^{10}$; and R$^{10}$ is C$_{1-4}$ alkyl. In certain embodiments, X is NR$^{10}$; and R$^{10}$ is methyl.

In certain embodiments, Y is O or NR$^{10}$. In certain embodiments, Y is O or NR$^{10}$; and R$^{10}$ is hydrogen or alkyl. In certain embodiments, Y is O. In certain embodiments, Y is NR$^{10}$. In certain embodiments, Y is NR$^{10}$; and R$^{10}$ is alkyl. In certain embodiments, Y is NR$^{10}$; and R$^{10}$ is C$_{1-4}$ alkyl. In certain embodiments, Y is NR$^{10}$; and R$^{10}$ is methyl.

In certain embodiments, X is O or NR$^{10}$; and Y is O or NR$^{10}$. In certain embodiments, X is O or NR$^{10}$; Y is O or NR$^{10}$; and R$^{10}$ is hydrogen or alkyl. In certain embodiments, X is O or NR$^{10}$; Y is O or NR$^{10}$; and R$^{10}$ is hydrogen or C$_{1-4}$ alkyl. In certain embodiments, X is O or NR$^{10}$; Y is O or NR$^{10}$; and R$^5$ is C$_{1-4}$ alkyl. In certain embodiments, X is O or NR$^{10}$; Y is O or NR$^{10}$; and R$^{10}$ is methyl, ethyl, propyl, or butyl. In certain embodiments, X is O; Y is NR$^{10}$; and R$^{10}$ is C$_{1-4}$ alkyl. In certain embodiments, X is O; Y is NR$^{10}$; and R$^{10}$ is methyl, ethyl, propyl, or butyl. In certain embodiments, X is O; Y is NR$^{10}$; and R$^{10}$ is methyl.

In certain embodiments, the compound of Formula I is a compound of the formula:

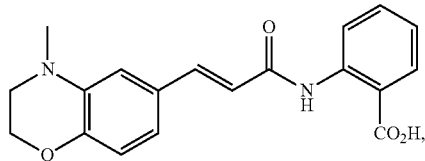 [SMILES: CN1CCOc2ccc(/C=C/C(=O)Nc3ccccc3C(=O)O)cc21]

or a pharmaceutically acceptable salt thereof.

Examples of the compound of Formula I include, but are not limited to
(E)-N-(2-fluorophenyl)-3-(3-methoxy-4-(prop-2-yn-1-yloxy)phenyl)acrylamide (1);
(E)-3-(3-methoxy-4-(prop-2-yn-1-yloxy)phenyl)-N-(2-(5-methyl-1H-1,2,4-triazol-3-yl)phenyl)acrylamide (2);
(E)-N-(2-chlorophenyl)-3-(3-methoxy-4-(prop-2-yn-1-yloxy)phenyl)acrylamide (3);
(E)-N-(2-bromophenyl)-3-(3-methoxy-4-(prop-2-yn-1-yloxy)phenyl)acrylamide (4);
(E)-3-(3-methoxy-4-(prop-2-yn-1-yloxy)phenyl)-N-(o-tolyl)acrylamide (5);
(E)-N-(2-cyanophenyl)-3-(3-methoxy-4-(prop-2-yn-1-yloxy)phenyl)acrylamide (6);
(E)-N-(3,4-dichlorophenyl)-3-(3-methoxy-4-(prop-2-yn-1-yloxy)phenyl)acrylamide (7);
(E)-N-(2-(2H-tetrazol-5-yl)phenyl)-3-(3-methoxy-4-(prop-2-yn-1-yloxy)phenyl)acrylamide (16);
(E)-N-(2-(1,2,4-oxadiazol-3-yl)phenyl)-3-(3-methoxy-4-(prop-2-yn-1-yloxy)phenyl)acrylamide (17);
(E)-3-(3-methoxy-4-(prop-2-yn-1-yloxy)phenyl)-N-(2-(5-methyl-1,2,4-oxadiazol-3-yl)phenyl)-acrylamide (18);
(E)-3-(3-methoxy-4-(prop-2-yn-1-yloxy)phenyl)-N-(2-(5-oxo-4,5-dihydro-1,2,4-oxadiazol-3-yl)phenyl)acrylamide (19);
(E)-N-(2-(1,2,4-oxadiazol-5-yl)phenyl)-3-(3-methoxy-4-(prop-2-yn-1-yloxy)phenyl)acrylamide (20);
(E)-N-(2-(1,3,4-oxadiazol-2-yl)phenyl)-3-(3-methoxy-4-(prop-2-yn-1-yloxy)phenyl)acrylamide (21);
(E)-3-(3-methoxy-4-(prop-2-yn-1-yloxy)phenyl)-N-(2-(1-methyl-1H-pyrazol-4-yl)phenyl)-acrylamide (22);
(E)-3-(3-methoxy-4-(prop-2-yn-1-yloxy)phenyl)-N-(2-(3-methyl-1H-1,2,4-triazol-1-yl)phenyl)acryl-amide (23);
(E)-N-(2-(1H-pyrazol-4-yl)phenyl)-3-(3-methoxy-4-(prop-2-yn-1-yloxy)phenyl)acrylamide (24);
(E)-N-(2-(1H-imidazol-4-yl)phenyl)-3-(3-methoxy-4-(prop-2-yn-1-yloxy)phenyl)acrylamide (25);
(E)-3-(3-methoxy-4-(prop-2-yn-1-yloxy)phenyl)-N-(2-(1-methyl-1H-imidazol-4-yl)phenyl)acrylamide (26);
(E)-2-(3-(3-methoxy-4-(prop-2-yn-1-yloxy)phenyl)acrylamido)-N-(methylsulfonyl)benzamide (27);
(E)-3-(3-methoxy-4-(prop-2-yn-1-yloxy)phenyl)-N-(2-(3-methyl-1,2,4-oxadiazol-5-yl)phenyl)acryl-amide (28);
(E)-3-(3-methoxy-4-(prop-2-yn-1-yloxy)phenyl)-N-(2-(5-methyl-1,3,4-oxadiazol-2-yl)phenyl)-acrylamide (29);
(E)-2-(3-(3-methoxy-4-(prop-2-yn-1-yloxy)phenyl)acrylamido)-N-(2H-tetrazol-5-yl)benzamide (31);
(E)-2-(3-(3-methoxy-4-(prop-2-yn-1-yloxy)phenyl)acrylamido)-N-(1-methylpiperidin-4-yl)benzamide (36);
(E)-2-(3-(3-methoxy-4-(prop-2-yn-1-yloxy)phenyl)acrylamido)-N-(oxetan-3-yl)benzamide (38);
(E)-2-(3-(3-methoxy-4-(prop-2-yn-1-yloxy)phenyl)acrylamido)-N-(pyridin-4-yl)benzamide (44);
(E)-2-(3-(3-methoxy-4-(prop-2-yn-1-yloxy)phenyl)acrylamido)-N-(1-methyl-1H-pyrazol-4-yl)benzamide (47);
(E)-2-(3-(3-methoxy-4-(prop-2-yn-1-yloxy)phenyl)acrylamido)-N-(1-methyl-1H-pyrazol-3-yl)benzamide (48);
(E)-2-(3-(3-methoxy-4-(prop-2-yn-1-yloxy)phenyl)acrylamido)-N-(piperidin-4-yl)benzamide (49);
(E)-2-(3-(3-methoxy-4-((1-methylpyrrolidin-3-yl)oxy)phenyl)acrylamido)benzoic acid (51);
(E)-N-(3-cyanophenyl)-3-[2-[2-(dimethylamino)ethoxy]-3-methoxy-4-prop-2-ynoxy-phenyl]prop-2-enamide (76);
((E)-N-(2-cyanophenyl)-3-(2-(2-(dimethylamino)ethoxy)-3-methoxy-4-(prop-2-yn-1-yloxy)phenyl)acrylamide (77);
(E)-2-(3-(2-(2-(dimethylamino)ethoxy)-3-methoxy-4-(prop-2-yn-1-yloxy)phenyl)acrylamido)-benzoic acid (78);
(E)-N-(2-cyanophenyl)-3-[3-methoxy-2-(1-methylazetidin-3-yl)oxy-4-prop-2-ynoxy-phenyl]prop-2-enamide (79);
2-[[(E)-3-(3-methoxy-4-prop-2-ynoxy-2-pyrrolidin-3-yloxyphenyl)prop-2-enoyl]amino]benzoic acid (80);
(E)-N-(2-cyanophenyl)-3-[3-methoxy-2-(1-methylpyrrolidin-3-yl)oxy-4-prop-2-ynoxy-phenyl]prop-2-enamide (81);
(E)-N-(2-cyanophenyl)-3-(3-methoxy-4-prop-2-ynoxy-2-pyrrolidin-3-yloxy-phenyl)prop-2-enamide (82);
2-[[(E)-3-[3-methoxy-2-(4-piperidyloxy)-4-prop-2-ynoxy-phenyl]prop-2-enoyl]amino]benzoic acid (83);
2-[[(E)-3-[3-methoxy-2-(2-morpholinoethoxy)-4-prop-2-ynoxy-phenyl]prop-2-enoyl]amino]benzoic acid (84);
(E)-N-(2-cyanophenyl)-3-[3-methoxy-2-(2-morpholinoethoxy)-4-prop-2-ynoxy-phenyl]prop-2-enamide (85);
2-[[(E)-3-[2-[3-(dimethylamino)propoxy]-3-methoxy-4-prop-2-ynoxy-phenyl]prop-2-enoyl]amino]benzoic acid (86);
(E)-N-(2-cyanophenyl)-3-[2-[3-(dimethylamino)propoxy]-3-methoxy-4-prop-2-ynoxy-phenyl]prop-2-enamide (87);
(E)-N-(2-cyanophenyl)-3-[3-methoxy-2-(4-piperidyloxy)-4-prop-2-ynoxy-phenyl]prop-2-enamide (88);

(E)-N-(2-cyanophenyl)-3-[3-methoxy-2-[(1-methyl-4-piperidyl)oxy]-4-prop-2-ynoxy-phenyl]prop-2-enamide (89);
2-[[(E)-3-[4-(cyclopropylmethoxy)-2-[2-(dimethylamino)ethoxy]-3-methoxy-phenyl]prop-2-enoyl]amino]benzoic acid (90);
(E)-N-(3-cyanophenyl)-3-(2-(2-(dimethylamino)ethoxy)-3-methoxyphenyl)acrylamide (91);
(E)-N-(2-cyanophenyl)-3-(2-(2-(dimethylamino)ethoxy)-3-methoxyphenyl)acrylamide (92);
(E)-N-(3-cyanophenyl)-3-(2-(2-(dimethylamino)ethoxy)-4-methoxyphenyl)acrylamide (93);
(E)-N-(2-cyanophenyl)-3-[2-[2-(dimethylamino)ethoxy]-4-methoxy-phenyl]prop-2-enamide (94);
(E)-2-(3-(3,4-dimethoxy-2-(prop-2-yn-1-yloxy)phenyl)acrylamido)benzoic acid (95);
(E)-2-(3-(3,4-dimethoxy-2-(pyridin-3-ylmethoxy)phenyl)acrylamido)benzoic acid (96);
(E)-2-(3-(3-methoxy-4-(4-methylpiperazin-1-yl)phenyl)acrylamido)benzoic acid (97);
(E)-2-(3-(3-methoxy-4-(1,2,3,6-tetrahydropyridin-4-yl)phenyl)acrylamido)benzoic acid (98);
(E)-2-(3-(3-methoxy-4-(1-methyl-1,2,3,6-tetrahydropyridin-4-yl)phenyl)acrylamido)benzoic acid (99);
(E)-2-(3-(4-methoxy-3-morpholinophenyl)acrylamido)benzoic acid (101);
(E)-2-(3-(3-methoxy-4-morpholinophenyl)acrylamido)benzoic acid (103);
(E)-2-(3-(4-methoxy-3-(1-methyl-1,2,3,6-tetrahydropyridin-4-yl)phenyl)acrylamido)benzoic acid (104);
2-[[(E)-3-(4-methyl-2,3-dihydro-1,4-benzoxazin-6-yl)prop-2-enoyl]amino]benzoic acid (107);
(E)-N-(2-(1,2,4-oxadiazol-5-yl)phenyl)-3-(3-methoxy-4-(prop-2-yn-1-yloxy)phenyl)acrylamide (108);
(E)-2-(3-(4-methyl-3-oxo-3,4-dihydro-2H-benzo[b][1,4]oxazin-7-yl)acrylamido)benzoic acid (109);
(E)-2-(3-(4-methyl-3,4-dihydro-2H-benzo[b][1,4]oxazin-7-yl)acrylamido)benzoic acid (110);
(E)-2-(3-(3-oxo-3,4-dihydro-2H-benzo[b][1,4]oxazin-6-yl)acrylamido)benzoic acid (111);
(E)-2-(3-(4-methyl-3-oxo-3,4-dihydro-2H-benzo[b][1,4]oxazin-6-yl)acrylamido)benzoic acid (112);
(E)-3-(3-ethyl-4-(prop-2-yn-1-yloxy)phenyl)-N-(2-(3-methyl-1H-1,2,4-triazol-1-yl)phenyl)-acrylamide (114);
(E)-2-(3-(2-(2-(dimethylamino)ethoxy)-3,4-dimethoxyphenyl)acrylamido)benzoic acid (116);
(E)-4-chloro-2-(3-(2-(2-(dimethylamino)ethoxy)-3,4-dimethoxyphenyl)acrylamido)benzoic acid (117);
(E)-N-(4-fluorophenyl)-3-(3-methoxy-4-(1,2,3,6-tetrahydropyridin-4-yl)phenyl)acrylamide (120);
N-(4-cyanophenyl)-2-(3-methoxy-4-(1,2,3,6-tetrahydropyridin-4-yl)phenyl)cyclopropane carboxamide (121);
2-(2-(2-(dimethylamino)ethoxy)-3,4-dimethoxyphenyl)-N-(4-fluorophenyl)cyclopropane-1-carboxamide (122);
(E)-3-(3-ethyl-4-(prop-2-yn-1-yloxy)phenyl)-N-(2-fluorophenyl)acrylamide (123);
(E)-N-(4-cyanophenyl)-3-(3-ethyl-4-(prop-2-yn-1-yloxy)phenyl)acrylamide (124);
(E)-3-(3-ethyl-4-(prop-2-yn-1-yloxy)phenyl)-N-(4-fluorophenyl)acrylamide (125);
(E)-3-(2-(2-(dimethylamino)ethoxy)-3,4-dimethoxyphenyl)-N-(2-fluorophenyl)acrylamide (127);
(E)-3-(2-(2-(dimethylamino)ethoxy)-3,4-dimethoxyphenyl)-N-(4-fluorophenyl)acrylamide (128);
(E)-N-(4-cyanophenyl)-3-(2-(2-(dimethylamino)ethoxy)-3,4-dimethoxyphenyl)acrylamide (129);
(E)-2-(3-(4-methyl-3,4-dihydro-2H-benzo[b][1,4]oxazin-7-yl)acrylamido)benzoic acid (130);
(E)-N-(4-cyanophenyl)-3-(3-methoxy-4-((1-methylpyrrolidin-3-yl)oxy)phenyl)acrylamide (131);
(E)-N-(4-fluorophenyl)-3-(3-methoxy-4-((1-methylpyrrolidin-3-yl)oxy)phenyl)acrylamide (132);
N-(4-fluorophenyl)-2-(3-methoxy-4-(prop-2-yn-1-yloxy)phenyl)cyclopropanecarboxamide (133);
N-(4-cyanophenyl)-2-(3-methoxy-4-(prop-2-yn-1-yloxy)phenyl)cyclopropanecarboxamide (135);
N-(4-fluorophenyl)-2-(3-methoxy-4-((1-methylpyrrolidin-3-yl)oxy)phenyl)cyclopropane-1-carboxamide (136);
N-(4-cyanophenyl)-2-(3-methoxy-4-((1-methylpyrrolidin-3-yl)oxy)phenyl)cyclopropane-1-carboxamide (137);
N-(2-fluorophenyl)-2-(3-methoxy-4-((1-methylpyrrolidin-3-yl)oxy)phenyl)cyclopropane carboxamide (138);
(E)-N-(4-cyanophenyl)-3-(3-methoxy-4-(1,2,3,6-tetrahydropyridin-4-yl)phenyl)acrylamide (139);
(E)-3-(3-methoxy-4-(1,2,3,6-tetrahydropyridin-4-yl)phenyl)-N-(2-(3-methyl-1H-1,2,4-triazol-1-yl)phenyl)acrylamide (140);
(E)-N-(2-fluorophenyl)-3-(3-methoxy-4-(1,2,3,6-tetrahydropyridin-4-yl)phenyl)acrylamide (141);
N-(4-fluorophenyl)-2-(3-methoxy-4-(1,2,3,6-tetrahydropyridin-4-yl)phenyl)cyclopropane carboxamide (143);
2-(3-methoxy-4-(1,2,3,6-tetrahydropyridin-4-yl)phenyl)-N-(2-(3-methyl-1H-1,2,4-triazol-1-yl)phenyl)cyclopropanecarboxamide (144);
N-(2-fluorophenyl)-2-(3-methoxy-4-(1,2,3,6-tetrahydropyridin-4-yl)phenyl)cyclopropane carboxamide (145);
(E)-N-(3-chlorophenyl)-3-(3-methoxy-4-(oxetan-3-ylmethoxy)phenyl)acrylamide (147);
N-(3-chlorophenyl)-2-(3-methoxy-4-(oxetan-3-ylmethoxy)phenyl)cyclopropane-1-carboxamide (148);
N-(4-chlorophenyl)-2-(4-methoxy-3-((1-methyl-1H-pyrazol-4-yl)methoxy)phenyl)cyclopropane-1-carboxamide (149);
(E)-N-(3-chlorophenyl)-3-(4-methoxy-3-morpholinophenyl)acrylamide (151);
(E)-N-(2-chlorophenyl)-3-(3-methoxy-4-(oxetan-3-ylmethoxy)phenyl)acrylamide (152);
(E)-N-(4-chlorophenyl)-3-(3-methoxy-4-(oxetan-3-ylmethoxy)phenyl)acrylamide (153);
N-(4-chlorophenyl)-2-(3-methoxy-4-(oxetan-3-ylmethoxy)phenyl)cyclopropane-1-carboxamide (154);
N-(2-chlorophenyl)-2-(3-methoxy-4-(oxetan-3-ylmethoxy)phenyl)cyclopropane-1-carboxamide (155);
N-(3-chlorophenyl)-2-(4-methoxy-3-((1-methyl-1H-pyrazol-4-yl)methoxy)phenyl)cyclopropane-1-carboxamide (156);
N-(2-chlorophenyl)-2-(4-methoxy-3-((1-methyl-1H-pyrazol-4-yl)methoxy)phenyl)cyclopropane-1-carboxamide (157);
2-(4-methoxy-3-((1-methyl-1H-pyrazol-4-yl)methoxy)phenyl)-N-(3-(methylsulfonyl)phenyl) cyclopropane-1-carboxamide (158);
(E)-N-(2-chlorophenyl)-3-(4-methoxy-3-((1-methyl-1H-pyrazol-4-yl)methoxy)phenyl)acrylamide (159);
(E)-N-(3-chlorophenyl)-3-(4-methoxy-3-((1-methyl-1H-pyrazol-4-yl)methoxy)phenyl)acrylamide (160); and pharmaceutically acceptable salts thereof.

In another aspect, disclosed are the following compounds:
(E)-3-(3-methoxy-4-(prop-2-yn-1-yloxy)phenyl)-N-phenylacrylamide (8);
methyl (E)-1-(3-(3-methoxy-4-(prop-2-yn-1-yloxy)phenyl)acryloyl)-1,2,3,4-tetrahydroquinoline-4-carboxylate (9)

(E)-1-(3,4-dihydroquinolin-1(2H)-yl)-3-(3-methoxy-4-(prop-2-yn-1-yloxy)phenyl)prop-2-en-1-one (10);
(E)-1-(3,4-dihydroquinoxalin-1(2H)-yl)-3-(3-methoxy-4-(prop-2-yn-1-yloxy)phenyl)prop-2-en-1-one (11);
(E)-1-(2,3-dihydro-4H-benzo[b][1,4]oxazin-4-yl)-3-(3-methoxy-4-(prop-2-yn-1-yloxy)phenyl)prop-2-en-1-one (12);
(E)-N-((trans)-2-aminocyclohexyl)-3-(3-methoxy-4-(prop-2-yn-1-yloxy)phenyl)acrylamide (13);
(E)-1-(4-hydroxy-3,4-dihydroquinolin-1(2H)-yl)-3-(3-methoxy-4-(prop-2-yn-1-yloxy)phenyl)prop-2-en-1-one (14);
(E)-1-(3-hydroxy-1H-indazol-1-yl)-3-(3-methoxy-4-(prop-2-yn-1-yloxy)phenyl)prop-2-en-1-one (15);
(E)-N-(2-(dimethylamino)ethyl)-2-(3-(3-methoxy-4-(prop-2-yn lyloxy) phenyl) acrylamido) benzamide (30);
(E)-N-(3-(dimethylamino)propyl)-2-(3-(3-methoxy-4-(prop-2-yn-1-yloxy)phenyl)acrylamido) benzamide (32);
(E)-2-(3-(3-methoxy-4-(prop-2-yn-1-yloxy)phenyl)acrylamido)-N-(2-methoxyethyl)benzamide (33);
(E)-2-(3-(3-methoxy-4-(prop-2-yn-1-yloxy)phenyl)acrylamido)-N-(2-(4-methylpiperazin-1-yl)ethyl)benzamide (34);
(E)-2-(3-(3-methoxy-4-(prop-2-yn-1-yloxy)phenyl)acrylamido)-N-(2-morpholino ethyl)benzamide (35);
(E)-2-(3-(3-methoxy-4-(prop-2-yn-1-yloxy)phenyl)acrylamido)-N-((1-methylpiperidin-4-yl)methyl)benzamide (37);
(E)-2-(3-(3-methoxy-4-(prop-2-yn-1-yloxy)phenyl)acrylamido)-N-((tetrahydrofuran-3-yl)methyl)benzamide (39);
(E)-2-(3-(3-methoxy-4-(prop-2-yn-1-yloxy)phenyl)acrylamido)-N-((1-methyl-1H-imidazol-5-yl)methyl)benzamide (40);
(E)-2-(3-(3-methoxy-4-(prop-2-yn-1-yloxy)phenyl)acrylamido)-N-(pyridin-2-ylmethyl)benzamide (41);
(E)-2-(3-(3-methoxy-4-(prop-2-yn-1-yloxy)phenyl)acrylamido)-N-(2-(pyridin-2-yl)ethyl)benzamide (42);
(E)-2-(3-(3-methoxy-4-(prop-2-yn-1-yloxy)phenyl)acrylamido)-N-(pyridin-3-ylmethyl)benzamide (43);
(E)-2-(3-(3-methoxy-4-(prop-2-yn-1-yloxy)phenyl)acrylamido)-N-(pyridin-4-ylmethyl)benzamide (45);
(E)-2-(3-(3-methoxy-4-(prop-2-yn-1-yloxy)phenyl)acrylamido)-N-(2-(pyridin-4-yl)ethyl)benzamide (46);
(E)-2-(3-(3-methoxy-4-(piperidin-4-ylmethoxy)phenyl)acrylamido)benzoic acid (50);
(E)-2-(3-(4-(((3,5-dimethylisoxazol-4-yl)methoxy)-3-methoxyphenyl)acrylamido)benzoic acid (52);
(E)-2-(3-(3-methoxy-4-((1-methyl-1H-pyrazol-4-yl)methoxy)phenyl)acrylamido)benzoic acid (53);
(E)-2-(3-(3-methoxy-4-(oxetan-3-ylmethoxy)phenyl)acrylamido)benzoic acid (54);
(E)-2-(3-(3-methoxy-4-(pyridin-2-ylmethoxy)phenyl)acrylamido)benzoic acid (55);
(E)-2-(3-(3-methoxy-4-(2-(pyridin-2-yl)ethoxy)phenyl)acrylamido)benzoic acid (56);
(E)-2-(3-(3-methoxy-4-(2-(pyridin-3-yl)ethoxy)phenyl)acrylamido)benzoic acid (57);
(E)-2-(3-(3-methoxy-4-(pyridin-4-ylmethoxy)phenyl)acrylamido)benzoic acid (58);
(E)-2-(3-(3-methoxy-4-(2-(pyridin-4-yl)ethoxy)phenyl)acrylamido)benzoic acid (59);
(E)-2-(3-(3-methoxy-4-((1-methyl-1H-pyrazol-5-yl)methoxy)phenyl)acrylamido)benzoic acid (60);
(E)-2-(3-(4-methoxy-3-(2-methoxyethoxy)phenyl)acrylamido)benzoic acid (61);
(E)-2-(3-(4-methoxy-3-(2-(pyridin-2-yl)ethoxy)phenyl)acrylamido)benzoic acid (62);
(E)-2-(3-(4-methoxy-3-(pyridin-3-ylmethoxy)phenyl)acrylamido)benzoic acid (63);
(E)-2-(3-(4-methoxy-3-(2-(pyridin-3-yl)ethoxy)phenyl)acrylamido)benzoic acid (64);
(E)-2-(3-(4-methoxy-3-(2-(pyridin-4-yl)ethoxy)phenyl)acrylamido)benzoic acid (65);
(E)-2-(3-(4-methoxy-3-((1-methyl-1H-pyrazol-4-yl)methoxy)phenyl)acrylamido)benzoic acid (66);
(E)-2-(3-(4-methoxy-3-((1-methyl-1H-pyrazol-5-yl)methoxy)phenyl)acrylamido)benzoic acid (67);
(E)-2-(3-(3-methoxy-4-((4-methylpiperazin-1-yl)methyl)phenyl)acrylamido)benzoic acid (68);
(E)-2-(3-(3-methoxy-4-(morpholinomethyl)phenyl)acrylamido)benzoic acid (69);
(E)-2-(3-(4-methoxy-3-(((1-methylpiperidin-4-yl)oxy)methyl)phenyl)acrylamido)benzoic acid (70)
(E)-2-(3-(4-methoxy-3-((prop-2-yn-1-yloxy)methyl)phenyl)acrylamido)benzoic acid (71);
(E)-2-(3-(3-methoxy-4-((prop-2-yn-1-yloxy)methyl)phenyl)acrylamido)benzoic acid (72);
(E)-2-(3-(4-methoxy-3-(methoxymethyl)phenyl)acrylamido)benzoic acid (73);
(E)-2-(3-(4-methoxy-3-((prop-2-yn-1-ylamino)methyl)phenyl)acrylamido)benzoic acid (74);
(E)-2-(3-(3-methoxy-4-((prop-2-yn-1-ylamino)methyl)phenyl)acrylamido)benzoic acid (75);
(E)-2-(3-(4-ethyl-3-methoxyphenyl)acrylamido)benzoic acid (100);
2-[[(E)-3-[4-(cyclopropylmethyl)-3-methoxyphenyl]prop-2-enoyl]amino]benzoic acid (102);
(E)-2-(3-(3-ethyl-4-methoxyphenyl)acrylamido)benzoic acid (105);
(E)-2-(3-(3-(cyclopropylmethyl)-4-methoxyphenyl)acrylamido)benzoic acid (106);
(E)-1-(2H-benzo[b][1,4]oxazin-4(3H)-yl)-3-(3-ethyl-4-(prop-2-yn-1-yloxy)phenyl)prop-2-en-1-one (113);
(E)-1-(2H-benzo[b][1,4]oxazin-4(3H)-yl)-3-(2-(2-(dimethylamino)ethoxy)-3,4-dimethoxyphenyl)-prop-2-en-1-one (115);
(E)-1-(2H-benzo[b][1,4]oxazin-4(3H)-yl)-3-(3-methoxy-4-((1-methylpyrrolidin-3-yl)oxy)phenyl)prop-2-en-1-one (118);
(2H-benzo[b][1,4]oxazin-4(3H)-yl)(2-(3-methoxy-4-(prop-2-yn-1-yloxy) phenyl) cyclopropyl) methanone (119);
(E)-3-(3-ethyl-4-(prop-2-yn-1-yloxy)phenyl)-1-(3-hydroxy-1H-indazol-1-yl)prop-2-en-1-one (126);
(3-hydroxy-1H-indazol-1-yl)(2-(3-methoxy-4-(prop-2-yn-1-yloxy)phenyl)cyclopropyl) methanone (134);
(E)-1-(3-hydroxy-1H-indazol-1-yl)-3-(3-methoxy-4-(1,2,3,6-tetrahydropyridin-4-yl)phenyl)prop-2-en-1-one (142);
(3-hydroxy-1H-indazol-1-yl)(2-(3-methoxy-4-(1,2,3,6-tetrahydropyridin-4-yl)phenyl) cyclopropyl)methanone (146);
(E)-3-(4-methoxy-3-((1-methyl-1H-pyrazol-4-yl)methoxy)phenyl)-N-(pyridin-3-yl)acrylamide (150); and pharmaceutically acceptable salts thereof.

For example, disclosed is a compound of the formula:

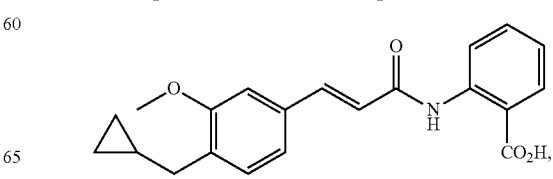

or a pharmaceutically acceptable salt thereof.

In certain embodiments, the compound of Formula I inhibits TGF-β induced proline incorporation in cells with an $IC_{50}$ of less than 100,000 μM, less than 50,000 μM, less than 20,000 μM, less than 10,000 μM, less than 5,000 μM, less than 2,500 μM, less than 1,000 μM, less than 900 μM, less than 800 μM, less than 700 μM, less than 600 μM, less than 500 μM, less than 400 μM, less than 300 μM, less than 200 μM, less than 100 μM, less than 90 μM, less than 80 μM, less than 70 μM, less than 60 μM, less than 50 μM, less than 40 μM, less than 30 μM, less than 20 μM, less than 10 μM, less than 5 μM, less than 4 μM, less than 3 μM, less than 2 μM, or less than 1 μM.

In certain embodiments, any compound disclosed herein (e.g., 2-[[(E)-3-[4-(cyclopropylmethyl)-3-methoxyphenyl]prop-2-enoyl]amino]benzoic acid) inhibits TGF-3 induced proline incorporation in cells with an $IC_{50}$ of less than 100,000 μM, less than 50,000 μM, less than 20,000 μM, less than 10,000 μM, less than 5,000 μM, less than 2,500 μM, less than 1,000 μM, less than 900 μM, less than 800 μM, less than 700 μM, less than 600 μM, less than 500 μM, less than 400 μM, less than 300 μM, less than 200 μM, less than 100 μM, less than 90 μM, less than 80 μM, less than 70 μM, less than 60 μM, less than 50 μM, less than 40 μM, less than 30 μM, less than 20 μM, less than 10 μM, less than 5 μM, less than 4 μM, less than 3 μM, less than 2 μM, or less than 1 μM.

Pharmaceutical Compositions, Kits, and Administration

The present disclosure provides pharmaceutical compositions comprising a compound (e.g., compound of Formula I, 2-[[(E)-3-[4-(cyclopropylmethyl)-3-methoxyphenyl]prop-2-enoyl]amino]benzoic acid) or a pharmaceutically acceptable salt, co-crystal, tautomer, stereoisomer, solvate, hydrate, polymorph, isotopically enriched derivative, or prodrug thereof, and optionally a pharmaceutically acceptable excipient. In certain embodiments, the pharmaceutical composition described herein comprises a compound (e.g., compound of Formula I, 2-[[(E)-3-[4-(cyclopropylmethyl)-3-methoxyphenyl]prop-2-enoyl]amino]benzoic acid), or a pharmaceutically acceptable salt thereof, and a pharmaceutically acceptable excipient.

In certain embodiments, the compound (e.g., compound of Formula I, 2-[[(E)-3-[4-(cyclopropylmethyl)-3-methoxyphenyl]prop-2-enoyl]amino]benzoic acid) is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a disease or condition associated with fibrosis in a subject in need thereof. In certain embodiments, the effective amount is an amount effective for preventing disease or condition associated with fibrosis in a subject in need thereof. In certain embodiments, the effective amount is an amount effective for treating fibrotic skin disorders (e.g., keloids, hypertrophic scars, scleroderma) in a subject in need thereof. In certain embodiments, the effective amount is an amount effective for preventing fibrotic skin disorders (e.g., keloids, hypertrophic scars, scleroderma) in a subject in need thereof. In certain embodiments, the effective amount is an amount effective for treating kidney disease in a subject in need thereof. In certain embodiments, the effective amount is an amount effective for preventing kidney disease in a subject in need thereof. In certain embodiments, the effective amount is an amount effective for treating an inflammatory disease in a subject in need thereof. In certain embodiments, the effective amount is an amount effective for preventing an inflammatory disease in a subject in need thereof. In certain embodiments, the effective amount is an amount effective for treating a benign or malignant neoplastic disease in a subject in need thereof. In certain embodiments, the effective amount is an amount effective for preventing a benign or malignant neoplastic disease in a subject in need thereof. In certain embodiments, the effective amount is an amount effective for reducing the risk of developing a disease (e.g., fibrosis, fibrotic skin disorders, kidney disease, inflammatory disease, or benign or malignant neoplastic disease) in a subject in need thereof. In certain embodiments, the effective amount is an amount effective for inhibiting the activity (e.g., aberrant activity, such as increased activity) of a protein in a subject or cell.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the effective amount is an amount effective for inhibiting the activity of the TGF-β signaling pathway by at least about 10%, at least about 20%, at least about 30%, at least about 40%, at least about 50%, at least about 60%, at least about 70%, at least about 80%, at least about 90%, at least about 95%, at least about 98%, or at least about 99%. In certain embodiments, the effective amount is an amount effective for inhibiting the activity of the TGF-β signaling pathway by a range between a percentage described in this paragraph and another percentage described in this paragraph, inclusive.

The present disclosure provides pharmaceutical compositions comprising a compound (e.g., compound of Formula I, 2-[[(E)-3-[4-(cyclopropylmethyl)-3-methoxyphenyl]prop-2-enoyl]amino]benzoic acid) for use in treating a disease or condition associated with fibrosis in a subject in need thereof. In certain embodiments, the composition is for use in treating fibrotic skin disorders (e.g., keloids, hypertrophic scars, scleroderma). In certain embodiments, the composition is for use in treating a lung disease (e.g., pulmonary fibrosis). In certain embodiments, the composition is for use in treating heart disease (e.g., ischaemic heart disease, valvular heart disease, hypertensive heart disease, diabetic cardiomyopathy, hypertension). In certain embodiments, the composition is for use in treating kidney disease. In certain embodiments, the composition is for use in treating cirrhosis of the liver. In certain embodiments, the composition is for use in treating kidney disease, wherein the kidney disease is progressive kidney disease, glomerulonephritis, diabetic kidney disease, diabetic nephropathy, systemic lupus, primary glomerulonephritis, membranous nephropathy, focal segmental glomerulosclerosis, membranoproliferative glomerulonephritis, diffuse proliferative glomerulonephritis, membranous focal segmental glomerulosclerosis, secondary glomerulonephritis, or ischemic nephropathy.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, and/or in reducing the risk to develop a disease in a subject in need thereof), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent exhibit a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological cancer, autoimmune disease, and/or inflammatory disease). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, and anti-viral agents. In certain embodiments, the additional pharmaceutical agent is an anti-viral agent. In certain embodiments, the additional pharmaceutical agent is an immunotherapy. In certain embodiments, the additional pharmaceutical agent is an anti-proliferative agent. In certain embodiments, the additional pharmaceutical agent is an anti-cancer agent. In certain embodiments, the anti-cancer agents include, but are not limited to, epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), cell signaling pathway inhibitors (e.g., tyrosine protein kinase inhibitors), modulators of protein stability (e.g., proteasome inhibitors), Hsp90 inhibitors, glucocorticoids, all-trans retinoic acids, anti-estrogens (e.g., tamoxifen, raloxifene, and megestrol), LHRH agonists (e.g., goserelin and leuprolide), anti-androgens (e.g. flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), Ca2+ ATPase inhibitors (e.g. thapsigargin), thalidomide, lenalidomide, pomalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (Astra-Zeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the compounds described herein or pharmaceutical compositions can be administered in combination with an anti-cancer therapy including, but not limited to, surgery, radiation therapy, and transplantation (e.g., stem cell transplantation, bone marrow transplantation).

In certain embodiments, the compound or pharmaceutical composition is a solid. In certain embodiments, the compound or pharmaceutical composition is a powder. In certain embodiments, the compound or pharmaceutical composition can be dissolved in a liquid to make a solution. In certain embodiments, the compound or pharmaceutical composition is dissolved in water to make an aqueous solution. In certain embodiments, the pharmaceutical composition is a liquid for parental injection. In certain embodiments, the pharmaceutical composition is a liquid for oral administration (e.g., ingestion). In certain embodiments, the pharmaceutical composition is a liquid (e.g., aqueous solution) for intravenous injection. In certain embodiments, the pharmaceutical composition is a liquid (e.g., aqueous solution) for subcutaneous injection.

After formulation with an appropriate pharmaceutically acceptable excipient in a desired dosage, the pharmaceutical compositions of this invention can be administered to humans and other animals orally, parenterally, intracisternally, intraperitoneally, topically, bucally, or the like, depending on the disease or condition being treated.

In certain embodiments, a pharmaceutical composition comprising a compound (e.g., compound of Formula I, 2-[[(E)-3-[4-(cyclopropylmethyl)-3-methoxyphenyl]prop-2-enoyl]amino]benzoic acid) is administered, orally or parenterally, at dosage levels of each pharmaceutical composition sufficient to deliver from about 0.001 mg/kg to about 200 mg/kg in one or more dose administrations for one or several days (depending on the mode of administration). In certain embodiments, the effective amount per dose varies from about 0.001 mg/kg to about 200 mg/kg, about 0.001 mg/kg to about 100 mg/kg, about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, of subject body weight per day, one or more times a day, to obtain the desired therapeutic and/or prophylactic effect. In certain embodiments, the compounds described herein may be at dosage levels sufficient to deliver from about 0.001 mg/kg to about 200 mg/kg, from about 0.001 mg/kg to about 100 mg/kg, from about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In certain embodiments, the composition described herein is administered at a dose that is below the dose at which the agent causes non-specific effects.

In certain embodiments, the pharmaceutical composition is administered at a dose of about 0.001 mg to about 1000 mg per unit dose. In certain embodiments, the pharmaceutical composition is administered at a dose of about 0.01 mg to about 200 mg per unit dose. In certain embodiments, the pharmaceutical composition is administered at a dose of about 0.01 mg to about 100 mg per unit dose. In certain embodiments, pharmaceutical composition is administered at a dose of about 0.01 mg to about 50 mg per unit dose. In certain embodiments, the pharmaceutical composition is administered at a dose of about 0.01 mg to about 10 mg per unit dose. In certain embodiments, the pharmaceutical composition is administered at a dose of about 0.1 mg to about 10 mg per unit dose.

Pharmaceutical compositions described herein can be prepared by any method known in the art of pharmacology. In general, such preparatory methods include the steps of bringing the composition comprising a compound (e.g., compound of Formula I, 2-[[(E)-3-[4-(cyclopropylmethyl)-3-methoxyphenyl]prop-2-enoyl]amino]benzoic acid) into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazelnut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include, but are not limited to, pharmaceutically acceptable emulsions, microemulsions, solutions, suspensions, syrups, and elixirs. In addition to the active agents, the liquid dosage forms may contain inert diluents commonly used in the art such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can also include adjuvants such as wetting agents, emulsifying and suspending agents, sweetening, flavoring, and perfuming agents. In certain embodiments for parenteral administration, agents of the invention are mixed with solubilizing agents such CREMOPHOR EL® (polyethoxylated castor oil), alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. Sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used. Ophthalmic formulation, ear drops, and eye drops are also contemplated as being within the scope of this invention. Additionally, the present disclosure contemplates the use of transdermal patches, which have the added advantage of providing controlled delivery of an agent to the body. Such dosage forms can be made by dissolving or dispensing the agent in the proper medium. Absorption enhancers can also be used to increase the flux of the agent across the skin. The rate can be controlled by either providing a rate controlling membrane or by dispersing the agent in a polymer matrix or gel.

Additionally, the carrier for a topical formulation can be in the form of a hydroalcoholic system (e.g., quids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, hematological cancer, autoimmune disease, inflammatory disease) in a subject in need thereof. In certain embodiments, the kits are useful for preventing a disease (e.g., a disease or condition associated with fibrosis, a benign or malignant neoplastic disease, inflammatory disease) in a subject in need thereof. In certain embodiments, the kits are useful for reducing the risk of developing a disease (e.g., a disease or condition associated with fibrosis, a benign or malignant neoplastic disease, inflammatory disease) in a subject in need thereof. In certain embodiments, the kits are useful for inhibiting the activity (e.g., aberrant activity, such as increased activity) of the TGF-β signaling pathway in a subject or cell.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., a disease or condition associated with fibrosis, a benign or malignant neoplastic disease, inflammatory disease) in a subject in need thereof. In certain embodiments, the kits and instructions provide for preventing a disease (e.g., a disease or condition associated with fibrosis, a benign or malignant neoplastic disease, inflammatory disease) in a subject in need thereof. In certain embodiments, the kits and instructions provide for reducing the risk of developing a disease (e.g., a disease or condition associated with fibrosis, a benign or malignant neoplastic disease, inflammatory disease) in a subject in need thereof. In certain embodiments, the kits and instructions provide for inhibiting the activity (e.g., aberrant activity, such as increased activity) of the TGF-β signaling pathway in a subject or cell. A kit described herein may include one or more additional pharmaceutical agents described herein as a separate composition.

Methods of Treatment

Fibrosis is the formation of excess fibrous connective tissue in an organ or tissue in a reparative or reactive process, and the deposition of connective tissue can obliterate the architecture and function of the underlying organ or tissue. Fibrosis is the pathological state of excess deposition of fibrous tissue, as well as the process of connective tissue deposition in healing. Defined by the pathological accumulation of extracellular matrix (ECM) proteins, fibrosis results in scarring and thickening of the affected tissue. Thus, it is an exaggerated wound healing response which interferes with normal organ function.

The most well characterized pro-fibrotic mediator is TGF-β, which is released by macrophages as well as any damaged tissue between surfaces called interstitium. Other soluble mediators of fibrosis include connective tissue growth factor (CTGF), platelet-derived growth factor (PDGF), and Interleukin 4 (IL-4). These initiate signal transduction pathways such as the AKT/mTOR and SMAD pathways that ultimately lead to the proliferation and activation of fibroblasts, which deposit extracellular matrix into the surrounding connective tissue. Therefore, use of a compound that inhibits mediators of fibrosis (e.g., TGF-β) provides a method of treating diseases that rely on fibrotic activity.

The present disclosure provides methods for treating a disease or condition associated with fibrosis. In certain embodiments, the application provides a method of treating fibrotic skin disorders (e.g., keloids, hypertrophic scars, scleroderma). In certain embodiments, the application provides a method of treating lung disease (e.g., pulmonary fibrosis). In certain embodiments, the application provides a method of treating heart disease (e.g., ischaemic heart disease, valvular heart disease, hypertensive heart disease, diabetic cardiomyopathy, hypertension). In certain embodiments, the application provides a method of treating cirrhosis of the liver. In certain embodiments, the application provides a method of treating kidney disease. In certain embodiments, the application provides a method of treating progressive kidney disease, glomerulonephritis, diabetic kidney disease, diabetic nephropathy, systemic lupus, primary glomerulonephritis, membranous nephropathy, focal segmental glomerulosclerosis, membranoproliferative glomerulonephritis, diffuse proliferative glomerulonephritis, membranous focal segmental glomerulosclerosis, secondary glomerulonephritis, or ischemic nephropathy. In certain embodiments, the application provides a method of treating focal segmental glomerulosclerosis. In certain embodiments, the application provides a method of treating benign or malignant neoplastic disease. In certain embodiments, the application provides a method of treating inflammation. In certain embodiments, the application provides a method of inhibiting the TGF-β signaling pathway.

In certain embodiments, the methods comprise administering to a subject in need thereof (e.g., a subject suffering from a disease associated with fibrosis) a compound that interacts with TGF-β, for example, a compound that is an inhibitor of TGF-β or the TGF-β signaling pathway. In certain embodiments, the methods comprise administering a compound (e.g., compound of Formula I, 2-[[(E)-3-[4-(cyclopropylmethyl)-3-methoxyphenyl]prop-2-enoyl]amino] benzoic acid), or a pharmaceutically acceptable salt, co-crystal, tautomer, stereoisomer, solvate, hydrate, polymorph, isotopically enriched derivative, or prodrug, or composition thereof, to a subject in need thereof. In some embodiments, the method comprises administering a pharmaceutical composition comprising a compound (e.g., compound of Formula I, 2-[[(E)-3-[4-(cyclopropylmethyl)-3-methoxyphenyl]prop-2-enoyl]amino]benzoic acid), or a pharmaceutically acceptable salt, co-crystal, tautomer, stereoisomer, solvate, hydrate, polymorph, isotopically enriched derivative, or prodrug, or composition thereof, to a subject in need thereof.

The present disclosure also provides a compound (e.g., compound of Formula I, 2-[[(E)-3-[4-(cyclopropylmethyl)-3-methoxyphenyl]prop-2-enoyl]amino]benzoic acid), or a pharmaceutically acceptable salt, co-crystal, tautomer, stereoisomer, solvate, hydrate, polymorph, isotopically enriched derivative, or prodrug, or composition thereof, for use in the treatment of a disease or condition associated with fibrosis, benign or malignant neoplastic disease, or inflammation. In certain embodiments, the disease or condition associated with fibrosis is fibrotic skin disorders (e.g., keloids, hypertrophic scars, scleroderma). In certain embodiments, the disease or condition associated with fibrosis is lung disease (e.g., pulmonary fibrosis). In certain embodiments, the disease or condition associated with fibrosis is heart disease (e.g., ischaemic heart disease, valvular heart disease, hypertensive heart disease, diabetic cardiomyopathy, hypertension). In certain embodiments, the disease or condition associated with fibrosis is cirrhosis of the liver. In certain embodiments, the disease or condition associated with fibrosis is kidney disease. In certain embodiments, the kidney disease is kidney disease is progressive kidney disease, glomerulonephritis, diabetic kidney disease, diabetic nephropathy, systemic lupus, primary glomerulonephritis, membranous nephropathy, focal segmental glomerulosclerosis, membranoproliferative glomerulonephritis, diffuse proliferative glomerulonephritis, membranous focal segmental glomerulosclerosis, secondary glomerulonephritis, or ischemic nephropathy.

The present disclosure also provides uses of a compound (e.g., compound of Formula I, 2-[[(E)-3-[4-(cyclopropylmethyl)-3-methoxyphenyl]prop-2-enoyl]amino]benzoic acid), or a pharmaceutically acceptable salt, co-crystal, tautomer, stereoisomer, solvate, hydrate, polymorph, isotopically enriched derivative, or prodrug, or composition thereof, in the manufacture of a medicament for the treatment of a disease or condition associated with fibrosis, benign or malignant neoplastic disease, or inflammation. In certain embodiments, the disease or condition associated with fibrosis is fibrotic skin disorders (e.g., keloids, hypertrophic scars, scleroderma). In certain embodiments, the disease or condition associated with fibrosis is lung disease (e.g., pulmonary fibrosis). In certain embodiments, the disease or condition associated with fibrosis is heart disease (e.g., ischaemic heart disease, valvular heart disease, hypertensive heart disease, diabetic cardiomyopathy, hypertension). In certain embodiments, the disease or condition associated with fibrosis is cirrhosis of the liver. In certain embodiments, the disease or condition associated with fibrosis is kidney disease. In certain embodiments, the kidney disease is kidney disease is progressive kidney disease, glomerulonephritis, diabetic kidney disease, diabetic nephropathy, systemic lupus, primary glomerulonephritis, membranous nephropathy, focal segmental glomerulosclerosis, membranoproliferative glomerulonephritis, diffuse proliferative glomerulonephritis, membranous focal segmental glomerulosclerosis, secondary glomerulonephritis, or ischemic nephropathy.

In certain embodiments, the methods of the invention comprise administering to the subject an effective amount of a compound (e.g., compound of Formula I, 2-[[(E)-3-[4-(cyclopropylmethyl)-3-methoxyphenyl]prop-2-enoyl] amino]benzoic acid), or a pharmaceutically acceptable salt, co-crystal, tautomer, stereoisomer, solvate, hydrate, polymorph, isotopically enriched derivative, or prodrug, or composition thereof. In some embodiments, the effective amount is a therapeutically effective amount. In some embodiments, the effective amount is a prophylactically effective amount.

In certain embodiments, the subject being treated is an animal. The animal may be of either sex and may be at any stage of development. In certain embodiments, the subject is a mammal. In certain embodiments, the subject being treated is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Certain methods described herein may comprise administering one or more additional pharmaceutical agent(s) in combination with the compounds described herein. The additional pharmaceutical agent(s) may be administered at the same time as the compound (e.g., compound of Formula I, 2-[[(E)-3-[4-(cyclopropylmethyl)-3-methoxyphenyl]prop-2-enoyl]amino]benzoic acid), or at different times than the compound (e.g., compound of Formula I, 2-[[(E)-3-[4-(cyclopropylmethyl)-3-methoxyphenyl]prop-2-enoyl]amino] benzoic acid). For example, the compound (e.g., compound of Formula I, 2-[[(E)-3-[4-(cyclopropylmethyl)-3-methoxyphenyl]prop-2-enoyl]amino]benzoic acid) and any additional pharmaceutical agent(s) may be on the same dosing schedule or different dosing schedules. All or some doses of the compound (e.g., compound of Formula I, 2-[[(E)-3-[4-(cyclopropylmethyl)-3-methoxyphenyl]prop-2-enoyl] amino]benzoic acid) may be administered before all or some doses of an additional pharmaceutical agent, after all or some does an additional pharmaceutical agent, within a dosing schedule of an additional pharmaceutical agent, or a combination thereof. The timing of administration of the compound (e.g., compound of Formula I, 2-[[(E)-3-[4-(cyclopropylmethyl)-3-methoxyphenyl]prop-2-enoyl]amino] benzoic acid) and additional pharmaceutical agents may be different for different additional pharmaceutical agents.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Mass spectra were recorded on a Micromass ZQ™, single quadrapole mass spectrometer. $^1$H Nuclear magnetic resonance (NMR) spectroscopy was carried out using a Bruker instrument operating at 400 MHz using the stated solvent at around room temperature, unless otherwise stated. Characeristic chemical shifts (6) are given in parts-per-million using conventional abbreviations for designation of major peaks: e.g., s, singlet; d, doublet; t, triplet; q, quartet; dd, doublet of doublets; dt, doublet of triplets; m, multiplet; br, broad.

Preparative HPLC purification was accomplished using the following platforms: Reverse phase preparative-HPLC using a Gilson preparative HPLC system (322 pump; 156 UV/VIS detector; GX281 liquid handler). The GX281 liquid handler acted as both auto-sampler and fraction collector. Preparative purification was performed using Phenomenex Gemini C18 at 150×25 mm×10 m or YMC-Actus Triart C18 150×30 mm×5 m columns. Appropriate focused gradients were selected based on acetonitrile and methanol solvent systems under acidic or basic conditions. The standard gradient used 20% gradient difference over 10 min. After each run a 2.0 min 100% acetonitrile wash was performed followed by a 1.5 min re-equilibration at the initial conditions. A flow rate of 25 mL/min was used throughout. The modifiers used for acidic/basic conditions were trifluoroacetic acid aqueous (0.1% v/v), ammonia (0.05% v/v; pH=10) and hydrochloric acid aqueous (0.1% v/v) respectively. The purification was controlled by Trilution LC software and triggered by a threshold collection value at 220 nm or 254 nm. Collected fractions were analyzed by LCMS (Agilent LCMS with 1100/1200 LC systems and 6110/6140 Mass System). The fractions that contained desired product were concentrated by vacuum centrifugation and the resultant residue passed through a freeze-drying cycle.

Alternatively, preparative HPLC purification was performed by reverse phase HPLC using a Waters Fractionlynx™ preparative HPLC system (2525 pump, 2996/2998 UV/VIS detector, 2767 liquid handler) or an equivalent HPLC system such as a Gilson Trilution® UV directed system. The Waters® 2767 liquid handler acted as both auto-sampler and fraction collector. The columns used for the preparative purification of the compounds were a Waters Sunfire® OBD Phenomenex Luna® Phenyl Hexyl or Waters Xbridge® Phenyl at 10 m 19×150 mm or Waters CSH™ Phenyl Hexyl, 19×150 mm, 5 m column. Appropriate focused gradients were selected based on acetonitrile and methanol solvent systems under either acidic or basic conditions. The modifiers used under acidic/basic conditions were formic acid or trifluoroacetic acid (0.1% V/V) and ammonium bicarbonate (10 mM) respectively. The purification was controlled by Waters Fractionlynx™ software through monitoring at 210-400 nm, and triggered a threshold collection value at 260 nm and, when using the Fractionlynx™, the presence of target molecular ion as observed under APi conditions. Collected fractions were analyzed by LCMS (Waters Acquity® systems with Waters® SQD).

Analytical Methods

Analytical Method 1: Using an Agilent 1200\G1956A LC-MS spectrometer and an Agilent 1200\G1956A. Method details are: 1) mobile phase: A: 0.025% NH3.H2O in water (v/v); B: Acetonitrile; 2) Gradient: B % from 10% to 80% within 3.5 mins. 3) Flow rate: 0.8 mL/min. 4) Column Temp: 40° C.; 5) Detector: DAD 220 nm & 254 nm.

Analytical Method 2: Analytical UPLC-MS was performed on a Waters Acquity I-Class UPLC with Waters Diode Array Detector (210-400 nm) coupled to a Waters SQD2 single quadrapole UPLC mass spectrometer using an HSS C18 column (1.8 um 100×2.1 mm plus guard). Method details are: 1) mobile phase: A: 0.1% formic acid (v/v) in water; B: 0.1% formic acid (v/v) in acetonitrile; 2) Gradient 0-1.2 min 95% A 5% B, 1.2-3.5 min linear gradient to 0% A 100% B, 3.5-4.9 min 0% A 100% B, 4.9-5.0 min gradient to 95% A 5% B, 5.0 min-6.0 min 95% A to 5% B. 3) Flow rate 0.5 mL/min.

Analytical Method 3: Analytical UPLC-MS was performed on a Waters Acquity I-Class UPLC with Waters Diode Array Detector (210-400 nm) coupled to a Waters SQD2 single quadrapole UPLC mass spectrometer using a BEH Shield RP18 column (1.7 um 100×2.1 mm. plus guard cartridge). Method details are: 1) mobile phase: A: 10 mM ammonium bicarbonate in water; B: acetonitrile; 2) Gradient 0-1.2 min 95% A 5% B, 1.2-3.5 min linear gradient to 0% A 100% B, 3.5-4.9 min 0% A 100% B, 4.9-5.0 min gradient to 95% A 5% B, 5.0 min-6.0 min 95% A to 5% B. 3) Flow rate 0.5 mL/min.

Analytical Method 4: Using an Agilent 1200 LC & Agilent 6110 MSD system and an Agilent Eclipse Plus C18 4.6*100 mm 3.5 m. Method details are: 1) mobile phase: A: 0.0375% TFA in water (v/v); B: 0.01875% TFA in Acetonitrile (v/v)); 2) Gradient: B % from 0% to 60% within 6 mins. 3) Flow rate: 1.0 mL/min. 4) Column Temp: 50° C.; 5) Detector: DAD 210 nm, 215 nm, 220 nm & 254 nm.

Analytical Method 5: Using a SHIMADZU LCMS-2020 system and a Chromolith@Flash RP-18E 25-2 MM. Method details are: 1) mobile phase: A: 0.0375% TFA in water (v/v); B: 0.01875% TFA in Acetonitrile (v/v)); 2) Gradient: B % from 0% to 60% within 3.5 mins. 3) Flow rate: 0.8 mL/min. 4) Column Temp: 50° C.; 5) Detector: PDA 220 nm & 254 nm.

Analytical Method 6: Using an Agilent 1200\G1956A system and a Xbridge C18 2.1*50 mm, 5 um. Method details are: 1) mobile phase: A: 0.025% $NH_3.H_2O$ in water (v/v) B: Acetonitrile; 2) Gradient: B % from 0% to 60% within 3.5 mins. 3) Flow rate: 0.8 mL/min. 4) Column Temp: 40° C.; 5) Detector: DAD 220 nm & 254 nm.

Analytical Method 7: Using a SHIMADZU LC-20AB system and an Innovation C18 UPLC Column 2.1×30 mm, 2.6 um. Method details are: 1) mobile phase: A: 0.0375% TFA in water (v/v); B: 0.01875% TFA in Acetonitrile (v/v); 2) Gradient: B % from 0% to 80% within 5.5 mins. 3) Flow rate: 0.8 mL/min. 4) Column Temp: 50° C.; 5) Detector: PDA (220 nm, 254 nm & 215 nm).

Analytical Method 8: Using an Agilent 1200\G1956A system and a Xbridge C18 2.1*50 mm, 5 um. Method details are: 1) mobile phase: A: 0.025% $NH_3.H_2O$ in water (v/v; B: Acetonitrile; 2) Gradient: B % from 0% to 80% within 3.5 mins. 3) Flow rate: 0.8 mL/min. 4) Column Temp: 40° C.; 5) Detector: DAD (220 & 254 nm).

Analytical Method 9: Using a SHIMADZU LCMS-2020 system and a Chromolith@Flash RP-18E 25-2 MM. Method details are: 1) mobile phase: A: 0.0375% TFA in water (v/v); B: 0.01875% TFA in Acetonitrile (v/v); 2) Gradient: B % from 0% to 95% within 3.5 mins. 3) Flow rate: 0.8 mL/min. 4) Column Temp: 50° C.; 5) Detector: PDA (220 nm & 254 nm).

Analytical Method 10: Using an Agilent 1200\G1956A system and a Chromolith@Flash RP-18E 25-2 MM. Method details are: 1) mobile phase: A: 0.0375% TFA in water (v/v); B: 0.01875% TFA in Acetonitrile (v/v); 2) Gradient: B % from 0% to 95% within 3.5 mins. 3) Flow rate: 0.8 mL/min. 4) Column Temp: 50° C.; 5) Detector: DAD (220 nm & 254 nm).

Analytical Method 11: Using an Agilent 1200 LC & Agilent 6110 MSD system and an Agilent ZORBAX 5 μm SB-Aq, 2.1*50 mm. Method details are: 1) mobile phase: A: 0.0375% TFA in water (v/v); B: 0.01875% TFA in Acetonitrile (v/v); 2) Gradient: B % from 0% to 90% within 3.4 mins. 3) Flow rate: 0.8 mL/min. 4) Column Temp: 50° C.; 5) Detector: DAD (210 nm, 215 nm, 220 nm & 254 nm).

Analytical Method 12: Using an Agilent 1200 LC & Agilent 6110 MSD system and an Agilent ZORBAX 5 μm SB-Aq, 2.1*50 mm. Method details are: 1) mobile phase: A: 0.0375% TFA in water (v/v); B: 0.01875% TFA in Acetonitrile (v/v); 2) Gradient: B % from 10% to 100% within 3.4 mins. 3) Flow rate: 0.8 mL/min. 4) Column Temp: 50° C.; 5) Detector: DAD (210 nm, 215 nm, 220 nm & 254 nm).

Analytical Method 13: Using an Agilent 1200 LC & Agilent 6110 MSD system and a Agilent ZORBAX 5 μm SB-Aq, 2.1*50 mm. Method details are: 1) mobile phase: A: A: 0.05% $NH_3$—$H_2O$ in water (v/v); B: Acetonitrile (v/v); 2) Gradient: B % from 5% to 90% within 3.4 mins. 3) Flow rate: 0.8 mL/min. 4) Column Temp: 40° C.; 5) Detector: DAD (210 nm, 215 nm, 220 nm & 254 nm).

General Methods

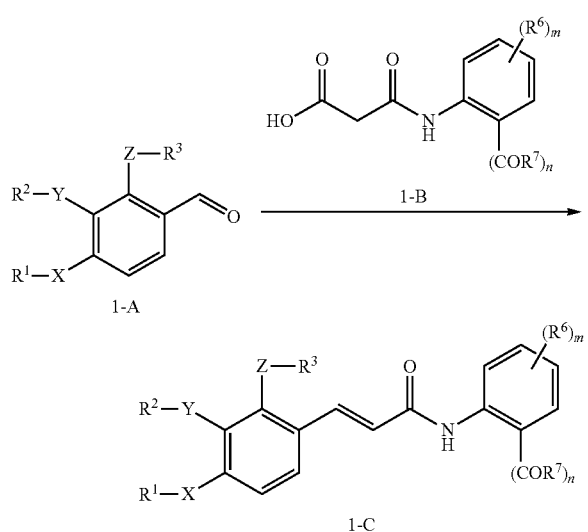

Many of the compounds described below can be prepared according to the scheme above. An aldehyde (1-A where X—$R^1$, Y—$R^2$, and Z—$R^3$ can represent appropriate substituents) is reacted with an 3-oxo-3-(phenylamino)propanoic acid (1-B in which $R^6$ and $R^7$ can be appropriate substituents) to afford the desired N-phenylcinnamamide analogues (1-C). This condensation is typically performed at an elevated temperature, for example 110° C., in a suitable solvent such as toluene or pyridine over a reaction time consistent with the reactivity of the substrates, for example 16 hours. The reaction is typically catalyzed by a suitable base such as piperidine. The starting materials 1-A and 1-B can be commercially available or prepared according to methods known to those skilled in the art. Suitable substituted N-phenylcinnamamide products (1-C) can also be further derivatized.

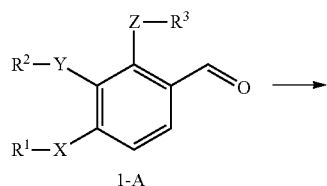

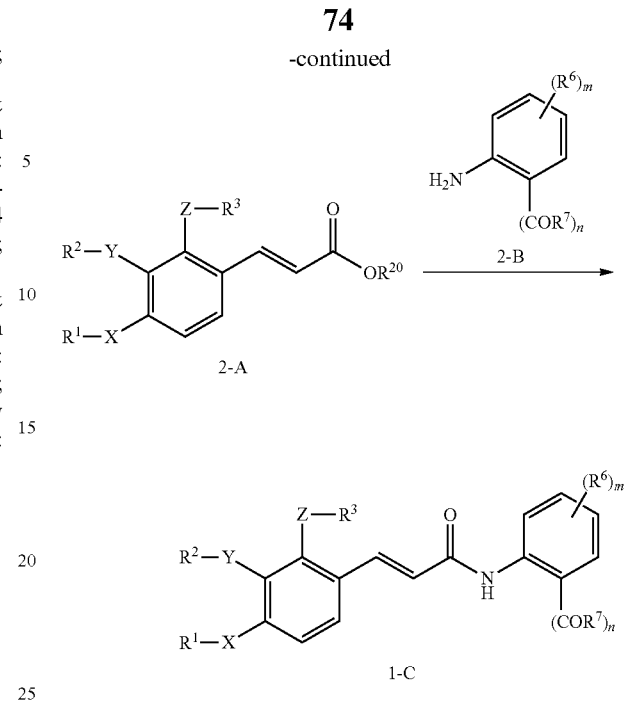

Alternatively, aldehyde 1-A can be converted to the cinnamic acid (2-A, where $R^{20}$ can be either H or a substituent such as methyl or ethyl) by reaction with malonic acid or a malonic acid monoester (scheme above). Such reactions are typically performed in a solvent such as pyridine in the presence of a suitable base, for example piperidine, and are conducted at an elevated temperature for example 100 to 120° C. Alternatively, the transformation can be accomplished using a Wittig or Wadsworth-Emmons reaction in which the aldehyde is reacted with a phosphonate, such as triethylphosphonoacetate, in the presence of a base, such as sodium hydride, and in an aprotic solvent such as THF. These reactions are commonly performed at ambient temperature. Cinnamyl esters formed in this way can be converted to the acid using a hydroxide base. Alternatively the cinnamic acids or cinnamyl esters can be commercially available or prepared from commercially available cinnamic acids or esters.

The cinnamic acid 2-A is converted to the N-phenylcinnamamide 1-C using a coupling agent such as HATU in the presence of a suitable base, for example diisopropylethylamine and the aniline 2-B. These reactions are performed in an inert solvent such as dichloromethane or N,N-dimethylformamide and can be performed at room temperature or elevated temperature depending on the reactivity of the substrates. Alternatively, the acid (2-B) can first be transformed into an acid chloride using, for example, oxalyl chloride. The acid chloride is then reacted with an aniline (2-C) in the presence of a suitable base such as trimethylamine or pyridine and in an inert solvent such as dichloromethane or tetrahydrofuran.

The starting materials 2-A or 2-B can be commercially available or prepared according to methods known to those skilled in the art. The N-phenylcinnamamide products can also be further modified.

Compound Synthesis

(E)-N-(2-fluorophenyl)-3-(3-methoxy-4-(prop-2-yn-1-yloxy)phenyl)acrylamide (1)

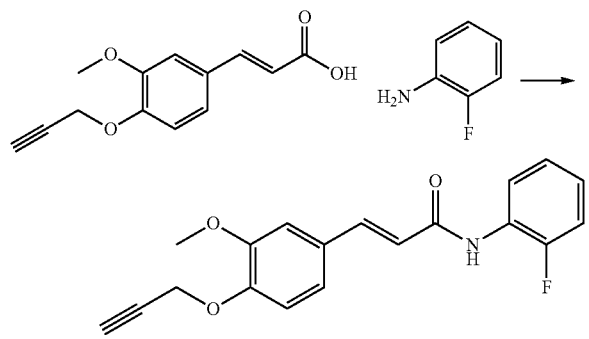

To a suspension of (E)-3-(3-methoxy-4-prop-2-ynoxy-phenyl)prop-2-enoic acid (0.5 g, 2.15 mmol, 1.0 equiv.) in dichloromethane (5 mL) was added oxalyl chloride (376 μL, 4.30 mmol, 2.0 equiv.) and the mixture was stirred at 25° C. for 30 minutes. The reaction mixture was concentrated under reduced pressure to give (E)-3-(3-methoxy-4-(prop-2-yn-1-yloxy)phenyl)acryloyl chloride as a yellow solid, which was used directly without further purification (0.6 g).

To a solution of 2-fluoroaniline (46 μL, 0.479 mmol, 1.2 equiv.) in dichloromethane (5 mL) was added (E)-3-(3-methoxy-4-prop-2-ynoxy-phenyl)prop-2-enoyl chloride (0.1 g, 0.399 mmol, 1.0 equiv.) and triethylamine (166 μL, 1.20 mmol, 3.0 equiv.) and the mixture was stirred at 25° C. for 12 hours. The mixture was concentrated under reduced pressure and the residue purified by preparative HPLC to give the desired product as a yellow solid (0.030 g, 23%); $^1$H NMR (CD$_3$OD, 400 MHz) δ 8.07-8.05 (m, 1H), 7.63 (d, J=15.6 Hz, 1H), 7.26-7.24 (m, 1H), 7.20-7.16 (m, 4H), 7.09 (d, J=8.4 Hz, 1H), 6.84 (d, J=15.6 Hz, 1H), 4.81 (d, J=2.4 Hz, 2H), 3.91 (s, 3H), 2.98 (t, J=2.4 Hz, 1H); MS (ESI+) m/z 326.2 (M+H)+; 99.5% purity, RT 2.31 min (Method 10).

| Ex | Structure | Data | Method |
|---|---|---|---|
| 2 | (E)-3-(3-methoxy-4-(prop-2-yn-1-yloxy)phenyl)-N-(2-(5-methyl-1H-1,2,4-triazol-3-yl)phenyl)acrylamide | $^1$H NMR (DMSO-d$_6$, 400 MHz) δ 12.99 (br. s., 1H), 8.66 (d, J = 7.2 Hz, 1H), 8.13 (d, J = 8.0 Hz, 1H), 7.61 (d, J = 15.6 Hz, 1H), 7.35 (s, 1H), 7.26-7.23 (m, 2H), 7.09-7.07 (m, 2H), 6.69 (d, J = 15.6 Hz, 1H), 4.85 (d, J = 2.0 Hz, 2H), 3.86 (s, 3H), 3.59 (t, J = 2.0 Hz, 1H), 2.41 (s, 3H); MS (ESI+) m/z 389.3 (M + H)+; 98.6% purity, RT 1.99 min (Method 8) | Prepared according to the method for 1 starting from 2-(5-methyl-1H-1,2,4-triazol-3-yl)aniline |
| 3 | (E)-N-(2-chlorophenyl)-3-(3-methoxy-4-(prop-2-yn-1-yloxy)phenyl)acrylamide | $^1$H NMR (CD$_3$OD, 400 MHz) δ 7.96 (d, J = 8.0 Hz, 1H), 7.64 (d, J = 15.6 Hz, 1H), 7.47 (d, J = 6.8 Hz, 1H), 7.30-7.29 (m, 1H), 7.28-7.27 (m, 1H), 7.19-7.18 (m, 2H), 7.12-7.10 (m, 1H), 7.00 (d, J = 15.6 Hz, 1H), 4.81 (d, J = 2.4 Hz, 2H), 3.90 (s, 3H), 2.98 (t, J = 2.4 Hz, 1H); MS (ESI+) m/z 342.2/344.1 (M + H)+; 99.6% purity, RT 2.22 min (Method 10) | Prepared according to the method for 1 starting from 2-chloroaniline |
| 4 | (E)-N-(2-bromophenyl)-3-(3-methoxy-4-(prop-2-yn-1-yloxy)phenyl)acrylamide | $^1$H NMR (CDCl$_3$, 400 MHz) δ 8.52 (d, J = 8.0 Hz, 1H), 7.78 (s, 1H), 7.72 (d, J = 16.0 Hz, 1H), 7.60-7.56 (m, 1H), 7.38-7.34 (m, 1H), 7.19-7.16 (m, 1H), 7.12-7.11 (m, 1H), 7.07-6.98 (m, 2H), 6.48 (d, J = 16.0 Hz, 1H), 4.82 (d, J = 4.0 Hz, 2H), 3.96 (s, 3H), 2.55 (t, J = 4.0 Hz, 1H); MS (ESI+) m/z 386.1/388.1 (M + H)+; 96.3% purity, RT 2.18 min (Method 10) | Prepared according to the method for 1 starting from 2-bromoaniline |

| Ex | Structure | Data | Method |
|---|---|---|---|
| 5 | 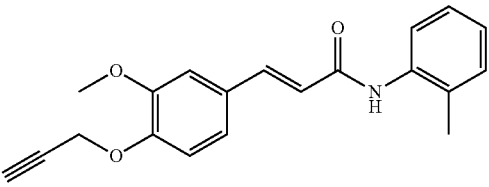<br>(E)-3-(3-methoxy-4-(prop-2-yn-1-yloxy)phenyl)-N-(o-tolyl)acrylamide | $^1$H NMR (DMSO-d$_6$, 400 MHz) δ 9.37 (s, 1H), 7.52 (d, J = 15.6 Hz, 1H), 7.25 (d, J = 10.8 Hz, 1H), 7.22-7.18 (m, 4H), 7.09-7.07 (m, 2H), 6.88 (d, J = 15.6 Hz, 1H), 4.84 (d, J = 2.4 Hz, 2H), 3.84 (s, 3H), 3.59 (t, J = 2.4 Hz, 1H), 2.25 (s, 3H); MS (ESI+) m/z 322.2 (M + H)+; 100% purity, RT 2.01 min (Method 10) | Prepared according to the method for 1 starting from o-toluidine |
| 6 | 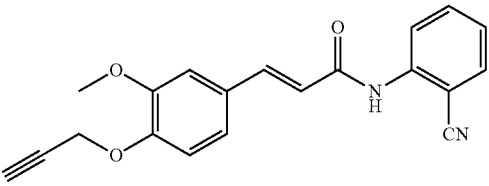<br>(E)-N-(2-cyanophenyl)-3-(3-methoxy-4-(prop-2-yn-1-yloxy)phenyl)acrylamide | $^1$H NMR (CD$_3$OD, 400 MHz) δ 7.40 (d, J = 8.8 Hz, 1H), 7.72 (d, J = 15.6 Hz, 1H), 7.68-7.66 (m, 2H), 7.36-7.34 (m, 1H), 7.27-7.26 (m, 1H), 7.20-7.19 (m, 1H), 7.11-7.09 (m, 1H), 6.80 (d, J = 15.6 Hz, 1H), 4.81 (d, J = 2.4 Hz, 2H), 3.91 (s, 3H), 2.98 (t, J = 2.4 Hz, 1H); MS (ESI+) m/z 333.2 (M + H)+; 96.7% purity, RT 1.92 min (Method 10) | Prepared according to the method for 1 starting from 2-aminobenzonitrile |
| 7 | 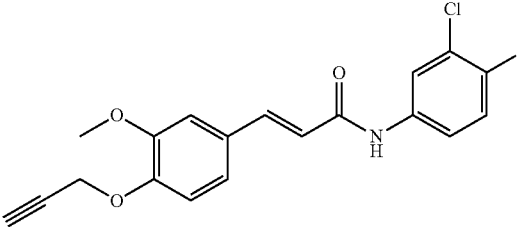<br>(E)-N-(3,4-dichlorophenyl)-3-(3-methoxy-4-(prop-2-yn-1-yloxy)phenyl)acrylamide | $^1$H NMR (DMSO-d$_6$, 400 MHz) δ 10.44 (s, 1H), 8.11 (d, J = 1.2 Hz, 1H), 7.60-7.55 (m, 3H), 7.26-7.25 (m, 1H), 7.20 (d, J = 8.4 Hz, 1H), 7.09 (d, J = 8.4 Hz, 1H), 6.67 (d, J = 15.6 Hz, 1H), 4.84 (d, J = 2.0 Hz, 2H), 3.84 (s, 3H), 3.59 (t, J = 2.0 Hz, 1H); MS (ESI+) m/z 376.1/378.1/380.1 (M + H)+; 95.8% purity, RT 2.4 min (Method 10) | Prepared according to the method for 1 starting from 3,4-dichloroaniline |

(E)-3-(3-methoxy-4-(prop-2-yn-1-yloxy)phenyl)-N-phenylacrylamide (8)

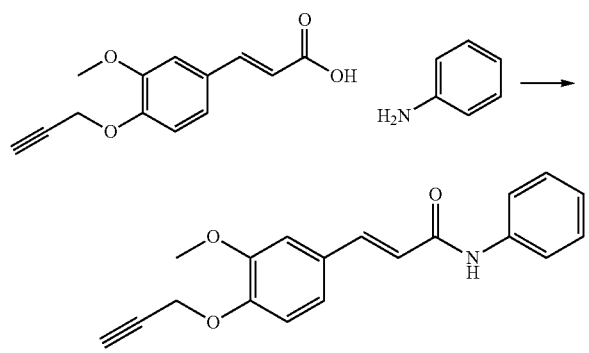

To a solution of (E)-3-(3-methoxy-4-prop-2-ynoxy-phenyl)prop-2-enoic acid (0.1 g, 0.431 mmol, 1.0 equiv.) and HATU (0.327 g, 0.861 mmol, 2.0 equiv.) in N,N-dimethylformamide (2 mL) was added diisopropylethylamine (015 mL, 0.861 mmol, 2.0 equiv.) and the mixture was stirred at 30° C. for 1 hour. Then aniline (59 μL, 0.646 mmol, 1.5 equiv.) was added and the reaction was stirred at 30° C. for another 2 hours. The reaction liquid was diluted with methanol (3 mL) and the resulting mixture was purified by preparative HPLC to give the desired product as a yellow solid (25 mg, 19%); $^1$H NMR (DMSO-d$_6$, 400 MHz) δ 10.14 (s, 1H), 7.72-7.69 (m, 2H), 7.54 (d, J=16.0 Hz, 1H), 7.35-7.31 (m, 2H), 7.26-7.25 (m, 1H), 7.24-7.23 (m, 1H), 7.10-7.04 (m, 2H), 6.73 (d, J=15.6 Hz, 1H), 4.85 (d, J=2.4 Hz, 2H), 3.85 (s, 3H), 3.60 (t, J=2.4 Hz, 1H). MS (ESI+) m/z 308.1 (M+H)+; 100% purity, RT 2.94 min (Method 11).

| Ex | Structure | Data | Method |
|---|---|---|---|
| 9 | methyl (E)-1-(3-(3-methoxy-4-(prop-2-yn-1-yloxy)phenyl)acryloyl)-1,2,3,4-tetrahydroquinoline-4-carboxylate | $^1$H NMR (400 MHz, CDCl3): d, ppm 7.68 (1H, d, J = 15.3 Hz), 7.32-7.24 (2H, m), 7.26 (2H, s), 7.22-7.16 (2H, m), 7.06 (2H, dd, J = 1.8, 8.3 Hz), 7.08-6.98 (2H, m), 7.00 (2H, d, J = 8.3 Hz), 6.96-6.95 (1H, m), 6.68 (1H, d, J = 15.8 Hz), 4.79 (2H, d, J = 2.3 Hz), 4.22-4.14 (1H, m), 3.90-3.85 (4H, m), 3.85-3.77 (1H, m), 3.73-3.72 (3H, m), 2.53-2.51 (1H, m), 2.47-2.37 (1H, m), 2.23-2.13 (1H, m). MS: (ESI+) m/z 406 (M + H)+ 97.74% purity, RT = 3.33 min., (Method 2). | Prepared according to the method for 8 starting from (E)-3-(3-methoxy-4-prop-2-ynoxy-phenyl)prop-2-enoic acid and methyl 1,2,3,4-tetrahydroquinoline-4-carboxylate |
| 10 | (E)-1-(3,4-dihydroquinolin-1(2H)-yl)-3-(3-methoxy-4-(prop-2-yn-1-yloxy)phenyl)prop-2-en-1-one | $^1$H NMR (400 MHz, CDCl3): d, ppm 7.68 (1H, d, J = 16.2 Hz), 7.24-7.11 (4H, m), 7.08-6.94 (3H, m), 6.74 (1H, d, J = 15.8 Hz), 4.78 (2H, d, J = 2.5 Hz), 3.95-3.90 (2H, m), 3.85 (3H, s), 2.79-2.74 (2H, m), 2.53-2.51 (1H, m), 2.06-1.97 (2H, m). MS: (ESI+) m/z 348.2 (M + H)+ 99.45% purity, RT = 3.47 min., (Method 2). | Prepared according to the method for 8 starting from (E)-3-(3-methoxy-4-prop-2-ynoxy-phenyl)prop-2-enoic acid and 1,2,3,4-tetrahydroquinoline |
| 11 | (E)-1-(3,4-dihydroquinoxalin-1(2H)-yl)-3-(3-methoxy-4-(prop-2-yn-1-yloxy)phenyl)prop-2-en-1-one | $^1$H NMR (400 MHz, CDCl3): d, ppm 7.69 (1H, d, J = 14.9 Hz), 7.11-6.98 (5H, m), 6.92 (1H, d, J = 15.3 Hz), 6.68-6.63 (2H, m), 4.79 (2H, d, J = 2.5 Hz), 4.16-4.07 (1H, m), 4.02-3.97 (2H, m), 3.86 (3H, s), 3.54-3.50 (2H, m), 2.53-2.51 (1H, m). MS: (ESI+) m/z 349 (M + H)+ 92.91% purity, RT = 3.23 min., (Method 2). | Prepared according to the method for 8 starting from (E)-3-(3-methoxy-4-prop-2-ynoxy-phenyl)prop-2-enoic acid and 1,2,3,4-tetrahydroquinoxaline |
| 12 | (E)-1-(2,3-dihydro-4H-benzo[b][1,4]oxazin-4-yl)-3-(3-methoxy-4-(prop-2-yn-1-yloxy)phenyl)prop-2-en-1-one | $^1$H NMR (400 MHz, CDCl3): d, ppm 7.73 (1H, d, J = 15.3 Hz), 7.22-7.15 (1H, m), 7.14-7.08 (2H, m), 7.05-6.99 (2H, m), 6.98-6.87 (3H, m), 4.80 (2H, d, J = 2.3 Hz), 4.39-4.35 (2H, m), 4.10-4.06 (2H, m), 3.88 (3H, s), 2.54-2.52 (1H, m). MS: (ESI+) m/z 350 (M + H)+ 99% purity, RT = 3.39 min., (Method 2). | Prepared according to the method for 8 starting from (E)-3-(3-methoxy-4-prop-2-ynoxy-phenyl)prop-2-enoic acid and 3,4-dihydro-2H-benzo[b][1,4]oxazine |
| 13 | (E)-N-((trans)-2-aminocyclohexyl)-3-(3-methoxy-4-(prop-2-yn-1-yloxy)phenyl)acrylamide | $^1$H NMR (400 MHz, CDCl3) 7.51 (1H, d, J = 15.4 Hz), 7.10-7.07 (1H, m), 7.06-7.02 (1H, m), 6.97 (1H, d, J = 8.3 Hz), 6.41 (1H, d, J = 14.9 Hz), 6.00-5.93 (1H, m), 4.78 (2H, d, J = 2.5 Hz), 3.89 (3H, s), 3.77-3.66 (1H, m), 2.68-2.59 (1H, m), 2.54-2.51 (1H, m), 2.01-1.96 (2H, m), 1.77-1.66 (2H, m), 1.33-1.19 (4H, m); MS: (ESI+) m/z 329.2 (M + H)+ 99.01% purity, RT = 2.87 min., (Method 3). | Prepared according to the method for 8 starting from (E)-3-(3-methoxy-4-prop-2-ynoxy-phenyl)prop-2-enoic acid and trans-cyclohexane-1,2-diamine |

| Ex | Structure | Data | Method |
|---|---|---|---|
| 14 | (E)-1-(4-hydroxy-3,4-dihydroquinolin-1(2H)-yl)-3-(3-methoxy-4-(prop-2-yn-1-yloxy)phenyl)prop-2-en-1-one | $^1$H NMR (400 MHz, DMSO) δ 7.59 (d, J = 15.7 Hz, 1H), 7.54 (d, J = 6.9 Hz, 1H), 7.34-7.29 (m, 2H), 7.28-7.17 (m, 3H), 7.09 (d, J = 8.6 Hz, 1H), 6.92 (d, J = 15.7 Hz, 1H), 5.54 (d, J = 5.6 Hz, 1H), 4.87 (d, J = 2.3 Hz, 2H), 4.70-4.64 (m, 1H), 4.13-4.05 (m, 1H), 3.83 (s, 3H), 3.76-3.67 (m, 1H), 3.63 (t, J = 2.3 Hz, 1H), 2.23-2.13 (m, 1H), 1.90-1.80 (m, 1H). MS (ESI+) m/z 364.2 (M + H)+; 99.8% purity, RT 3.06 min (Method 2) | Prepared according to the method for 16 starting from (E)-3-(3-methoxy-4-(prop-2-yn-1-yloxy)phenyl)acrylic acid and 1,2,3,4-tetrahydroquinolin-4-ol |
| 15 | (E)-1-(3-hydroxy-1H-indazol-1-yl)-3-(3-methoxy-4-(prop-2-yn-1-yloxy)phenyl)prop-2-en-1-one | $^1$H NMR (400 MHz, DMSO) δ 12.21-12.16 (m, 1H), 8.46 (d, J = 8.3 Hz, 1H), 7.87 (d, J = 6.6 Hz, 2H), 7.74-7.69 (m, 2H), 7.49-7.43 (m, 2H), 7.39 (dd, J = 8.3 Hz, J = 1.8 Hz, 1H), 7.18 (d, J = 8.6 Hz, 1H), 4.93 (d, J = 2.3 Hz, 2H), 3.92 (s, 3H), 3.66 (t, J = 2.3 Hz, 1H); MS (ESI+) m/z 349.3 (M + H)+; 98.9% purity, RT 2.60 min (Method 3) | Prepared according to the method for 16 starting from (E)-3-(3-methoxy-4-(prop-2-yn-1-yloxy)phenyl)acrylic acid and 3-indazolinone |

(E)-N-(2-(2H-tetrazol-5-yl)phenyl)-3-(3-methoxy-4-(prop-2-yn-1-yloxy)phenyl)acrylamide (16)

(E)-N-(2-(1,2,4-oxadiazol-3-yl)phenyl)-3-(3-methoxy-4-(prop-2-yn-1-yloxy)phenyl)acrylamide (17)

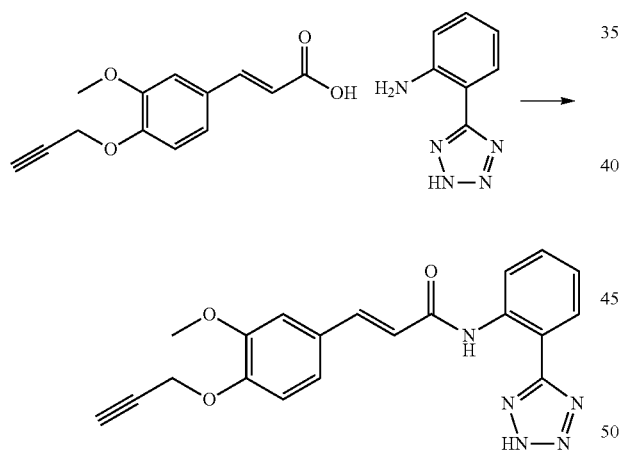

a) ((E)-N-(2-(N-hydroxycarbamimidoyl)phenyl)-3-(3-methoxy-4-(prop-2-yn-1-yloxy)phenyl)-acrylamide

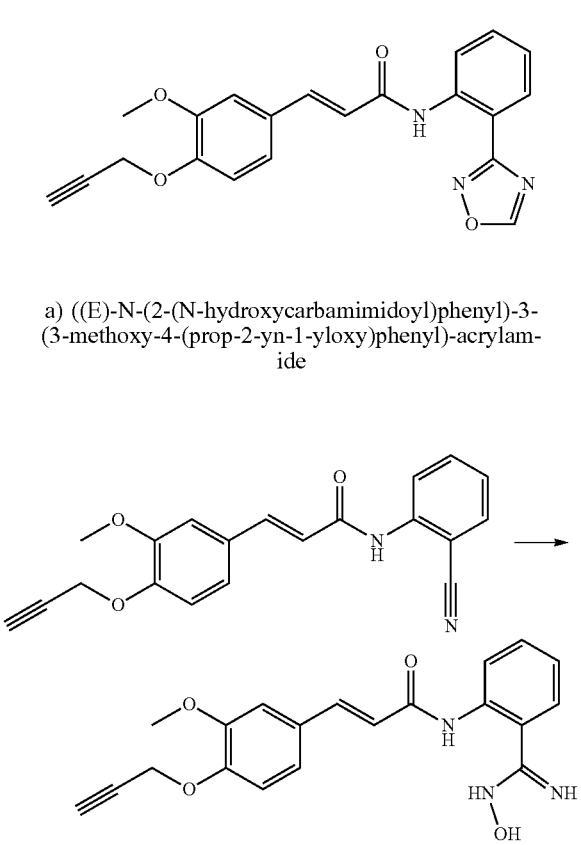

To a solution of (E)-3-(3-methoxy-4-(prop-2-yn-1-yloxy)phenyl)acrylic acid (0.1 g, 0.431 mmol, 1.0 equiv.) and 2-(2H-tetrazol-5-yl)aniline (0.083 g, 0.516 mmol, 1.2 equiv.) in dichloromethane (3 mL) were added N,N-diisopropylethylamine (0.225 mL, 1.29 mmol, 3.0 equiv.) and HATU (0.245 g, 0.645 mmol, 1.5 equiv.). The reaction mixture was stirred at 25° C. for 16 hours and concentrated under reduced pressure. The residue was purified by preparative HPLC to give the desired product as a light yellow solid (0.025 g, 15%); $^1$H NMR (DMSO-d$_6$, 400 MHz) δ 12.45 (br. s., 1H), 8.71-7.65 (m, 1H), 7.19 (dd, $J_1$=8.0 Hz, $J_2$=2.0 Hz, 1H), 7.63 (d, J=15.6 Hz, 1H), 7.38-7.25 (m, 3H), 7.16-7.08 (m, 3H), 6.75 (d, J=15.6 Hz, 1H), 4.85 (d, J=2.0 Hz, 2H), 3.88 (s, 3H), 3.61 (t, J=2.0 Hz, 1H); MS (ESI+) m/z 398.1 (M+Na)+; 95.9% purity, RT 1.95 min (Method 10).

To a solution of (E)-N-(2-cyanophenyl)-3-(3-methoxy-4-(prop-2-yn-1-yloxy)phenyl)acrylamide (1.00 g, 3.01 mmol, 1.0 equiv.) (6) and hydroxylamine hydrochloride (0.418 g, 6.02 mmol, 2.0 equiv.) in ethanol (13 mL) was added a solution of sodium bicarbonate (0.505 g, 6.02 mmol, 2.0 equiv.) in water (2 mL) and the mixture was stirred at 80° C. for 12 hours. The mixture was cooled to 20° C. and concentrated under reduced pressure to give a residue, which was dissolved in dichloromethane/ethanol (20/1, 200 mL) and filtered. The filtrate was concentrated under reduced pressure to give a residue, which was triturated in dichloromethane/methanol (50/1, 40 mL) to give the desired product as a light yellow solid. (0.6 g, 69%); MS (ESI+) m/z 366.1 (M+H)+.

b) (E)-N-(2-(1,2,4-oxadiazol-3-yl)phenyl)-3-(3-methoxy-4-(prop-2-yn-1-yloxy)phenyl)acrylamide

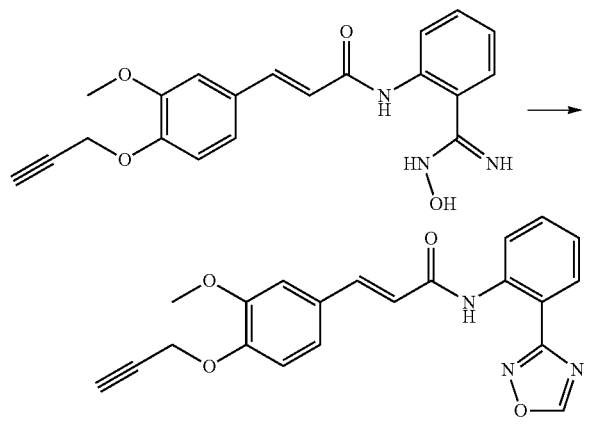

To a suspension of ((E)-N-(2-(N-hydroxycarbamimidoyl)phenyl)-3-(3-methoxy-4-(prop-2-yn-1-yloxy)phenyl)acrylamide (0.08 g, 0.218 mmol, 1.0 equiv.) in trimethoxymethane (2.91 g, 27.4 mmol, 3 mL, 125 equiv.) was added 4-methylbenzenesulfonic acid (0.004 g, 0.022 mmol, 0.1 equiv.) and the mixture stirred at 100° C. for 12 hours. The mixture was concentrated under reduced pressure to give a residue, which was triturated with methanol (2 mL) and the solid collected by filtration to give the desired product as a light yellow solid (0.045 g, 52%); $^1$H NMR (DMSO-d$_6$, 400 MHz) δ 10.07 (br. s., 1H), 9.81 (s, 1H), 8.24 (d, J=8.0 Hz, 1H), 8.03 (d, J=8.0 Hz, 1H), 7.61-7.59 (m, 1H), 7.56 (d, J=15.6 Hz, 1H), 7.34-7.33 (m, 2H), 7.2 (d, J=8.4 Hz, 1H), 7.08 (d, J=8.4 Hz, 1H), 6.80 (d, J=15.6 Hz, 1H), 4.85 (d, J=2.0 Hz, 2H), 3.82 (s, 3H), 3.60 (t, J=2.0 Hz, 1H); MS (ESI+) m/z 398.2 (M+Na)$^+$; 94.4% purity, RT 2.18 min (Method 10).

(E)-3-(3-methoxy-4-(prop-2-yn-1-yloxy)phenyl)-N-(2-(5-methyl-1,2,4-oxadiazol-3-yl)phenyl)-acrylamide (18)

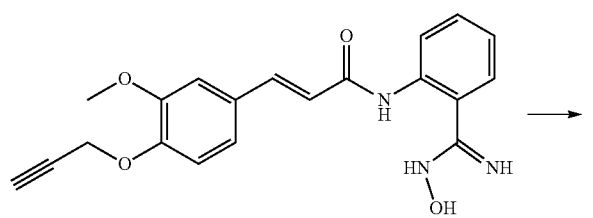

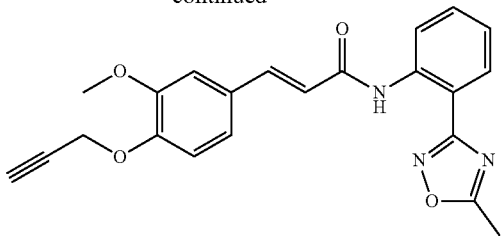

To a solution of ((E)-N-(2-(N-hydroxycarbamimidoyl)phenyl)-3-(3-methoxy-4-(prop-2-yn-1-yloxy)phenyl)acrylamide (0.1 g, 0.273 mmol, 1.0 equiv.) in toluene (1 mL) and pyridine (1 mL) was added acetyl chloride (0.043 g, 0.547 mmol, 2.0 equiv.) and the mixture was stirred at 20° C. for 30 minutes, then heated to 110° C. for 12 hours. The mixture was concentrated under reduced pressure to give a residue, which was triturated in methanol (2 mL) and the solid collected by filtration to give the desired product as a light yellow solid (0.042 g, 38%); 1H NMR (DMSO-d$_6$, 400 MHz) δ 10.18 (s, 1H), 8.36 (d, J=7.6 Hz, 1H), 8.02 (d, J=7.6 Hz, 1H), 7.61-7.56 (m, 2H), 7.35-7.24 (m, 3H), 7.08 (d, J=8.0 Hz, 1H), 6.81 (d, J=16.0 Hz, 1H), 4.85 (d, J=2.0 Hz, 2H), 3.85 (s, 3H), 3.60 (t, J=2.0 Hz, 1H), 2.73 (s, 3H); MS (ESI+) m/z 390.1 (M+H)+; 95.5% purity, RT 2.95 min (Method 8).

(E)-3-(3-methoxy-4-(prop-2-yn-1-yloxy)phenyl)-N-(2-(5-oxo-4,5-dihydro-1,2,4-oxadiazol-3-yl)phenyl)acrylamide (19)

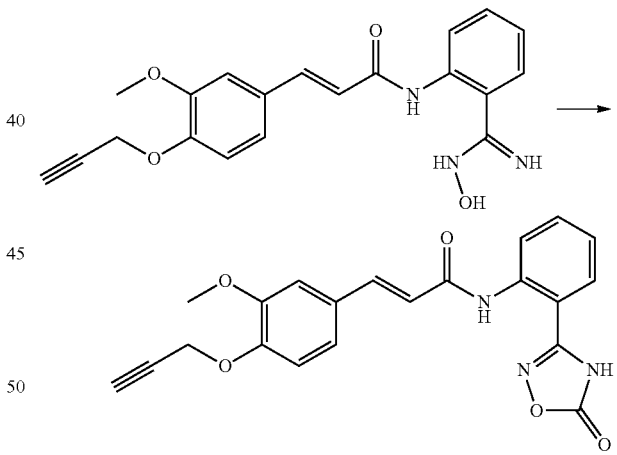

To a suspension of ((E)-N-(2-(N-hydroxycarbamimidoyl)phenyl)-3-(3-methoxy-4-(prop-2-yn-1-yloxy)phenyl)acrylamide (0.120 g, 0.328 mmol, 1.0 equiv.) in ethanol (2.5 mL) was added sodium methoxide (0.213 g, 0.985 mol, 25%, 3.0 equiv.) and dimethyl carbonate (110 μL, 1.31 mmol, 4.0 equiv.). The mixture was stirred at 90° C. for 15 hours, cooled to 20° C. and filtered. The filtrate was concentrated under reduced pressure and the residue was purified by preparative HPLC to give the desired product as a light yellow solid (0.020 g, 15%); $^1$H NMR (DMSO-d$_6$, 400 MHz) δ 10.63 (br. s., 1H), 8.23 (d, J=8.0 Hz, 1H), 7.71 (d, J=8.0 Hz, 1H), 7.59-7.52 (m, 2H), 7.30 (s, 1H), 7.27-7.22 (m, 2H), 7.08 (d, J=8.0 Hz, 1H), 6.71 (d, J=16.0 Hz, 1H), 4.85 (d, J=2.0 Hz, 2H), 3.84 (s, 3H), 3.59 (t, J=2.0 Hz, 1H); MS (ESI+) m/z 414.1 (M+Na)+; 96.4% purity, RT 1.59 min (Method 8).

(E)-N-(2-(1,2,4-oxadiazol-5-yl)phenyl)-3-(3-methoxy-4-(prop-2-yn-1-yloxy)phenyl)acrylamide (20)

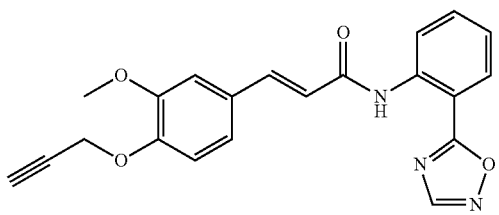 [SMILES: C#CCOc1ccc(/C=C/C(=O)Nc2ccccc2-c2ncno2)cc1OC]

a) (E)-N-((dimethylamino)methylene)-2-nitrobenzamide

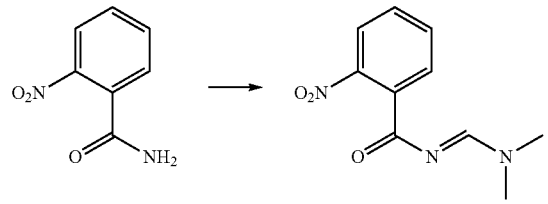 [SMILES: NC(=O)c1ccccc1[N+](=O)[O-] ; CN(C)/C=N/C(=O)c1ccccc1[N+](=O)[O-]]

To the solution of 2-nitrobenzamide (1.4 g, 8.43 mmol, 1.0 equiv.) was added N,N-dimethylformamide dimethyl acetal (5.02 g, 42.1 mmol, 5.0 equiv.) and the reaction mixture was stirred at 120° C. for 2 hours. The mixture was concentrated under reduced pressure and the residue purified by silica gel chromatography (petroleum ether:ethyl acetate=10:1 to 1:1) to afford (E)-N-((dimethylamino)methylene)-2-nitrobenzamide as a yellow solid (1.20 g crude) which was used without further purification. MS (ESI+) m/z 222.1 (M+H)+.

b) 5-(2-nitrophenyl)-1,2,4-oxadiazole

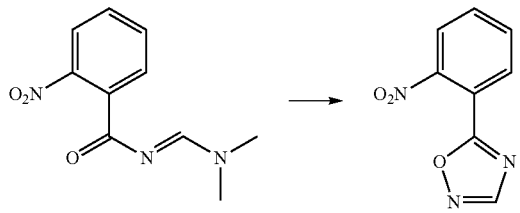 [SMILES: CN(C)/C=N/C(=O)c1ccccc1[N+](=O)[O-] ; O=[N+]([O-])c1ccccc1-c1ncno1]

To a solution of hydroxylamine hydrochloride (0.98 g, 14.1 mmol, 1.3 equiv.) in sodium hydroxide (5 M, 2.8 mL, 1.3 equiv.) was added (E)-N-(dimethylaminomethylene)-2-nitrobenzamide (2.4 g, 10.8 mmol, 1.0 equiv.) portion-wise over 5 minutes at 20° C. and the mixture stirred at 20° C. for 0.5 hour. The mixture was diluted with water (10 mL) and extracted with dichloromethane (10 mL×3). The organic layer was dried and concentrated under reduced pressure to give (E)-N-((hydroxyamino)methylene)-2-nitrobenzamide (1.20 g) which was used directly without further purification.

A mixture of (E)-N-((hydroxyamino)methylene)-2-nitrobenzamide (0.9 g, 4.30 mmol, 1.0 equiv.) in acetic acid (7 mL) and dioxane (7 mL) was stirred at 90° C. for 2 hours. The mixture was concentrated under reduced pressure and the residue was purified by silica gel chromatography (petroleum ether:ethyl acetate 10:1 to 5:1) to give the desired product as a light yellow solid (0.4 g, 49%); 1H NMR (DMSO-d6, 400 MHz) δ 9.25 (s, 1H), 8.23-8.21 (m, 1H), 8.13-7.11 (m, 1H), 7.99-7.95 (m, 2H).

c) 2-(1,2,4-oxadiazol-5-yl)aniline

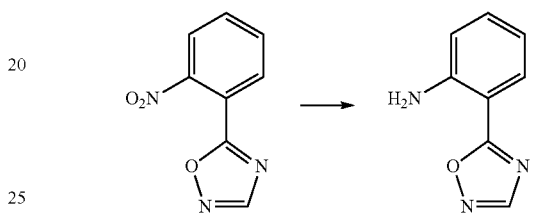

To a solution of 5-(2-nitrophenyl)-1,2,4-oxadiazole (0.3 g, 1.57 mmol, 1.0 equiv.) in ethanol (5 mL) was added tin(II) chloride dihydrate (1.42 g, 6.28 mmol, 4.0 equiv.) and the mixture was stirred at 90° C. for 12 hours. The mixture was concentrated under reduced pressure and the residue was dissolved in ethyl acetate (10 mL) and washed with saturated aqueous sodium bicarbonate (5 mL) and brine (5 mL). The organic layer was dried and concentrated under reduced pressure and the residue was purified by silica gel chromatography (petroleum ether:ethyl acetate 1:1 to ethyl acetate) to give the desired product as a light yellow solid (0.1 g, 35%); $^1$H NMR (DMSO-$d_6$, 400 MHz) δ 10.96 (s, 1H), 7.88-7.86 (m, 1H), 7.57-7.53 (m, 1H), 7.19 (d, J=8.0 Hz, 1H), 7.11-7.07 (m, 1H), 6.37 (br. s., 2H); MS (ESI+) m/z 162.1 (M+H)+.

d) (E)-N-(2-(1,2,4-oxadiazol-5-yl)phenyl)-3-(3-methoxy-4-(prop-2-yn-1-yloxy)phenyl)acrylamide

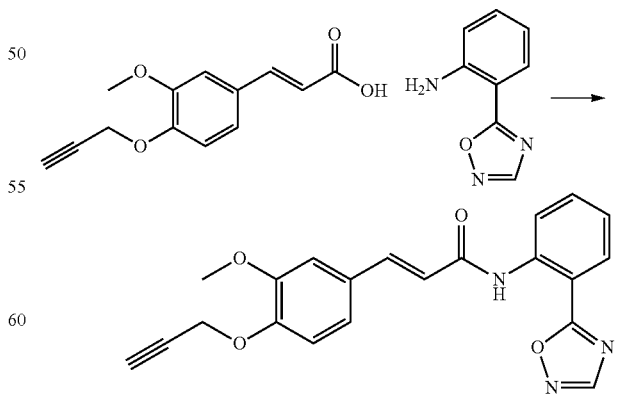

To a solution of (E)-3-(3-methoxy-4-prop-2-ynoxy-phenyl)prop-2-enoic acid (0.056 g, 0.242 mmol, 1.0 equiv.) and 2-(1,2,4-oxadiazol-5-yl)aniline (0.039 g, 0.242 mmol, 1.0 equiv.) in pyridine (2 mL) was added phosphorus oxychloride (0.037 g, 0.242 mmol, 1.0 equiv.) at 0° C. and the mixture was stirred at 20° C. for 12 hours. The mixture was quenched with water (1 mL), diluted with ethyl acetate (20 mL) and washed with 1N hydrochloric acid (20 mL) and then saturated aqueous sodium bicarbonate (5 mL). The organic layer was dried and concentrated under reduced pressure to give a residue, which was triturated in methanol (3 mL) and the solid collected by filtration to give the desired product as a light yellow solid (4 mg, 5%); $^1$H NMR (DMSO-$d_6$, 400 MHz) δ 12.23 (s, 1H), 11.69 (s, 1H), 8.06 (d, J=7.6 Hz, 1H), 7.79-7.72 (m, 2H), 7.51 (d, J=8.0 Hz, 1H), 7.40 (t, J=8.0 Hz, 1H), 7.27-7.25 (m, 2H), 7.12 (d, J=8.0 Hz, 1H), 6.86 (d, J=16.0 Hz, 1H), 4.86 (d, J=2.0 Hz, 2H), 3.83 (s, 3H), 3.61 (t, J=2.0 Hz, 1H); MS (ESI+) m/z 376.3 (M+H)+; 100% purity, RT 1.97 min (Method 10).

-continued

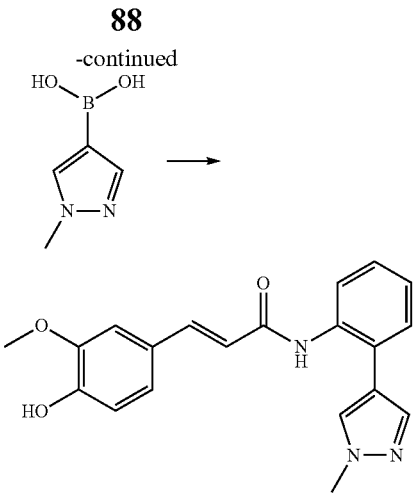

| Ex | Structure | Data | Method |
|---|---|---|---|
| 21 | 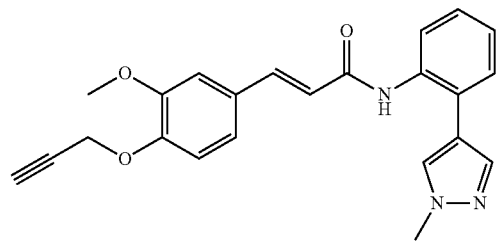<br>(E)-N-(2-(1,3,4-oxadiazol-2-yl)phenyl)-3-(3-methoxy-4-(prop-2-yn-1-yloxy)phenyl)acrylamide | $^1$H NMR (DMSO-$d_6$, 400 MHz) δ 10.71 (s, 1H), 9.44 (s, 1H), 8.47 (d, J = 8.0 Hz, 1H), 7.98 (d, J = 8.0 Hz, 1H), 7.66 (d, J = 8.0 Hz, 1H), 7.61 (d, J = 16.0 Hz, 1H), 7.39 (d, J = 2.4 Hz, 1H), 7.36-7.32 (m, 1H), 7.27 (d, J = 8.0 Hz, 1H), 7.08 (d, J = 8.0 Hz, 1H), 6.63 (d, J = 16.0 Hz, 1H), 4.86 (d, J = 2.0 Hz, 2H), 3.86 (s, 3H), 3.60 (t, J = 2.0 Hz, 1H); MS (ESI+) m/z 398.1 (M + Na)+; 98.9% purity, RT 2.71 min (Method 8) | Prepared according to the method for 20 (step d) starting from 2-(1,3,4-oxadiazol-2-yl)aniline and (E)-3-(3-methoxy-4-prop-2-ynoxy-phenyl)prop-2-enoic acid |

(E)-3-(3-methoxy-4-(prop-2-yn-1-yloxy)phenyl)-N-(2-(1-methyl-1H-pyrazol-4-yl)phenyl)-acrylamide (22)

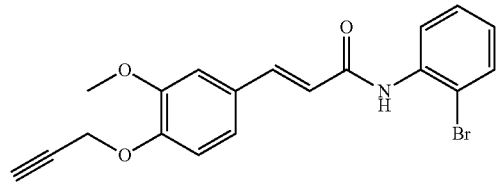

a) (E)-3-(4-hydroxy-3-methoxyphenyl)-N-(2-(1-methyl-1H-pyrazol-4-yl)phenyl)acrylamide A mixture of (E)-N-(2-bromophenyl)-3-(3-methoxy-4-prop-2-ynoxy-phenyl)prop-2-enamide (0.16 g, 0.414 mmol, 1.0 equiv.) (4), (1-methylpyrazol-4-yl)boronic acid (0.104 g, 0.828 mmol, 2.0 equiv.), [1,1'-bis(diphenylphosphino)ferrocene]dichloropalladium(II) (0.03 g, 0.041 mmol, 0.1 equiv.) and sodium carbonate (0.131 g, 1.24 mmol, 3.0 equiv.) in dioxane (6 mL) and water (1 mL) was stirred at 80° C. for 24 hours under nitrogen. The mixture was concentrated under reduced pressure to give a residue which was purified by silica gel chromatography (petroleum ether:ethyl acetate 1:1) to give the title compound as light yellow gum (0.1 g, 19%); MS (ESI+) m/z 350.2 (M+H)+.

b) (E)-3-(3-methoxy-4-(prop-2-yn-1-yloxy)phenyl)-N-(2-(1-methyl-1H-pyrazol-4-yl)phenyl)acryl-amide

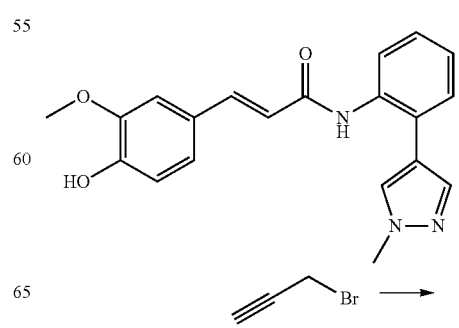

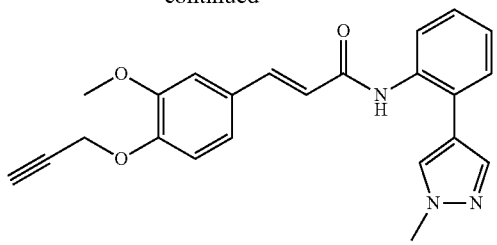

A mixture of (E)-3-(4-hydroxy-3-methoxy-phenyl)-N-[2-(1-methylpyrazol-4-yl)phenyl]prop-2-enamide (0.1 g, 0.286 mmol, 1.0 equiv.), 3-bromoprop-1-yne (0.068 g, 0.572 mmol, 2.0 equiv.) and potassium carbonate (0.119 g, 0.858 mmol, 3.0 equiv.) in acetone (5 mL) was stirred at 20° C. for 12 hours. The mixture was filtered and the filtrate was concentrated under reduced pressure to give a residue which was purified by preparative HPLC to give the desired product as a light yellow solid (7 mg, 6%); $^1$H NMR (CDCl$_3$, 400 MHz) δ 8.36 (br. s., 1H), 7.71-7.68 (m, 2H), 7.54 (s, 1H), 7.45 (s, 1H), 7.39-7.34 (m, 1H), 7.29-7.28 (m, 1H), 7.19-7.17 (m, 1H), 7.13-7.11 (m, 1H), 7.08-7.06 (m, 1H), 7.03 (d, J=8.0 Hz, 1H), 6.32 (d, J=16.0 Hz, 1H), 4.82 (d, J=2.4 Hz, 2H), 4.02 (s, 3H), 3.93 (s, 3H), 2.54 (t, J=2.4 Hz, 1H); MS (ESI+) m/z 388.1 (M+H)+; 95.1% purity, RT 2.88 min (Method 11).

(E)-3-(3-methoxy-4-(prop-2-yn-1-yloxy)phenyl)-N-(2-(3-methyl-1H-1,2,4-triazol-1-yl)phenyl)acrylamide (23)

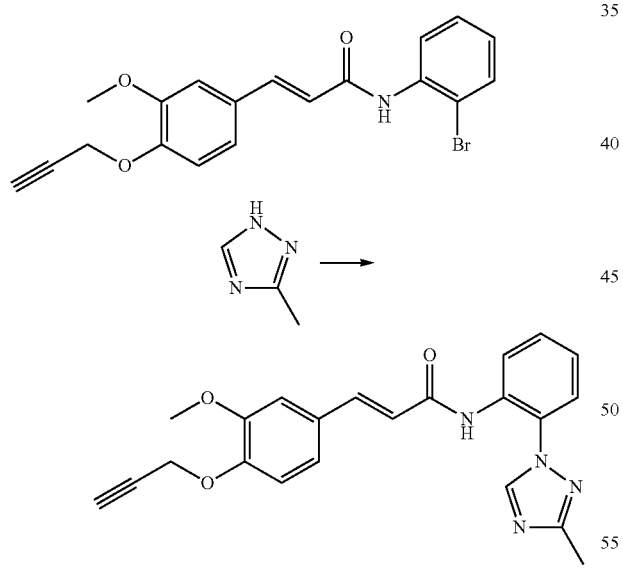

A mixture of (E)-N-(2-bromophenyl)-3-(3-methoxy-4-prop-2-ynoxy-phenyl)prop-2-enamide (0.2 g, 0.517 mmol, 1.0 equiv.) (4), 3-methyl-1H-1,2,4-triazole (0.258 g, 3.11 mmol, 6.0 equiv.), cuprous iodide (0.049 g, 0.258 mmol, 0.5 equiv.) and cesium carbonate (0.506 g, 1.55 mmol, 3.0 equiv.) in dimethyl sulfoxide (2 mL) was stirred at 100° C. under nitrogen in microwave for 3 hours. The mixture was cooled to 25° C., diluted with ethyl acetate (20 mL) and filtered. The filtrate was concentrated under reduced pressure to give a residue which was purified by preparative HPLC to give the desired product as a light yellow solid (5 mg, 2%); $^1$H NMR (CDCl$_3$, 400 MHz) δ 9.89 (s, 1H), 8.63 (d, J=8.0 Hz, 1H), 8.37 (s, 1H), 7.64 (d, J=16.0 Hz, 1H), 7.46 (t, J=8.0 Hz, 1H), 7.35 (d, J=8.0 Hz, 1H), 7.21 (t, J=8.0 Hz, 1H), 7.15 (d, J=8.0 Hz, 1H), 7.08-7.05 (m, 2H), 6.36 (d, J=16.0 Hz, 1H), 4.82 (d, J=2.0 Hz, 2H), 3.94 (s, 3H), 2.60 (s, 3H), 2.55 (t, J=2.0 Hz, 1H); MS (ESI+) m/z 389.1 (M+H)+; 99% purity, RT 2.34 min (Method 8).

(E)-N-(2-(1H-pyrazol-4-yl)phenyl)-3-(3-methoxy-4-(prop-2-yn-1-yloxy)phenyl)acrylamide (24)

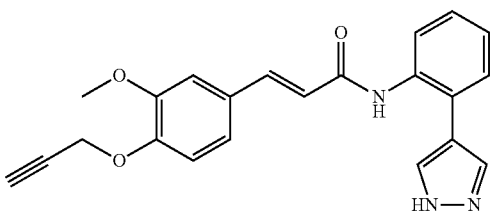 [SMILES: C#CCOc1ccc(/C=C/C(=O)Nc2ccccc2-c2cn[nH]c2)cc1OC]

a) 4,4,5,5-tetramethyl-2-(2-nitrophenyl)-1,3,2-dioxaborolane

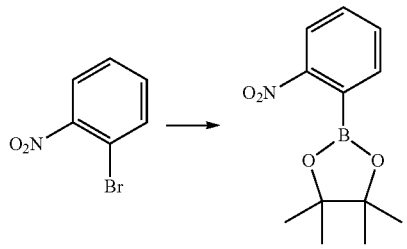 [SMILES: O=[N+]([O-])c1ccccc1Br ; CC1(C)OB(c2ccccc2[N+](=O)[O-])OC1(C)C]

A mixture of 1-bromo-2-nitro-benzene (10.0 g, 49.5 mmol, 1.0 equiv.), 4,4,5,5-tetramethyl-2-(4,4,5,5-tetramethyl-1,3,2-dioxaborolan-2-yl)-1,3,2-dioxaborolane (15.08 g, 59.4 mmol, 1.2 equiv.), potassium acetate (14.57 g, 148 mmol, 3.0 equiv.) and [1,1'-bis(diphenylphosphino)ferrocene]dichloropalladium(II) (1.09 g, 1.49 mmol, 0.03 equiv.) in dioxane (180 mL) was stirred at 80° C. for 12 hours under nitrogen. The mixture was concentrated under reduced pressure to give a residue which was purified by silica gel chromatography (petroleum ether:ethyl acetate 100:1 to 80:1) to give the desired product as yellow oil (12.0 g, 97%); $^1$H NMR (DMSO-d$_6$, 400 MHz) δ 8.17 (d, J=8.0 Hz, 1H), 7.67-7.65 (m, 1H), 7.58-7.54 (m, 2H), 1.44 (s, 12H).

b) 4-(2-nitrophenyl)-1-((2-(trimethylsilyl)ethoxy)methyl)-1H-pyrazole

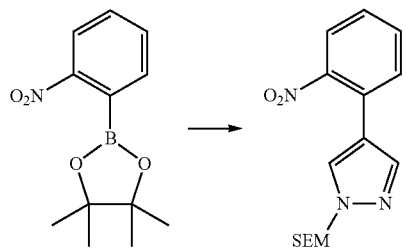 [SMILES: CC1(C)OB(c2ccccc2[N+](=O)[O-])OC1(C)C ; C[Si](C)(C)CCOCn1cc(-c2ccccc2[N+](=O)[O-])cn1]

A mixture of 2-[(4-bromopyrazol-1-yl)methoxy]ethyl-trimethylsilane (0.8 g, 2.89 mmol, 1.0 equiv.), 4,4,5,5-tetramethyl-2-(2-nitrophenyl)-1,3,2-dioxaborolane (2.16 g, 8.67 mmol, 3.0 equiv.), [1,1'-bis(diphenylphosphino)ferrocene]dichloropalladium(II) (0.211 g, 0.289 mmol, 0.1 equiv.) and potassium phosphate tribasic (1.84 g, 8.67 mmol, 3.0 equiv.) in dioxane (20 mL) and water (2 mL) was stirred at 100° C. for 12 hours under nitrogen. The mixture was concentrated under reduced pressure to give a residue which was purified by silica gel chromatography (petroleum ether: ethyl acetate 30:1 to 15:1) to give the desired product as light yellow gum (0.16 g, 16%); $^1$H NMR (CDCl$_3$, 400 MHz) δ 7.76-7.74 (m, 2H), 7.67 (s, 1H), 7.60-7.56 (m, 1H), 7.52-7.49 (m, 1H), 7.44-7.40 (m, 1H), 5.46 (s, 2H), 3.61 (t, J=8.0 Hz, 2H), 0.94 (t, J=8.0 Hz, 2H), 0.00 (s, 9H).

c) 2-(1-((2-(trimethylsilyl)ethoxy)methyl)-1H-pyrazol-4-yl)aniline

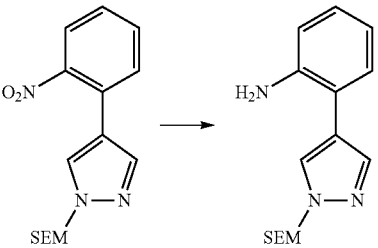 [SMILES: C[Si](C)(C)CCOCn1cc(-c2ccccc2[N+](=O)[O-])cn1 ; C[Si](C)(C)CCOCn1cc(-c2ccccc2N)cn1]

To a solution of trimethyl-[2-[[4-(2-nitrophenyl)pyrazol-1-yl]methoxy]ethyl]silane (0.16 g, 0.500 mmol, 1.0 equiv.) in methanol (10 mL) was added Pd/C (0.05 g, 5% purity) and the mixture was stirred at 20° C. under a hydrogen atmosphere for 1.5 hours. The mixture was filtered and the filtrate was concentrated under reduced pressure to give the desired product as light yellow gum, which was used directly without further purification (0.15 g); MS (ESI+) m/z 290.1 (M+H)+.

d) (E)-3-(3-methoxy-4-(prop-2-yn-1-yloxy)phenyl)-N-(2-(1-((2-(trimethylsilyl)ethoxy)methyl)-1H-pyrazol-4-yl)phenyl)acrylamide

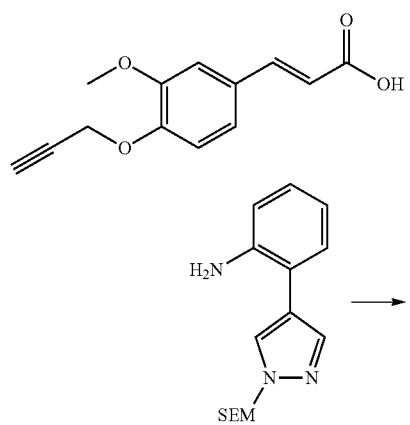

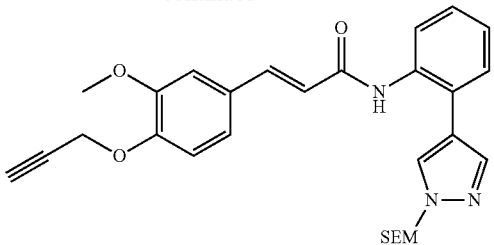

The title compound was prepared according to the procedure described for the synthesis of (1) starting from (E)-3-(3-methoxy-4-prop-2-ynoxy-phenyl)prop-2-enoic acid and 2-(1-((2-(trimethylsilyl)ethoxy)methyl)-1H-pyrazol-4-yl)aniline. MS (ESI+) m/z 504.2 (M+H)+.

e) (E)-N-(2-(1H-pyrazol-4-yl)phenyl)-3-(3-methoxy-4-(prop-2-yn-1-yloxy)phenyl)acrylamide

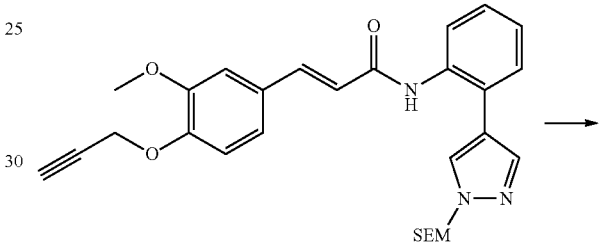

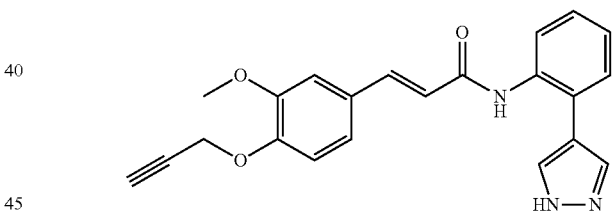

To a solution of (E)-3-(3-methoxy-4-prop-2-ynoxy-phenyl)-N-[2-[1-(2-trimethylsilylethoxymethyl)pyrazol-4-yl]phenyl]prop-2-enamide (0.09 g, 0.178 mmol, 1.0 equiv.) in methanol (2 mL) was added 4M hydrogen chloride in methanol (6 mL) solution and the mixture was stirred at 20° C. for 5 hours. The mixture was concentrated under reduced pressure to give a residue which was purified by preparative HPLC to give the desired product as an off-white solid (8 mg, 12%); $^1$H NMR (CDCl$_3$, 400 MHz) δ 8.40 (br. s., 1H), 7.80 (s, 2H), 8.69 (d, J=16.0 Hz, 1H), 7.40-7.32 (m, 3H), 7.21-7.18 (m, 1H), 7.13-7.10 (m, 1H), 7.08-7.06 (m, 1H), 7.03 (d, J=8.0 Hz, 1H), 6.30 (d, J=16.0 Hz, 1H), 4.81 (d, J=4.0 Hz, 2H), 3.93 (s, 3H), 2.54 (t, J=2.0 Hz, 1H); MS (ESI+) m/z 374.1 (M+H)+; 98.7% purity, RT 2.28 min (Method 8).

| Ex | Structure | Data | Method |
|---|---|---|---|
| 25 | (E)-N-(2-(1H-imidazol-4-yl)phenyl)-3-(3-methoxy-4-(prop-2-yn-1-yloxy)phenyl)acrylamide | ¹H NMR (DMSO-d₆, 400 MHz) δ 12.83 (s, 1H), 12.59 (br. s., 1H), 8.57 (d, J = 8.0 Hz, 1H), 8.01 (s, 1H), 7.79-7.74 (m, 2H), 7.58 (d, J = 8.0 Hz, 1H), 7.35 (s, 1H), 7.27-7.19 (m, 2H), 7.08-7.05 (m, 2H), 6.68 (d, J = 16.0 Hz, 1H), 4.85 (d, J = 2.4 Hz, 2H), 3.85 (s, 3H), 3.59 (t, J = 2.4 Hz, 1H); MS (ESI+) m/z 374.1 (M + H)+; 93.6% purity, RT 2.48 min (Method 8) | Prepared according to the method for 24 starting from 4-bromo-1-((2-(trimethylsilyl)ethoxy)methyl)-1H-imidazole |
| 26 | (E)-3-(3-methoxy-4-(prop-2-yn-1-yloxy)phenyl)-N-(2-(1-methyl-1H-imidazol-4-yl)phenyl)acrylamide | ¹H NMR (DMSO-d₆, 400 MHz) δ 12.64 (s, 1H), 8.56 (d, J = 8.0 Hz, 1H), 7.94 (s, 1H), 7.76 (s, 1H), 7.67 (d, J = 8.0 Hz, 1H), 7.57 (d, J = 16.0 Hz, 1H), 7.35 (s, 1H), 7.26-7.20 (m, 2H), 7.09-7.05 (m, 2H), 6.68 (d, J = 16.0 Hz, 1H), 4.84 (d, J = 2.0 Hz, 2H), 3.86 (s, 3H), 3.76 (s, 3H), 3.58 (t, J = 2.0 Hz, 1H); MS (ESI+) m/z 388.1 (M + H)+; 95.5% purity, RT 2.72 min (Method 8) | Prepared according to the method for 24 starting from 4-bromo-1-methyl-1H-imidazole |

(E)-2-(3-(3-methoxy-4-(prop-2-yn-1-yloxy)phenyl)acrylamido)-N-(methylsulfonyl)benzamide (27)

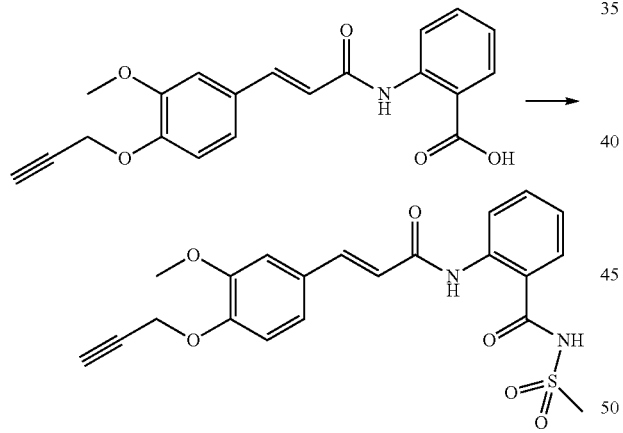

To a solution of 2-[[(E)-3-(3-methoxy-4-prop-2-ynoxy-phenyl)prop-2-enoyl]amino]benzoic acid (0.08 g, 0.227 mmol, 1.0 equiv.) in tetrahydrofuran (5 mL) was added 1,1′-carbonyldiimidazole (0.074 g, 0.455 mmol, 2.0 equiv.). The mixture was stirred at 50° C. for 1 hour and then a solution of methanesulfonamide (0.043 g, 0.455 mmol, 2.0 equiv.) and 1,8-diazabicyclo[5.4.0]undec-7-ene (0.103 g, 0.683 mmol, 3.0 equiv.) in tetrahydrofuran (5 mL) was slowly added. The reaction was stirred for another 5 hours at 20° C. The reaction mixture was diluted with ethyl acetate (5 mL) and washed with water (5 mL×3). The organic layers were dried and concentrated under reduced pressure to give a residue which was purified by preparative HPLC to give the desired product as a white solid (20 mg, 21%); 1H NMR (DMSO-d6, 400 MHz) δ 10.74 (br. s., 1H), 7.92 (d, J=7.6 Hz, 1H), 7.69 (d, J=7.2 Hz, 1H), 7.58-7.56 (m, 2H), 7.33 (s, 1H), 7.22-7.21 (m, 2H), 7.08-7.06 (m, 1H), 6.77 (d, J=16.0 Hz, 1H), 4.84 (d, J=2.0 Hz, 2H), 3.84 (s, 3H), 3.59 (t, J=2.0 Hz, 1H), 3.32 (s, 3H); MS (ESI+) m/z 451.1 (M+Na)+; 98% purity, RT 2.81 min (Method 11).

(E)-3-(3-methoxy-4-(prop-2-yn-1-yloxy)phenyl)-N-(2-(3-methyl-1,2,4-oxadiazol-5-yl)phenyl)acrylamide (28)

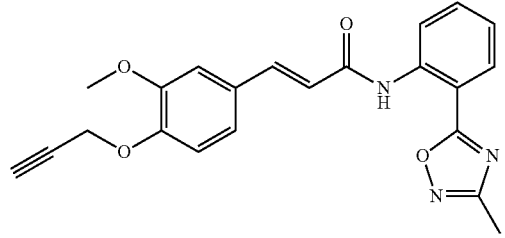

a) N-((E)-1-(hydroxyimino)ethyl)-2-((E)-3-(3-methoxy-4-(prop-2-yn-1-yloxy)phenyl)acrylamido)-benzamide

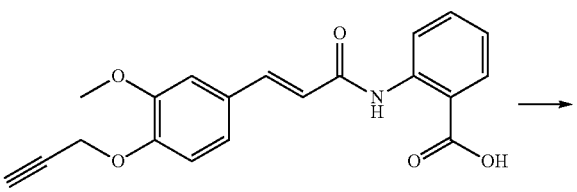

-continued

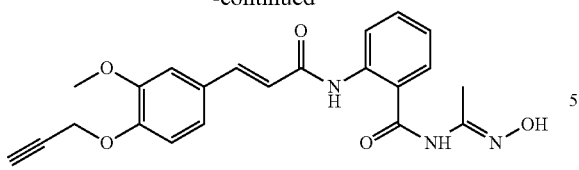

To a solution of 2-[[(E)-3-(3-methoxy-4-prop-2-ynoxyphenyl)prop-2-enoyl]amino]benzoic acid (0.1 g, 0.284 mmol, 1.0 equiv.) in N,N-dimethylformamide (5 mL) was added HATU (0.129 g, 341 umol, 1.2 equiv.), N,N-diisopropylethylamine (0.110 g, 0.853 mmol, 3.0 equiv.) and N-hydroxyacetamidine (0.042 g, 0.569 mmol, 2.0 equiv.) and the mixture stirred for 12 hours at 25° C. The reaction mixture was filtered and concentrated to give a residue which was purified by silica gel chromatography (petroleum ether:ethyl acetate 5:1 to ethyl acetate) to give the desired product as a light yellow solid and used without further purification (0.15 g crude); 1H NMR (CDCl3, 400 MHz) δ 11.33 (s, 1H), 8.86 (d, J=8.4 Hz, 1H), 7.99-7.96 (m, 1H), 7.66 (d, J=15.2 Hz, 1H), 7.59-7.58 (m, 1H), 7.12-7.07 (m, 3H), 7.03 (d, J=8.8 Hz, 1H), 6.49 (d, J=15.2 Hz, 1H), 4.81 (d, J=2.0 Hz, 2H), 3.95 (s, 3H), 2.54 (t, J=2.0 Hz, 1H), 2.15 (s, 3H).

b) (E)-3-(3-methoxy-4-(prop-2-yn-1-yloxy)phenyl)-N-(2-(3-methyl-1,2,4-oxadiazol-5-yl)phenyl)-acrylamide

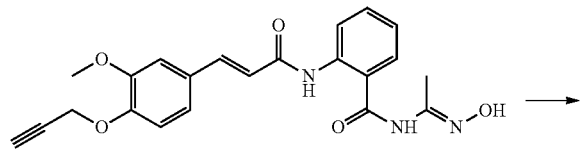

A solution of N-((E)-1-(hydroxyimino)ethyl)-2-((E)-3-(3-methoxy-4-(prop-2-yn-1-yloxy)phenyl)-acrylamido)benzamide (0.15 g, 0.368 mmol, 1.0 equiv.) in N,N-dimethylformamide (3 mL) was heated to 110° C. for 10 hours. The reaction mixture was filtered and the filtrate was concentrated under reduced pressure to give a residue which was purified by preparative HPLC to give the desired product as a light yellow solid (10 mg, 21%); 1H NMR (DMSO-d6, 400 MHz) δ 11.39 (s, 1H), 8.97 (d, J=8.0 Hz, 1H), 8.13 (d, J=8.4 Hz, 1H), 7.75 (d, J=15.6 Hz, 1H), 7.63 (t, J=8.4 Hz, 1H), 7.26-7.25 (m, 2H), 7.14 (s, 1H), 7.09 (d, J=8.8 Hz, 1H), 6.53 (d, J=15.6 Hz, 1H), 4.83 (d, J=2.0 Hz, 2H), 3.96 (s, 3H), 2.58 (s, 3H), 2.56 (t, J=2.0 Hz, 1H); MS (ESI+) m/z 412.1 (M+Na)+; 93% purity, RT 3.33 min (Method 11).

(E)-3-(3-methoxy-4-(prop-2-yn-1-yloxy)phenyl)-N-(2-(5-methyl-1,3,4-oxadiazol-2-yl)phenyl)-acrylamide (29)

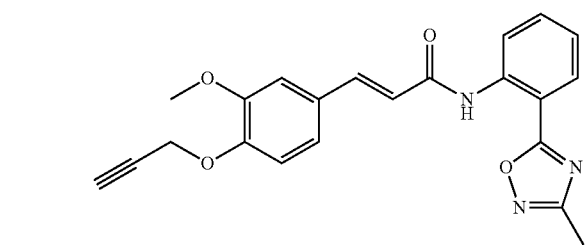 [SMILES: C#CCOc1ccc(/C=C/C(=O)Nc2ccccc2-c2nc(C)no2)cc1OC]

To a solution of 2-[[(E)-3-(3-methoxy-4-prop-2-ynoxyphenyl)prop-2-enoyl]amino]benzoic acid (0.5 g, 1.42 mmol, 1.0 equiv.) in acetonitrile (30 mL) was added acetohydrazide (0.126 g, 1.70 mmol, 1.2 equiv.) and phosphorus oxychloride (1.09 g, 7.10 mmol, 5.0 equiv.). The reaction mixture was stirred at 106° C. for 16 hours. The reaction mixture was concentrated under reduced pressure to give a residue which was purified by preparative HPLC to afford the desired product as a yellow solid (28 mg, 5%); $^1$H NMR (DMSO-d$_6$, 400 MHz) δ 11.04 (s, 1H), 8.12 (d, J=8.0 Hz, 1H), 7.97 (d, J=16.0 Hz, 1H), 7.88-7.86 (m, 1H), 7.73 (d, J=8.0 Hz, 1H), 7.53 (t, J=8.0 Hz, 1H), 7.37-7.36 (m, 2H), 7.14-7.10 (m, 2H), 4.87 (d, J=2.0 Hz, 2H), 3.86 (s, 3H), 3.34 (t, J=2.0 Hz, 1H), 2.19 (s, 3H); MS (ESI+) m/z 390.1 (M+H)+; 95.5% purity, RT 1.77 min (Method 10).

(E)-N-(2-(dimethylamino)ethyl)-2-(3-(3-methoxy-4-(prop-2-yn lyloxy) phenyl) acrylamido) benzamide (30)

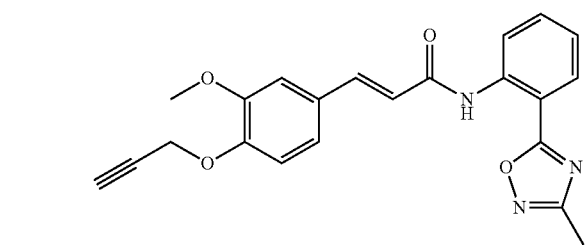 [SMILES: C#CCOc1ccc(/C=C/C(=O)Nc2ccccc2-c2nc(C)no2)cc1OC]

To a solution of N',N'-dimethylethane-1,2-diamine (42.9 mg, 0.487 mmol, 1.5 equiv.) in dichloromethane (5 mL) was added 2-[[(E)-3-(3-methoxy-4-prop-2-ynoxy-phenyl)prop-2-enoyl]amino]benzoyl chloride (120 mg, 0.325 mmol, 1.0 equiv.) (prepared from 2-[[(E)-3-(3-methoxy-4-prop-2-ynoxy-phenyl)prop-2-enoyl]amino]benzoic acid and thionyl chloride) and triethylamine (99 mg, 0.974 mmol, 3.0 equiv.) and the resulting mixture was stirred at 20° C. for 12 hrs. The reaction mixture was filtered and the filtrate was concentrated under reduced pressure to give a residue which was purified by preparative HPLC to afford the title compound as a light yellow solid as the trifluoroacetic acid salt (27.8 mg, 19%); $^1$H NMR (CDCl$_3$, 400 MHz) δ 12.45 (br. s., 1H), 11.63 (s, 1H), 8.87 (br. s., 1H), 8.76 (d, J=8.4 Hz, 1H), 8.02 (d, J=8.0 Hz, 1H), 7.68 (d, J=15.6 Hz, 1H), 7.52 (t, J=8.4 Hz, 1H), 7.18-7.12 (m, 3H), 7.02 (d, J=8.4 Hz, 1H), 6.50 (d, J=16.0 Hz, 1H), 4.82 (s, 2H), 3.95 (s, 3H), 3.91 (br. s., 2H), 3.31 (br. s., 2H) 2.91 (s, 6H), 2.55 (s, 1H); MS (ESI+) m/z 422.2 (M+H)+; 93.7% purity, RT 2.46 min (Method 11).

| Ex | Structure | Data | Method |
|---|---|---|---|
| 31 | (E)-2-(3-(3-methoxy-4-(prop-2-yn-1-yloxy)phenyl)acrylamido)-N-(2H-tetrazol-5-yl)benzamide | $^1$H NMR (DMSO-d$_6$, 400 MHz) δ 16.00 (br. s. 1H), 12.45 (br. s., 1H), 10.37 (s, 1H), 7.90 (d, J = 6.4 Hz, 1H), 7.78 (d, J = 6.4 Hz, 1H), 7.59 (t, J = 7.6 Hz, 1H), 7.52 (d, J = 15.6 Hz, 1H), 7.28-7.26 (m, 2H), 7.19-7.18 (m, 1H), 7.07 (d, J = 18.4 Hz, 1H), 6.72 (d, J = 15.6 Hz, 1H), 4.84 (d, J = 2.0 Hz, 2H), 3.83 (s, 3H), 3.34 (t, J = 2.0 Hz, 1H); MS (ESI+) m/z 419.0 (M + H)+; 97% purity, RT 2.73 min (Method 11) | Prepared according to the method for 1 starting from 2-amino-N-(2H-tetrazol-5-yl)benzamide (J. Med. Chem. 1986, 29, 2403) |
| 32 | (E)-N-(3-(dimethylamino)propyl)-2-(3-(3-methoxy-4-(prop-2-yn-1-yloxy)phenyl)acrylamido) benzamide trifluoroacetic acid salt | $^1$H NMR (CDCl$_3$, 400 MHz) δ 12.73 (br. s., 1H), 11.68 (s, 1H), 8.76 (d, J = 8.4 Hz, 1H), 8.07 (br. s., 1H), 7.80 (d, J = 8.0 Hz, 1H), 7.69 (d, J = 15.6 Hz, 1H), 7.53-7.52 (m, 1H), 7.16-7.13 (m, 3H), 7.03 (d, J = 8.0 Hz, 1H), 6.50 (d, J = 15.6 Hz, 1H), 4.81 (s, 2H), 3.95 (s, 3H), 3.59 (d, J = 5.6 Hz, 2H), 3.17 (t, J = 6.8 Hz, 2H), 2.85 (s, 6H), 2.55 (s, 1H), 2.19 (t, J = 6.0 Hz, 2H); MS (ESI+) m/z 436.2 (M + H)+; 96.4% purity, RT 2.45 min (Method 11) | Prepared according to the method for 30 starting from N,N-dimethylpropane-1,3-diamine |
| 33 | (E)-2-(3-(3-methoxy-4-(prop-2-yn-1-yloxy)phenyl)acrylamido)-N-(2-methoxyethyl)benzamide | $^1$H NMR (DMSO, 400 MHz) δ11.46 (s, 1H), 8.81 (d, J = 5.2 Hz, 1H), 8.54 (d, J = 8.4 Hz, 1H), 7.75 (d, J = 8.4 Hz, 1H), 7.56-7.51 (m, 2H), 7.41 (d, J = 1.2 Hz, 1H), 7.24 (d, J = 8.8 Hz, 1H), 7.17-7.15 (m, 1H), 7.05 (d, J = 8.4 Hz, 1H), 6.78 (d, J = 15.6 Hz, 1H), 4.84 (s, 2H), 3.85 (s, 3H), 3.59 (s, 1H), 3.50-3.40 (m, 4H), 3.28 (s, 3H); MS (ESI+) m/z 409.2 (M + H)+; 96.9% purity, RT 2.93 min (Method 11) | Prepared according to the method for 30 starting from 2-methoxyethanamine |

-continued

| Ex | Structure | Data | Method |
|---|---|---|---|
| 34 | (E)-2-(3-(3-methoxy-4-(prop-2-yn-1-yloxy)phenyl)acrylamido)-N-(2-(4-methylpiperazin-1-yl)ethyl)benzamide trifluoroacetic acid salt | $^1$H NMR (DMSO-d$_6$, 400 MHz) δ 11.34 (s, 1H), 8.81 (br. s, 1H), 8.49 (d, J = 8.4 Hz, 1H), 7.75 (d, J = 7.2 Hz, 1H), 7.57-7.52 (m, 2H), 7.40 (s, 1H), 7.24 (d, J = 8.0 Hz, 1H), 7.18 (t, J = 8.0 Hz, 1H), 7.06 (d, J = 8.4 Hz, 1H), 6.77 (d, J = 15.6 Hz, 1H), 5.40-4.20 (m, 6H), 3.85 (s, 3H), 3.59 (s, 1H), 3.54-3.52 (m, 2H), 3.50-2.99 (m, 4H), 2.94-2.92 (m, 2H), 2.76 (s, 3H); MS (ESI+) m/z 477.2 (M + H)+; 97% purity, RT 2.38 min (Method 11) | Prepared according to the method for 30 starting from 2-(4-methylpiperazin-1-yl)ethanamine |
| 35 | (E)-2-(3-(3-methoxy-4-(prop-2-yn-1-yloxy)phenyl)acrylamido)-N-(2-morpholino ethyl)benzamide trifluoroacetic acid salt | $^1$H NMR (CDCl$_3$, 400 MHz) δ 11.56 (s., 1H), 8.76 (d, J = 8.0 Hz, 1H), 8.55 (br. s, 1H), 8.71-7.67 (m, 2H), 7.52 (t, J = 4.0 Hz, 1H), 7.15-7.12 (m, 3H), 7.04 (d, J = 8.0 Hz, 1H), 6.48 (d, J = 15.2 Hz, 1H), 4.82 (d, J = 2.0 Hz, 2H), 4.02-4.01 (m, 4H), 3.95 (s., 3H), 3.91 (d, J = 4.8 Hz, 2H), 3.70-3.50 (m, 2H), 3.36 (d, J = 4.8 Hz, 2H), 3.10-2.80 (m, 2H), 2.55 (s, 1H). MS (ESI+) m/z 464.2 (M + H)+; 94.2% purity, RT 2.47 min (Method 11) | Prepared according to the method for 30 starting from 2-morpholinoethanamine |
| 36 | (E)-2-(3-(3-methoxy-4-(prop-2-yn-1-yloxy)phenyl)acrylamido)-N-(1-methylpiperidin-4-yl)benzamide trifluoroacetic acid salt | $^1$H NMR (DMSO-d$_6$, 400 MHz) δ 11.21 (s, 1H), 9.56 (br. s, 1H), 8.75 (d, J = 7.2 Hz, 1H), 8.45 (d, J = 8.0 Hz, 1H), 7.75 (d, J = 7.6 Hz, 1H), 7.56-7.52 (m, 2H), 7.39 (s., 1H), 7.23 (d, J = 8.0 Hz, 1H), 7.18 (t, J = 8.0 Hz, 1H), 7.06 (d, J = 8.4 Hz, 1H), 6.76 (d, J = 15.6 Hz, 1H), 4.85 (s, 2H), 4.05-4.02 (m, 1H), 3.85 (s, 3H), 3.69 (s, 1H), 3.60-3.58 (m, 2H), 3.12-3.07 (m, 2H), 2.78 (d, J = 3.6 Hz, 3H), 2.08-2.05 (m, 2H), 1.80-1.74 (m, 2H); MS (ESI+) m/z 448.2 (M + H)+; 99% purity, RT 2.47 min (Method 11) | Prepared according to the method for 30 starting from 1-methylpiperidin-4-amine |
| 37 | (E)-2-(3-(3-methoxy-4-(prop-2-yn-1-yloxy)phenyl)acrylamido)-N-((1-methylpiperidin-4-yl)methyl)benzamide trifluoroacetic acid salt | $^1$H NMR (DMSO-d$_6$, 400 MHz) δ 11.39 (s, 1H), 9.46 (br. s, 1H), 8.87 (t, J = 5.2 Hz, 1H), 8.51 (d, J = 8.0 Hz, 1H), 7.77 (d, J = 7.2 Hz, 1H), 7.56-7.52 (m, 2H), 7.41 (s, 1H), 7.24 (d, J = 8.0 Hz, 1H), 7.19 (t, J = 7.6 Hz, 1H), 7.06 (d, J = 8.4 Hz, 1H), 6.77 (d, J = 15.6 Hz, 1H), 4.85 (s, 2H), 3.85 (s, 3H), 3.59 (s, 1H), 3.44-3.41 (m, 2H), 3.21 (t, J = 5.6 Hz, 2H), 2.94-2.85 (m, 2H), 2.74 (d, J = 4.4 Hz, 3H), 1.90 (d, J = 14.4 Hz, 2H), 1.87-1.82 (m, 1H), 1.44-1.38 (m, 2H); MS (ESI+) m/z 462.2 (M + H)+; 98.9% purity, RT 2.49 min (Method 11) | Prepared according to the method for 30 starting from (1-methylpiperidin-4-yl)methanamine |

| Ex | Structure | Data | Method |
|---|---|---|---|
| 38 | 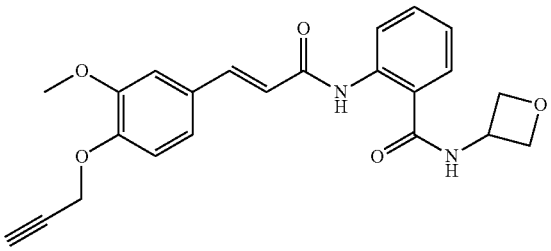<br>(E)-2-(3-(3-methoxy-4-(prop-2-yn-1-yloxy)phenyl)acrylamido)-N-(oxetan-3-yl)benzamide | $^1$H NMR (DMSO-d$_6$, 400 MHz) δ 11.21 (s, 1H), 9.38 (d, J = 6.4 H, 1H), 8.50 (d, J = 7.6 Hz, 1H), 7.83 (d, J = 1.2 Hz. 1H), 7.55-7.51 (m, 2H), 7.40 (d, J = 2.0 Hz, 1H), 7.23-7.19 (m, 2H), 7.05 (d, J = 8.4 Hz, 1H), 6.78 (d, J = 15.6 Hz, 1H), 5.05-5.02 (m, 1H), 4.84 (d, J = 2.4 Hz, 2H), 4.78 (t, J = 6.8 Hz, 2H), 4.63 (d, J = 6.4 Hz, 2H), 3.85 (s, 3H), 3.59 (t, J = 2.4 Hz, 1H); MS (ESI+) m/z 407.2 (M + H)+; 98.4% purity, RT 1.82 min (Method 10) | Prepared according to the method for 30 starting from oxetan-3-amine |
| 39 | 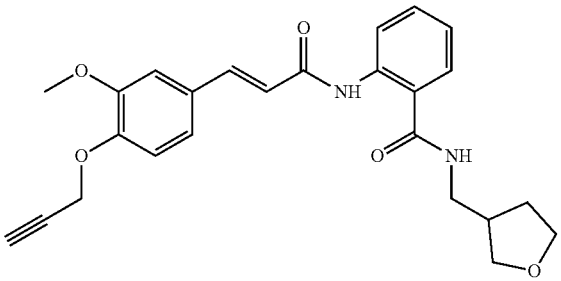<br>(E)-2-(3-(3-methoxy-4-(prop-2-yn-1-yloxy)phenyl)acrylamido)-N-((tetrahydrofuran-3-yl)methyl)benzamide | $^1$H NMR (DMSO-d$_6$, 400 MHz) δ 11.30 (s, 1H), 8.75 (d, J = 8.4 Hz, 1H), 7.77 (d, J = 15.2 Hz, 1H), 7.55-7.45 (m, 2H), 7.14-7.09 (m, 3H), 7.03 (d, J = 8.8 Hz, 1H), 6.58 (br. s, 1H), 6.49 (d, J = 15.6 Hz, 1H), 4.81 (d, J = 2.4 Hz, 2H), 4.00-3.95 (m, 4H), 3.85-3.78 (m, 1H), 3.80-3.74 (m, 1H), 3.70-3.67 (d, J = 4.4 Hz, 1H), 3.55-3.44 (m, 2H), 2.70-2.60 (m, 1H), 2.54 (t, J = 2.4 Hz, 1H), 2.17-2.12 (m, 1H), 1.73-1.70 (m, 1H); MS (ESI+) m/z 435.3 (M + H)+; 99.2% purity, RT 1.92 min (Method 10) | Prepared according to the method for 30 starting from (tetrahydrofuran-3-yl)methanamine |
| 40 | 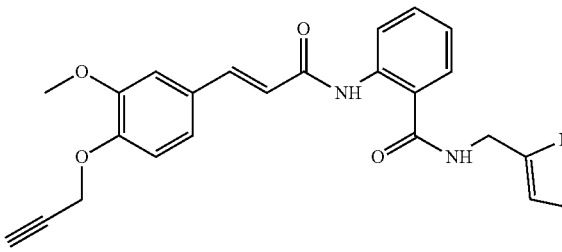<br>(E)-2-(3-(3-methoxy-4-(prop-2-yn-1-yloxy)phenyl)acrylamido)-N-((1-methyl-1H-imidazol-5-yl)methyl)benzamide trifluoroacetic acid salt | $^1$H NMR (DMSO-d$_6$, 400 MHz) δ 11.11 (s, 1H), 9.23 (t, J = 5.2 Hz, 1H), 9.01 (s, 1H), 8.38 (d, J = 7.6 Hz, 1H), 7.75 (d, J = 8.0 Hz, 1H), 7.65 (s, 1H), 7.54-7.50 (m, 2H), 7.37 (d, J = 2.0 Hz, 1H), 7.23-7.19 (m, 2H), 7.07 (d, J = 8.4 Hz, 1H), 6.75 (d, J = 15.6 Hz, 1H), 4.85 (d, J = 2.4 Hz, 2H), 4.59 (d, J = 2.0 Hz, 2H), 3.88 (s, 3H), 3.85 (s, 3H) 3.60 (t, J = 2.4 Hz, 1H); MS (ESI+) m/z 445.3 (M + H)+; 96.3% purity, RT 1.54 min (Method 10) | Prepared according to the method for 30 starting from (1-methyl-1H-imidazol-5-yl)methanamine |
| 41 | 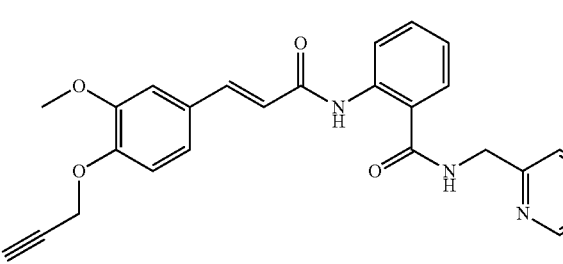<br>(E)-2-(3-(3-methoxy-4-(prop-2-yn-1-yloxy)phenyl)acrylamido)-N-(pyridin-2-ylmethyl)benzamide | $^1$H NMR (DMSO-d$_6$, 400 MHz) δ 11.35 (s, 1H), 9.39 (d, J = 6.0 Hz, 1H), 8.59 (br. s, 1H), 8.52 (d, J = 8.4 Hz, 1H), 7.89-7.87 (m, 2H), 7.55-7.51 (m, 3H), 7.38-7.37 (m, 2H), 7.21 (d, J = 8.4 Hz, 2H), 7.04 (d, J = 8.4 Hz, 1H), 6.75 (d, J = 15.6 Hz, 1H), 4.83 (d, J = 2.4 Hz, 2H), 4.65 (d, J = 5.6 Hz, 2H), 3.83 (s, 3H), 3.57 (t, J = 2.4 Hz, 1H); MS (ESI+) m/z 442.2 (M + H)+; 97.6% purity, RT 1.59 min (Method 10) | Prepared according to the method for 30 starting from pyridin-2-ylmethanamine |

| Ex | Structure | Data | Method |
|---|---|---|---|
| 42 | (E)-2-(3-(3-methoxy-4-(prop-2-yn-1-yloxy)phenyl)acrylamido)-N-(2-(pyridin-2-yl)ethyl)benzamide | $^1$H NMR (CDCl$_3$, 400 MHz) δ 11.59 (s, 1H), 8.78 (d, J = 8.4 Hz, 1H), 8.60 (s, 1H), 8.00 (br. s, 1H), 7.70-7.67 (m, 2H), 7.65-7.53 (m, 2H), 7.24-7.22 (m, 2H), 7.17-7.10 (m, 3H), 7.03 (d, J = 8.4 Hz, 1H), 6.51 (d, J = 15.6 Hz, 1H), 4.81 (d, J = 1.6 Hz, 2H), 3.96 (s, 3H), 3.89-3.85 (m, 2H), 3.13 (t, J = 6.0 Hz, 2H), 2.55 (t, J = 2.4 Hz, 1H); MS (ESI+) m/z 456.2 (M + H)+; 98.2% purity, RT 2.86 min (Method 13) | Prepared according to the method for 30 starting from 2-(pyridin-2-yl)ethanamine |
| 43 | (E)-2-(3-(3-methoxy-4-(prop-2-yn-1-yloxy)phenyl)acrylamido)-N-(pyridin-3-ylmethyl)benzamide trifluoroacetic acid salt | $^1$H NMR (DMSO-d$_6$, 400 MHz) δ 11.27 (s, 1H), 9.42 (br. s, 1H), 8.81 (br. s, 1H), 8.69 (br. s, 1H), 8.46 (d, J = 8.4 Hz, 1H), 8.24 (br. s, 1H), 7.84 (d, J = 7.6 Hz, 1H), 7.55 (br. s, 1H), 7.55-7.50 (m, 2H), 7.39 (s, 1H), 7.23-7.21 (m, 2H), 7.06 (d, J = 8.4 Hz, 1H), 6.76 (d, J = 15.6 Hz, 1H), 4.85 (d, J = 2.4 Hz, 2H), 4.63 (d, J = 4.0 Hz, 2H), 3.85 (s, 3H), 3.60 (t, J = 2.4 Hz, 1H); MS (ESI+) m/z 442.1 (M + H)+; 99.2% purity, RT 1.49 min (Method 10) | Prepared according to the method for 30 starting from pyridin-3-ylmethanamine |
| 44 | (E)-2-(3-(3-methoxy-4-(prop-2-yn-1-yloxy)phenyl)acrylamido)-N-(pyridin-4-yl)benzamide | $^1$H NMR (CDCl$_3$, 400 MHz) δ 10.62 (s, 1H), 9.09 (s, 1H), 8.64 (d, J = 6.4 Hz, 2H), 8.46-8.45 (m, 1H), 7.78-7.73 (m, 3H), 7.56-7.55 (m, 1H), 7.36-7.35 (m, 1H), 7.25-7.24 (m, 1H), 7.20 (s, 1H), 7.15 (s, 1H), 7.09-7.01 (m, 1H), 6.45 (d, J = 15.6 Hz, 1H), 4.83 (d, J = 2.4 Hz, 2H), 3.98 (s, 3H), 2.56 (t, J = 2.4 Hz, 1H); MS (ESI+) m/z 428.1 (M + H)+; 96.3% purity, RT 2.44 min (Method 8) | Prepared according to the method for 30 starting from pyridin-4-amine |
| 45 | (E)-2-(3-(3-methoxy-4-(prop-2-yn-1-yloxy)phenyl)acrylamido)-N-(pyridin-4-ylmethyl)benzamide trifluoroacetic acid salt | $^1$H NMR (DMSO-d$_6$, 400 MHz) δ 11.24 (s, 1H), 9.48 (t, J = 6.0 Hz, 1H), 8.72 (d, J = 6.0 Hz, 2H), 8.46 (d, J = 8.0 Hz, 1H), 7.89 (d, J = 6.8 Hz, 1H), 7.76 (d, J = 6.0 Hz, 2H), 7.55-7.51 (m, 2H), 7.37 (d, J = 1.6 Hz, 1H), 7.23-7.20 (m, 2H), 7.04 (d, J = 8.4 Hz, 1H), 6.74 (d, J = 15.6 Hz, 1H), 4.83 (d, J = 2.4 Hz, 2H), 4.68 (d, J = 5.6 Hz, 2H), 3.83 (s, 3H), 3.59 (t, J = 2.4 Hz, 1H); MS (ESI+) m/z 442.1 (M + H)+; 98.7% purity, RT 2.5 min (Method 11) | Prepared according to the method for 30 starting from pyridin-4-ylmethanamine |

| Ex | Structure | Data | Method |
|---|---|---|---|
| 46 | (E)-2-(3-(3-methoxy-4-(prop-2-yn-1-yloxy)phenyl)acrylamido)-N-(2-(pyridin-4-yl)ethyl)benzamide | ¹H NMR (DMSO-d₆, 400 MHz) δ 11.31 (s, 1H), 8.94-8.93 (m, 1H), 8.81 (d, J = 6.4 Hz, 2H), 8.54 (d, J = 8.0 Hz, 1H), 7.89 (d, J = 6.4 Hz, 2H), 7.72 (d, J = 7.6 Hz, 1H), 7.62-7.58 (m, 2H), 7.47 (d, J = 1.2 Hz, 1H), 7.37-7.33 (m, 1H), 7.24-7.21 (m, 1H), 7.12 (d, J = 8.4 Hz, 1H), 6.81 (d, J = 15.6 Hz, 1H), 4.90 (d, J = 2.0 Hz, 2H), 3.92 (s, 3H), 3.76-3.70 (m, 2H), 3.65 (s, 1H), 3.18 (t, J = 6.4 Hz, 2H); MS (ESI+) m/z 456.2 (M + H)+; 95.1% purity, RT 1.54 min (Method 10) | Prepared according to the method for 30 starting from 2-(pyridin-4-yl)ethanamine |
| 47 | (E)-2-(3-(3-methoxy-4-(prop-2-yn-1-yloxy)phenyl)acrylamido)-N-(1-methyl-1H-pyrazol-4-yl)benzamide | ¹H NMR (DMSO-d₆, 400 MHz) δ 11.07 (s, 1H), 10.67 (s, 1H), 8.47 (d, J = 7.2 Hz, 1H), 8.04 (s, 1H), 7.82 (d, J = 6.8 Hz, 1H), 7.62 (s, 1H), 7.60-7.52 (m, 2H), 7.39 (d, J = 2.0 Hz, 1H), 7.24-7.23 (m, 2H), 7.06 (d, J = 8.0 Hz, 1H), 6.79 (d, J = 15.6 Hz, 1H), 4.84 (d, J = 2.4 Hz, 2H), 3.85 (s, 3H), 3.83 (s, 3H), 3.59 (t, J = 2.4 Hz, 1H); MS (ESI+) m/z 431.1 (M + H)+; 96.3% purity, RT 2.62 min (Method 12) | Prepared according to the method for 30 starting from 1-methyl-1H-pyrazol-4-amine |
| 48 | (E)-2-(3-(3-methoxy-4-(prop-2-yn-1-yloxy)phenyl)acrylamido)-N-(1-methyl-1H-pyrazol-3-yl)benzamide | ¹H NMR (DMSO-d₆, 400 MHz) δ 10.98 (s, 1H), 10.93 (s, 1H), 8.42 (d, J = 8.0 Hz, 1H), 7.86 (d, J = 8.0 Hz, 1H), 7.64 (d, J = 2.0 Hz, 1H), 7.56-7.52 (m, 2H), 7.40 (s, 1H), 7.23-7.18 (m, 2H), 7.05 (d, J = 8.4 Hz, 1H), 6.83 (d, J = 15.6 Hz, 1H), 6.60 (s, 1H), 4.84 (s, 2H), 3.84 (s, 3H), 3.79 (s, 3H), 3.58 (s, 1H); MS (ESI+) m/z 431.2 (M + H)+; 94% purity, RT 1.93 min (Method 10) | Prepared according to the method for 30 starting from 1-methyl-1H-pyrazol-3-amine |

(E)-2-(3-(3-methoxy-4-(prop-2-yn-1-yloxy)phenyl)acrylamido)-N-(piperidin-4-yl)benzamide (49)

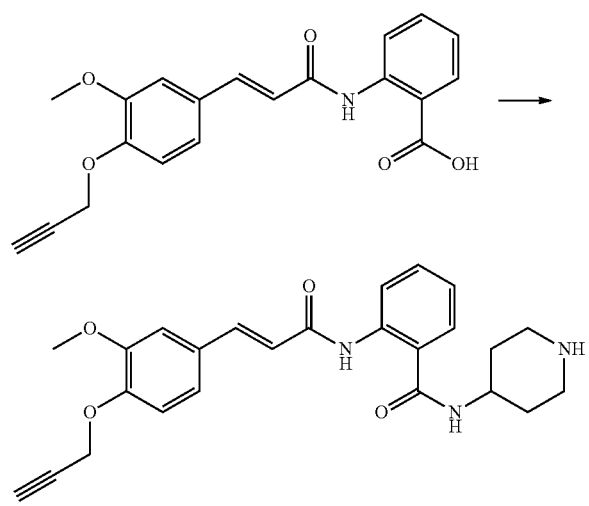

To a solution of 2-[[(E)-3-(3-methoxy-4-prop-2-ynoxy-phenyl)prop-2-enoyl]amino]benzoic acid (100 mg, 0.285 mmol, 1.0 equiv.), tert-butyl 4-aminopiperidine-1-carboxylate (114 mg, 0.569 mmol, 2.0 equiv.) and diisopropylethylamine (149 uL, 0.854 mmol, 3.0 equiv.) in N,N-dimethylformamide (2 mL) was added HATU (163 mg, 0.427 mmol, 1.5 equiv.) and the reaction mixture stirred at 40° C. for 16 hours. The mixture was diluted with water (20 mL) and extracted with ethyl acetate (30 mL×3). The combined organic layer was washed with brine (20 mL×2), dried over sodium sulfate, filtered and concentrated. The residue was purified by preparative-TLC (petroleum ether:ethyl acetate 1:1) to give the intermediate tert-butyl 4-[[2-[[(E)-3-(3-methoxy-4-prop-2-ynoxy-phenyl)prop-2-enoyl]amino]benzoyl]amino]-piperidine-1-carboxylate (113 mg, 45% yield). This was stirred in 4M hydrochloric acid in dioxane (20 mL) at 25° C. for 2 hours. The solvent was removed in vacuo, and the residue purified by preparative-HPLC to afford 2-[[(E)-3-(3-methoxy-4-prop-2-ynoxy-phenyl)prop-2-enoyl]amino]-N-(4-piperidyl)benzamide as a light yellow solid as a trifluoroacetic acid salt (15.6 mg, 15%); ¹H NMR (DMSO-d₆, 400 MHz) δ 11.17 (s, 1H), 8.74 (d, J=7.6 Hz, 1H), 8.50

(br. s, 1H), 8.43 (d, J=7.6 Hz, 1H), 8.30 (br. s, 1H), 7.76 (d, J=8.0 Hz, 1H), 7.56-7.40 (m, 2H), 7.40 (d, J=2.0 Hz, 1H), 7.25-7.19 (m, 2H), 7.07 (d, J=8.4 Hz, 1H), 6.76 (d, J=15.6 Hz, 1H), 4.85 (d, J=2.4 Hz, 2H), 4.11-4.09 (m, 1H), 3.86 (s, 3H), 3.61 (t, J=2.0 Hz, 1H), 3.40-3.30 (m, 2H), 3.07-2.99 (m, 2H), 2.03-2.00 (m, 2H), 1.78-1.70 (m, 2H); MS (ESI+) m/z 434.2 (M+H)+; 99.1% purity, RT 2.46 min (Method 11).

(E)-2-(3-(3-methoxy-4-(piperidin-4-ylmethoxy)phenyl)acrylamido)benzoic acid (50)

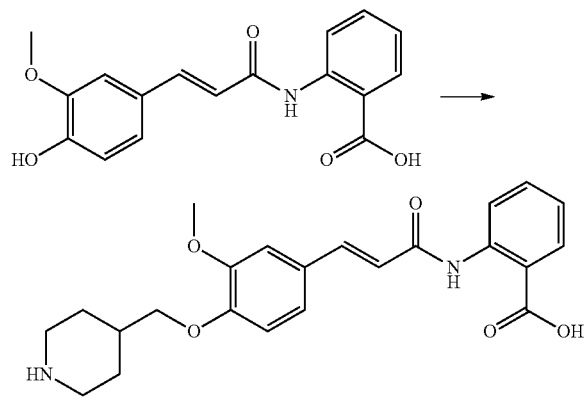

A mixture of 2-[[(E)-3-(4-hydroxy-3-methoxy-phenyl)prop-2-enoyl]amino]benzoic acid (150 mg, 0.479 mmol, 1.0 equiv. Bioorg. Med. Chem. Lett. 2009, 19, 7003-7006), tert-butyl 4-(p-tolylsulfonyloxymethyl)piperidine-1-carboxylate (265 mg, 0.718 mmol, 1.5 equiv.) and potassium hydroxide (0.5 M, 3.8 mL, 4.0 equiv.) in acetone (3 mL) was stirred at 80° C. for 16 hours. The mixture was concentrated under reduced pressure and the residue stirred in 4M hydrogen chloride in dioxane (10 mL). The solvent was removed in vacuo and the residue purified by preparative HPLC to give the desired product as a yellow solid as the trifluoroacetic acid salt (60.5 mg, 26.6%); $^1$H NMR (DMSO-d$_6$, 400 MHz) δ 11.32 (s, 1H), 8.65-8.60 (m, 2H), 8.32 (br. s, 1H), 8.02 (dd, J=8.0 Hz, J=1.2 Hz, 1H), 7.62 (t, J=8.0 Hz, 1H), 7.57 (d, J=15.6 Hz, 1H), 7.40 (d, J=1.6 Hz, 1H), 7.25 (d, J=8.0 Hz, 1H), 7.18 (t, J=8.0 Hz, 1H), 7.03 (d, J=8.4 Hz, 1H), 6.81 (d, J=15.6 Hz, 1H), 3.92 (d, J=6.4 Hz, 2H), 3.88 (s, 3H), 3.20-3.35 (m, 2H), 2.85-3.00 (m, 2H), 2.00-2.20 (m, 1H), 1.80-2.00 (m, 2H), 1.40-1.55 (m, 2H); MS (ESI+) m/z 411.2 (M+H)+; 90.3% purity, RT 2.16 min (Method 11).

(E)-2-(3-(3-methoxy-4-((1-methylpyrrolidin-3-yl)oxy)phenyl)acrylamido)benzoic acid (51)

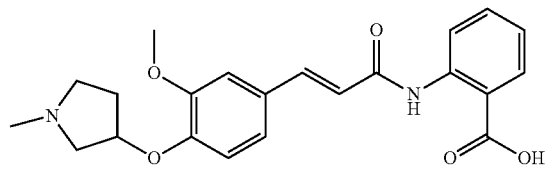 [SMILES: COc1cc(/C=C/C(=O)Nc2ccccc2C(=O)O)ccc1OC1CCN(C)C1]

a) 1-methylpyrrolidin-3-yl 4-methylbenzenesulfonate

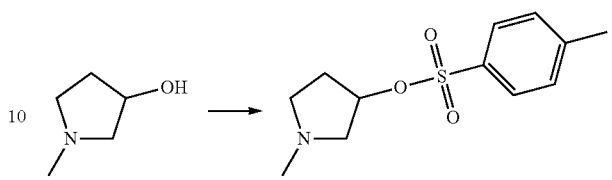

To the solution of 1-methylpyrrolidin-3-ol (300 mg, 2.97 mmol, 1.00 equiv) and potassium hydroxide (666 mg, 11.86 mmol, 4.00 equiv) in tetrahydrofuran (5 mL) was added 4-methylbenzenesulfonyl chloride (848 mg, 4.45 mmol, 1.50 equiv) portion-wise maintaining the temperature at 0° C. and the resultant yellow slurry was stirred at 25° C. for 16 hours. The reaction mixture was filtered and the filtrate was concentrated in vacuo to afford the desired product as yellow oil (523 mg, 65%) which was used without further purification; MS (ESI$^+$) m/z 256.1 (M+H)+.

b) (E)-2-(3-(3-methoxy-4-((1-methylpyrrolidin-3-yl)oxy)phenyl)acrylamido)benzoic acid

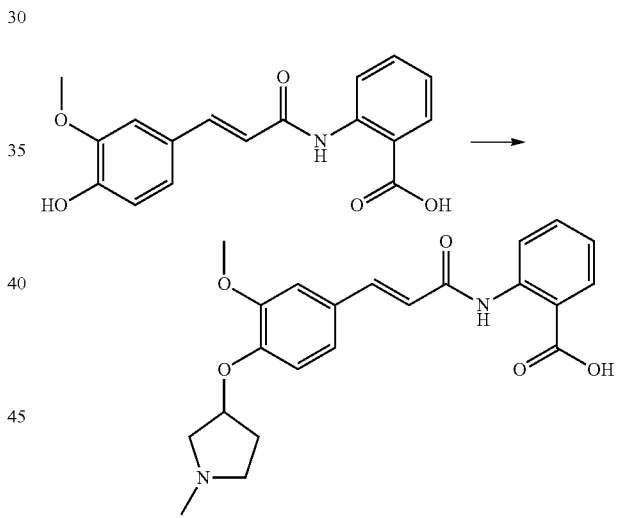

A mixture of 2-[[(E)-3-(4-hydroxy-3-methoxy-phenyl)prop-2-enoyl]amino]benzoic acid (100 mg, 0.32 mmol, 1.00 equiv), (1-methylpyrrolidin-3-yl) 4-methylbenzenesulfonate (130 mg, 0.48 mmol, 1.50 equiv) and potassium hydroxide (0.5 M, 2.55 mL, 4.00 equiv) in acetone (3 mL) was stirred at 60° C. for 16 hours. The reaction mixture was concentrated in vacuo and the residue purified by preparative HPLC to afford the desired product as a light yellow solid (72 mg, 44%) as a trifluoroacetate salt; $^1$H NMR (CDCl$_3$, 400 MHz) δ 11.48 (s, 1H), 8.87 (d, J=8.8 Hz, 1H), 8.18 (dd, J=8.0 Hz, J=1.2 Hz, 1H), 7.61-7.65 (m, 2H), 7.16 (t, J=8.0 Hz, 1H), 7.02-7.07 (m, 2H), 6.83 (d, J=8.0 Hz, 1H), 6.42 (d, J=15.6 Hz, 1H), 5.17 (s, 1H), 4.10-4.40 (m, 1H), 3.90-4.00 (m, 1H), 3.86 (s, 3H), 3.20-3.40 (m, 2H), 3.07 (s, 3H), 2.40-2.55 (m, 2H); MS (ESI+) m/z 397.3 (M+H)+; 98.8% purity; RT=1.93 min (Method 10).

(E)-2-(3-(4-((3,5-dimethylisoxazol-4-yl)methoxy)-3-methoxyphenyl)acrylamido)benzoic acid (52)

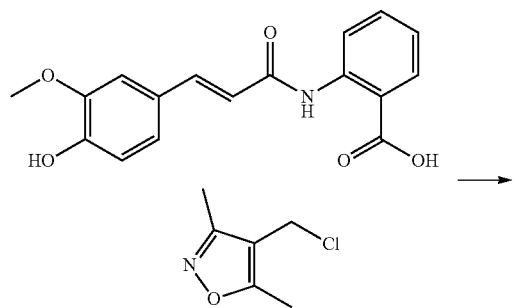

A solution of 2-[[(E)-3-(4-hydroxy-3-methoxy-phenyl)prop-2-enoyl]amino]benzoic acid (100 mg, 0.32 mmol, 1.00 equiv.), 4-(chloromethyl)-3,5-dimethyl-isoxazole (87 mg, 0.48 mmol, 1.50 equiv.) and potassium hydroxide (0.5 M, 2.6 mL, 4.00 equiv.) in acetone (2 mL) was stirred at 60° C. for 16 hours. The reaction mixture was concentrated in vacuo and the residue was purified by preparative HPLC to afford the desired product as a light yellow solid (65 mg, 47%); $^1$H NMR (DMSO-d$_6$, 400 MHz) δ 11.28 (s, 1H), 8.62 (d, J=8.4 Hz, 1H), 8.01 (d, J=8.0 Hz, 1H), 7.62 (t, J=8.0 Hz, 1H), 7.57 (d, J=15.2 Hz, 1H), 7.39 (s, 1H), 7.28 (d, J=8.0 Hz, 1H), 7.17 (t, J=7.6 Hz, 1H), 7.12 (d, J=8.4 Hz, 1H), 6.81 (d, J=15.6 Hz, 1H), 4.95 (s, 2H), 3.83 (s, 3H), 2.39 (s, 3H), 2.21 (s, 3H); MS (ESI+) m/z 423.1 (M+H)+; 98.2% purity; RT=1.49 min (Method 1).

(E)-2-(3-(3-methoxy-4-((1-methyl-1H-pyrazol-4-yl)methoxy)phenyl)acrylamido)benzoic acid (53)

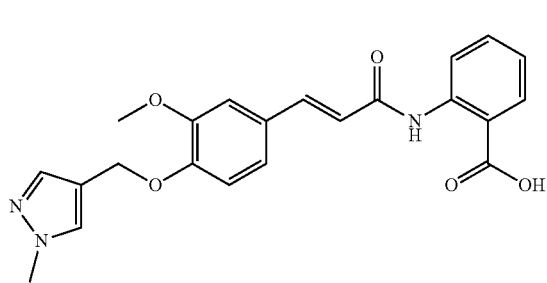 [SMILES: COc1cc(/C=C/C(=O)Nc2ccccc2C(=O)O)ccc1OCc1cnn(C)c1]

a) 3-methoxy-4-((1-methyl-1H-pyrazol-4-yl)methoxy)benzaldehyde

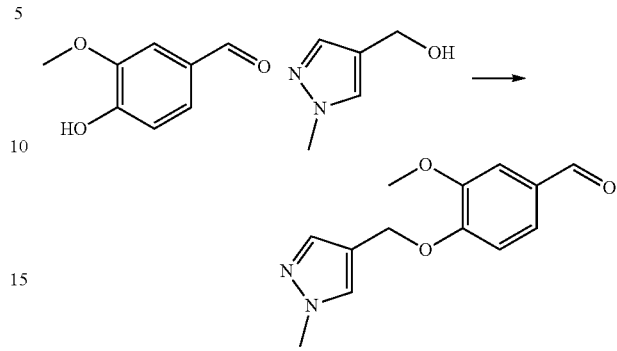

To a solution of (1-methylpyrazol-4-yl) methanol (300 mg, 2.68 mmol, 1.00 equiv.), 4-hydroxy-3-methoxybenzaldehyde (448 mg, 2.95 mmol, 1.10 equiv.) and triphenylphosphine (773 mg, 2.95 mmol, 1.10 equiv.) in tetrahydrofuran (3 mL) was added diisopropyl azodicarboxylate (573 uL, 2.95 mmol, 1.10 equiv.) drop-wise maintaining the temperature at 0° C. under a nitrogen atmosphere and the reaction mixture was stirred at 25° C. for 16 hours. The reaction mixture was diluted with water (20 mL) and the aqueous layer extracted with ethyl acetate (20 mL×3). The combined organic layer was washed with brine (20 mL), dried over sodium sulfate, filtered and concentrated in vacuo. The crude product was purified by preparative HPLC to afford the desired product as a brown solid. MS (ESI+) m/z 247.0 (M+H)+.

b) (E)-2-(3-(3-methoxy-4-((1-methyl-1H-pyrazol-4-yl)methoxy)phenyl)acrylamido)benzoic acid

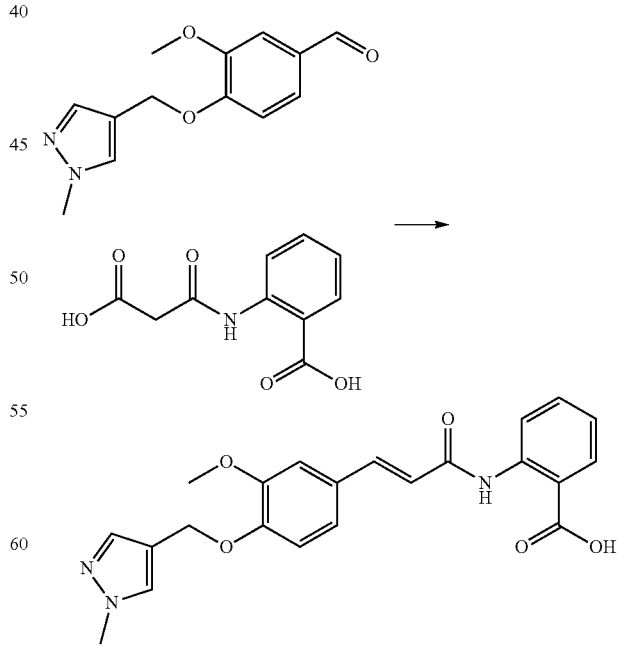

To a solution of 2-[(2-carboxyacetyl)amino]benzoic acid (80 mg, 0.36 mmol, 1.0 equiv.) and 3-methoxy-4-[(1-methylpyrazol-4-yl)methoxy]benzaldehyde (97 mg, 0.39 mmol, 1.1 equiv.) in chloroform (5 mL) was added piperidine (15 mg, 0.18 mmol, 0.5 equiv.) and the reaction mixture was stirred at 70° C. for 16 hours. The solvent was removed in vacuo and the residue was purified by preparative HPLC to give the desired product as a yellow solid (15 mg, 8%); $^1$H NMR (DMSO-$d_6$, 400 MHz) δ 11.63 (br. s, 1H), 8.62 (d, J=7.6 Hz, 1H), 8.01 (d, J=6.4 Hz, 1H), 7.79 (s, 1H), 7.40-7.70 (m, 3H), 7.35 (d, J=2.0 Hz, 1H), 7.25 (t, J=7.6 Hz, 1H), 7.00-7.18 (m, 2H), 6.76 (d, J=15.6 Hz, 1H), 4.97 (s, 2H), 3.82 (s, 3H), 3.80 (s, 3H); MS (ESI+) m/z 408.1 (M+H)+; 97.6% purity, RT 1.92 min (Method 10).

| Ex | Structure | Data | Method |
|---|---|---|---|
| 54 | 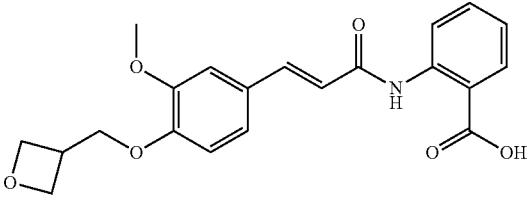<br>(E)-2-(3-(3-methoxy-4-(oxetan-3-ylmethoxy)phenyl)acrylamido) benzoic acid | $^1$H NMR (DMSO-$d_6$, 400 MHz) δ 11.29 (s, 1H), 8.63 (d, J = 8.4 Hz, 1H), 8.01 (d, J = 6.4 Hz, 1H), 7.61 (t, J = 10.0 Hz, 1H), 7.57 (d, J = 15.6 Hz, 1H), 7.38 (d, J = 2.0 Hz, 1H), 7.25 (d, J = 8.4 Hz, 1H), 7.17 (t, J = 8.0 Hz, 1H), 7.05 (d, J = 8.4 Hz, 1H), 6.80 (d, J = 15.6 Hz, 1H), 4.71 (dd, J = 8.0 Hz, J = 6.0 Hz, 2H), 4.41 (t, J = 6.0 Hz, 2H), 4.24 (d, J = 6.8 Hz, 2H), 3.84 (s, 3H), 3.30-3.40 (m, 1H); MS (ESI+) m/z 384.1 (M + H)+; 97.7% purity, RT 2.86 min (Method 12) | Prepared according to the method for 51 starting from 2-[[(E)-3-(4-hydroxy-3-methoxy-phenyl)prop-2-enoyl]amino] benzoic acid and oxetan-3-ylmethanol |
| 55 | 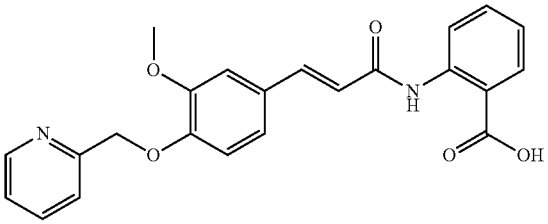<br>(E)-2-(3-(3-methoxy-4-(pyridin-2-ylmethoxy)phenyl)acrylamido) benzoic acid hydrochloric acid salt | $^1$H NMR (DMSO-$d_6$, 400 MHz) δ 11.19 (s, 1H), 8.62 (d, J = 8.4 Hz, 1H), 8.58 (d, J = 4.4 Hz, 1H), 8.00 (dd, J = 7.2 Hz, J = 2.0 Hz, 1H), 7.85 (t, J = 7.6 Hz, 1H), 7.61 (t, J = 7.6 Hz, 1H), 7.56 (d, J = 15.6 Hz, 1H), 7.52 (d, J = 7.6 Hz, 1H), 7.42 (d, J = 2.0 Hz, 1H), 7.36 (dd, J = 7.2 Hz, J = 4.2 Hz, 1H), 7.23 (dd, J = 8.4 Hz, J = 1.2 Hz, 1H), 7.17 (t, J = 8.0 Hz, 1H), 7.07 (d, J = 8.4 Hz, 1H), 6.80 (d, J = 15.6 Hz, 1H), 5.22 (s, 2H), 3.88 (s, 3H); MS (ESI+) m/z 405.1 (M + H)+; 95.8% purity, RT 2.63 min (Method 11) | Prepared according to the method for 51 starting from 2-[[(E)-3-(4-hydroxy-3-methoxy-phenyl)prop-2-enoyl]amino] benzoic acid and pyridine-2-ylmethanol |
| 56 | 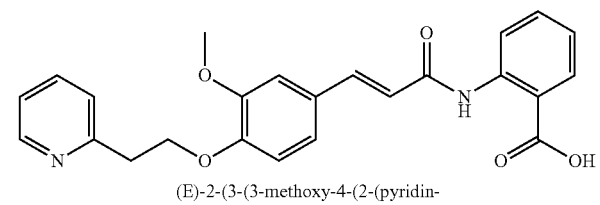<br>(E)-2-(3-(3-methoxy-4-(2-(pyridin-2-yl)ethoxy)phenyl)acrylamido) benzoic acid trifluoroacetic acid salt | $^1$H NMR (DMSO-$d_6$, 400 MHz) δ 11.28 (s, 1H), 8.62 (d, J = 8.0 Hz, 1H), 8.55 (d, J = 3.6 Hz, 1H), 8.00 (dd, J = 7.6 Hz, J = 1.2 Hz, 1H), 7.81 (t, J = 7.2 Hz, 1H), 7.61 (t, J = 8.0 Hz, 1H), 7.56 (d, J = 15.6 Hz, 1H), 7.45 (d, J = 7.6 Hz, 1H), 7.37 (d, J = 1.2 Hz, 1H), 7.31 (dd, J = 6.4 Hz, J = 5.2 Hz, 1H), 7.24 (dd, J = 8.8 Hz, J = 1.2 Hz, 1H), 7.17 (t, J = 7.6 Hz, 1H), 7.05 (d, J = 8.4 Hz, 1H), 6.79 (d, J = 15.6 Hz, 1H), 4.40 (t, J = 6.8 Hz, 2H), 3.80 (s, 3H), 3.24 (t, J = 6.8 Hz, 2H); MS (ESI+) m/z 419.1 (M + H)+; 93.9% purity, RT 2.49 min (Method 11) | Prepared according to the method for 51 starting from 2-[[(E)-3-(4-hydroxy-3-methoxy-phenyl)prop-2-enoyl]amino] benzoic acid and 2-(pyridin-2-yl)ethan-1-ol |
| 57 | 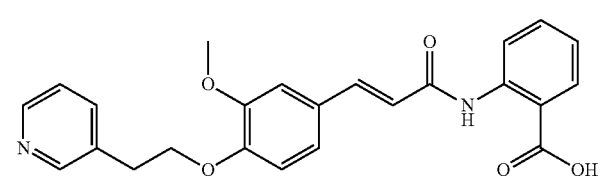<br>(E)-2-(3-(3-methoxy-4-(2-(pyridin-3-yl)ethoxy)phenyl)acrylamido) benzoic acid trifluoroacetic acid salt | $^1$H NMR (DMSO-$d_6$, 400 MHz) δ 11.28 (s, 1H), 8.64-8.60 (m, 2H), 8.52 (d, J = 4.0 Hz, 1H), 8.00 (dd, J = 7.6 Hz, J = 1.2 Hz, 1H), 7.94 (d, J = 7.6 Hz, 1H), 7.61 (t, J = 8.4 Hz, 1H), 7.56 (d, J = 15.6 Hz, 1H), 7.49 (dd, J = 7.6 Hz, J = 4.8 Hz, 1H), 7.38 (d, J = 2.0 Hz, 1H), 7.23 (dd, J = 8.0 Hz, J = 2.0 Hz, 1H), 7.17 (t, J = 7.6 Hz, 1H), 7.03 (d, J = 8.8 Hz, 1H), 6.80 (d, J = 15.6 Hz, 1H), 4.27 (t, J = 6.8 Hz, 2H), 3.82 (s, 3H), 3.12 (t, J = 6.8 Hz, 2H); MS (ESI+) m/z 419.3 (M + H)+; 99.1% purity, RT 1.61 min (Method 10) | Prepared according to the method for 51 starting from 2-[[(E)-3-(4-hydroxy-3-methoxy-phenyl)prop-2-enoyl]amino] benzoic acid and 2-(pyridin-3-yl)ethan-1-ol |

| Ex | Structure | Data | Method |
|---|---|---|---|
| 58 | 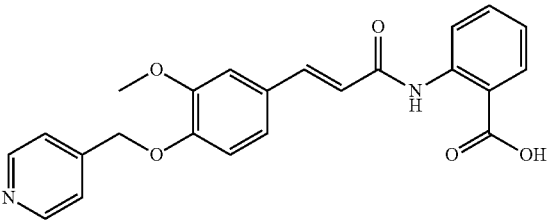<br>(E)-2-(3-(3-methoxy-4-(pyridin-4-ylmethoxy)phenyl)acrylamido) benzoic acid trifluoroacetic acid salt | $^1$H NMR (DMSO-d$_6$, 400 MHz) δ 11.30 (s, 1H), 8.75 (d, J = 6.4 Hz, 2H), 8.64 (d, J = 7.6 Hz, 1H), 8.02 (d, J = 6.4 Hz, 1H), 7.71 (d, J = 6.4 Hz, 2H), 7.62 (t, J = 8.4 Hz, 1H), 7.57 (d, J = 15.6 Hz, 1H), 7.46 (d, J = 1.2 Hz, 1H), 7.25 (d, J = 8.4 Hz, 1H), 7.17 (t, J = 7.6 Hz, 1H), 7.06 (d, J = 8.4 Hz, 1H), 6.83 (d, J = 15.6 Hz, 1H), 5.38 (s, 2H), 3.91 (s, 3H); MS (ESI+) m/z 405.3 (M + H)+; 99.6% purity, RT 1.99 min (Method 10) | Prepared according to the method for 51 starting from 2-[[(E)-3-(4-hydroxy-3-methoxy-phenyl)prop-2-enoyl]amino] benzoic acid and pyridin-4-ylmethanol |
| 59 | 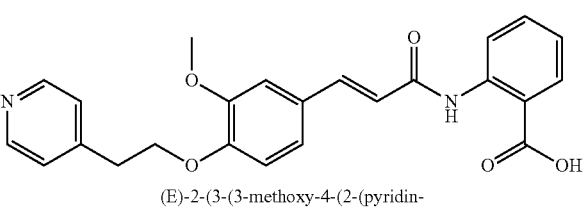<br>(E)-2-(3-(3-methoxy-4-(2-(pyridin-4-yl)ethoxy)phenyl)acrylamido) benzoic acid trifluoroacetic acid salt | $^1$H NMR (DMSO-d$_6$, 400 MHz) δ 11.28 (s, 1H), 8.78 (d, J = 6.4 Hz, 2H), 8.63 (d, J = 8.0 Hz, 1H), 8.01 (d, J = 8.0 Hz, 1H), 7.89 (d, J = 6.4 Hz, 2H), 7.62 (t, J = 8.0 Hz, 1H), 7.56 (d, J = 15.6 Hz, 1H), 7.39 (d, J = 1.2 Hz, 1H), 7.25 (d, J = 8.4 Hz, 1H), 7.17 (t, J = 7.6 Hz, 1H), 7.06 (d, J = 8.4 Hz, 1H), 6.80 (d, J = 15.6 Hz, 1H), 4.38 (t, J = 6.4 Hz, 2H), 3.82 (s, 3H), 3.32 (t, J = 6.0 Hz, 2H); MS (ESI+) m/z 419.1 (M + H)+; 98.8% purity, RT 2.49 min (Method 11) | Prepared according to the method for 51 starting from 2-[[(E)-3-(4-hydroxy-3-methoxy-phenyl)prop-2-enoyl]amino] benzoic acid and 2-(pyridin-4-yl)ethan-1-ol |
| 60 | 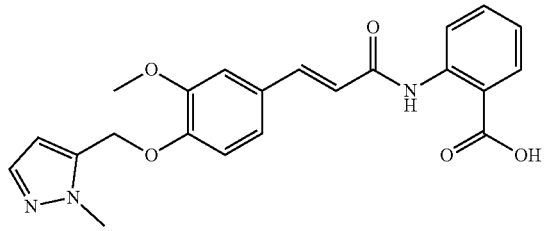<br>(E)-2-(3-(3-methoxy-4-((1-methyl-1H-pyrazol-5-yl)methoxy)phenyl)acrylamido) benzoic acid | $^1$H NMR (DMSO-d$_6$, 400 MHz) δ 11.74 (br. s, 1H), 8.64 (d, J = 9.2 Hz, 1H), 8.02 (d, J = 7.2 Hz, 1H), 7.55-7.59 (m, 2H), 7.38-7.41 (m, 2H), 7.24-7.27 (m, 1H), 7.15-7.18 (m, 2H), 6.80 (d, J = 15.2 Hz, 1H), 6.38 (s, 1H), 5.21 (s, 2H), 3.85 (s, 3H); MS (ESI+) m/z 408.3 (M + H)+; 95.9% purity, RT 1.94 min (Method 10) | Prepared according to the method for 52 starting from 2-[[(E)-3-(4-hydroxy-3-methoxy-phenyl)prop-2-enoyl]amino] benzoic acid and 5-(chloromethyl)-1-methyl-1H-pyrazole |
| 61 | 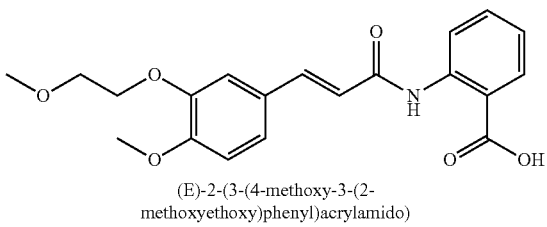<br>(E)-2-(3-(4-methoxy-3-(2-methoxyethoxy)phenyl)acrylamido) benzoic acid | $^1$H NMR (CDCl$_3$, 400 MHz) δ 11.23 (s, 1H), 8.86 (d, J = 8.4 Hz, 1H), 8.13 (d, J = 8.0 Hz, 1H), 7.67 (d, J = 15.6 Hz, 1H), 7.63 (t, J = 7.6 Hz, 1H), 7.16-7.10 (m, 3H), 6.83 (d, J = 8.4 Hz, 1H), 6.41 (d, J = 15.2 Hz, 1H), 4.25 (t, J = 4.4 Hz, 2H), 3.87 (t, J = 4.8 Hz, 2H), 3.82 (s, 3H), 3.51 (s, 3H); MS (ESI+) m/z 372.1 (M + H)+; 99% purity, RT 2.9 min (Method 11) | Prepared according to the method for 52 starting from (E)-2-(3-(3-hydroxy-4-methoxyphenyl) acrylamido)benzoic acid and 1-bromo-2-methoxyethane |
| 62 | 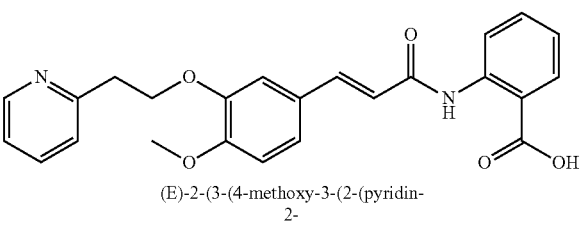<br>(E)-2-(3-(4-methoxy-3-(2-(pyridin-2-yl)ethoxy)phenyl)acrylamido) benzoic acid trifluoroacetic acid salt | $^1$H NMR (CD$_3$OD, 400 MHz) δ 8.74 (d, J = 5.2 Hz, 1H), 8.69 (d, J = 8.4 Hz, 1H), 8.44 (t, J = 8.0 Hz, 1H), 8.12 (d, J = 7.6 Hz, 1H), 8.03 (d, J = 8.0 Hz, 1H), 7.86 (t, J = 6.4 Hz, 1H), 7.62-7.56 (m, 2H), 7.27-7.24 (m, 2H), 7.17 (t, J = 7.6 Hz, 1H), 6.98 (d, J = 8.0 Hz, 1H), 6.60 (d, J = 15.6 Hz, 1H), 4.48 (t, J = 5.2 Hz, 2H), 3.81 (s, 3H), 3.52 (t, J = 4.8 Hz, 2H); MS (ESI+) m/z 419.2 (M + H)+; 95.1% purity, RT 2.52 min (Method 11) | Prepared according to the method for 51 starting from 2-[[(E)-(E)-2-(3-(3-hydroxy-4-methoxyphenyl) acrylamido)benzoic acid and 2-(pyridin-2-yl)ethan-1-ol |

| Ex | Structure | Data | Method |
|---|---|---|---|
| 63 | 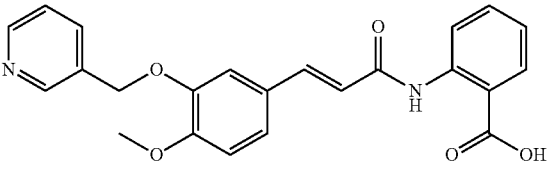<br>(E)-2-(3-(4-methoxy-3-(pyridin-3-ylmethoxy)phenyl)acrylamido)benzoic acid trifluoroacetic acid salt | $^1$H NMR (CD$_3$OD, 400 MHz) δ 8.95 (s, 1H), 8.78 (d, J = 5.6 Hz, 1H), 8.71 (d, J = 8.4 Hz, 1H), 8.61 (d, J = 8.0 Hz, 1H), 8.13 (d, J = 6.6 Hz, 1H), 7.98-8.02 (m, 1H), 7.65-7.59 (m, 2H), 7.44 (d, J = 1.2 Hz, 1H), 7.33 (d, J = 4.8 Hz, 1H), 7.17 (t, J = 7.6 Hz, 1H), 7.09 (d, J = 8.4 Hz, 1H), 6.66 (d, J = 15.6 Hz, 1H), 5.39 (s, 2H), 3.92 (s, 3H); MS (ESI+) m/z 405.1 (M + H)+; 93.4% purity, RT 1.54 min (Method 10) | Prepared according to the method for 51 starting from 2-[[(E)-(E)-2-(3-(3-hydroxy-4-methoxyphenyl)acrylamido)benzoic acid and pyridin-3-ylmethanol |
| 64 | 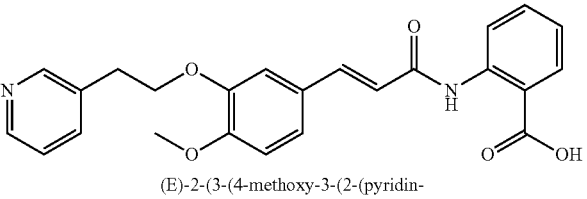<br>(E)-2-(3-(4-methoxy-3-(2-(pyridin-3-yl)ethoxy)phenyl)acrylamido)benzoic acid trifluoroacetic acid salt | $^1$H NMR (CD$_3$OD, 400 MHz) δ 8.91 (s, 1H), 8.74 (d, J = 5.2 Hz, 1H), 8.67-8.63 (m, 2H), 8.09 (dd, J = 8.0 Hz, J = 1.2 Hz, 1H), 8.02 (dd, J = 7.6 Hz, J = 6.0 Hz, 1H), 7.58-7.52 (m, 2H), 7.23-7.12 (m, 3H), 6.95 (d, J = 8.4 Hz, 1H), 6.56 (d, J = 15.6 Hz, 1H), 4.36 (t, J = 4.8 Hz, 2H), 3.83 (s, 3H), 3.36 (t, J = 4.8 Hz, 2H); MS (ESI+) m/z 419.2 (M + H)+; 95.3% purity, RT 2.54 min (Method 12) | Prepared according to the method for 51 starting from 2-[[(E)-(E)-2-(3-(3-hydroxy-4-methoxyphenyl)acrylamido)benzoic acid and 2-(pyridin-3-yl)ethan-1-ol |
| 65 | 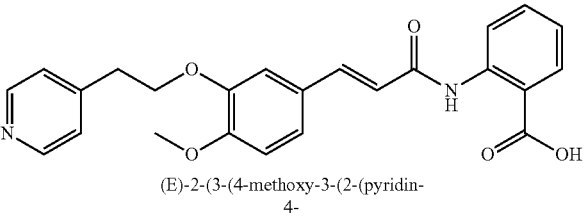<br>(E)-2-(3-(4-methoxy-3-(2-(pyridin-4-yl)ethoxy)phenyl)acrylamido)benzoic acid trifluoroacetic acid salt | $^1$H NMR (CD$_3$OD, 400 MHz) δ 8.76 (d, J = 8.0 Hz, 2H), 8.70 (d, J = 11.2 Hz, 1H), 8.15-8.05 (m, 3H), 7.63-7.56 (m, 2H), 7.29 (s, 1H), 7.26 (d, J = 11.2 Hz, 1H), 7.17 (t, J = 7.6 Hz, 1H), 7.00 (d, J = 11.2 Hz, 1H), 6.63 (d, J = 16.8 Hz, 1H), 4.46 (t, J = 7.6 Hz, 2H), 3.84 (s, 3H), 3.45 (t, J = 7.2 Hz, 2H); MS (ESI+) m/z 419.1 (M + H)+; 96.1% purity, RT 2.52 min (Method 12) | Prepared according to the method for 51 starting from 2-[[(E)-(E)-2-(3-(3-hydroxy-4-methoxyphenyl)acrylamido)benzoic acid and 2-(pyridin-4-yl)ethan-1-ol |
| 66 | 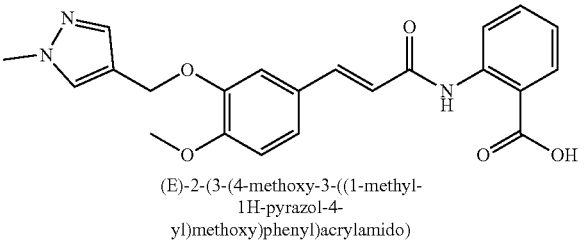<br>(E)-2-(3-(4-methoxy-3-((1-methyl-1H-pyrazol-4-yl)methoxy)phenyl)acrylamido)benzoic acid | $^1$H NMR (DMSO-d$_6$, 400 MHz) δ 11.60 (br. s, 1H), 8.63 (d, J = 8.4 Hz, 1H), 8.01 (d, J = 7.2 Hz, 1H), 7.81 (s, 1H), 7.64-7.40 (m, 4H), 7.24 (t, J = 8.4 Hz, 1H), 7.15 (t, J = 7.6 Hz, 1H), 6.99 (t, J= 8.0 Hz, 1H), 6.79 (d, J = 15.6 Hz, 1H), 5.01 (s, 2H), 3.83 (s, 3H), 3.78 (s, 3H); MS (ESI+) m/z 408.2 (M + H)+; 96.8% purity, RT 1.94 min (Method 10) | Prepared according to the method for 53 starting from 3-hydroxy-4-methoxy-benzaldehyde |
| 67 | 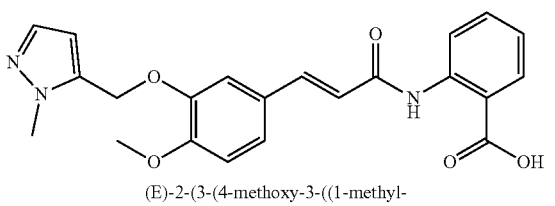<br>(E)-2-(3-(4-methoxy-3-((1-methyl-1H-pyrazol-5-yl)methoxy)phenyl)acrylamido)benzoic acid | $^1$H NMR (CD$_3$OD, 400 MHz) δ 8.70 (d, J = 11.2 Hz, 1H), 8.12 (d, J = 9.6 Hz, 1H), 7.66-7.50 (m, 2H), 7.45-7.39 (m, 2H), 7.27 (d, J = 10.8 Hz, 1H), 7.16 (t, J = 10.4 Hz, 1H), 7.03 (d, J = 11.2 Hz, 1H), 6.63 (d, J = 16.8 Hz, 1H), 6.40 (s, 1H), 5.22 (s, 2H), 3.95 (s, 3H), 3.87 (s, 3H); MS (ESI+) m/z 408.1 (M + H)+; 97.4% purity, RT 2.95 min (Method 12) | Prepared according to the method for 52 starting from 2-[[(E)-(E)-2-(3-(3-hydroxy-4-methoxyphenyl)acrylamido)benzoic acid and 5-(chloromethyl)-1-methyl-1H-pyrazole |

(E)-2-(3-(3-methoxy-4-((4-methylpiperazin-1-yl)methyl)phenyl)acrylamido)benzoic acid (68)

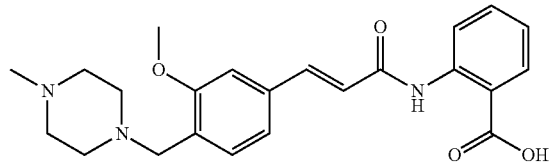 [SMILES: COc1cc(/C=C/C(=O)Nc2ccccc2C(=O)O)ccc1CN1CCN(C)CC1]

a)
1-(4-bromo-2-methoxybenzyl)-4-methylpiperazine

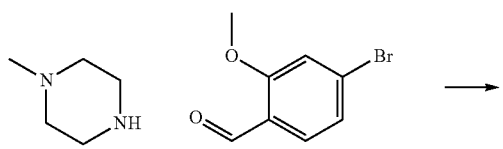

To a solution of 4-bromo-2-methoxy-benzaldehyde (500 mg, 2.3 mmol, 1.0 equiv.), 1-methylpiperazine (389 μL, 3.5 mmol, 1.5 equiv.) and acetic acid (40 μL, 0.699 mmol, 0.3 equiv.) in 1,2-dichloroethane (10 mL) was added sodium triacetoxyborohydride (741 mg, 3.5 mmol, 1.5 equiv.) portion-wise maintaining the temperature at 0° C. The mixture was stirred at 25° C. for 3 hours and was then quenched with saturated aqueous sodium bicarbonate solution (20 mL). Then the mixture was extracted with dichloromethane (20 mL×3) and the combined organic layer washed with brine (20 mL), dried over sodium sulfate, filtered and concentrated to give the desired product as yellow oil (560 mg, crude) which was used without further purification; 1H NMR (CDCl₃, 400 MHz) δ 7.23 (d, J=8.0 Hz, 1H), 7.07 (dd, J=8.0 Hz, J₂=2.0 Hz 1H), 6.99 (d, J=1.6 Hz, 1H), 3.81 (s, 3H), 3.50 (s, 2H), 2.60-2.35 (m, 8H), 2.29 (s, 3H).

b) 3-methoxy-4-((4-methylpiperazin-1-yl)methyl)benzaldehyde

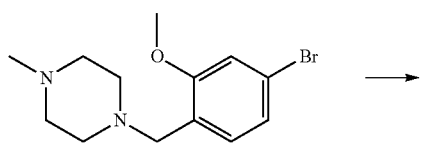

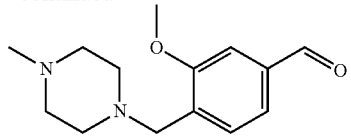

To a solution of 1-(4-bromo-2-methoxybenzyl)-4-methylpiperazine (250 mg, 0.836 mmol, 1.0 equiv.) in anhydrous tetrahydrofuran (10 mL) at −78° C. under a nitrogen atmosphere was added n-butyllithium (2.5 M in hexane, 1.00 mL, 3.0 equiv.) via syringe drop-wise over a period of 10 minutes. The resulting solution was stirred at −78° C. for 10 minutes and then N,N-dimethylformamide (644 μL, 8.4 mmol, 10.0 equiv.) was added at −78° C. over 10 minutes. The mixture was then stirred at 25° C. for 1 hour. The reaction was quenched with saturated ammonium chloride aqueous solution (10 mL) and the resultant mixture was extracted with ethyl acetate (20 mL×3). The combined organic layer was washed with brine (20 mL), dried over sulfate sodium, filtered and concentrated to give the desired product as yellow oil (225 mg, crude) which was used without further purification; MS (ESI+) m/z 249.1 (M+H)+.

c) (E)-2-(3-(3-methoxy-4-((4-methylpiperazin-1-yl)methyl)phenyl)acrylamido)benzoic acid

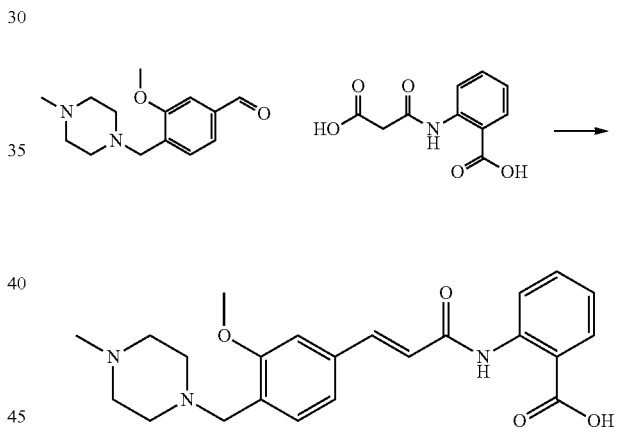

To a solution of 2-[(2-carboxyacetyl)amino]benzoic acid (100 mg, 0.448 mmol, 1.0 equiv.) and 3-methoxy-4-((4-methylpiperazin-1-yl)methyl)benzaldehyde (223 mg, 0.896 mmol, 2.0 equiv.) in toluene (5 mL) was added piperidine (44 μL, 0.448 mmol, 1.0 equiv.) and the reaction mixture stirred at 110° C. for 16 hours. The mixture was concentrated in vacuo and the residue purified by preparative HPLC to give the desired product as a white solid (15 mg, 8%) as the trifluoroacetic acid salt; $^1$H NMR (CD₃OD, 400 MHz) δ 8.71 (d, J=8.0 Hz, 1H), 8.14 (d, J=6.4 Hz, 1H), 7.69 (d, J=15.6 Hz, 1H), 7.61 (t, J=7.2 Hz, 1H), 7.43 (d, J=7.6 Hz, 1H), 7.34 (s, 1H), 7.29 (d, J=8.0 Hz, 1H), 7.19 (t, J=8.0 Hz, 1H), 6.84 (d, J=16.0 Hz, 1H), 3.97 (s, 2H), 3.95 (s, 3H), 3.30-3.20 (m, 4H), 3.10-2.90 (m, 4H), 2.85 (s, 3H). MS (ESI+) m/z 410.2 (M+H)+; 96.5% purity, RT 1.89 min (Method 11).

| Ex | Structure | Data | Method |
|---|---|---|---|
| 69 | -2-(3-(3-methoxy-4-(morpholinomethyl)phenyl)acrylamido)benzoic acid trifluoroacetic acid salt | $^1$H NMR (DMSO-$d_6$, 400 MHz) δ 11.23 (s, 1H), 8.59 (d, J = 8.0 Hz, 1H), 8.03 (dd, J = 8.0 Hz, J = 2.0 Hz, 1H), 7.67-7.55 (m, 2H), 7.52-7.43 (m, 2H), 7.36 (d, J = 7.6 Hz, 1H), 7.19 (t, J = 8.0 Hz, 1H), 6.93 (d, J = 16.0 Hz, 1H), 4.22 (s, 2H), 3.96 (s, 3H), 3.81 (br. s, 4H), 3.11 (br. s, 4H). MS (ESI+) m/z 397.1 (M + H)+; 95.1% purity, RT 5.41 min (Method 4) | Prepared according to the method for 68 starting from 4-bromo-2-methoxybenzaldehyde and morpholine |

(E)-2-(3-(4-methoxy-3-(((1-methylpiperidin-4-yl)oxy)methyl)phenyl)acrylamido)benzoic acid (70)

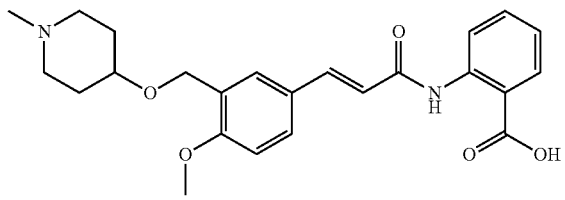 [SMILES: COc1ccc(/C=C/C(=O)Nc2ccccc2C(=O)O)cc1COC1CCN(C)CC1]

a) 4-bromo-2-(chloromethyl)-1-methoxybenzene

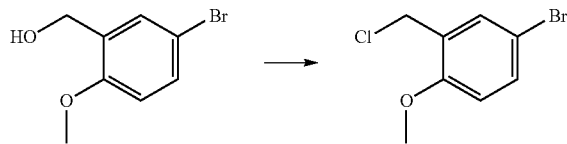

To the solution of (4-bromo-2-methoxy-phenyl)methanol (2.9 g, 13.4 mmol, 1.0 equiv.) and N,N-dimethylformamide (51 μL, 0.668 mmol, 0.05 equiv.) in dichloromethane (30 mL) was added thionyl chloride (1.5 mL, 20 mmol, 1.5 equiv.) drop-wise maintaining the temperature at 0° C. The reaction mixture was then stirred at 40° C. for 2 hours, cooled to room temperature and concentrated in vacuo. The residue was diluted with dichloromethane (30 mL) and the resulting solution washed with saturated aqueous sodium bicarbonate (10 mL) and brine (10 mL), dried over sulfate sodium, filtered and concentrated to give the desired product as a light yellow solid (1.2 g) which was used without further purification; $^1$H NMR (CDCl$_3$, 400 MHz) δ 7.49 (d, J=2.4 Hz, 1H), 7.41 (dd, J=8.8 Hz, J=2.0 Hz, 1H), 6.78 (d, J=8.8 Hz, 1H), 4.60 (s, 2H), 3.87 (s, 3H).

b) 4-((5-bromo-2-methoxybenzyl)oxy)-1-methylpiperidine

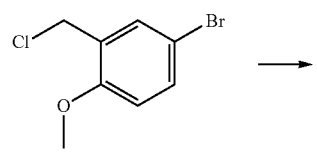

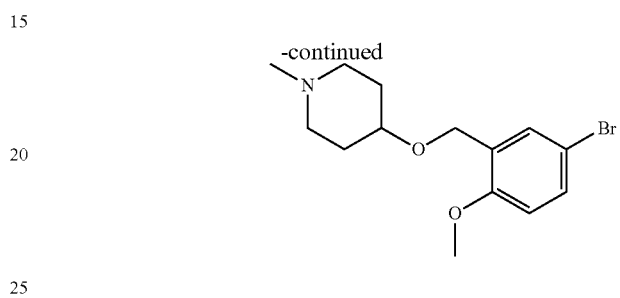

To a solution of 1-methylpiperidin-4-ol (178 μL, 1.5 mmol, 1.2 equiv.) in tetrahydrofuran (5 mL) was added sodium hydride (76.4 mg, 1.9 mmol, 60% purity in mineral oil, 1.5 equiv.) at 0° C. The mixture was stirred at 25° C. for 1 hour. 4-Bromo-2-(chloromethyl)-1-methoxybenzene (300 mg, 1.3 mmol, 1.0 equiv.) was then added and the mixture stirred for 11 hours at 60° C. The reaction was quenched by saturated aqueous ammonium chloride (10 mL) under stirring and extracted with ethyl acetate (5 mL×3). The combined organic layer was washed with brine (10 mL), dried over sulfate sodium, filtered and concentrated to give a residue which was purified by column chromatography (silica gel, dichloromethane:methanol=100:1 to 10:1) to give the desired product as light yellow oil (270 mg); $^1$H NMR (CDCl$_3$, 400 MHz) δ 7.53 (d, J=3.2 Hz, 1H), 7.34 (dd, J=7.6 Hz, J=3.2 Hz, 1H), 6.71 (d, J=13.6 Hz, 1H), 4.52 (s, 2H), 3.80 (s, 3H), 3.40-3.50 (m, 1H), 2.80-2.65 (m, 2H), 2.30 (s, 3H), 2.30-2.10 (m, 2H), 2.05-1.90 (m, 2H), 1.85-1.65 (m, 2H).

c) 4-methoxy-3-(((1-methylpiperidin-4-yl)oxy)methyl)benzaldehyde

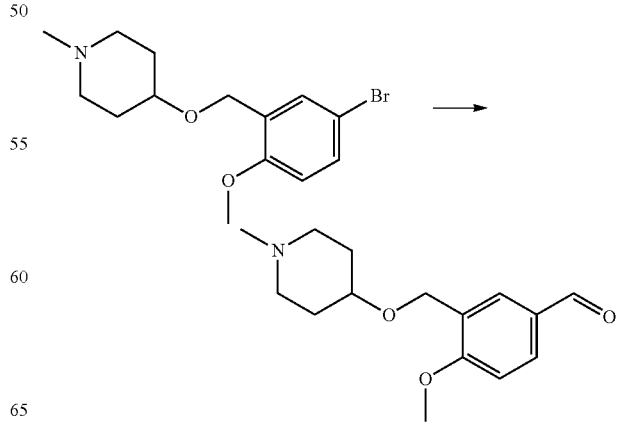

121

The title compound was prepared according to the procedure described for the synthesis of 3-methoxy-4-((4-methylpiperazin-1-yl)methyl)benzaldehyde starting from 4-((5-bromo-2-methoxybenzyl)oxy)-1-methylpiperidine. MS (ESI+) m/z 264.1 (M+H)+.

d) (E)-2-(3-(4-methoxy-3-(((1-methylpiperidin-4-yl)oxy)methyl)phenyl)acrylamido)benzoic acid

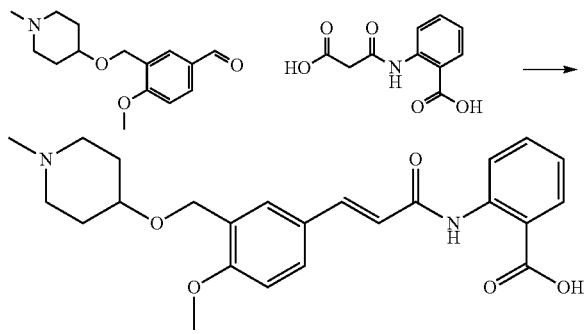

The title compound was prepared as the trifluoroacetic acid salt according to the procedure described for the synthesis of (E)-2-(3-(3-methoxy-4-((4-methylpiperazin-1-yl)methyl)phenyl)acrylamido)benzoic acid (68) starting from 2-[(2-carboxyacetyl)amino]benzoic acid and 4-methoxy-3-(((1-methylpiperidin-4-yl)oxy)methyl)benzaldehyde (11%); $^1$H NMR (DMSO-$d_6$, 400 MHz, performed at 80° C.) δ 11.17 (br. s, 1H), 8.58 (d, J=10.8 Hz, 1H), 8.02 (d, J=8.4 Hz, 1H), 7.70-7.55 (m, 4H), 7.18-7.05 (m, 2H), 6.65 (d, J=20.8 Hz, 1H), 4.57 (s, 2H), 3.88 (s, 3H), 3.75 (br.s, 1H, partially obscured by water signal), 3.25-3.10 (m, 4H, partially obscured by water signal), 2.80 (s, 3H), 2.10-1.80 (m, 4H); MS (ESI+) m/z 425.2 (M+H)+; 98% purity, RT 2.52 min (Method 11).

122

(E)-2-(3-(4-methoxy-3-(methoxymethyl)phenyl)acrylamido)benzoic acid (73)

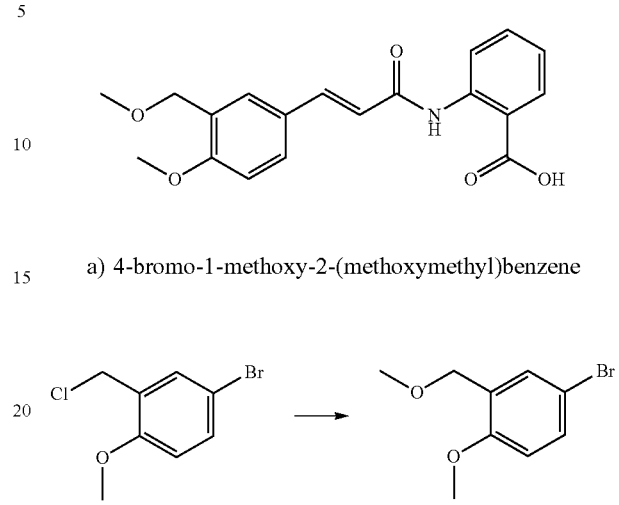

a) 4-bromo-1-methoxy-2-(methoxymethyl)benzene

To a solution of 4-bromo-2-(chloromethyl)-1-methoxybenzene (600 mg, 2.6 mmol, 1.0 equiv.) in tetrahydrofuran (5 mL) was added sodium methoxide (165 mg, 3.1 mmol, 1.2 equiv.) and the resultant mixture stirred under reflux for 12 hours. The reaction mixture was concentrated under vacuum to give a residue which was diluted with ethyl acetate (10 mL) and washed with water (10 mL×3). The combined organic layer was washed with brine (10 mL×2), dried over sodium sulfate, filtered and concentrated to give the desired product as yellow oil (430 mg) which was used without further purification; $^1$H NMR (CDCl$_3$, 400 MHz) δ 7.49 (d, J=2.0 Hz, 1H), 7.36 (dd, J=8.8 Hz, J=2.4 Hz, 1H), 6.74 (d, J=7.6 Hz, 1H), 4.46 (s, 2H), 3.82 (s, 3H), 3.44 (s, 3H).

| Ex | Structure | Data | Method |
|---|---|---|---|
| 71 | (E)-2-(3-(4-methoxy-3-((prop-2-yn-1-yloxy)methyl)phenyl)acrylamido)benzoic acid | $^1$H NMR (CD$_3$OD, 400 MHz) δ 8.70 (d, J = 8.0 Hz, 1H), 8.12 (d, J = 7.2 Hz, 1H), 7.68-7.55 (m, 4H), 7.16 (t, J = 7.6 Hz, 1H), 7.03 (d, J = 7.6 Hz, 1H), 6.61 (d, J = 16.0 Hz, 1H), 4.64 (s, 2H), 4.26 (d, J = 2.0 Hz, 2H), 3.89 (s, 3H), 2.91 (t, J = 2.0 Hz, 1H); MS (ESI+) m/z 388.1 (M + Na)+; 99% purity, RT 2.13 min (Method 10) | Prepared according to the method for 70 starting from 4-bromo-2-(chloromethyl)-1-methoxybenzene and prop-2-yn-1-ol |
| 72 | (E)-2-(3-(3-methoxy-4-((prop-2-yn-1-yloxy)methyl)phenyl)acrylamido)benzoic acid | $^1$H NMR (DMSO-$d_6$, 400 MHz) δ 11.45 (br. s, 1H), 8.61 (d, J = 8.4 Hz, 1H), 8.01 (d, J = 8.0 Hz, 1H), 7.64-7.56 (m, 2H), 7.39 (s, 1H), 7.35-7.30 (m, 2H), 7.18 (t, J = 7.6 Hz, 1H), 6.94 (d, J = 15.6 Hz, 1H), 4.54 (s, 2H), 4.23 (d, J = 2.4 Hz, 2H), 3.88 (s, 3H), 3.48 (t, J = 2.0 Hz, 1H); MS (ESI+) m/z 366.2 (M + H)+; 97.8% purity, RT 2.18 min (Method 10) | Prepared according to the method for 70 starting from 4-bromo-1-(chloromethyl)-2-methoxybenzene and prop-2-yn-1-ol | b) 4-methoxy-3-(methoxymethyl)benzaldehyde

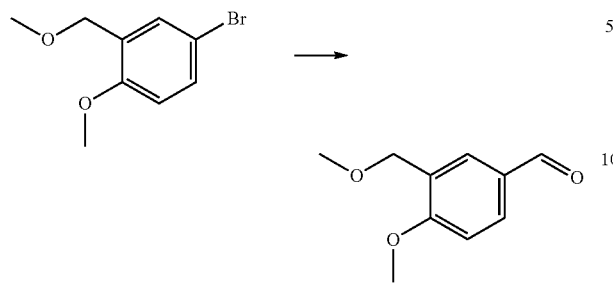

The title material was prepared according to the procedure described for the synthesis of 4-methoxy-3-((4-methylpiperazin-1-yl)methyl)benzaldehyde starting from 4-bromo-1-methoxy-2-(methoxymethyl)benzene. $^1$H NMR (CDCl$_3$, 400 MHz) δ 9.91 (s, 1H), 7.92 (s, 1H), 7.84 (dd, J=8.4 Hz, J=2.0 Hz, 1H), 6.99 (d, J=8.4 Hz, 1H), 4.53 (s, 2H), 3.94 (s, 3H), 3.47 (s, 3H).

c) (E)-2-(3-(4-methoxy-3-(methoxymethyl)phenyl)acrylamido)benzoic acid

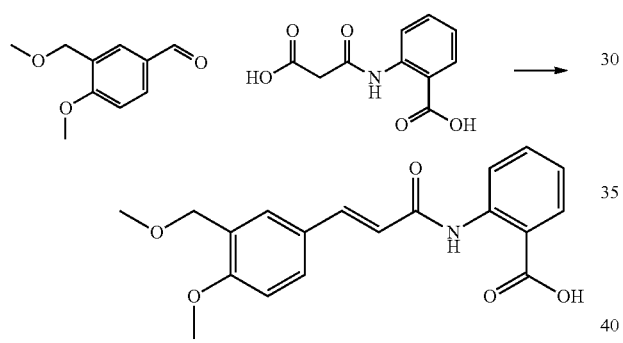

The title compound was prepared according to the procedure described for the synthesis of (E)-2-(3-(3-methoxy-4-((4-methylpiperazin-1-yl)methyl)phenyl)acrylamido)benzoic acid (68) starting from 2-[(2-carboxyacetyl)amino]benzoic acid and 4-methoxy-3-(methoxymethyl)benzaldehyde (25%); $^1$H NMR (CD$_3$OD, 400 MHz) δ 8.69 (d, J=8.0 Hz, 1H), 8.11 (d, J=7.2 Hz, 1H), 7.65-7.54 (m, 4H), 7.15 (t, J=7.6 Hz, 1H), 7.02 (d, J=8.8 Hz, 1H), 6.60 (d, J=15.6 Hz, 1H), 4.50 (s, 2H), 3.88 (s, 3H), 3.43 (s, 3H); MS (ESI+) m/z 342.1 (M+H)+; 99.2% purity, RT 2.94 min (Method 11).

(E)-2-(3-(4-methoxy-3-((prop-2-yn-1-ylamino)methyl)phenyl)acrylamido)benzoic acid (74)

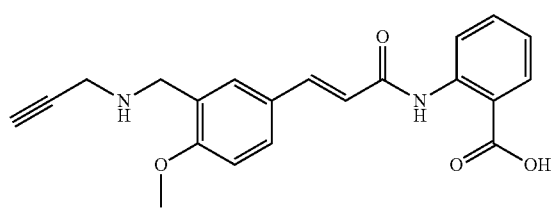 [SMILES: C#CCNCc1cc(/C=C/C(=O)Nc2ccccc2C(=O)O)ccc1OC]

124 a) N-(5-bromo-2-methoxybenzyl)prop-2-yn-1-amine

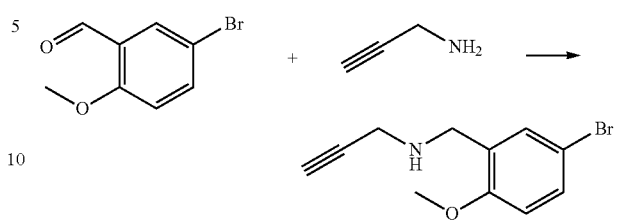

A mixture of 5-bromo-2-methoxybenzaldehyde (1.00 g, 4.65 mmol, 1.00 equiv.) and prop-2-yn-1-amine (298 uL, 4.65 mmol, 1.00 equiv.) in 1,2-dichloroethane (15.00 mL) was stirred for 0.5 hours at 25° C. Sodium triacetoxyborohydride (1.48 g, 6.98 mmol, 1.50 equiv.) and acetic acid (28 mg, 0.46 mmol, 0.10 equiv.) were then added at 0° C. and the resulting reaction stirred for 11.5 hours at 25° C. The reaction mixture was quenched with 1 N hydrochloric acid (10 mL) and the solvent was removed under reduced pressure. The residue was diluted with dichloromethane (30 mL) and washed with saturated sodium bicarbonate aqueous (10 mL), water (10 mL×3) and brine (10 mL). The organic layer was dried over sodium sulfate and concentrated under reduced pressure. The residue was purified by silica gel column chromatography (petroleum ether:ethyl acetate 1:0 to 10:1) to afford the desired product as colourless oil (1.10 g, 58%); 1H NMR (CDCl$_3$, 400 MHz) δ 7.39 (d, J=2.0 Hz, 1H), 7.36 (dd, J=8.8 Hz, J=2.4 Hz. 1H), 6.75 (d, J=8.4 Hz, 1H), 3.84 (s, 2H), 3.82 (s, 3H), 3.43 (d, J=2.4 Hz, 2H), 2.26 (t, J=2.4 Hz, 1H).

b) tert-butyl 5-bromo-2-methoxybenzyl(prop-2-yn-1-yl)carbamate

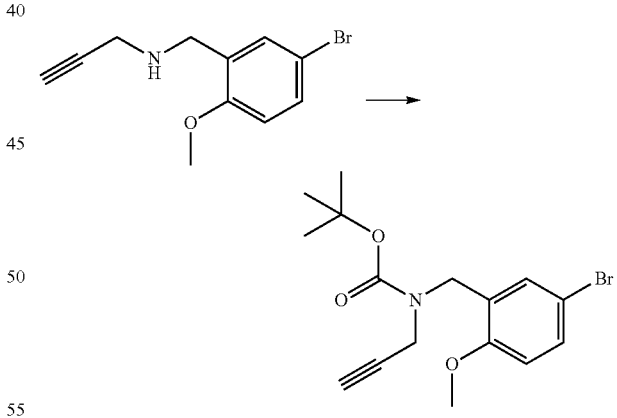

To the mixture of N-(5-bromo-2-methoxybenzyl)prop-2-yn-1-amine (0.500 g, 1.97 mmol, 1.00 equiv.), di-tert-butyl dicarbonate (1.29 g, 5.91 mmol, 3.00 equiv.) and 4-(dimethylamino)pyridine (0.024 g, 0.19 mmol, 0.10 equiv.) in methanol (10 mL) was added triethylamine (199.34 mg, 1.97 mmol, 1.00 equiv.) and the resulting reaction mixture was stirred for 6 hours at 25° C. The reaction mixture was concentrated under reduced pressure to give a residue which was purified by silica gel column chromatography (petroleum ether:ethyl acetate=50:1 to 20:1) to afford the desired product as colourless oil (0.41 g) which was used without further purification; 1H NMR (CDCl₃, 400 MHz) δ 7.34 (dd, J=8.8 Hz, J=2.4 Hz, 1H), 7.31 (d, J=2.0 Hz, 1H), 6.73 (d, J=8.4 Hz, 1H), 4.60-4.45 (m, 2H), 4.20-3.90 (m, 2H), 3.82 (s, 3H), 2.30-2.15 (m, 1H), 1.70-1.40 (m, 9H).

c) tert-butyl 5-formyl-2-methoxybenzyl(prop-2-yn-1-yl)carbamate

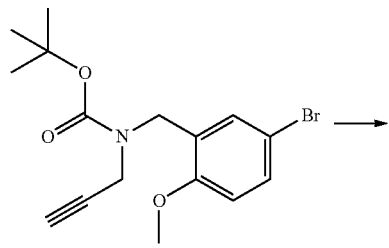

To a solution of tert-butyl 5-bromo-2-methoxybenzyl (prop-2-yn-1-yl)carbamate (0.300 g, 0.85 mmol, 1.00 equiv.) in tetrahydrofuran (5 mL) at −78° C. under a nitrogen atmosphere was added n-BuLi (2.5 M, 0.68 mL, 2.00 equiv.) slowly and the reaction stirred for 10 minutes at −78° C. Dimethyl formamide (619 mg, 8.47 mmol, 10.00 equiv.) was then added and the resulting solution stirred for 30 minutes at −78° C. The reaction mixture was warmed to 20° C., quenched by the addition of aqueous saturated ammonium chloride (5 mL) and extracted with ethyl acetate (5 mL×3). The combined organic layer was dried over sodium sulfate, and concentrated under reduced pressure to give a residue which was purified by silica gel column chromatography (petroleum ether:ethyl acetate 20:1 to 5:1) to afford the desired product as yellow oil (0.150 g) which was used without further purification; MS (ESI⁺) m/z 326.0 (M+Na)⁺.

d) (E)-2-(3-(3-(((tert-butoxycarbonyl)(prop-2-yn-1-yl)amino)methyl)-4-methoxyphenyl)-acrylamido) benzoic acid

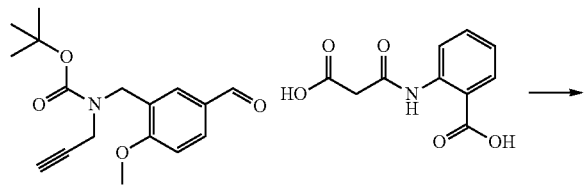

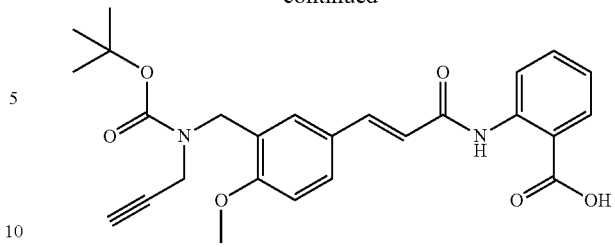

To a solution of 2-[(2-carboxyacetyl)amino]benzoic acid (100 mg, 0.45 mmol, 1.00 equiv.) and tert-butyl 5-formyl-2-methoxybenzyl(prop-2-yn-1-yl)carbamate (136 mg, 0.45 mmol, 1.00 equiv.) in chloroform (5 mL) was added piperidine (4 mg, 0.04 mmol, 0.10 equiv.) and the resulting mixture stirred at 60° C. for 12 hours. The reaction was concentrated under reduced pressure to afford the desired product as light yellow oil, which was used in the next step without further purification (250 mg); MS (ESI⁺) m/z 487.1 (M+Na)⁺.

e) (E)-2-(3-(4-methoxy-3-((prop-2-yn-1-ylamino) methyl)phenyl)acrylamido)benzoic acid

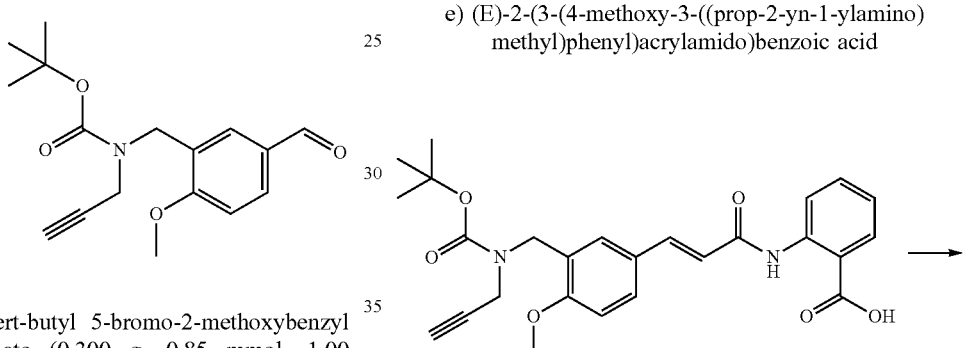

To a solution of (E)-2-(3-(3-(((tert-butoxycarbonyl)(prop-2-yn-1-yl)amino)methyl)-4-methoxyphenyl)-acrylamido) benzoic acid (250 mg, crude) in dioxane (5 mL) was added 4M hydrochloric acid in dioxane (3 mL) and the mixture stirred at 25° C. for 3 hours. The mixture was concentrated under reduced pressure and the residue was washed with methanol (5 mL×3) to afford the desired product as a yellow solid (56.2 mg, 24.6%) as the hydrochloride salt; ¹H NMR (DMSO-d₆, 400 MHz) δ 12.77 (br. s, 1H), 8.60 (d, J=8.0 Hz, 1H), 8.00 (d, J=6.8 Hz, 1H), 7.74 (s, 1H), 7.62 (d, J=8.4 Hz, 1H), 7.54 (d, J=15.2 Hz, 1H), 7.47 (t, J=7.2 Hz, 1H), 7.10-7.05 (m, 2H), 6.62 (d, J=15.6 Hz, 1H), 3.94 (s, 2H), 3.85 (s, 3H), 3.62 (s, 2H), 3.37 (s, 1H); MS (ESI+) m/z 365.3 (M+H)+; 94.4% purity; RT=1.54 min (Method 10).

| Ex | Structure | Data | Method |
|---|---|---|---|
| 75 | 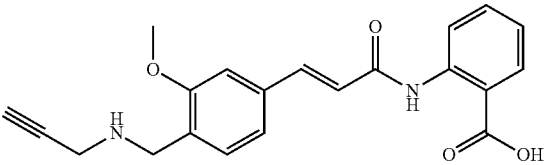<br>(E)-2-(3-(3-methoxy-4-((prop-2-yn-1-ylamino)methyl)phenyl)acrylamido)benzoic acid | $^1$H NMR (DMSO-$d_6$, 400 MHz) δ 11.37 (s, 1H), 9.47 (br. s, 1H), 8.61 (d, J = 8.4 Hz, 1H), 8.02 (d, J = 6.4 Hz, 1H), 7.66-7.60 (m, 2H), 7.49-7.45 (m, 2H), 7.37 (d, J = 7.6 Hz, 1H), 7.18 (t, J = 7.6 Hz, 1H), 7.02 (d, J = 15.6 Hz, 1H), 4.18 (s, 2H), 3.93-3.90 (m, 5H), 3.75 (t, J = 2.4 Hz, 1H); MS (ESI+) m/z 365.2 (M + H)+; 99.6% purity, RT 1.57 min (Method 10) | Prepared according to the method for 74 starting from 4-bromo-2-methoxy-benzaldehyde and prop-2-yn-1-amine |

(E)-N-(3-cyanophenyl)-3-[2-[2-(dimethylamino)ethoxy]-3-methoxy-4-prop-2-ynoxy-phenyl]prop-2-enamide (76)

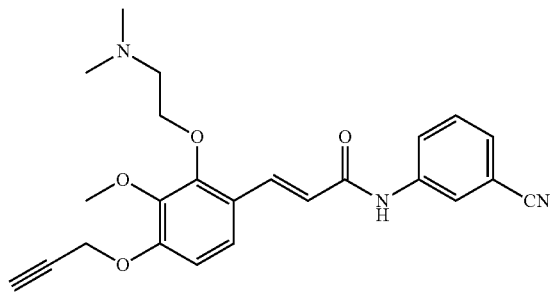 [SMILES: C#CCOc1ccc(/C=C/C(=O)Nc2cccc(C#N)c2)c(OCCN(C)C)c1OC]

a) 6-formyl-2-methoxy-3-(prop-2-yn-1-yloxy)phenyl acetate

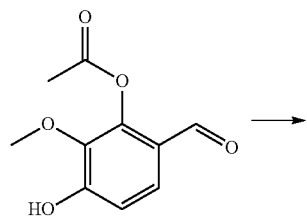

To a solution of (6-formyl-3-hydroxy-2-methoxyphenyl) acetate (0.38 g, 1.81 mmol 1.0 equiv., J. Med. Chem. 2000, 43, 1550-1562) and 3-bromoprop-1-yne (1.26 g, 9.03 mmol, 5.0 equiv.) in acetone (10 mL) was added potassium carbonate (1.50 g, 10.8 mmol, 6.0 equiv.) and the mixture stirred at 20° C. for 12 hours. The mixture was filtered and the filtrate concentrated in vacuo to give a residue which was purified by silica gel chromatography (petroleum ether:ethyl acetate 10:1 to 5:1) to give the desired product as light yellow gum (0.2 g) which was used without further purification; $^1$H NMR (CDCl$_3$, 400 MHz) δ 9.96 (s, 1H), 7.61 (d, J=8.0 Hz, 1H), 7.07 (d, J=8.0 Hz, 1H), 4.85 (d, J=2.4 Hz, 2H), 3.88 (s, 3H), 2.59 (t, J=2.4 Hz, 1H), 2.43 (s, 3H).

b) 2-hydroxy-3-methoxy-4-prop-2-ynoxy-benzaldehyde

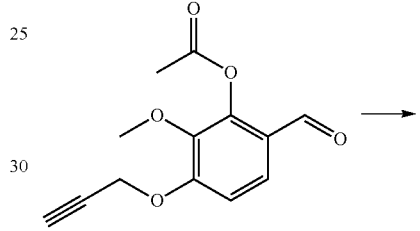

To a solution of (6-formyl-2-methoxy-3-prop-2-ynoxy-phenyl) acetate (2.10 g, 8.46 mmol, 1.0 equiv.) in water (10 mL) and tetrahydrofuran (10 mL) was added lithium hydroxide (0.79 g, 16.9 mmol, 2.0 equiv.) and the reaction stirred at 20° C. for 1 hour. The mixture was concentrated under reduced pressure to remove the tetrahydrofuran and the aqueous mixture was extracted with ethyl acetate (10 mL×2). The organic layer was concentrated under reduced pressure to give a residue, which was purified by silica gel chromatography (petroleum ether:ethyl acetate=15:1 to 10:1) to give the desired product as a light yellow solid (1.50 g, 86%); 1H NMR (CDCl$_3$, 400 MHz) δ 11.22 (s, 1H), 9.78 (s, 1H), 7.31 (d, J=8.8 Hz, 1H), 6.75 (d, J=8.8 Hz, 1H), 4.86 (s, 2H), 3.93 (s, 3H), 2.58 (t, J=2.4 Hz, 1H).

c) 2-[2-(dimethylamino)ethoxy]-3-methoxy-4-prop-2-ynoxybenzaldehyde

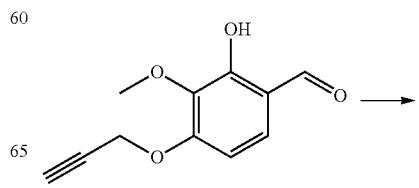

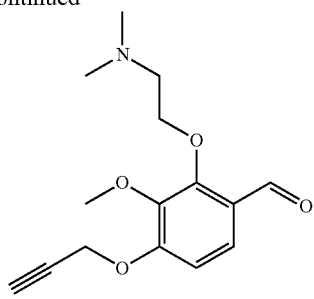

To a solution of 2-hydroxy-3-methoxy-4-prop-2-ynoxy-benzaldehyde (0.33 g, 1.60 mmol, 1.0 equiv.) in acetonitrile (8 mL) was added 2-chloro-N,N-dimethylethanamine (0.35 g, 2.40 mmol, 1.5 equiv.), sodium iodide (0.048 g, 320 umol, 0.2 equiv.) and caesium carbonate (1.30 g, 4.00 mmol, 2.5 equiv.) and the reaction stirred at 90° C. for 3 hours. The mixture was then cooled to 20° C., diluted with ethyl acetate (20 mL) and filtered. The filtrate was concentrated under reduced pressure to give a residue which was purified by silica gel chromatography (petroleum ether:ethyl acetate 5:1 to 1:1) to give the desired product as light yellow gum (0.3 g, 68%); $^1$H NMR (CDCl$_3$, 400 MHz) δ 10.33 (s, 1H), 7.62 (d, J=8.8 Hz, 1H), 6.89 (d, J=8.8 Hz, 1H), 4.83 (d, J=2.0 Hz, 2H), 4.29 (t, J=5.6 Hz, 2H), 3.91 (s, 3H), 2.71 (t, J=5.6 Hz, 2H), 2.57 (t, J=2.4 Hz, 1H), 2.32 (s, 6H).

d) (E)-3-[2-[2-(dimethylamino)ethoxy]-3-methoxy-4-prop-2-ynoxy-phenyl]prop-2-enoic acid

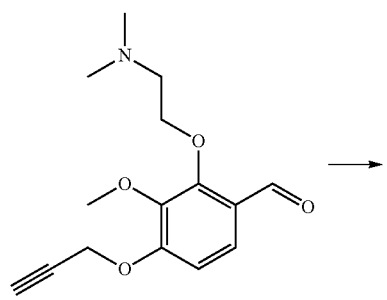

To a solution of 2-[2-(dimethylamino)ethoxy]-3-methoxy-4-prop-2-ynoxybenzaldehyde (0.22 g, 0.793 mmol, 1.0 equiv.) and malonic acid (0.165 g, 1.59 mmol, 2.0 equiv.) in pyridine (5 mL) was added piperidine (10.1 mg, 0.119 mmol, 0.15 equiv.) and the reaction stirred at 100° C. for 1 hour. The mixture was cooled and concentrated under reduced pressure. The residue was diluted with water (5 mL) and the pH adjusted to 9 by the addition of saturated sodium carbonate solution. The aqueous mixture was extracted with ethyl acetate (5 mL×4), filtered and concentrated to give a crude product as a light yellow solid (0.25 g) as the sodium salt which was used without further purification; $^1$H NMR (DMSO-d$_6$, 400 MHz) δ 7.74 (d, J=16.0 Hz, 1H), 7.53 (d, J=9.2 Hz, 1H), 6.97 (d, J=9.2 Hz, 1H), 6.47 (d, J=16.4 Hz, 1H), 4.92 (d, J=2.0 Hz, 2H), 4.20 (t, J=5.2 Hz, 2H), 3.80 (s, 3H), 3.66 (t, J=2.4 Hz, 1H), 3.19-3.17 (m, 2H), 2.65 (s, 6H).

e) (E)-N-(3-cyanophenyl)-3-[2-[2-(dimethylamino)ethoxy]-3-methoxy-4-prop-2-ynoxy-phenyl]prop-2-enamide

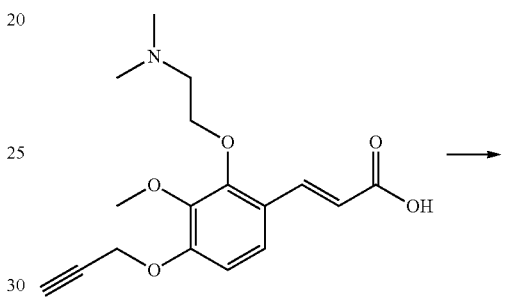

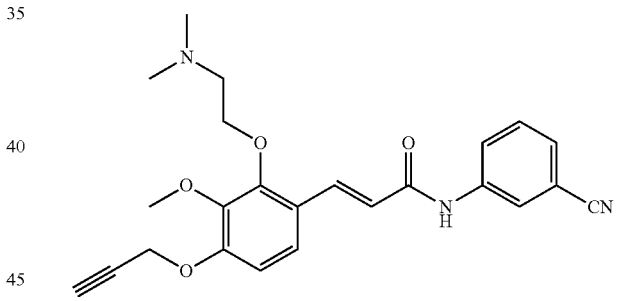

To a solution of (E)-3-[2-[2-(dimethylamino)ethoxy]-3-methoxy-4-prop-2-ynoxy-phenyl]prop-2-enoic acid (0.1 g, 0.313 mmol, 1.0 equiv.) and 3-aminobenzonitrile (0.037 g, 0.313 mmol, 1.0 equiv.) in pyridine (2 mL) was added phosphoryl chloride (29.10 µL, 0.313 mmol, 1.0 equiv.) at 0° C. and the mixture was stirred at 0° C. for 15 minutes. The mixture was concentrated in vacuo and the residue was purified by preparative HPLC to afford the desired compound as a light yellow solid (12 mg, 9%); 1H NMR (DMSO-d$_6$, 400 MHz) δ 10.49 (s, 1H), 8.23 (s, 1H), 7.88-7.83 (m, 2H), 7.56-7.52 (m, 2H), 7.38 (d, J=8.8 Hz, 1H), 6.98 (d, J=8.8 Hz, 1H), 6.73 (d, J=16.0 Hz, 1H), 4.91 (d, J=2.4 Hz, 2H), 4.06 (t, J=5.8 Hz, 2H), 3.78 (s, 3H), 3.65 (t, J=2.2 Hz, 1H), 2.63 (t, J=5.8 Hz, 2H), 2.22 (s, 6H); MS (ESI+) m/z 420.2 (M+H)+; 99.1% purity, RT 2.79 min (Method 8).

| Ex | Structure | Data | Method |
|---|---|---|---|
| 77 | ((E)-N-(2-cyanophenyl)-3-(2-(2-(dimethylamino)ethoxy)-3-methoxy-4-(prop-2-yn-1-yloxy)phenyl)acrylamide | ¹H NMR (DMSO-d₆, 400 MHz) δ 10.29 (s, 1H), 7.88-7.82 (m, 2H), 7.75-7.72 (m, 2H), 7.41 (d, J = 8.4 Hz, 1H), 7.38-7.33 (m, 1H), 6.99 (d, J = 8.8 Hz, 1H), 6.88 (d, J = 15.6 Hz, 1H), 4.91 (d, J = 2.4 Hz, 2H), 4.06 (t, J = 5.8 Hz, 2H), 3.78 (s, 3H), 3.65 (t, J = 2.4 Hz, 1H), 2.63 (t, J = 5.8 Hz, 2H), 2.22 (s, 6H); MS (ESI+) m/z 420.2 (M + H)+; 99% purity, RT 2.66 min (Method 8) | Prepared according to the method for 76 final step starting from (E)-3-[2-[2-(dimethylamino)-ethoxy]-3-methoxy-4-prop-2-ynoxy-phenyl]prop-2-enoic acid and 2-aminobenzonitrile |

(E)-2-(3-(2-(2-(dimethylamino)ethoxy)-3-methoxy-4-(prop-2-yn-1-yloxy)phenyl)acrylamido)-benzoic acid (78)

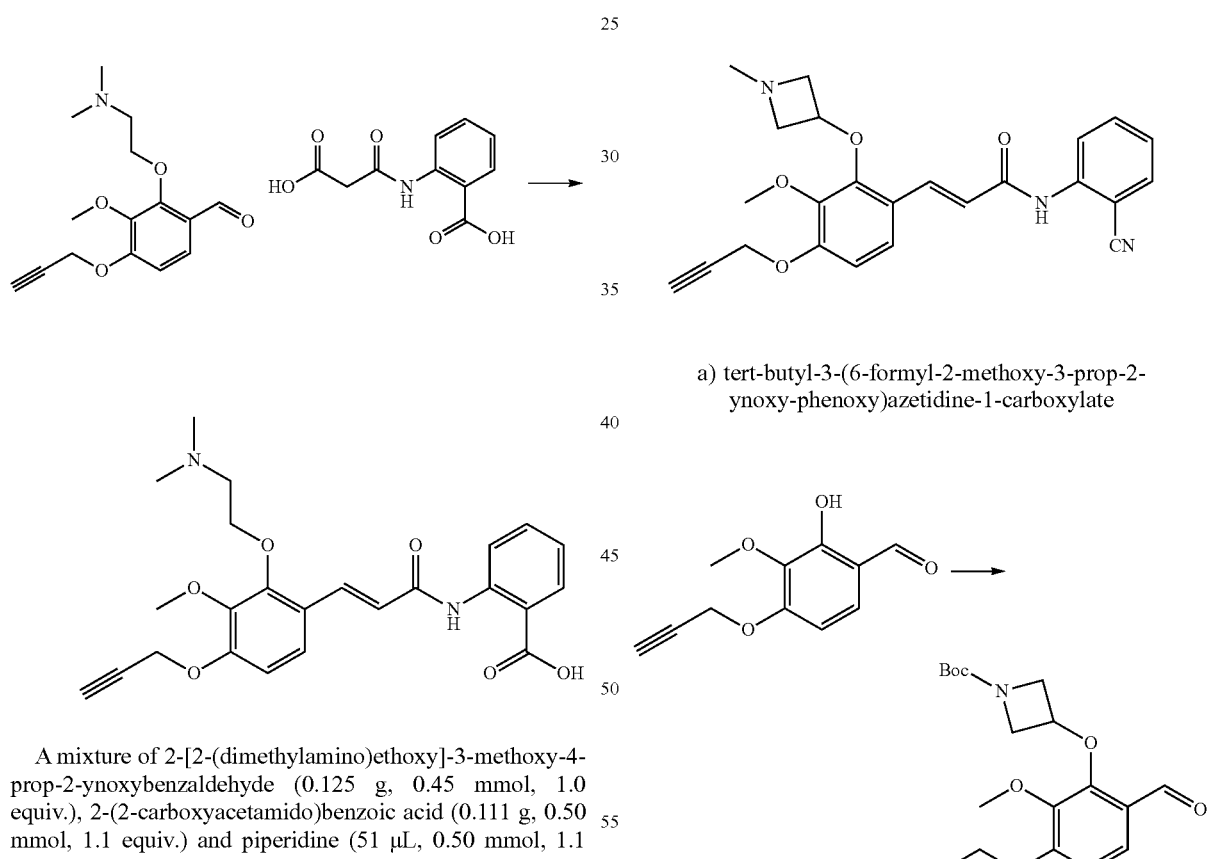

A mixture of 2-[2-(dimethylamino)ethoxy]-3-methoxy-4-prop-2-ynoxybenzaldehyde (0.125 g, 0.45 mmol, 1.0 equiv.), 2-(2-carboxyacetamido)benzoic acid (0.111 g, 0.50 mmol, 1.1 equiv.) and piperidine (51 μL, 0.50 mmol, 1.1 equiv.) in anhydrous toluene was stirred under reflux for 4 hours. The reaction was then cooled to room temperature and the solvent removed in vacuo. The residue was purified by preparative HPLC to provide the title compound (14 mg, 7%); ¹H NMR (400 MHz, DMSO) δ 14.33 (s, 1H), 8.63-8.60 (m, 1H), 8.10 (dd, J=7.8 Hz, J=1.8 Hz, 1H), 7.96 (d, J=17.4 Hz, 1H), 7.66 (d, J=8.8 Hz, 1H), 7.44-7.39 (m, 1H), 7.09-7.03 (m, 2H), 6.59 (d, J=16.5 Hz, 1H), 4.98 (d, J=2.3 Hz, 2H), 4.39 (t, J=4.5 Hz, 2H), 3.86 (s, 3H), 3.68 (t, J=2.4 Hz, 1H), 3.65-3.59 (m, 2H), 2.98 (s, 6H); MS (ESI+) m/z 439.7 (M+H)+; 98% purity, RT 2.66 min (Method 2).

(E)-N-(2-cyanophenyl)-3-[3-methoxy-2-(1-methyl-azetidin-3-yl)oxy-4-prop-2-ynoxy-phenyl]prop-2-enamide (79)

a) tert-butyl-3-(6-formyl-2-methoxy-3-prop-2-ynoxy-phenoxy)azetidine-1-carboxylate To a solution of 2-hydroxy-3-methoxy-4-prop-2-ynoxy-benzaldehyde (0.160 g, 0.77 mmol, 1.0 equiv.) in N,N-dimethylformamide (3 mL) was added potassium carbonate (0.322 g, 2.33 mmol, 3.0 equiv.) and tert-butyl 3-methyl-sulfonyloxyazetidine-1-carboxylate (0.293 g, 1.16 mmol, 1.5 equiv.) and the resulting mixture was stirred at 65° C. for 16 hours. The mixture was cooled to room temperature, diluted with water (10 mL) and extracted with ethyl acetate (10 mL×3). The combined organic phase was washed with brine (10 mL), filtered and concentrated in vacuo. The residue was purified by silica gel column chromatography (petroleum ether:ethyl acetate 20:1 to 5:1) to provide the desired product as a red oil (70 mg) which was used without further purification. $^1$H NMR (CDCl$_3$, 400 MHz) δ 10.28 (s, 1H), 7.60 (d, J=8.8 Hz, 1H), 6.87 (d, J=8.8 Hz, 1H), 5.22-5.19 (m, 1H), 4.83 (d, J=2.0 Hz, 2H), 4.30-4.27 (m, 2H), 4.26-4.16 (m, 2H), 3.85 (s, 3H), 2.57 (t, J=2.4 Hz, 1H), 1.45 (s, 9H).

b) tert-butyl-3-[6-[(E)-3-(2-cyanoanilino)-3-oxo-prop-1-enyl]-2-methoxy-3-prop-2-ynoxy-phenoxy]azetidine-1-carboxylate

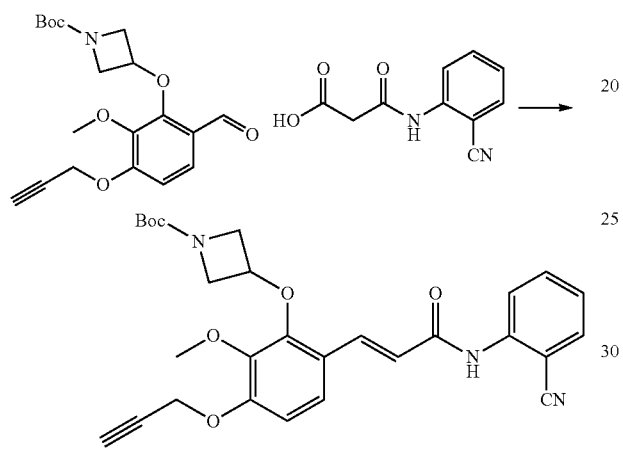

The title compound was prepared according to the procedure described for the synthesis of (E)-2-(3-(2-(2-(dimethylamino)ethoxy)-3-methoxy-4-(prop-2-yn-1-yloxy)phenyl)acrylamido)benzoic acid (78) starting from tert-butyl-3-(6-formyl-2-methoxy-3-prop-2-ynoxy-phenoxy)azetidine-1-carboxylate and 3-(2-cyanoanilino)-3-oxo-propanoic acid (42%); MS (ESI$^+$) m/z 526.2 (M+Na)$^+$.

c) (E)-3-[2-(azetidin-3-yloxy)-3-methoxy-4-prop-2-ynoxyphenyl]-N-(2-cyanophenyl)prop-2-enamide

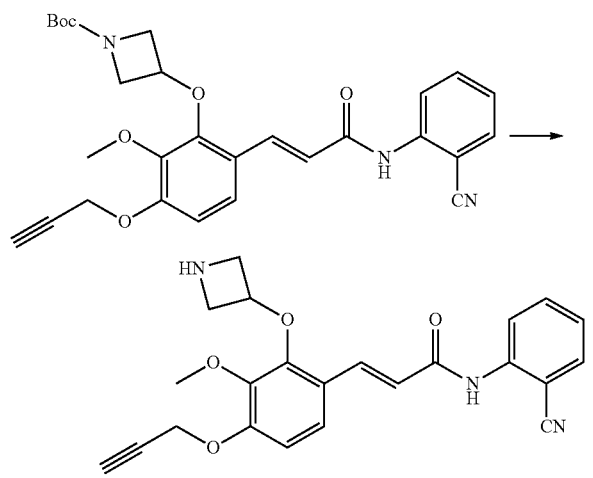

To a solution of tert-butyl-3-[6-[(E)-3-(2-cyanoanilino)-3-oxo-prop-1-enyl]-2-methoxy-3-prop-2-ynoxy-phenoxy]azetidine-1-carboxylate (0.190 g, 0.37 mmol, 1.0 equiv.) in dichloromethane (6 mL) was added zinc bromide (0.850 g, 3.77 mmol, 10.0 equiv.) and the reaction mixture stirred at 25° C. for 4 hours. The mixture was concentrated and the residue added into saturated aqueous sodium bicarbonate solution (15 mL). The aqueous mixture was extracted with ethyl acetate (10 mL×3) and the combined organic phase was concentrated in vacuo to give the title compound as yellow oil (100 mg) which was used without further purification; MS (ESI$^+$) m/z 403.9 (M+H)+.

d) (E)-N-(2-cyanophenyl)-3-[3-methoxy-2-(1-methylazetidin-3-yl)oxy-4-prop-2-ynoxy-phenyl]prop-2-enamide

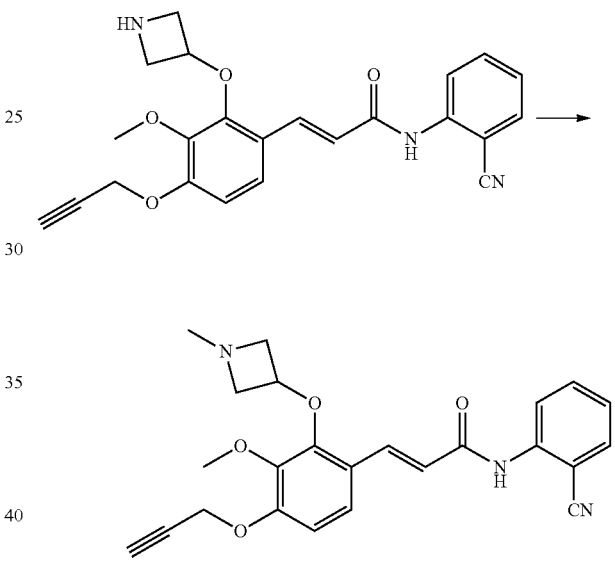

To a solution of (E)-3-[2-(azetidin-3-yloxy)-3-methoxy-4-prop-2-ynoxyphenyl]-N-(2-cyanophenyl)prop-2-enamide (100 mg, 0.24 mmol, 1.00 equiv.) in methanol (5 mL) was added sodium bicarbonate (42 mg, 0.49 mmol, 2.00 equiv.) and aqueous formaldehyde (40 mg, 0.49 mmol, 37%, 2.00 equiv.) and the resulting mixture stirred at 25° C. for 0.3 hours. Sodium cyanoborohydride (31 mg, 0.49 mmol, 2.00 equiv.) was added and stirring continued at 25° C. for 1 hour. The mixture was filtered and the filtrate concentrated under vacuum to afford a residue which was purified by preparative HPLC to provide the desired product as a white solid (12.0 mg, 11%); $^1$H NMR (CD$_3$OD, 400 MHz) δ 7.93 (d, J=15.6 Hz, 1H), 7.81 (d, J=8.4 Hz, 1H), 7.74 (d, J=8.0 Hz, 1H), 7.70 (t, J=8.0 Hz, 1H), 7.40 (d, J=9.2 Hz, 1H), 7.37 (t, J=7.6 Hz, 1H), 6.95 (d, J=8.8 Hz, 1H), 6.82 (d, J=16.0 Hz, 1H), 4.72-4.68 (m, 1H), 3.82 (s, 3H), 3.80-3.76 (m, 2H), 3.42-3.34 (m, 2H), 3.01 (t, J=2.4 Hz, 1H), 2.43 (s, 3H), propargyl CH$_2$ masked by residual water signal; LCMS: m/z 418.1 [M+H]$^+$; 95.1% purity; RT=2.55 min (Method 12).

135

2-[[(E)-3-(3-methoxy-4-prop-2-ynoxy-2-pyrrolidin-3-yloxyphenyl)prop-2-enoyl]amino]benzoic acid (80)

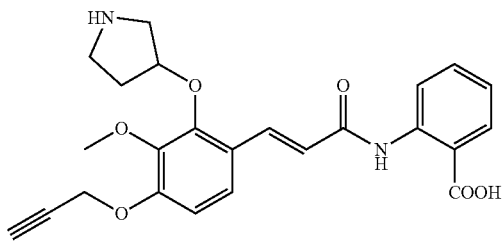 [SMILES: C#CCOc1ccc(/C=C/C(=O)Nc2ccccc2C(=O)O)c(OC2CCNC2)c1OC]

a) tert-butyl 3-(6-formyl-2-methoxy-3-prop-2-ynoxyphenoxy)pyrrolidine-1-carboxylate

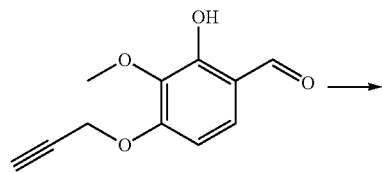

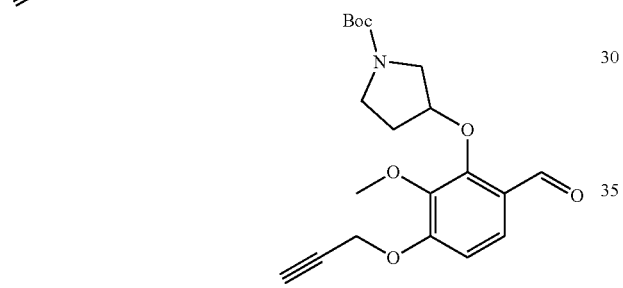

The title compound was prepared according to the procedure described for the synthesis of tert-butyl-3-(6-formyl-2-methoxy-3-prop-2-ynoxyphenoxy)azetidine-1-carboxylate starting from 2-hydroxy-3-methoxy-4-prop-2-ynoxybenzaldehyde and tert-butyl 3-((methylsulfonyl)oxy)pyrrolidine-1-carboxylate (79%); ¹H NMR (CDCl₃, 400 MHz) δ 10.15 (s, 1H), 7.63 (t, J=8.0 Hz, 1H), 6.91 (t, J=8.4 Hz, 1H), 5.27 (d, J=37.6 Hz, 1H), 4.86 (d, J=2.4 Hz, 2H), 3.88 (s, 3H), 3.71-3.45 (m, 4H), 2.57 (t, J=2.4 Hz, 1H), 2.24 (m, 1H), 2.06-2.03 (m, 1H), 1.47 (s, 9H).

b) 2-[[(E)-3-[2-(1-tert-butoxycarbonylpyrrolidin-3-yl)oxy-3-methoxy-4-prop-2-ynoxy-phenyl]prop-2-enoyl]amino]benzoic acid

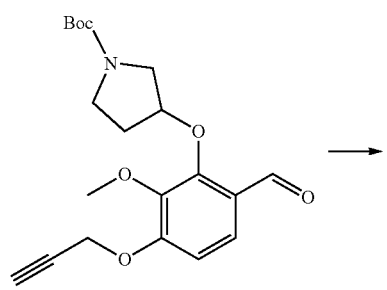

136

-continued

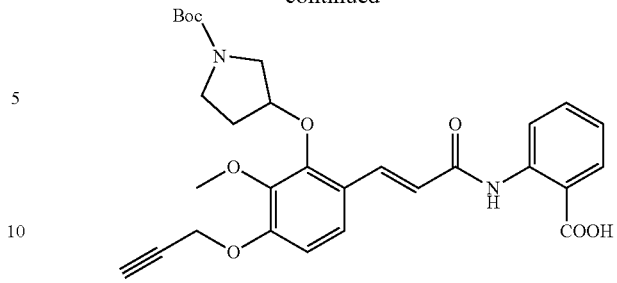

The title compound was prepared according to the procedure described for the synthesis of tert-butyl-3-[6-[(E)-3-(2-cyanoanilino)-3-oxo-prop-1-enyl]-2-methoxy-3-prop-2-ynoxyphenoxy]azetidine-1-carboxylate starting from tert-butyl 3-(6-formyl-2-methoxy-3-prop-2-ynoxyphenoxy)pyrrolidine-1-carboxylate and 2-(2-carboxyacetamido)benzoic acid. MS (ESI+) m/z 537.2 (M+H)+.

c) 2-[[(E)-3-(3-methoxy-4-prop-2-ynoxy-2-pyrrolidin-3-yloxyphenyl)prop-2-enoyl]amino]benzoic acid

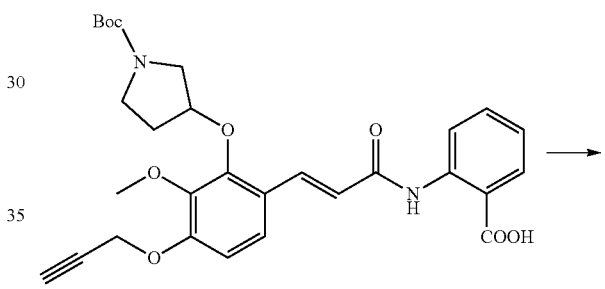

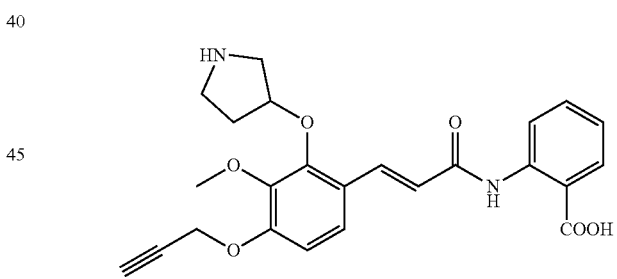

To a solution of 2-[[(E)-3-[2-(1-tert-butoxycarbonylpyrrolidin-3-yl)oxy-3-methoxy-4-prop-2-ynoxyphenyl]prop-2-enoyl]amino]benzoic acid (200 mg, 0.37 mmol, 1.00 equiv.) in dichloromethane (4 mL) was added trifluoroacetic acid (4 mL) and the resultant mixture stirred at 20° C. for 1 hour. The reaction was concentrated in vacuo and the residue purified by preparative HPLC to provide the desired product as a white solid as the trifluoroacetic acid salt (108 mg, 52%); ¹H NMR (CD₃OD, 400 MHz) δ 8.72 (d, J=8.4 Hz, 1H), 8.15 (dd, J=8.0 Hz, J=1.6 Hz, 1H), 7.91 (d, J=16.0 Hz, 1H), 7.62-7.56 (m, 2H), 7.22-7.20 (t, J=8.4 Hz, 1H), 7.04 (d, J=8.8 Hz, 1H), 6.69 (d, J=16.0 Hz, 1H), 5.23 (t, J=4.4 Hz, 1H), 4.90 (d, J=2.4 Hz, 2H), 3.89 (s, 3H), 3.74 (d, J=13.2 Hz, 1H), 3.68-3.61 (m, 1H), 3.54-3.50 (m, 2H), 3.06 (t, J=2.4 Hz, 1H), 2.37 (m, 1H), 2.19-2.17 (m, 1H); MS (ESI+) m/z 437.1 [M+H]⁺; 100.0% purity; RT=2.67 min. (Method 12).

| Ex | Structure | Data | Method |
|---|---|---|---|
| 81 | (E)-N-(2-cyanophenyl)-3-[3-methoxy-2-(1-methylpyrrolidin-3-yl)oxy-4-prop-2-ynoxy-phenyl]prop-2-enamide trifluoroacetic acid salt | $^1$H NMR (CD$_3$OD, 400 MHz) δ 7.96 (d, J = 15.6 Hz, 1H), 7.77-7.70 (m, 3H), 7.49 (d, J = 8.8 Hz, 1H), 7.39 (t, J = 6.8 Hz, 1H), 7.03 (d, J = 8.8 Hz, 1H), 6.79 (d, J = 15.6 Hz, 1H), 5.16 (br. s, 1H), 4.87 (d, J = 2.4 Hz, 2H), 3.88 (s, 3H), 4.06-3.88 (m, 2H), 3.31-3.26 (m, 2H), 3.15-3.08 (m, 1H), 3.03 (s, 3H), 2.48-2.34 (m, 2H); MS (ESI+) m/z 432.1 [M + H]$^+$; 95.2% purity; RT = 2.50 min (Method 12). | Prepared according to the method for 79 starting from 2-hydroxy-3-methoxy-4-prop-2-ynoxy-benzaldehyde and tert-butyl 3-((methylsulfonyl)oxy)pyrrolidine-1-carboxylate. |
| 82 | (E)-N-(2-cyanophenyl)-3-(3-methoxy-4-prop-2-ynoxy-2-pyrrolidin-3-yloxy-phenyl)prop-2-enamide trifluoroacetic acid salt | $^1$H NMR (CD$_3$OD, 400 MHz) δ 7.94 (d, J = 15.6 Hz, 1H), 7.78-7.70 (m, 3H), 7.51 (d, J = 8.8 Hz, 1H), 7.39 (t, J = 7.2 Hz, 1H), 7.03 (d, J = 9.2 Hz, 1H), 6.78 (d, J = 15.6 Hz, 1H), 5.20 (br. s, 1H), 4.87 (d, J = 2.4 Hz, 2H), 3.88 (s, 3H), 3.73 (d, J = 13.2 Hz, 1H), 3.62-3.61 (m, 1H), 3.51-3.47 (m, 2H), 3.04 (s, 1H), 2.33-2.29 (m, 1H), 2.17-2.12 (m, 1H); MS (ESI+) m/z 418.1 [M + H]$^+$; 98.8% purity; RT = 2.55 min (Method 12). | Prepared according to the method for 79 steps a to c starting from 2-hydroxy-3-methoxy-4-prop-2-ynoxy-benzaldehyde and tert-butyl 3-((methylsulfonyl)oxy)pyrrolidine-1-carboxylate |
| 83 | 2-[[(E)-3-[3-methoxy-2-(4-piperidyloxy)-4-prop-2-ynoxy-phenyl]prop-2-enoyl]amino]benzoic acid trifluoroacetic acid salt | $^1$H NMR (CD$_3$OD, 400 MHz) δ 8.69 (d, J = 8.4 Hz, 1H), 8.14 (d, J = 7.6 Hz, 1H), 7.96 (d, J = 15.6 Hz, 1H), 7.60 (t, J = 7.6 Hz, 1H), 7.54 (d, J = 8.8 Hz, 1H), 7.20 (t, J = 7.6 Hz, 1H), 7.01 (d, J = 8.8 Hz, 1H), 6.68 (d, J = 15.6 Hz, 1H), 4.58 (br. s, 1H), 3.88 (s, 3H), 3.55-3.51 (m, 2H), 3.22-3.18 (m, 2H), 3.05 (s, 1H), 2.15-2.14 (m, 4H) propargyl CH$_2$ masked by residual water signal; MS (ESI+) m/z 451.2 [M + H]$^+$; 96.4% purity; RT = 2.69 min (Method 12). | Prepared according to the method for 80 starting from 2-hydroxy-3-methoxy-4-prop-2-ynoxy-benzaldehyde and tert-butyl 4-methylsulfonyloxy-piperidine-1-carboxylate |
| 84 | 2-[[(E)-3-[3-methoxy-2-(2-morpholinoethoxy)-4-prop-2-ynoxy-phenyl]prop-2-enoyl]amino]benzoic acid trifluoroacetic acid salt | $^1$H NMR (CD$_3$OD, 400 MHz) δ 8.69 (d, J = 8.0 Hz, 1H), 8.13 (dd, J = 8.4 Hz, J = 1.2 Hz, 1H), 7.89 (d, J = 16.0 Hz, 1H), 7.60 (t, J = 8.4 Hz, 1H), 7.54 (d, J = 8.8 Hz, 1H), 7.19 (t, J = 8.4 Hz, 1H), 7.05 (d, J = 8.8 Hz, 1H), 6.76 (d, J = 16.0 Hz, 1H), 4.38 (t, J = 4.8 Hz, 2H), 4.04 (br. s, 4H), 3.92 (s, 3H), 3.74 (t, J = 4.8 Hz, 2H), 3.58 (br. s, 4H), 3.05 (t, J = 2.4 Hz, 1H) propargyl CH$_2$ masked by residual water signal; MS (ESI+) m/z 481.2 [M + H]$^+$; 96.4% purity; RT = 2.69 min (Method 12) | Prepared according to the method for 80 steps a and b starting from 2-hydroxy-3-methoxy-4-prop-2-ynoxy-benzaldehyde and 2-morpholinoethyl methanesulfonate |

| Ex | Structure | Data | Method |
|---|---|---|---|
| 85 | (E)-N-(2-cyanophenyl)-3-[3-methoxy-2-(2-morpholinoethoxy)-4-prop-2-ynoxy-phenyl]prop-2-enamide trifluoroacetic acid salt | $^1$H NMR (CD$_3$OD, 400 MHz) δ 7.96 (d, J = 16.0 Hz, 1H), 7.77-7.70 (m, 3H), 7.50 (d, J = 8.8 Hz, 1H), 7.39 (t, J = 8.4 Hz, 1H), 7.05 (d, J = 9.2 Hz, 1H), 6.81 (d, J = 16.0 Hz, 1H), 4.89 (d, J = 2.4 Hz, 2H), 4.38 (t, J = 4.8 Hz, 2H), 4.10 (br. s, 2H), 3.92 (s, 3H), 3.91 (br. s, 2H), 3.72 (t, J = 4.8 Hz, 2H), 3.77-3.71 (m, 2H), 3.37-3.35 (m, 2H), 3.05 (t, J = 2.4 Hz, 1H). MS (ESI+) m/z 462.2 [M + H]$^+$; 95.7% purity; RT = 2.59 min (Method 12i) | Prepared according to the method for 79 steps a to b starting from 2-hydroxy-3-methoxy-4-prop-2-ynoxy-benzaldehyde and 2-morpholinoethyl methanesulfonate |
| 86 | 2-[[(E)-3-[2-[3-(dimethylamino)propoxy]-3-methoxy-4-prop-2-ynoxy-phenyl]prop-2-enoyl]amino]benzoic acid trifluoroacetic acid salt | $^1$H NMR (CD$_3$OD, 400 MHz) δ 8.68 (d, J = 8.4 Hz, 1H), 8.11 (dd, J = 8.0 Hz, J = 1.6 Hz, 1H), 7.88 (d, J = 16.0 Hz, 1H), 7.58 (t, J = 7.2 Hz, 1H), 7.47 (d, J = 9.2 Hz, 1H), 7.16 (t, J = 7.2 Hz, 1H), 6.96 (d, J = 9.2 Hz, 1H), 6.67 (t, J = 15.6 Hz, 1H), 4.85 (d, J = 2.4 Hz, 2H), 4.15 (t, J = 5.6 Hz, 2H), 3.88 (s, 3H), 3.50 (t, J = 8.0 Hz, 2H), 3.02 (t, J = 2.4 Hz, 1H), 3.01 (s, 6H), 2.28-2.23 (m, 2H); MS (ESI+) m/z 453.2 (M + H)$^+$; MS (ESI+) m/z 453.1 [M + H]$^+$; 95.4% purity; RT = 2.78 min (Method 12). | Prepared according to the method for 80 steps a and b starting from 2-hydroxy-3-methoxy-4-prop-2-ynoxy-benzaldehyde and 3-chloro-N,N-dimethyl-propan-1-amine. |
| 87 | (E)-N-(2-cyanophenyl)-3-[2-[3-(dimethylamino)propoxy]-3-methoxy-4-prop-2-ynoxy-phenyl]prop-2-enamide trifluoroacetic acid salt | $^1$H NMR (CD$_3$OD, 400 MHz) δ 7.97 (d, J = 15.6 Hz, 1H), 7.77-7.70 (m, 3H), 7.48 (d, J = 8.8 Hz, 1H), 7.38 (t, J = 7.6 Hz, 1H), 7.00 (d, J = 8.8 Hz, 1H), 6.78 (t, J = 15.6 Hz, 1H), 4.86 (d, J = 2.4 Hz, 2H), 4.18 (t, J = 5.6 Hz, 2H), 3.89 (s, 3H), 3.48 (t, J = 8.0 Hz, 2H), 3.03 (t, J = 2.4 Hz, 1H), 2.97 (s, 6H), 2.26-2.22 (m, 2H); MS (ESI+) m/z 434.2 [M + H]$^+$; 98.7% purity; RT = 2.65 min (Method 12) | Prepared according to the method for 79 steps a to b starting from 2-hydroxy-3-methoxy-4-prop-2-ynoxy-benzaldehyde and 3-chloro-N,N-dimethyl-propan-1-amine. |

| Ex | Structure | Data | Method |
|---|---|---|---|
| 88 | (E)-N-(2-cyanophenyl)-3-[3-methoxy-2-(4-piperidyloxy)-4-prop-2-ynoxy-phenyl]prop-2-enamide trifluoroacetic acid salt | $^1$H NMR (CD$_3$OD, 400 MHz) δ 8.02 (d, J = 15.6 Hz, 1H), 7.82-7.71 (m, 3H), 7.50 (d, J = 8.4 Hz, 1H), 7.39 (t, J = 8.0 Hz, 1H), 7.01 (d, J = 8.8 Hz, 1H), 6.77 (d, J = 16.0 Hz, 1H), 4.87 (d, J = 2.4 Hz, 2H), 4.52 (m, 1H), 3.86 (s, 3H), 3.51-3.31 (m, 2H), 3.18 (m, 2H), 3.04 (t, J = 2.4 Hz, 1H), 2.13-2.09 (m, 4H). MS (ES1+) m/z 432.2 [M + H]$^+$; 95.7% purity; RT = 2.45 min (Method 12) | Prepared according to the method for 79 steps a to c starting from 2-hydroxy-3-methoxy-4-prop-2-ynoxy-benzaldehyde and tert-butyl 4-methylsulfonyloxy-piperidine-1-carboxylate |
| 89 | (E)-N-(2-cyanophenyl)-3-[3-methoxy-2-[(1-methyl-4-piperidyl)oxy)-4-prop-2-ynoxy-phenyl]prop-2-enamide trifluoroacetic acid salt | $^1$H NMR (DMSO-d$_6$, 400 MHz) δ 10.06 (s, 1H), 7.81-7.70 (m, 4H), 7.41 (d, J = 8.8 Hz, 1H), 7.37 (t, J = 7.6 Hz, 1H), 7.03 (d, J = 8.8 Hz, 1H), 6.85 (d, J = 16.0 Hz, 1H), 4.90 (d, J = 2.4 Hz, 2H), 4.36 (br, 1H), 3.84 (s, 3H), 3.48 (t, J = 2.4 Hz, 1H), 3.50-3.25 (m, 4H), 2.81 (s, 3H), 2.11-2.01 (m, 4H). MS (ESI+) m/z 446.2 [M + H]$^+$; 99.4% purity; RT = 2.46 min (Method 12). | Prepared according to the method for 79 starting from 2-hydroxy-3-methoxy-4-prop-2-ynoxy-benzaldehyde and tert-butyl 4-methylsulfonyloxy-piperidine-1-carboxylate |

2-[[(E)-3-[4-(cyclopropylmethoxy)-2-[2-(dimethyl-amino)ethoxy]-3-methoxy-phenyl]prop-2-enoyl]amino]benzoic acid (90)

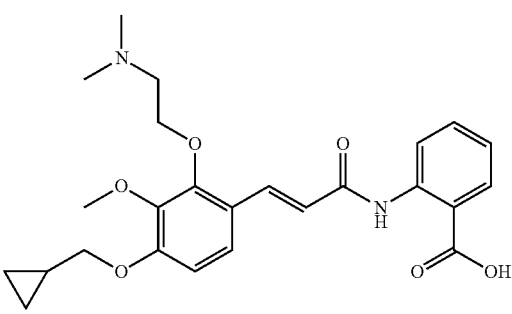 [SMILES: COc1c(OCC2CC2)ccc(/C=C/C(=O)Nc2ccccc2C(=O)O)c1OCCN(C)C]

a) [3-(cyclopropylmethoxy)-6-formyl-2-methoxy-phenyl] acetate

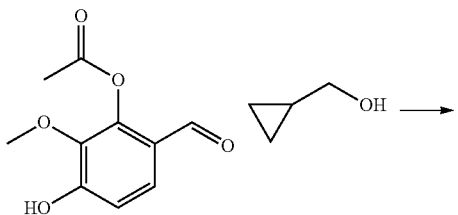

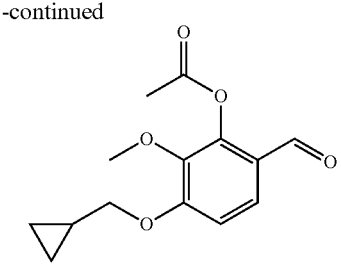

To a solution of (6-formyl-3-hydroxy-2-methoxyphenyl) acetate (0.350 g, 1.67 mmol, 1.00 equiv.) in tetrahydrofuran (6 mL) was added cyclopropylmethanol (0.241 g, 3.34 mmol, 2.00 equiv.), triphenylphosphine (0.876 g, 3.34 mmol, 2.00 equiv.) and diethyl azodicarboxylate (0.582 g, 3.34 mmol, 2.00 equiv.) under a nitrogen atmosphere and the resultant mixture stirred at 25° C. for 3 hours. The reaction mixture was concentrated in vacuo and the residue purified by silica gel column chromatography (petroleum ether:ethyl acetate 50:1 to 15:1) to give the desired product as a colorless oil (0.300 g, 67%); $^1$H NMR (CDCl$_3$, 400 MHz) δ 9.94 (s, 1H), 7.56 (d, J=8.8 Hz, 1H), 6.87 (d, J=8.8 Hz, 1H), 3.95 (d, J=7.2 Hz, 2H), 3.87 (s, 3H), 2.42 (s, 3H), 1.35-1.32 (m, 1H), 0.69-0.67 (m, 2H), 0.41-0.38 (m, 2H).

b) 4-(cyclopropylmethoxy)-2-hydroxy-3-methoxy-benzaldehyde

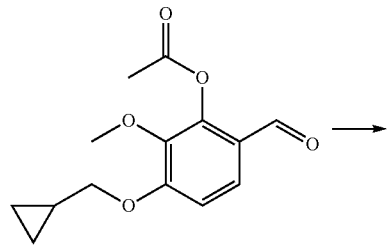

The title compound was prepared according to the procedure described for the synthesis of 2-hydroxy-3-methoxy-4-prop-2-ynoxybenzaldehyde starting from [3-(cyclopropylmethoxy)-6-formyl-2-methoxy-phenyl]acetate (59%); MS (ESI+) m/z 223.0 (M+H)+.

c) 4-(cyclopropylmethoxy)-2-[2-(dimethylamino)ethoxy]-3-methoxy-benzaldehyde

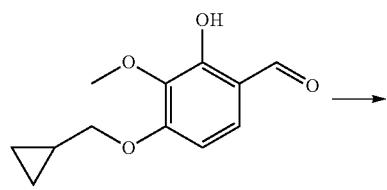

The title compound was prepared according to the procedure described for the synthesis of 2-[2-(dimethylamino)ethoxy]-3-methoxy-4-prop-2-ynoxybenzaldehyde starting from 4-(cyclopropylmethoxy)-2-hydroxy-3-methoxy-benzaldehyde and 2-chloro-N,N-dimethylethanamine. MS (ESI+) m/z 294.0 (M+H)+.

d) 2-[[(E)-3-[4-(cyclopropylmethoxy)-2-[2-(dimethylamino)ethoxy]-3-methoxy-phenyl]prop-2-enoyl]amino]benzoic acid

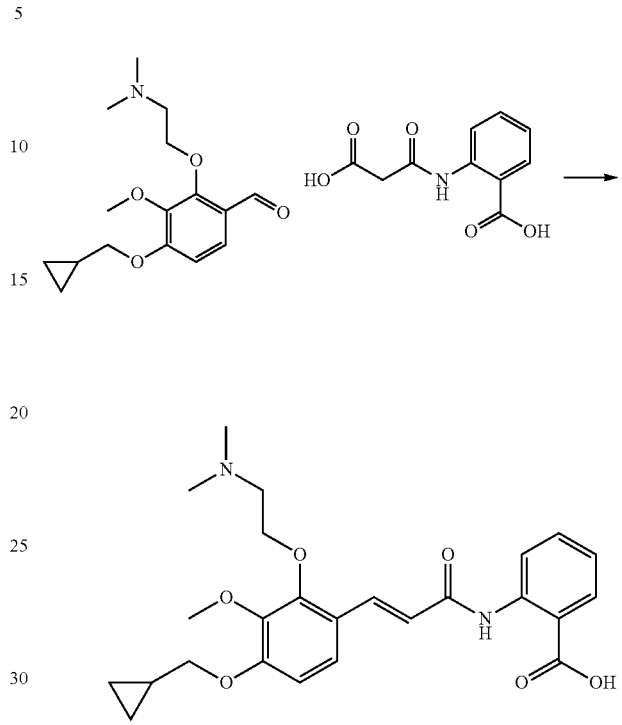

The title compound was prepared as the trifluoroacetic acid salt according to the procedure described for the synthesis of (E)-2-(3-(2-(2-(dimethylamino)ethoxy)-3-methoxy-4-(prop-2-yn-1-yloxy)phenyl)acrylamido)-benzoic acid starting from 4-(cyclopropylmethoxy)-2-[2-(dimethylamino)ethoxy]-3-methoxy-benzaldehyde and 2-[(2-carboxyacetyl)amino]benzoic acid (28%); ¹H NMR (CD₃OD, 400 MHz) δ 8.71 (d, J=8.4 Hz, J=1.2 Hz, 1H), 8.14 (dd, J=8.0 Hz, J=1.6 Hz, 1H), 7.92 (d, J=15.6 Hz, 1H), 7.60 (td, J=8.8 Hz, J=1.2 Hz, 1H), 7.48 (d, J=8.8 Hz, 1H), 7.18 (t, J=8.0 Hz, 1H), 6.91 (d, J=8.8 Hz, 1H), 6.69 (d, J=16.0 Hz, 1H), 4.32 (t, J=4.8 Hz, 2H), 3.96 (s, 3H), 3.94 (d, J=8.0 Hz, 2H), 3.67 (t, J=4.8 Hz, 2H), 3.11 (s, 6H), 1.34-1.30 (m, 1H), 0.67-0.64 (m, 2H), 0.40-0.39 (m, 2H); MS (ESI+) m/z 455.1 [M+H]⁺; 99.5% purity; RT=1.84 min. (Method 9)

(E)-N-(3-cyanophenyl)-3-(2-(2-(dimethylamino)ethoxy)-3-methoxyphenyl)acrylamide (91)

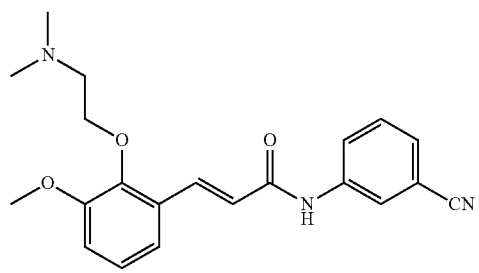 [SMILES: COc1cccc(/C=C/C(=O)Nc2cccc(C#N)c2)c1OCCN(C)C]

a) 2-[2-(dimethylamino)ethoxy]-3-methoxybenzaldehyde

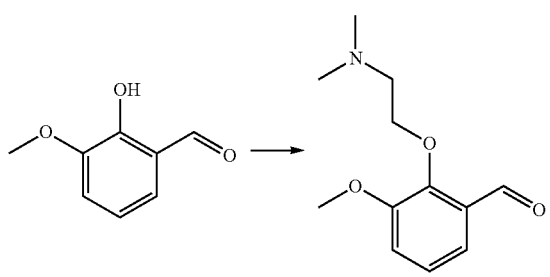 [SMILES: COc1cccc(C=O)c1O ; COc1cccc(C=O)c1OCCN(C)C]

The title compound was prepared according to the procedure described for the synthesis of 2-[2-(dimethylamino)ethoxy]-3-methoxy-4-prop-2-ynoxybenzaldehyde starting from 2-hydroxy-3-methoxybenzaldehyde and 2-chloro-N,N-dimethylethanamine and used directly without further purification.

b) (E)-3-[2-[2-(dimethylamino)ethoxy]-3-methoxyphenyl]prop-2-enoic acid

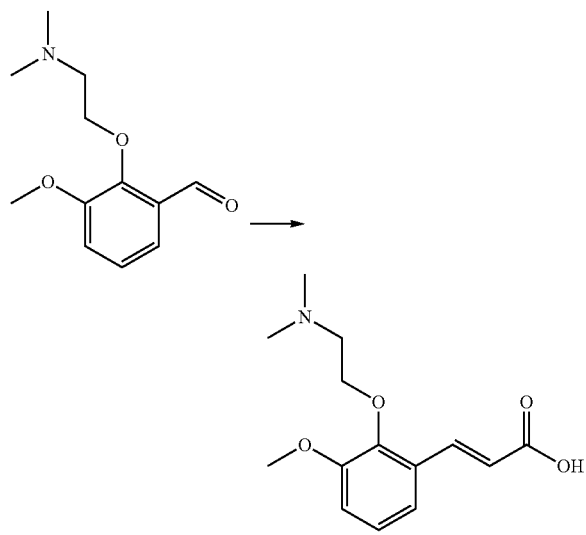

The title compound was prepared according to the procedure described for the synthesis of (E)-3-[2-[2-(dimethylamino)ethoxy]-3-methoxy-4-prop-2-ynoxyphenyl]prop-2-enoic acid starting from 2-[2-(dimethylamino)ethoxy]-3-methoxybenzaldehyde and malonic acid; MS (ESI+) m/z 266.2 (M+H)+.

c) (E)-N-(3-cyanophenyl)-3-(2-(2-(dimethylamino)ethoxy)-3-methoxyphenyl)acrylamide

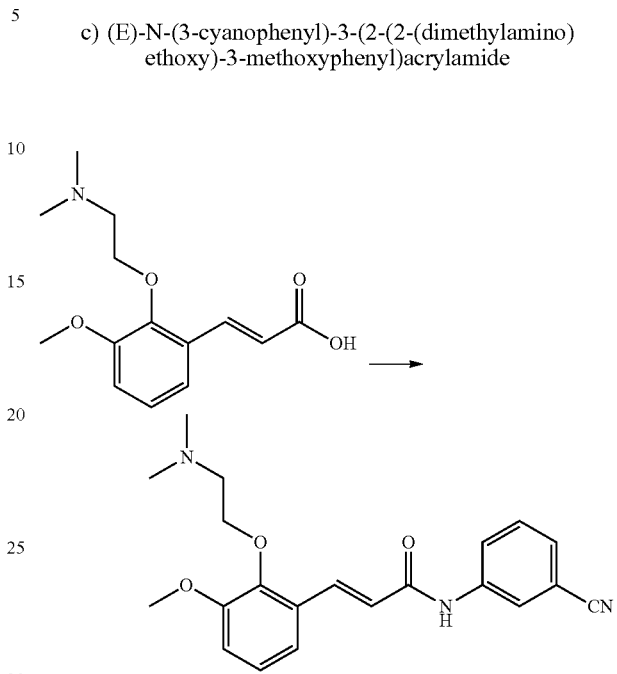

To a solution of (E)-3-[2-[2-(dimethylamino)ethoxy]-3-methoxyphenyl]prop-2-enoic acid (0.52 g, 0.471 mmol, 1.0 equiv.) in dichloromethane (5 mL) was added diisopropylethylamine (0.183 g, 1.41 mmol, 3.0 equiv.) and HATU (0.215 g, 0.565 mmol, 1.2 equiv.). The reaction was stirred at 20° C. for 30 minutes, 3-aminobenzonitrile (0.084 g, 0.707 mmol, 1.5 equiv.) was added and the resulting mixture stirred for 2 hours at 20° C. The reaction was washed with water (5 mL×3) and the organic phase was dried over anhydrous sodium sulfate, filtered and concentrated in vacuo. The residue was purified by preparative HPLC to afford the desired compound as a light yellow solid (40 mg, 23%); $^1$H NMR (DMSO-$d_6$, 400 MHz) δ 10.53 (s, 1H), 8.23 (s, 1H), 7.96 (d, J=16.0 Hz, 1H), 7.87 (d, J=7.6 Hz, 1H), 7.56-7.53 (m, 2H), 7.22-7.20 (m, 1H), 7.14-7.11 (m, 2H), 6.80 (d, J=15.6 Hz, 1H), 4.01 (t, J=5.6 Hz, 2H), 3.83 (s, 3H), 2.60 (t, J=6.0 Hz, 2H), 2.21 (s, 6H); MS (ESI+) m/z 366.2 (M+H)+; 100% purity, RT 2.71 min (Method 8).

| Ex | Structure | Data | Method |
|---|---|---|---|
| 92 | (E)-N-(2-cyanophenyl)-3-(2-(2-(dimethylamino)ethoxy)-3-methoxyphenyl)acrylamide | $^1$H NMR (DMSO-$d_6$, 400 MHz) δ 10.32 (s, 1H), 7.97 (d, J = 16.0 Hz, 1H), 7.84 (d, J = 8.0 Hz, 1H), 7.74-7.70 (m, 2H), 7.38-7.33 (m, 1H), 7.25-7.23 (m, 1H), 7.16-7.12 (m, 2H), 6.94 (d, J = 16.0 Hz, 1H), 4.01 (t, J = 5.6 Hz, 2H), 3.83 (s, 3H), 2.59 (t, J = 6.0 Hz, 2H), 2.20 (s, 6H); MS (ESI+) m/z 366.1 (M + H)+; 98.9% purity, RT 2.29 min (Method 11) | Prepared according to the method for 91 step c starting from (E)-3-[2-[2-(dimethylamino)ethoxy]-3-methoxyphenyl]prop-2-enoic acid and 2-aminobenzonitrile |

147

(E)-N-(3-cyanophenyl)-3-(2-(2-(dimethylamino)ethoxy)-4-methoxyphenyl)acrylamide (93)

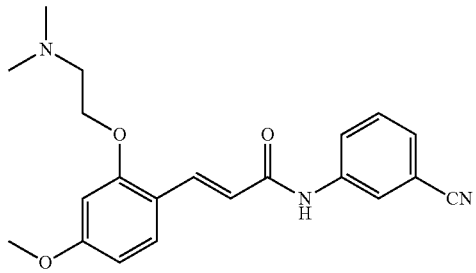 [SMILES: COc1ccc(/C=C/C(=O)Nc2cccc(C#N)c2)c(OCCN(C)C)c1]

a) 2-[2-(dimethylamino)ethoxy]-4-methoxybenzaldehyde

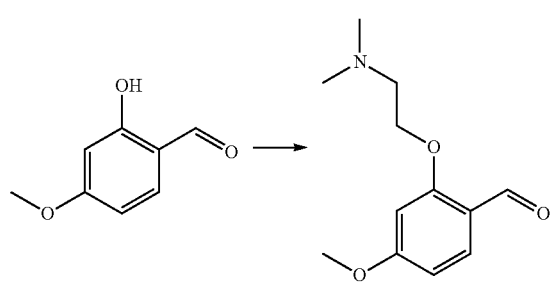 [SMILES: COc1ccc(C=O)c(O)c1 ; COc1ccc(C=O)c(OCCN(C)C)c1]

The title compound was prepared according to the procedure described for the synthesis of 2-[2-(dimethylamino)ethoxy]-3-methoxy-4-prop-2-ynoxybenzaldehyde starting from 2-hydroxy-4-methoxybenzaldehyde and 2-chloro-N,N-dimethylethanamine (27% yield); $^1$H NMR (CDCl$_3$, 400 MHz) δ 10.33 (s, 1H), 7.83 (d, J=8.4 Hz, 1H), 6.56 (d, J=8.8 Hz, 1H), 6.46 (s, 1H), 4.17 (t, J=5.8 Hz, 2H), 3.88 (s, 3H), 2.82 (t, J=5.6 Hz, 2H), 2.38 (s, 6H); MS (ESI+) m/z 224.0 (M+H)$^+$.

b) (E)-3-[2-[2-(dimethylamino)ethoxy]-4-methoxyphenyl]prop-2-enoic acid

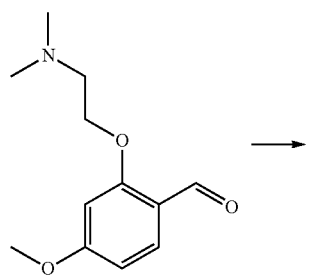

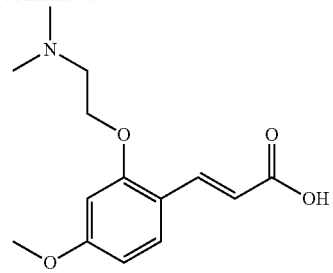

The title compound was prepared according to the procedure described for the synthesis of (E)-3-[2-[2-(dimethylamino)ethoxy]-3-methoxy-4-prop-2-ynoxyphenyl]prop-2-enoic acid starting from 2-(2-(dimethylamino)ethoxy)-4-methoxybenzaldehyde and malonic acid (83% yield); $^1$H NMR (CD$_3$OD, 400 MHz) δ 8.01 (d, J=21.6 Hz, 1H), 7.63 (d, J=11.2 Hz, 1H), 6.68-6.45 (m, 2H), 6.38 (d, J=21.2 Hz, 1H), 4.47 (t, J=6.4 Hz, 2H), 3.86 (s, 3H), 3.71 (t, J=6.6 Hz, 2H), 3.04 (s, 6H); MS (ESI+) m/z 266.3 (M+H)$^+$.

c) (E)-N-(3-cyanophenyl)-3-(2-(2-(dimethylamino)ethoxy)-4-methoxyphenyl)acrylamide

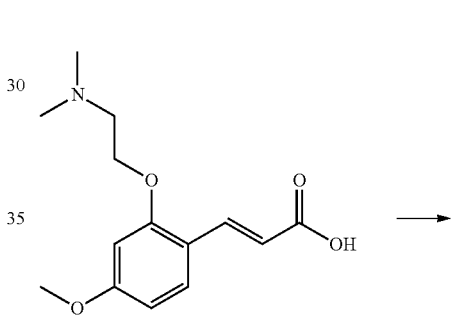

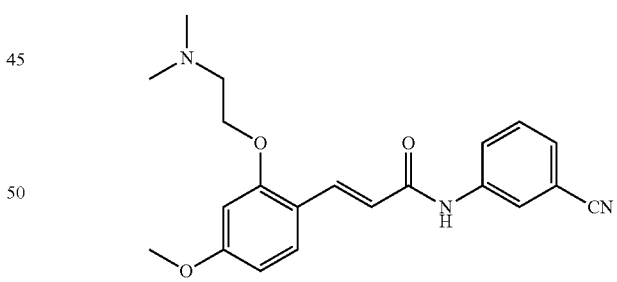

The title compound was prepared as the trifluoroacetic acid salt according to the procedure described for the synthesis of (E)-N-(3-cyanophenyl)-3-[2-[2-(dimethylamino)ethoxy]-3-methoxy-4-prop-2-ynoxy-phenyl]prop-2-enamide (76) starting from (E)-3-[2-[2-(dimethylamino)ethoxy]-4-methoxyphenyl]prop-2-enoic acid and 3-aminobenzonitrile (26% yield); $^1$H NMR (CDCl$_3$, 400 MHz) δ 8.31 (s, 1H), 8.04 (s, 1H), 7.92-7.88 (m, 2H), 7.45-7.36 (m, 3H), 6.76 (d, J=15.6 Hz, 1H), 6.53 (d, J=6.0 Hz, 1H), 6.48 (d, J=2.0 Hz, 1H), 4.15 (t, J=5.6 Hz, 2H), 3.85 (s, 3H), 2.85 (t, J=5.6 Hz, 2H), 2.40 (s, 6H); MS (ESI+) m/z 366 (M+H)+; 95.3% purity, RT 2.06 min (Method 5).

| Ex | Structure | Data | Method |
|---|---|---|---|
| 94 | (E)-N-(2-cyanophenyl)-3-[2-[2-(dimethylamino)ethoxy)-4-methoxy-phenyl]prop-2-enamide trifluoroacetic acid salt | $^1$H NMR (CD$_3$OD, 400 MHz) δ 8.11 (d, J = 16.0 Hz, 1H), 7.78-7.75 (d, J = 8.0 Hz, 2H), 7.72-7.68 (m, 2H), 7.38 (t, J = 8.0 Hz, 1H), 6.76-6.68 (m, 3H), 4.45 (t, J = 4.6 Hz, 2H), 3.88 (s, 3H), 3.71 (t, J = 4.6 Hz, 2H), 3.05 (s, 6H); MS (ESI+) m/z 366.1 (M + H)+; 94% purity, RT 2.91 min (Method 11) | Prepared according to the method for 93 step c starting from (E)-3-[2-[2-(dimethylamino)ethoxy]-4-methoxy-phenyl]prop-2-enoic acid and 2-aminobenzonitrile |

(E)-2-(3-(3,4-dimethoxy-2-(prop-2-yn-1-yloxy)phenyl)acrylamido)benzoic acid (95)

a)
3,4-dimethoxy-2-(prop-2-yn-1-yloxy)benzaldehyde

To a solution of 2-hydroxy-3,4-dimethoxybenzaldehyde (0.200 g, 1.09 mmol, 1 equiv., *Inorganic Chemistry*, 2004, 43, 4743-4750) in acetone (1.7 mL) was added potassium carbonate (0.300 g, 2.17 mmol, 2 equiv.) and propargyl bromide (0.19 mL, 1.28 mmol, 1.2 mmol, 80 wt % in toluene) and the resulting suspension stirred at 60° C. overnight. The reaction was cooled to room temperature and the solid removed by filtration and washed with acetone. The combined filtrate was concentrated in vacuo and the residue was partitioned between ethyl acetate and water. The organic phase was washed with water, dried over MgSO$_4$ and the solvent removed in vacuo. The residue was purified by silica gel chromatography (petroleum ether:ethyl acetate 1:0 to 2:1) to afford the title compound as a white solid (0.133 g, 54%); $^1$H NMR (400 MHz, CDCl$_3$) δ 10.32 (s, 1H), 7.65 (d, J=8.8 Hz, 1H), 6.81 (d, J=8.8 Hz, 1H), 4.92 (d, J=2.5 Hz, 2H), 3.94 (s, 3H), 3.90 (s, 3H), 2.49 (t, J=2.4 Hz, 1H).

b) (E)-2-(3-(3,4-dimethoxy-2-(prop-2-yn-1-yloxy)phenyl)acrylamido)benzoic acid

The title compound was prepared according to the procedure described for the synthesis of (E)-2-(3-(2-(2-(dimethylamino)ethoxy)-3-methoxy-4-(prop-2-yn-1-yloxy)phenyl)acrylamido)benzoic acid (78) starting from 3,4-dimethoxy-2-(prop-2-yn-1-yloxy)benzaldehyde and 2-(2-carboxyacetamido)benzoic acid (16% yield); $^1$H NMR (400 MHz, DMSO) δ 11.72 (s, 1H), 8.68 (d, J=7.6 Hz, 1H), 8.06 (dd, J=8.0 Hz, J=1.6 Hz, 1H), 7.89 (d, J=16.0 Hz, 1H), 7.67-7.60 (m, 2H), 7.23-7.18 (m, 1H), 6.98 (d, J=8.8 Hz, 1H), 6.81 (d, J=16.0 Hz, 1H), 4.88 (d, J=2.5 Hz, 2H), 3.92 (s, 3H), 3.83 (s, 3H), 3.59 (t, J=2.4 Hz, 1H); MS (ESI−) m/z 380.1 (M−H)−; 96.7% purity, RT 2.62 min (Method 3).

151

(E)-2-(3-(3,4-dimethoxy-2-(pyridin-3-ylmethoxy)phenyl)acrylamido)benzoic acid (96)

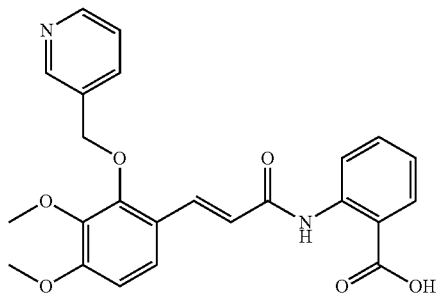 [SMILES: COc1ccc(/C=C/C(=O)Nc2ccccc2C(=O)O)c(OCc2cccnc2)c1OC]

a)
3,4-dimethoxy-2-(pyridin-3-ylmethoxy)benzaldehyde

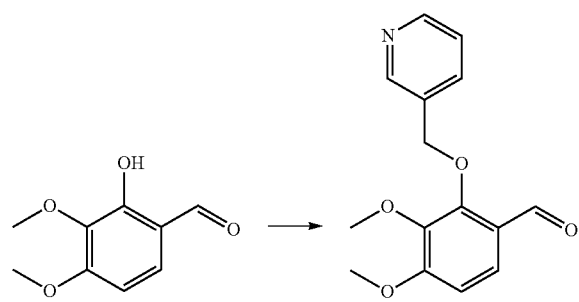 [SMILES: COc1ccc(C=O)c(O)c1OC ; COc1ccc(C=O)c(OCc2cccnc2)c1OC]

To a solution of 2-hydroxy-3,4-dimethoxybenzaldehyde (0.240 g, 1.32 mmol, 1 equiv., Inorganic Chemistry, 2004, 43, 4743-4750) in acetonitrile (10.5 mL) was added potassium carbonate (0.546 g, 3.95 mmol, 3 equiv.), 3-picolyl chloride hydrochloride (0.216 g, 1.32 mmol) and sodium iodide (0.02 g, 0.13 mmol, 0.1 equiv.) and the resulting mixture stirred at 95° C. for 16 hours. The reaction was cooled to room temperature and poured into saturated potassium carbonate solution. The acetonitrile was removed in vacuo and the aqueous phase extracted with ethyl acetate (×2). The combined organic phase was washed with saturated potassium carbonate solution, dried over MgSO$_4$ and the solvent removed in vacuo. The residue was purified by silica gel chromatography (petroleum ether:ethyl acetate 1:0 to 0:1) to afford the title compound as a white solid (0.182 g, 50%); $^1$H NMR (400 MHz, CDCl$_3$) δ 10.14 (s, 1H), 8.67 (d, J=1.8 Hz, 1H), 8.61 (dd, J=4.8, J=1.5 Hz, 1H), 7.82-7.77 (m, 1H), 7.60 (d, J=8.8 Hz, 1H), 7.33 (dd, J=7.8, 4.8 Hz, 1H), 6.80 (d, J=8.8 Hz, 1H), 5.24 (s, 2H), 3.96 (s, 3H), 3.90 (s, 3H).

152 b) (E)-2-(3-(3,4-dimethoxy-2-(pyridin-3-ylmethoxy)phenyl)acrylamido)benzoic acid

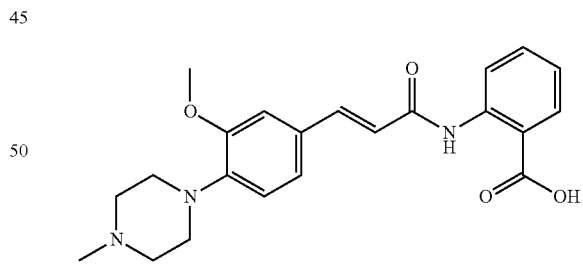

The title compound was prepared according to the procedure described for the synthesis of (E)-2-(3-(2-(2-(dimethylamino)ethoxy)-3-methoxy-4-(prop-2-yn-1-yloxy)phenyl)acrylamido)benzoic acid (78) starting from 3,4-dimethoxy-2-(pyridin-3-ylmethoxy)benzaldehyde and 2-(2-carboxyacetamido)benzoic acid (12% yield); $^1$H NMR (400 MHz, DMSO) δ 11.78 (s, 1H), 8.71 (d, J=1.8 Hz, 1H), 8.66 (d, J=7.6 Hz, 1H), 8.61 (dd, J=4.8 Hz, J=1.5 Hz, 1H), 8.06 (dd, J=7.8 Hz, J=1.5, Hz, 1H), 7.99-7.94 (m, 1H), 7.78 (d, J=15.8 Hz, 1H), 7.66-7.58 (m, 2H), 7.50 (dd, J=7.7 Hz, J=4.9, Hz, 1H), 7.23-7.17 (m, 1H), 6.98 (d, J=8.8 Hz, 1H), 6.75 (d, J=15.7 Hz, 1H), 5.16 (s, 2H), 3.93 (s, 3H), 3.86 (s, 3H); MS (ESI+) m/z 435.3 (M+H)+; 98.6% purity, RT 2.91 min (Method 2).

(E)-2-(3-(3-methoxy-4-(4-methylpiperazin-1-yl)phenyl)acrylamido)benzoic acid (97)

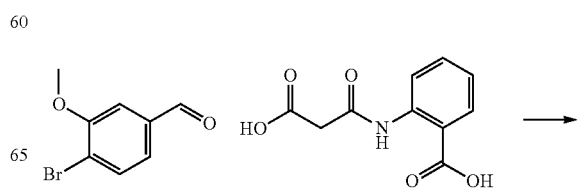

a) (E)-2-(3-(4-bromo-3-methoxyphenyl)acrylamido)benzoic acid

153
-continued

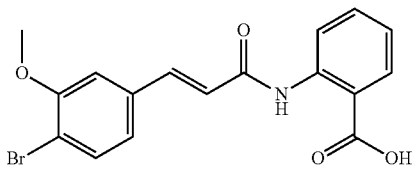

To a mixture of 2-[(2-carboxyacetyl)amino]benzoic acid (500 mg, 2.24 mmol, 1.0 equiv.) and 4-bromo-3-methoxybenzaldehyde (530 mg, 2.46 mmol, 1.1 equiv.) in toluene (5 mL) was added piperidine (19 mg, 0.224 mmol, 0.1 equiv.). The mixture was stirred at 110° C. for 10 hours. The precipitated solid was collected by filtration and suspended in 1N hydrochloric acid (20 mL) and stirred at 20° C. for 2 hours. The mixture was filtered and the collected solid dried under vacuum to afford the desired product as a yellow solid (400 mg, 47%). $^1$H NMR (400 MHz, DMSO-$d_6$) δ 11.34 (s, 1H), 8.61 ((d, J=8.0 Hz, 1H), 8.02 (dd, J 1.2 Hz, 7.6 Hz, 1H), 7.63-7.59 (m, 3H), 7.50 (s, 1H), 7.27 (d, J=8.0 Hz, 1H), 7.19 (t, J=8.0 Hz, 1H), 7.02 (d, J=8.0 Hz, 1H), 3.93 (s, 3H).

b) (E)-2-(3-(3-methoxy-4-(4-methylpiperazin-1-yl)phenyl)acrylamido)benzoic acid

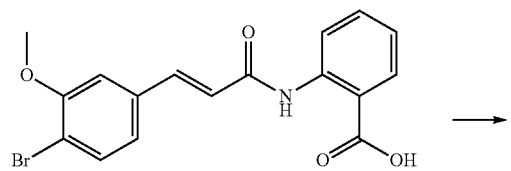

A mixture of (E)-2-(3-(4-bromo-3-methoxyphenyl)acrylamido)benzoic acid (100 mg, 0.266 mmol, 1.0 equiv.), 1-methylpiperazine (40 mg, 0.40 mmol, 1.5 equiv.), t-BuOK (90 mg, 0.799 mmol, 3.0 equiv.) and tBuXPhos Pd G1 (18 mg, 0.027 mmol, 0.1 equiv.) in tetrahydrofuran (3 mL) was de-gassed and then heated to 80° C. for 2 hours under a nitrogen atmosphere. The mixture was filtered and concentrated to dryness under vacuum. The residue was purified by preparative HPLC to afford the desired product as a yellow solid (16 mg, 12%) as the trifluoroacetic acid salt. $^1$H NMR (400 MHz, DMSO-$d_6$) δ 11.36 (s, 1H), 8.62 ((d, J=8.0 Hz, 1H), 8.02 (dd, J 1.2 Hz, 7.6 Hz, 1H), 7.62-7.56 (m, 2H), 7.38 (d, J=1.2 Hz, 1H), 7.25 (d, J=8.0 Hz, 1H), 7.18 (t, J=8.4 Hz, 1H), 6.98 (d, J=8.0 Hz, 1H), 6.83 (d, J=15.6 Hz, 1H), 3.89 (s, 3H), 2.87 (s, 3H) piperazine signals obscured under water signal; MS (ESI+) m/z 396.2 (M+H)+; 97.9% purity, RT 2.39 min (Method 11).

154
(E)-2-(3-(3-methoxy-4-(1,2,3,6-tetrahydropyridin-4-yl)phenyl)acrylamido)benzoic acid (98)

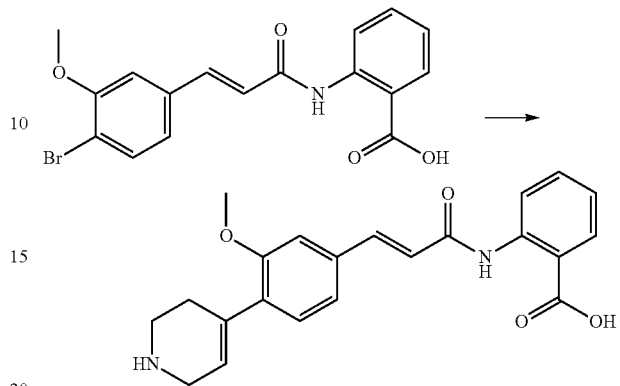

A mixture of 2-[[(E)-3-(4-bromo-3-methoxy-phenyl)prop-2-enoyl]amino]benzoic acid (150 mg, 0.399 mmol, 1.0 equiv.), tert-butyl 4-(4,4,5,5-tetramethyl-1,3,2-dioxaborolan-2-yl)-3,6-dihydro-2H-pyridine-1-carboxylate (1240 mg, 0.399 mmol, 1.0 equiv.), potassium carbonate (165 mg, 1.2 mmol, 3.0 equiv.) and Pd(dppf)Cl$_2$ (29 mg, 0.040 mmol, 1.0 equiv.) in N,N-dimethylformamide (1.5 mL) and water (0.3 mL) was de-gassed and then heated to 100° C. for 3 hours under a nitrogen atmosphere. After cooling to room temperature the mixture was diluted with dichloromethane:methanol (10:1), filtered through a silica pad and concentrated in vacuo. The residue was then stirred at 25° C. hydrochloric acid/methanol (2 mL, 8 mmol) for 30 minutes and concentrated under vacuum to give the desired product as a yellow solid (180 mg, 75%) as a hydrochloric acid salt. $^1$H NMR (CD$_3$OD, 400 MHz) δ 8.69 (d, J=8.4 Hz, 1H), 8.14 (d, J=6.4 Hz, 1H), 7.67 (d, J=15.6 Hz, 1H), 7.55 (t, J=7.6 Hz, 1H), 7.27 (d, J=14.4 Hz, 3H), 7.17 (t, J=7.2 Hz, 1H), 6.80 (d, J=15.6 Hz, 1H), 5.91 (s, 1H), 3.92 (s, 3H), 3.90-3.81 (m, 2H), 3.44 (t, J=6.0 Hz, 2H), 2.85-2.72 (m, 2H); MS (ESI+) m/z 379.1 (M+H)+; 100% purity, RT 1.54 min (Method 10).

(E)-2-(3-(3-methoxy-4-(1-methyl-1,2,3,6-tetrahydropyridin-4-yl)phenyl)acrylamido)benzoic acid (99)

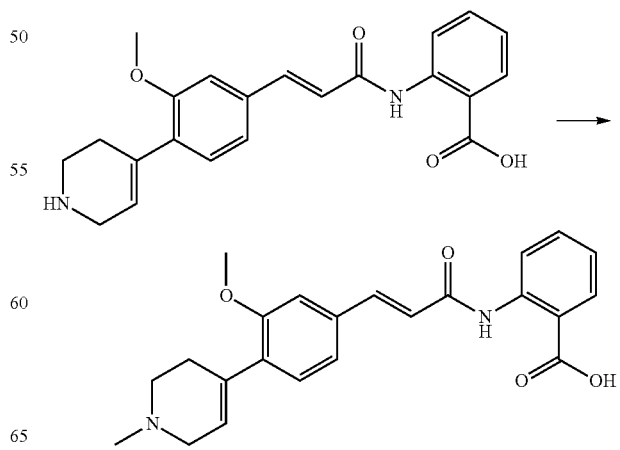

To a mixture of 2-[[(E)-3-[3-methoxy-4-(1,2,3,6-tetrahydropyridin-4-yl)phenyl]prop-2-enoyl]amino]benzoic acid (180 mg, 0.476 mmol, 1.0 equiv.) (98) in methanol (3 mL) was added formaldehyde (1 mL, 37% aqueous). After stirring at 25° C. for 30 minutes sodium triacetoxyborohydride (302 mg, 1.43 mmol, 3.0 equiv.) was added and the mixture stirred for 2 hours. The reaction was then concentrated in vacuo and the residue dissolved in dichloromethane:methanol (10:1) and filtered. The filtrate was concentrated in vacuo and the residue purified by preparative HPLC to give the desired product as a yellow solid (41 mg, 22%) as the trifluoroacetic acid salt; ¹H NMR (CD₃OD, 400 MHz) δ 8.72 (d, J=8.4 Hz, 1H), 8.13 (dd, J=8.0 Hz, J=1.6 Hz, 1H), 7.66 (d, J=14.2 Hz, 1H), 7.62 (d, J=7.2 Hz, 1H), 7.29 (d, J=16.8 Hz, 3H), 7.21 (t, J=6.8 Hz, 1H), 6.83 (d, J=15.6 Hz, 1H), 5.90 (s, 1H), 4.11-4.04 (m, 1H), 3.93 (s, 3H), 3.84-3.66 (m, 2H), 3.39-3.33 (m, 1H), 3.02 (s, 3H), 2.89-2.83 (m, 2H); MS (ESI+) m/z 393.1 (M+H)+; 95.3% purity, RT 1.61 min (Method 11).

(E)-2-(3-(4-ethyl-3-methoxyphenyl)acrylamido)benzoic acid (100)

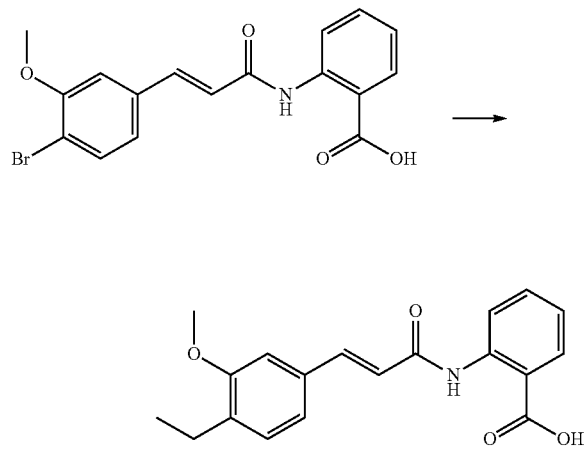

A mixture of 2-[[(E)-3-(4-bromo-3-methoxy-phenyl)prop-2-enoyl]amino]benzoic acid (150 mg, 0.399 mmol, 1.0 equiv.), ethylboronic acid (35.4 mg, 0.478 mmol, 1.2 equiv.), cesium carbonate (390 mg, 1.20 mmol, 3.0 equiv.) and Ad₂nBuP Biphenyl (26.7 mg, 0.04 mmol, 0.1 equiv.) in 2-methyl-2-butanol (1 mL) was de-gassed and then heated to 90° C. for 2 hours under a nitrogen atmosphere. The cooled mixture was diluted with ethyl acetate (20 mL), washed with brine (2×5 mL) and the organic phase concentrated to dryness in vacuo and the residue purified by preparative HPLC to afford the desired product as a yellow solid (43.0 mg, 32%); ¹H NMR (CD₃OD, 400 MHz) δ 8.72 (d, J=8.0 Hz, 1H), 8.14 (dd, J=1.6 Hz, J=9.6 Hz, 1H), 7.68 (d, J=16.0 Hz, 1H), 7.64-7.59 (m, 1H), 7.21-7.17 (m, 4H), 6.74 (d, J=15.6 Hz, 1H), 3.92 (s, 3H), 2.66 (q, J=7.2 Hz, 2H), 1.20 (t, J=7.6 Hz, 3H); MS (ESI−) m/z 324.1 (M−H)⁻. 97.9% purity, RT 1.61 min (Method 8).

(E)-2-(3-(4-methoxy-3-morpholinophenyl)acrylamido)benzoic acid (101)

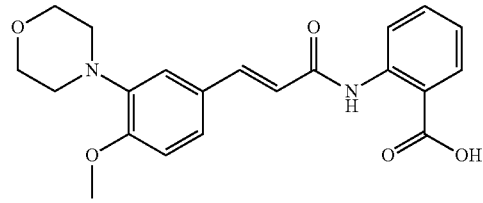 [SMILES: COc1ccc(/C=C/C(=O)Nc2ccccc2C(=O)O)cc1N1CCOCC1]

a) (E)-2-(3-(3-bromo-4-methoxyphenyl)acrylamido)benzoic acid

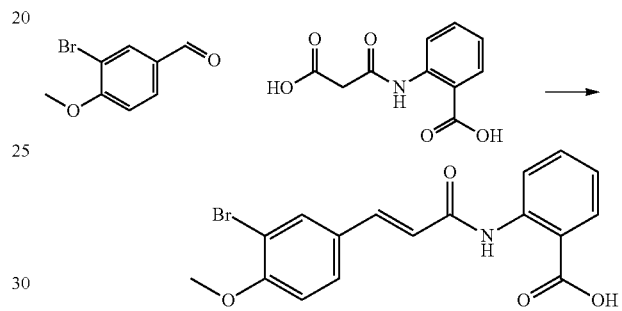

To a solution of 2-[(2-carboxyacetyl)amino]benzoic acid (500 mg, 2.24 mmol, 1.0 equiv.) in toluene (20 mL) was added 3-bromo-4-methoxybenzaldehyde (506 mg, 2.35 mmol, 1.05 equiv.) and piperidine (95.4 mg, 1.12 mmol, 0.5 equiv.) and the resulting mixture stirred at 110° C. for 16 hours. The reaction was cooled to room temperature, 1N hydrochloric acid (2 mL) was added and the mixture was extracted with ethyl acetate (100 mL×2). The combined organic phase was concentrated under reduced pressure to afford the desired product as a white solid (300 mg, 36%) which was used without further purification; MS (ESI+) m/z 376.0/378.0 (M+H)+.

b) (E)-2-(3-(4-methoxy-3-morpholinophenyl)acrylamido)benzoic acid

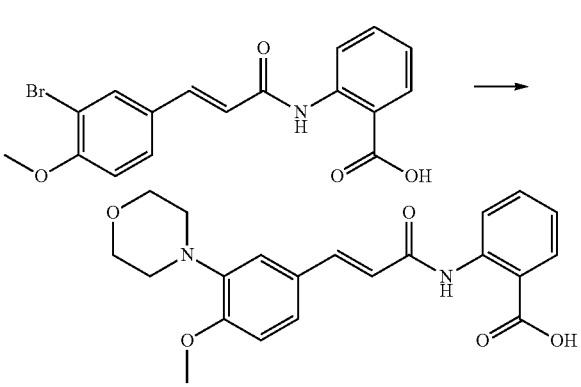

The title compound was prepared as the trifluoroacetic acid salt according to the procedure described for the synthesis of (E)-2-(3-(3-methoxy-4-(4-methylpiperazin-1-yl)phenyl)acrylamido)benzoic acid (97) starting from (E)-2-(3-(3-bromo-4-methoxyphenyl)acrylamido)benzoic acid and morpholine (14%); $^1$H NMR (DMSO-d$_6$, 400 MHz) δ 11.24 (s, 1H), 8.60 (d, J=8.4 Hz, 1H), 8.01 (d, J=7.2 Hz, 1H), 7.65-7.50 (m, 2H), 7.35 (d, J=8.0 Hz, 1H), 7.27 (s, 1H), 7.18 (t, J=7.6 Hz, 1H), 7.01 (d, J=8.4 Hz, 1H), 6.75 (d, J=15.6 Hz, 1H), 3.84 (s, 3H), 3.78-3.67 (m, 4H), 3.05-2.94 (m, 4H); MS (ESI+) m/z 383.1 (M+H)+; 98.4% purity, RT 2.69 min (Method 11).

2-[[(E)-3-[4-(cyclopropylmethyl)-3-methoxyphenyl]prop-2-enoyl]amino]benzoic acid (102)

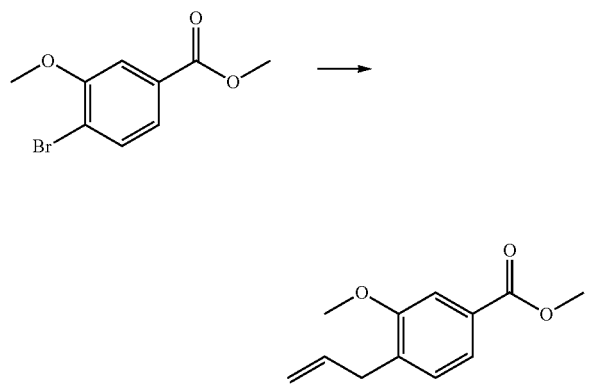

a) methyl 4-allyl-3-methoxybenzoate

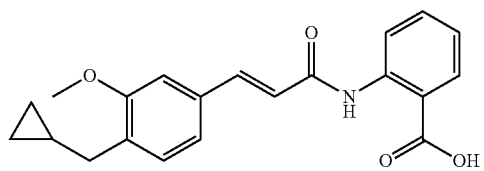 [SMILES: COc1cc(/C=C/C(=O)Nc2ccccc2C(=O)O)ccc1CC1CC1]

To a solution of methyl 4-bromo-3-methoxybenzoate (28.00 g, 114.25 mmol, 1.00 equiv.) in N,N-dimethylformamide (400 mL) was added allyl(tributyl)stannane (38.53 mL, 125.68 mmol, 1.10 equiv.) and Pd(PPh$_3$)$_4$(13.20 g, 11.43 mmol, 0.10 equiv.). The mixture was degassed under vacuum and purged with nitrogen 3 times and the resulting mixture stirred at 80° C. for 4 hours under a nitrogen atmosphere. Water (25 mL) and sodium fluoride (5 g) were added, the resultant mixture was stirred at 25° C. for 30 minutes and then filtered. The filter cake was washed with ethyl acetate (20 mL×2). The combined filtrate was extracted with ethyl acetate (250 ml×3). The organic phase was combined and washed with brine (100 mL×2), dried over sodium sulfate, filtered and concentrated in vacuo. The residue was purified by silica gel column chromatography (petroleum ether:ethyl acetate 1000:1 to 800:1) to give the desired product as colourless oil (21.2 g, 90%); $^1$H NMR (DMSO, 400 MHz) δ 7.51 (dd, J=8.0 Hz, J=1.6 Hz, 1H), 7.45 (s, 1H), 7.21 (d, J=7.6 Hz, 1H), 5.96-5.89 (m, 1H), 5.06-5.01 (m, 2H), 3.83 (s, 3H), 3.82 (s, 3H), 3.36 (s, 2H).

b) methyl 4-(cyclopropylmethyl)-3-methoxybenzoate

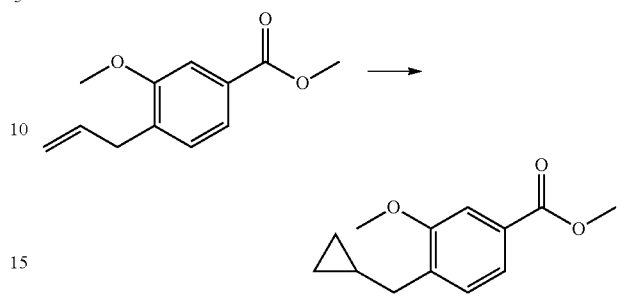

A solution of diethylzinc in toluene (1 M, 155.16 mL, 4.00 equiv.) was added to dichloromethane (100 mL) under a nitrogen atmosphere. The solution was cooled in an ice bath, a solution of trifluoroacetic acid (12.35 mL, 166.80 mmol, 4.30 equiv.) in dichloromethane (100 mL) was added dropwise and the reaction mixture stirred for 20 minutes at 0° C. A solution of diiodomethane (12.52 mL, 155.16 mmol, 4.00 equiv.) in dichloromethane (100 mL) was added and the reaction stirred for 20 minutes. Methyl 4-allyl-3-methoxybenzoate (8.00 g, 38.79 mmol, 1.00 equiv.) was then added and the resulting mixture stirred for 48 hours at 20° C. The mixture was poured into water (300 mL) and extracted with dichloromethane (200 mL×3). The combined organic phase was washed with brine (200 mL), dried over sodium sulfate and the solvent removed in vacuo. The residue was purified by preparative HPLC to provide the desired product as a yellow liquid (3.5 g, 41%); $^1$H NMR (CDCl$_3$, 400 MHz) δ 7.61 (dd, J=7.6 Hz, J=1.6 Hz, 1H), 7.51 (s, 1H), 7.36 (d, J=7.6 Hz, 1H), 3.90 (s, 3H), 3.88 (s, 3H), 2.58 (d, J=6.8 Hz, 2H), 1.05-1.01 (m, 1H), 0.52-0.50 (m, 2H), 0.20-0.18 (m, 2H).

c) [4-(cyclopropylmethyl)-3-methoxy-phenyl]methanol

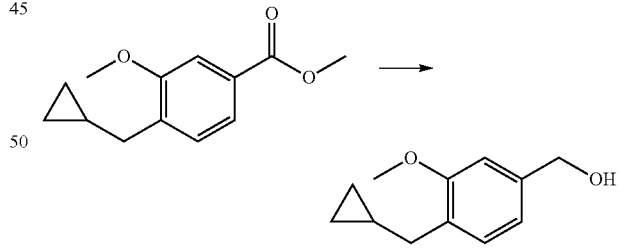

To a solution of methyl 4-(cyclopropylmethyl)-3-methoxybenzoate (3.50 g, 15.89 mmol, 1.00 equiv.) in tetrahydrofuran (50 mL) was added DIBAL-H (1 M, 47.7 mL, 3.00 equiv.) at 0° C. and the reaction was stirred at 25° C. for 1 hour. The mixture was quenched with water (100 mL) and acidified with 6 N hydrochloric acid until the pH was 6-7. The mixture was extracted with ethyl acetate (100 mL×3). The combined organic phase was washed with brine (100 mL), dried over sodium sulfate, filtered and concentrated in vacuo to afford the desired product as a yellow liquid (3.4 g) which was used without further purification; 1H NMR (CDCl$_3$, 400 MHz) δ 7.29 (d, J=8.0 Hz, 1H), 6.92-6.90 (m, 2H), 4.69 (s, 2H), 3.88 (s, 3H), 2.55 (d, J=6.8 Hz, 2H), 1.06-1.02 (m, 1H), 0.51-0.48 (m, 2H), 0.21-0.18 (m, 2H).

d) 4-(cyclopropylmethyl)-3-methoxy-benzaldehyde

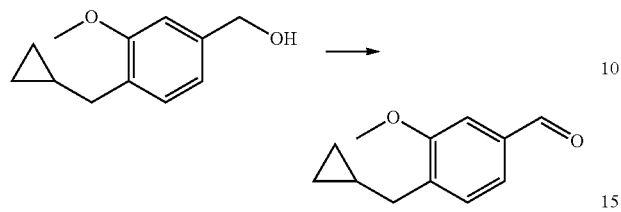

To a solution of [4-(cyclopropylmethyl)-3-methoxyphenyl]methanol (3.40 g, 17.69 mmol, 1.00 equiv.) in dichloromethane (30 mL) was added Dess-Martin periodinane (26.26 g, 61.92 mmol, 19.17 mL, 3.50 equiv.) at 0° C. and the reaction was stirred at 25° C. for 1 hour. The reaction was quenched with saturated aqueous sodium sulphite (80 mL) and saturated aqueous sodium carbonate (50 mL) at 0° C. and the resulting mixture extracted with ethyl acetate (100 mL×4). The combined organic phase was washed with brine (100 mL), dried over sodium sulfate, filtered and concentrated in vacuo. The residue was purified by silica gel column chromatography (petroleum ether:ethyl acetate 20:1) to provide the desired product as a colourless liquid (2.6 g, 77%); $^1$H NMR (CDCl$_3$, 400 MHz) δ 9.95 (s, 1H), 7.48 (d, J=7.6 Hz, 1H), 7.43 (d, J=7.6 Hz, 1H), 7.37 (s, 1H), 3.90 (s, 3H), 2.61 (d, J=6.8 Hz, 2H), 1.09-1.04 (m, 1H), 0.56-0.51 (m, 2H), 0.21-0.20 (m, 2H).

e) 2-[[(E)-3-[4-(cyclopropylmethyl)-3-methoxyphenyl]prop-2-enoyl]amino]benzoic acid

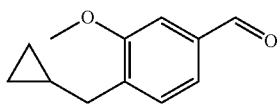

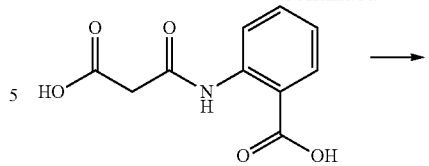

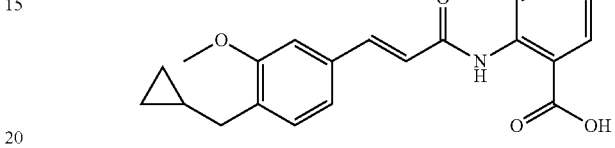

To a solution of 4-(cyclopropylmethyl)-3-methoxybenzaldehyde (2.30 g, 12.09 mmol, 1.00 equiv.) in toluene (50 mL) was added 2-[(2-carboxyacetyl)amino]benzoic acid (2.97 g, 13.30 mmol, 1.10 equiv.) and piperidine (120 μL, 1.21 mmol, 0.10 equiv.) and the mixture stirred at 130° C. for 6 hours. The mixture was concentrated in vacuo and the residue purified by preparative HPLC to provide the title compound as a white solid (2.0 g, 47%); $^1$H NMR (CD$_3$OD, 400 MHz) δ 8.72 (d, J=8.4 Hz, 1H), 8.13 (dd, J=8.0 Hz, J=1.6 Hz, 1H), 7.65 (d, J=15.6 Hz, 1H), 7.59 (t, J=6.8 Hz, 1H), 7.29 (d, J=7.6 Hz, 1H), 7.20-7.15 (m, 3H), 6.75 (d, J=15.6 Hz, 1H), 3.90 (s, 3H), 2.55 (d, J=6.8 Hz, 2H), 1.05-1.01 (m, 1H), 0.50-0.47 (m, 2H), 0.19-0.18 (m, 2H); MS (ESI+) m/z 352.1 [M+H]$^+$; 100% purity, RT 2.90 min (Method 9).

| Ex | Structure | Data | Method |
|---|---|---|---|
| 103 | (E)-2-(3-(3-methoxy-4-morpholinophenyl)acrylamido)benzoic acid trifluoroacetic acid salt | $^1$H NMR (DMSO-d$_6$, 400 MHz) δ11.29 (s, 1H), 8.62 (d, J = 8.4 Hz, 1H), 8.01 (dd, J = 1.2 Hz, 9.2 Hz, 1H), 7.62-7.55 (m, 2H), 7.34 (s, 1H), 7.24 (d, J = 8.4 Hz, 1H), 7.18 (t, J = 4.0 Hz, 1H), 6.90 (d, J = 8.4 Hz, 1H), 6.79 (d, J = 15.6 Hz, 1H), 3.88 (s, 3H), 3.75-3.72 (m, 4H), 3.05-3.03 (m 4H); MS (ESI+) m/z 383.1 (M + H)+; 99.5% purity, RT 2.76 min (Method 11) | Prepared according to the method for 97 starting from 4-bromo-3-methoxy-benzaldehyde, 2-[(2-carboxyacetyl)amino]benzoic acid and morpholine |

| Ex | Structure | Data | Method |
|---|---|---|---|
| 104 | (E)-2-(3-(4-methoxy-3-(1-methyl-1,2,3,6-tetrahydropyridin-4-yl)phenyl)acrylamido)benzoic acid trifluoroacetic acid salt | $^1$H NMR (CD$_3$OD, 400 MHz) δ 8.71 (d, J = 8.4 Hz, 1H), 8.14 (dd, J = 1.2 Hz, 7.6 Hz, 1H), 7.68-7.64 (m, 2H), 7.62 (t, J = 2.4 Hz, 1H), 7.51 (d, J = 2.4 Hz, 1H), 7.19 (t, J = 7.6 Hz, 1H), 7.10 (d, J = 8.8 Hz, 1H), 6.66 (d, J = 15.6 Hz, 1H), 5.88 (s, 1H), 4.11-3.41 (m, 6H), 3.10-2.76 (m, 6H); MS (ESI+) m/z 393.2 (M + H)+; 99.0% purity, RT 2.48 min (Method 11) | Prepared according to the method for 98 and then 99 starting from (E)-2-(3-(3-bromo-4-methoxyphenyl)acrylamido)benzoic acid |
| 105 | (E)-2-(3-(3-ethyl-4-methoxyphenyl)acrylamido)benzoic acid | $^1$H NMR (DMSO-d$_6$, 400 MHz) δ 11.30 (s, 1H), 8.62 (d, J = 7.6 Hz, 1H), 8.01 (dd, J = 1.6 Hz, 8.0 Hz, 1H), 7.64-7.45 (m, 4H), 7.17 (t, J = 8.0 Hz, 1H), 7.01 (d, J = 8.4 Hz, 1H), 6.73 (d, J = 15.6 Hz, 1H), 3.84 (s, 3H), 2.60 (q, J = 7.6 Hz, 2H), 1.16 (t, J = 7.6 Hz, 3H); MS (ESI+) m/z 348.1 (M + Na)$^+$; 95.9% purity, RT 3.16 min (Method 11) | Prepared according to the method for 100 starting from (E)-2-(3-(3-bromo-4-methoxyphenyl)acrylamido)benzoic acid |
| 106 | (E)-2-(3-(3-(cyclopropylmethyl)-4-methoxyphenyl)acrylamido)benzoic acid | $^1$H NMR (CDCl$_3$, 400 MHz) δ 11.18 (s, 1H), 8.92 (d, J = 8.8 Hz, 1H), 8.15 (dd, J = 1.6 Hz, 9.6 Hz, 1H), 7.74 (d, J = 15.6 Hz, 1H), 7.67-7.62 (m, 1H), 7.54 (d, J = 4.0 Hz, 1H), 7.44 (dd, J = 2.4 Hz, 10.8 Hz, 1H), 7.15-7.12 (m, 1H), 6.86 (d, J = 8.4 Hz, 1H), 6.49 (d, J = 15.2 Hz, 1H), 3.87 (s, 3H), 2.55 (d, J = 6.8 Hz, 2H), 1.08-1.05 (m, 1H), 0.55-0.52 (m, 2H), 0.24-0.20 (m, 2H); MS (ESI+) m/z 352.0 (M + H)+; 96.9% purity, RT 2.97 min (Method 12) | Prepared according to the method for 102 starting from methyl 3-bromo-4-methoxybenzoate |

2-[[(E)-3-(4-methyl-2,3-dihydro-1,4-benzoxazin-6-yl)prop-2-enoyl]amino]benzoic acid (107)

a) ethyl 2-(4-formyl-2-nitrophenoxy)acetate

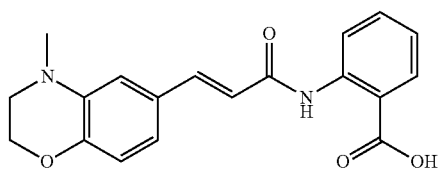 [SMILES: CN1CCOc2ccc(/C=C/C(=O)Nc3ccccc3C(=O)O)cc21]

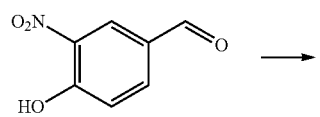

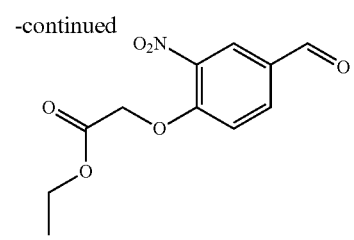

To a solution of 4-hydroxy-3-nitrobenzaldehyde (40.00 g, 239.35 mmol, 1.00 equiv.) in acetonitrile (100 mL) was added ethyl 2-chloroacetate (44.00 g, 359.03 mmol, 38.26 mL, 1.50 equiv.), sodium iodide (17.94 g, 119.68 mmol, 0.50 equiv.) and potassium carbonate (99.24 g, 718.05 mmol, 3.00 equiv.) and the resultant mixture stirred at 80° C. for 4 hours. The reaction mixture was cooled to 25° C. and filtered. The solid was washed with ethyl acetate (100 mL) and the combined filtrate was washed with brine (50 mL×2). The combined organic layers were dried over sodium sulfate, concentrated under reduced pressure and the residue purified by silica gel column chromatography (petroleum ether:ethyl acetate 10:1 to 3:1) to give the desired product as a yellow solid (15.50 g, 26%); $^1$H NMR (DMSO-d$_6$, 400 MHz) δ 9.95 (s, 1H), 8.44 (d, J=2.0 Hz, 1H), 8.16 (dd, J=8.8

Hz, J=2.4 Hz, 1H), 7.51 (d, J=8.8 Hz, 1H), 5.17 (s, 2H), 4.19 (q, J=6.8 Hz, 2H), 1.21 (t, J=6.8 Hz, 3H).

b) 3-oxo-4H-1,4-benzoxazine-6-carbaldehyde

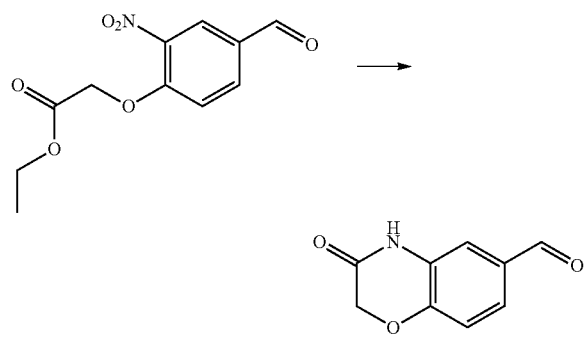

To a solution of ethyl 2-(4-formyl-2-nitrophenoxy)acetate (9.30 g, 36.73 mmol, 1.00 equiv.) in acetic acid (20.00 mL) was added iron powder (12.31 g, 220.37 mmol, 6.00 equiv.) and the mixture stirred at 60° C. for 16 hours. The reaction mixture was diluted with dichloromethane (50 mL) and methanol (50 mL), stirred at 25° C. for 1 hour and then filtered. The filtrate was concentrated in vacuo to give the desired product as a yellow solid which was used without further purification (4.40 g, 67%); ¹H NMR (DMSO-d₆, 400 MHz) δ 10.99 (br. s, 1H), 9.84 (s, 1H), 7.54 (dd, J=8.0 Hz, J=1.6 Hz, 1H), 7.38 (d, J=1.2 Hz, 1H), 7.15 (d, J=8.4 Hz, 1H), 4.72 (s, 2H).

c) 4-methyl-3-oxo-1,4-benzoxazine-6-carbaldehyde

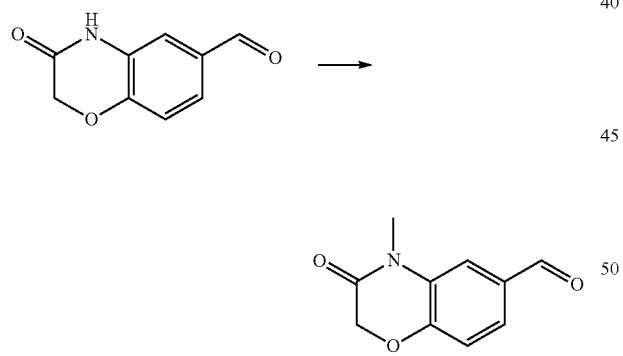

To a mixture of 3-oxo-4H-1,4-benzoxazine-6-carbaldehyde (3.27 g, 18.46 mmol, 1.00 equiv.) and caesium carbonate (18.04 g, 55.38 mmol, 3.00 equiv.) in acetonitrile (20.00 mL) was added methyl iodide (2.30 mL, 36.92 mmol, 2.00 equiv.) and the mixture stirred at 80° C. for 2 hours. The reaction was cooled to 25° C. and diluted with ethyl acetate (30 mL). The resultant mixture was filtered and the filtrate concentrated under reduced pressure to give the desired product which was used without further purification (3.50 g, 99%); ¹H NMR (DMSO-d₆, 400 MHz) δ 9.91 (s, 1H), 7.63-7.60 (m, 2H), 7.20 (d, J=8.8 Hz, 1H), 4.79 (s, 2H), 3.34 (s, 3H).

d) (4-methyl-2,3-dihydro-1,4-benzoxazin-6-yl)methanol

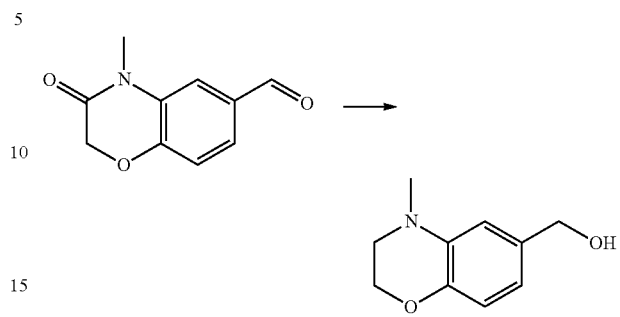

To a solution of 4-methyl-3-oxo-1,4-benzoxazine-6-carbaldehyde (5.90 g, 30.86 mmol, 1.00 equiv.) in tetrahydrofuran (100 mL) was added BH₃-Me₂S (10 M, 30.86 mL, 10.00 equiv.) drop-wise at 0° C. and the resultant mixture stirred at 60° C. for 2 hours. The reaction was quenched with methanol (100 mL) at 25° C. and concentrated in vacuo. The residue was dissolved in methanol (100 mL) and stirred at 60° C. for 2 hr. The solvent was removed under reduce pressure to give the crude product, which used directly in the next step (7.0 g); MS (ESI+) m/z 180.1 (M+H)+.

e) 4-methyl-2,3-dihydro-1,4-benzoxazine-6-carbaldehyde

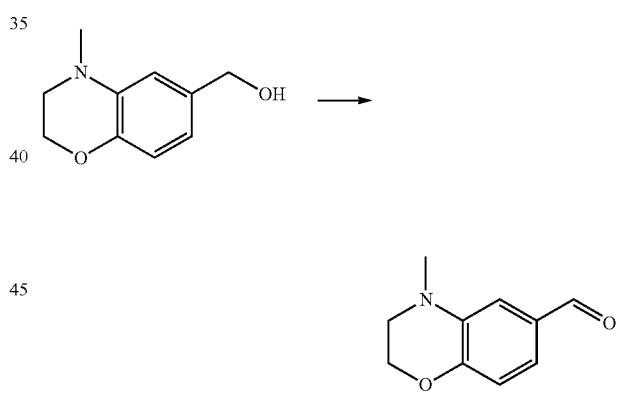

To a solution of (4-methyl-2,3-dihydro-1,4-benzoxazin-6-yl)methanol (7.00 g, 39.06 mmol, 1.00 equiv.) in dichloromethane (30.00 mL) was added Dess-Martin periodinane (24.85 g, 58.59 mmol, 18.14 mL, 1.50 equiv.) at 0° C. and the mixture stirred at 25° C. for 10 minutes. The reaction was quenched with saturated aqueous sodium thiosulfate (30 mL) and extracted with ethyl acetate (30 mL×3). The organic layer was washed with saturated sodium bicarbonate (30 mL×2) and brine (30 mL×2), dried over sodium sulfate and the solvent removed in vacuo. The residue was purified by silica gel column chromatography (petroleum ether:ethyl acetate 1:0 to 15:1) to give the desired product as a yellow oil (2.30 g, 33%); MS (ESI+) m/z 178.0 (M+H)+.

f) 2-[[(E)-3-(4-methyl-2,3-dihydro-1,4-benzoxazin-6-yl)prop-2-enoyl]amino]benzoic acid

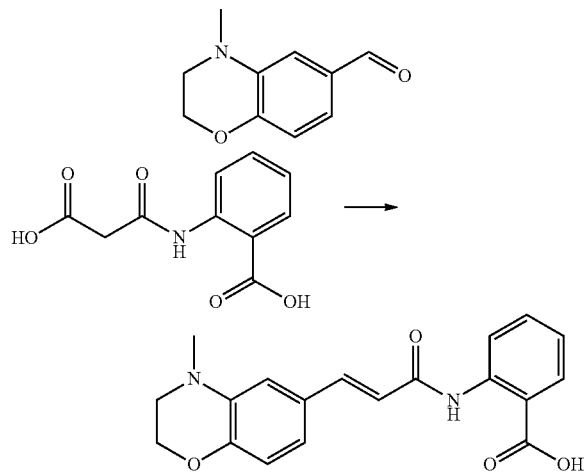

To a solution of 4-methyl-2,3-dihydro-1,4-benzoxazine-6-carbaldehyde (2.46 g, 13.88 mmol, 1.00 equiv.) and 2-[(2-carboxyacetyl)amino]benzoic acid (3.10 g, 13.88 mmol, 1.00 equiv.) in toluene (20 mL) was added piperidine (275 µL, 2.78 mmol, 0.20 equiv.) and the mixture stirred at 110° C. for 16 hours. The solvent was removed under reduced pressure and the residue was purified by preparative HPLC to provide the desired product as a yellow solid (3.26 g, 69%); $^1$H NMR (DMSO-$d_6$, 400 MHz) δ 11.29 (s, 1H), 8.62 (d, J=8.0 Hz, 1H), 8.00 (dd, J=8.0 Hz, J=1.6 Hz, 1H), 7.61 (t, J=8.0 Hz, 1H), 7.53 (d, J=15.2 Hz, 1H), 7.16 (t, J=8.0 Hz, 1H), 7.06 (d, J=2.0 Hz, 1H), 6.97 (d, J=8.4 Hz, 1H), 6.72-6.68 (m, 2H), 4.27 (t, J=4.4 Hz, 2H), 3.25 (t, J=4.4 Hz, 2H), 2.90 (s, 3H). MS (ESI+) m/z 339.1 [M+H]$^+$; 100% purity; RT=1.27 min (Method 6).

(E)-2-(3-(2-methyl-3-oxoisoindolin-5-yl)acrylamido)benzoic acid (108)

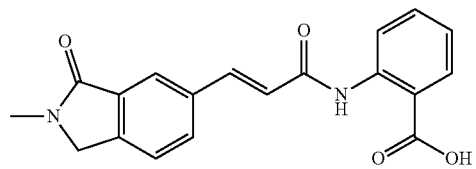 [SMILES: CN1Cc2ccc(/C=C/C(=O)Nc3ccccc3C(=O)O)cc2C1=O]

a) 6-vinylisoindolin-1-one

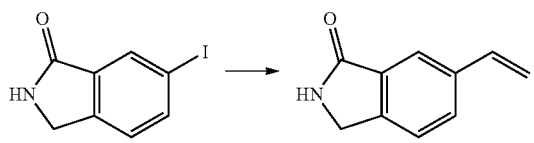

A mixture of 6-iodoisoindolin-1-one (1.00 g, 3.86 mmol, 1.0 equiv.), 4,4,5,5-tetramethyl-2-vinyl-1,3,2-dioxaborolane (0.892 g, 5.79 mmol, 1.5 equiv.), tetrakis(triphenylphosphine)palladium(0) (0.446 g, 0.386 mmol, 0.1 equiv.) and potassium carbonate (1.07 g, 7.72 mmol, 2.0 equiv.) in dioxane (15 mL) and water (3 mL) was degassed and purged with nitrogen 3 times and then stirred at 90° C. for 16 hours under a nitrogen atmosphere. The reaction mixture was concentrated under reduced pressure to give a residue which was washed petroleum ether/ethyl acetate (10/1, 30 mL) and the solid collected by filtration to give the desired product as a yellow solid (0.6 g, 73%); MS (ESI+) m/z 160.3 (M+H)+.

b) 2-methyl-6-vinylisoindolin-1-one

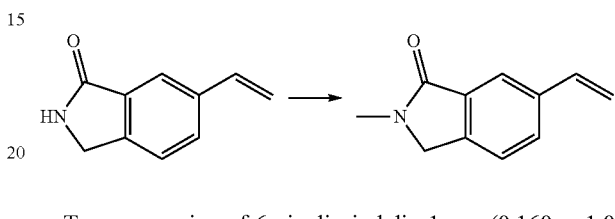

To a suspension of 6-vinylisoindolin-1-one (0.160 g, 1.0 mmol, 1.00 equiv.) in acetonitrile (5 mL) was added caesium carbonate (0.823 g, 2.53 mmol, 2.5 equiv.) and methyl iodide (75 µL, 1.21 mmol, 1.20 equiv.) and the resultant mixture was stirred at 80° C. for 1.5 hours. The mixture was cooled to 20° C., diluted with ethyl acetate (20 mL) and filtered. The filtrate was washed with brine (10 mL) and the organic phase was concentrated under reduced pressure to afford the desired product (0.180 g) as light yellow gum which was used without further purification; MS (ESI$^+$) m/z 174.1 (M+H)$^+$.

c) 2-methyl-3-oxoisoindoline-5-carbaldehyde

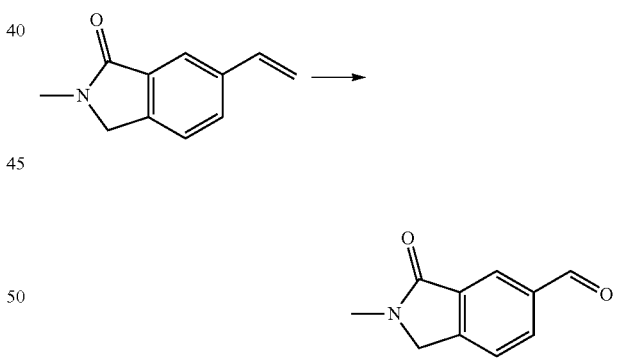

To a solution of 2-methyl-6-vinylisoindolin-1-one (0.160 g, 0.92 mmol, 1.00 equiv.) in dioxane (10 mL) and water (1 mL) was added 4-methylmorpholine N-oxide monohydrate (146 L, 1.39 mmol, 1.50 equiv.) and osmium(IV) oxide (0.070 g, 0.28 mmol, 0.30 equiv.) and mixture was stirred at 20° C. for 10 minutes. Sodium periodate (0.800 g, 3.74 mmol, 4.05 equiv.) was added and the resultant mixture was stirred at 20° C. for an additional 1.5 hours. The mixture was diluted with ethyl acetate (30 mL) and filtered. The filtrate was washed with brine (10 mL) and the organic layer was concentrated under reduced pressure to afford the desired product (0.170 g) as light yellow gum which was used without further purification; MS (ESI$^+$) m/z 176.1 (M+H)+.

d) (E)-2-(3-(2-methyl-3-oxoisoindolin-5-yl)acrylamido)benzoic acid

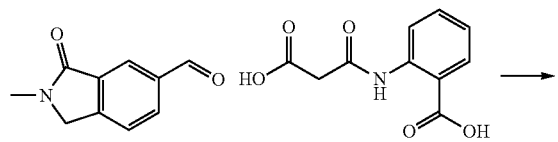

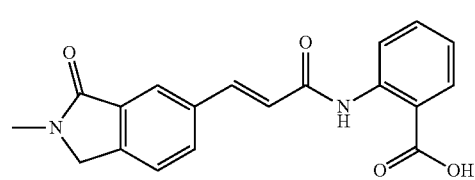

To a mixture of 2-methyl-3-oxoisoindoline-5-carbaldehyde (0.080 g, 0.46 mmol, 1.00 equiv.) and 2-[(2-carboxyacetyl)amino]benzoic acid (0.102 g, 0.46 mmol, 1.00 equiv.) in toluene (3 mL) was added piperidine (7 μL, 0.07 mmol, 0.15 equiv.) and the mixture was stirred at 120° C. for 2 hours. The reaction was concentrated under reduced pressure. The residue was triturated with methanol (5 mL) and 1N hydrochloric acid (2 mL) and the solid collected by filtration to afford the desired product (0.021 g, 13% yield) as a grey solid; $^1$H NMR (DMSO-$d_6$, 400 MHz) δ 11.40 (br. s., 1H), 8.60 (d, J=8.4 Hz, 1H), 8.03-7.94 (m, 2H), 7.93 (d, J=1.6 Hz, 1H), 7.72 (d, J=15.6 Hz, 1H), 7.65-7.62 (m, 2H), 7.03-7.02 (m, 1H), 7.10 (d, J=15.6 Hz, 1H), 4.50 (s, 2H), 3.08 (s, 3H); MS (ESI+) m/z 337.1 (M+H)+; 95.8% purity, RT 1.66 min (Method 6).

(E)-2-(3-(4-methyl-3-oxo-3,4-dihydro-2H-benzo[b][1,4]oxazin-7-yl)acrylamido)benzoic acid (109)

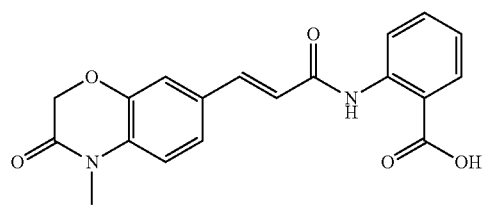 [SMILES: CN1C(=O)COc2cc(/C=C/C(=O)Nc3ccccc3C(=O)O)ccc21]

a) (E)-2-(3-(3-oxo-3,4-dihydro-2H-benzo[b][1,4]oxazin-7-yl)acrylamido)benzoic acid

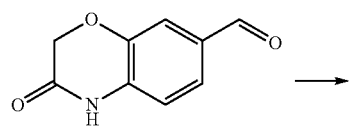

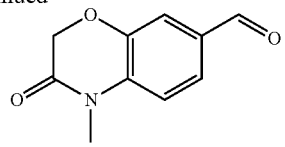

To a mixture of 3-oxo-4H-1,4-benzoxazine-7-carbaldehyde (0.600 g, 3.39 mmol, 1.00 equiv.) and caesium carbonate (3.31 g, 10.17 mmol, 3.00 equiv.) in N,N-dimethylformamide (6 mL) was added methyl iodide (0.42 mL, 6.78 mmol, 2.00 equiv.) and the mixture was stirred at 90° C. for 1 hour. The reaction was cooled to 20° C., diluted with water (20 mL) and extracted with ethyl acetate (20 mL×2). The organic phase was dried over sodium sulfate, filtered and concentrated under reduced pressure to give the title compound as a light yellow solid (0.600 g) which used without further purification; $^1$H NMR (CDCl$_3$, 400 MHz) δ 9.90 (s, 1H), 7.60 (dd, J=8.0 Hz, J=1.6 Hz, 1H), 7.50 (d, J=1.6 Hz, 1H), 7.12 (d, J=8.0 Hz, 1H), 4.69 (s, 2H), 3.42 (s, 3H).

b) (E)-2-(3-(4-methyl-3-oxo-3,4-dihydro-2H-benzo[b][1,4]oxazin-7-yl)acrylamido)benzoic acid

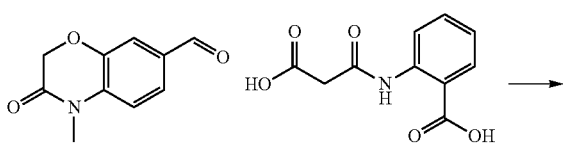

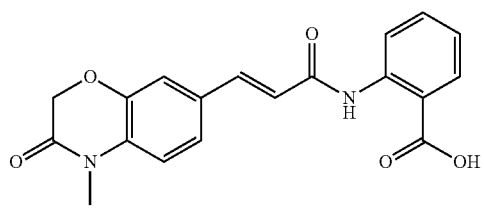

To a mixture of 4-methyl-3-oxo-1,4-benzoxazine-7-carbaldehyde (0.060 g, 0.31 mmol, 1.00 equiv.) and 2-[(2-carboxyacetyl)amino]benzoic acid (0.070 g, 0.31 mmol, 1.00 equiv.) in toluene (3 mL) was added piperidine (3 μL, 0.10 equiv.) and the resultant mixture stirred at 110° C. for 12 hours. The reaction was cooled to 20° C. and the resultant precipitate collected by filtration, washed with methanol (3 mL) and dried under vacuum to give the desired product as a light yellow solid (0.056 g, 48%); 56 mg (48%); $^1$H NMR (DMSO-$d_6$, 400 MHz) δ 13.61 (br. s., 1H), 11.36 (s, 1H), 8.61 (d, J=8.0 Hz, 1H), 8.02-7.99 (m, 1H), 7.64-7.54 (m, 2H), 7.47-7.43 (m, 2H), 7.21-7.15 (m, 2H), 6.86 (d, J=16.0 Hz, 1H), 4.70 (s, 2H), 3.30 (s, 3H); MS (ESI+) m/z 353.1 (M+H)+; 95% purity, RT 1.76 min (Method 6).

| Ex | Structure | Data | Method |
|---|---|---|---|
| 110 | (E)-2-(3-(4-methyl-3,4-dihydro-2H-benzo[b][1,4]oxazin-7-yl)acrylamido)benzoic acid | $^1$H NMR (DMSO-$d_6$, 400 MHz) δ 11.30 (s, 1H), 8.61 (d, J = 8.0 Hz, 1H), 8.00-7.98 (m, 1H), 7.61-7.57 (m, 1H), 7.44 (d, J = 16.0 Hz, 1H), 7.16-7.12 (m, 2H), 7.08-7.07 (m, 1H), 6.96 (d, J = 8.0 Hz, 1H), 6.55 (d, J = 16.0 Hz, 1H), 4.23-4.21 (m, 2H), 3.34-3.31 (m, 2H), 2.90 (s, 3H); MS (ESI+) m/z 339.1 (M + H)+; 98.7% purity, RT 1.86 min (Method 6) | Prepared according to the method for 108 (final step) starting from 4-methyl-3,4-dihydro-2H-benzo[b][1,4]oxazine-7-carbaldehyde and 2-(2-carboxyacetamido)benzoic acid |
| 111 | (E)-2-(3-(3-oxo-3,4-dihydro-2H-benzo[b][1,4]oxazin-6-yl)acrylamido)benzoic acid | $^1$H NMR (DMSO-$d_6$, 400 MHz) δ 13.60 (br. s., 1H), 11.33 (s, 1H), 10.80 (s, 1H), 8.58 (d, J = 8.0 Hz, 1H), 8.01-7.99 (m, 1H), 7.64-7.60 (m, 1H), 7.52 (d, J = 16.0 Hz, 1H), 7.34-7.31 (m, 1H), 7.19-7.16 (m, 2H), 7.00 (d, J = 8.0 Hz, 1H), 6.63 (d, J = 16.0 Hz, 1H ), 4.64 (s, 2H); MS (ESI+) m/z 339.0 (M + H)+; 95.2% purity, RT 1.67 min (Method 6) | Prepared according to the method for 108 (final step) starting from 3-oxo-3,4-dihydro-2H-benzo[b][1,4]oxazine-6-carbaldehyde and 2-(2-carboxyacetamido)benzoic acid |
| 112 | (E)-2-(3-(4-methyl-3-oxo-3,4-dihydro-2H-benzo[b][1,4]oxazin-6-yl)acrylamido)benzoic acid | $^1$H NMR (DMSO-$d_6$, 400 MHz) δ 11.37 (br. s., 1H), 8.63 (d, J = 8.0 Hz, 1H), 8.02-7.99 (m, 1H), 7.65-7.58 (m, 3H), 7.42-7.40 (m, 1H), 7.19-7.15 (m, 1H), 7.04 (d, J = 8.0 Hz, 1H), 6.88 (d, J = 16.0 Hz, 1H), 4.71 (s, 2H), 3.35 (s, 3H); MS (ESI+) m/z 353.0 (M + H)+; 94% purity, RT 1.88 min (Method 6) | Prepared according to the method for 108 (final step) starting from 4-methyl-3-oxo-1,4-benzoxazine-6-carbaldehyde and 2-(2-carboxyacetamido)benzoic acid |

(E)-1-(2H-benzo[b][1,4]oxazin-4(3H)-yl)-3-(3-ethyl-4-(prop-2-yn-1-yloxy)phenyl)prop-2-en-1-one (113)

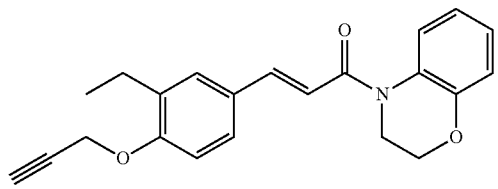 [SMILES: C#CCOc1ccc(/C=C/C(=O)N2CCOc3ccccc32)cc1CC]

a) (E)-3-(3-ethyl-4-(prop-2-yn-1-yloxy)phenyl) acrylic acid

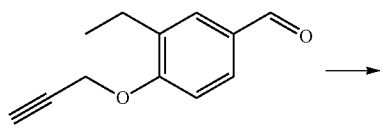

-continued

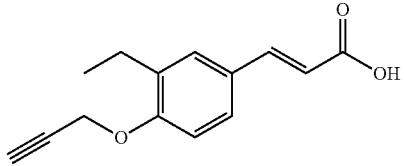

To a mixture of 3-ethyl-4-prop-2-ynoxybenzaldehyde (0.28 g, 1.49 mmol, 1.0 equiv.) and malonic acid (0.232 g, 2.23 mmol, 1.5 equiv.) in pyridine (5 mL) was added piperidine (0.013 g, 0.149 mmol, 0.1 equiv.) at 25° C. and the resulting solution stirred at 120° C. for 12 hours. The pH of the solution was adjusted to pH=3 with 1N hydrochloric acid and the resulting precipitate collected to afford the title compound as a yellow solid (0.32 g, 86%); $^1$H NMR (CDCl$_3$, 400 MHz) δ 7.74 (d, J=15.6 Hz, 1H), 7.39 (d, J=7.2 Hz, 2H), 6.98 (d, J=8.4 Hz, 1H), 6.34 (d, J=16.0 Hz, 1H), 4.77 (d, J=2.0 Hz, 2H), 2.67 (q, J=7.6 Hz, 2H), 2.53 (t, J=2.0 Hz, 1H), 1.22 (t, J=7.6 Hz, 3H); MS (ESI+) m/z 231.1 (M+H)+.

b) (E)-1-(2H-benzo[b][1,4]oxazin-4(3H)-yl)-3-(3-ethyl-4-(prop-2-yn-1-yloxy)phenyl)prop-2-en-1-one

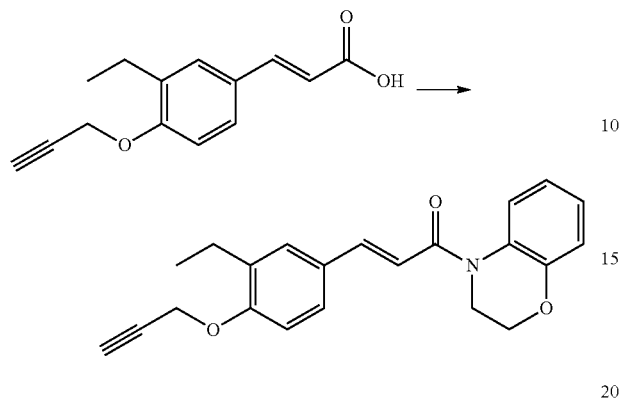

To a stirred solution of (E)-3-(3-ethyl-4-(prop-2-yn-1-yloxy)phenyl)acrylic acid (0.28 g, 1.22 mmol, 1.0 equiv.) in dichloromethane (5 mL) at 0° C. was added oxalyl chloride (0.463 g, 3.65 mmol, 3.0 equiv.) and the mixture stirred at 25° C. for 10 minutes. The reaction mixture was concentrated under reduced pressure to give a yellow solid and the residue was dissolved in dichloromethane (4 mL). 3,4-Dihydro-2H-1,4-benzoxazine (0.197 g, 1.46 mmol, 1.2 equiv.), triethylamine (0.057 g, 0.563 mmol, 2.0 equiv.) and dimethylaminopyridine (0.003 g, 0.028 mmol, 0.1 equiv.) were added at 25° C. and the resultant mixture was stirred at 25° C. for 12 hours. The reaction was diluted with water (30 mL) and extracted with dichloromethane (4×10 mL). The combined organic phase was dried over sodium sulfate and concentrated under reduced pressure. The residue was purified by preparative HPLC to afford the desired product as a white solid (48 mg, 47%); $^1$H NMR (CDCl$_3$, 400 MHz) δ 7.74 (d, J=15.6 Hz, 1H), 7.34-7.32 (m, 2H), 7.21 (d, J=6.8 Hz, 1H), 7.14-7.10 (m, 1H), 6.98-6.92 (m, 4H), 4.75 (d, J=2.4 Hz, 2H), 4.37 (t, J=4.4 Hz, 2H), 4.08 (t, J=4.8 Hz, 2H), 2.65 (q, J=7.6 Hz, 2H), 2.52 (t, J=2.4 Hz, 1H), 1.20 (t, J=7.6 Hz, 3H); MS (ESI+) m/z 348.1 (M+H)+; 100% purity, RT 2.42 min (Method 10).

(E)-3-(3-ethyl-4-(prop-2-yn-1-yloxy)phenyl)-N-(2-(3-methyl-1H-1,2,4-triazol-1-yl)phenyl)-acrylamide (114)

a) 3-methyl-1-(2-nitrophenyl)-1H-1,2,4-triazole

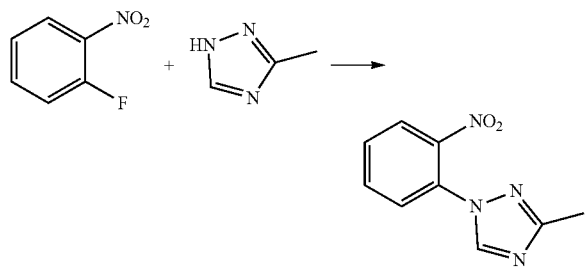

To a mixture of 1-fluoro-2-nitrobenzene (1 mL, 12.8 mmol, 1.0 equiv.) and 3-methyl-1H-1,2,4-triazole (1.27 g, 15.3 mmol, 1.2 equiv.) in acetonitrile (20 mL) was added potassium carbonate (5.29 g, 38.3 mmol, 3.0 equiv.) and the mixture was stirred at 60° C. for 12 hours. The mixture was cooled to 20° C., diluted with ethyl acetate (20 mL) and filtered. The filtrate was concentrated under reduced pressure to give a residue which was purified by silica gel chromatography (petroleum ether:ethyl acetate 2:1 to 1:1) to give the desired product as a light yellow solid (1.20 g, 46%); $^1$H NMR (DMSO-d$_6$, 400 MHz) δ 8.96 (s, 1H), 8.12 (d, J=8.0 Hz, 1H), 7.90-7.88 (m, 1H), 7.86-7.84 (m, 1H), 7.60 (t, J=8.0 Hz, 1H), 2.31 (s, 3H).

b) 2-(3-methyl-1H-1,2,4-triazol-1-yl)aniline

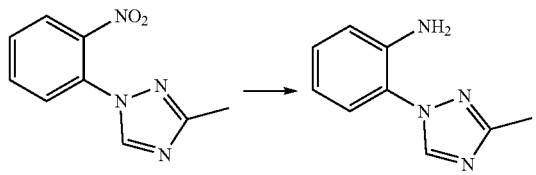

To a solution of 3-methyl-1-(2-nitrophenyl)-1,2,4-triazole (1.20 g, 5.88 mmol, 1.0 equiv.) in methanol (16 mL) was added Pd/C (0.2 g, 5%) and the mixture was stirred at 20° C. under a hydrogen atmosphere for 4 hours. The mixture was filtered and the filtrate concentrated under reduced pressure to give the desired product as light yellow gum which was used directly without further purification (1.00 g); 1H NMR (CDCl$_3$, 400 MHz) δ 8.24 (s, 1H), 7.20 (t, J=8.0 Hz, 1H), 7.15 (d, J=1.6 Hz, 1H), 6.85 (d, J=2.8 Hz, 1H), 6.83 (d, J=7.6 Hz, 1H), 4.54 (br. s., 2H), 2.50 (s, 3H).

c) (E)-3-(3-ethyl-4-(prop-2-yn-1-yloxy)phenyl)-N-(2-(3-methyl-1H-1,2,4-triazol-1-yl)phenyl)-acrylamide

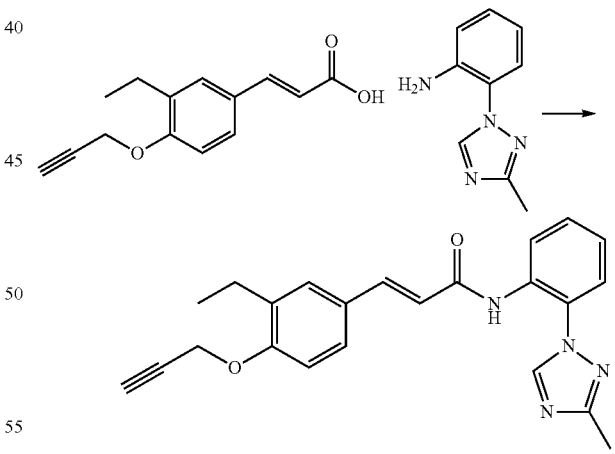

Prepared according to the procedure described for the synthesis of (E)-1-(2H-benzo[b][1,4]oxazin-4(3H)-yl)-3-(3-ethyl-4-(prop-2-yn-1-yloxy)phenyl)prop-2-en-1-one (113) starting from (E)-3-(3-ethyl-4-(prop-2-yn-1-yloxy)phenyl) acrylic acid and 2-(3-methyl-1H-1,2,4-triazol-1-yl)aniline (14%); $^1$H NMR (CDCl$_3$, 400 MHz) δ 9.80 (s, 1H), 8.62 (d, J=8.4 Hz, 1H), 8.41 (s, 1H), 7.65 (d, J=15.6 Hz, 1H), 7.50-7.40 (m, 1H), 7.39-7.34 (m, 3H), 7.28-7.20 (m, 1H), 6.98 (t, J=9.2 Hz, 1H), 6.35 (d, J=15.2 Hz, 1H), 4.76 (d, J=2.4 Hz, 2H), 2.68 (q, J=7.6 Hz, 2H), 2.62 (s, 3H), 2.52 (t, J=2.4 Hz, 1H), 1.23 (t, J=7.6 Hz, 3H); MS (ESI+) m/z 387.2 (M+H)+; 95.8% purity, RT 2.15 min (Method 10).

(E)-1-(2H-benzo[b][1,4]oxazin-4(3H)-yl)-3-(2-(2-(dimethylamino)ethoxy)-3,4-dimethoxyphenyl)-prop-2-en-1-one (115)

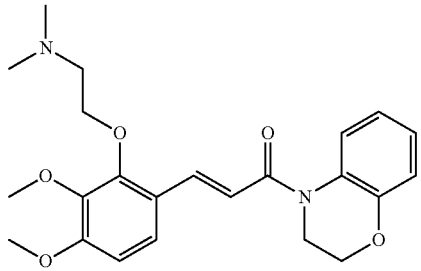 [SMILES: COc1ccc(/C=C/C(=O)N2CCOc3ccccc32)c(OCCN(C)C)c1OC]

a) 2-(2-(dimethylamino)ethoxy)-3,4-dimethoxybenzaldehyde

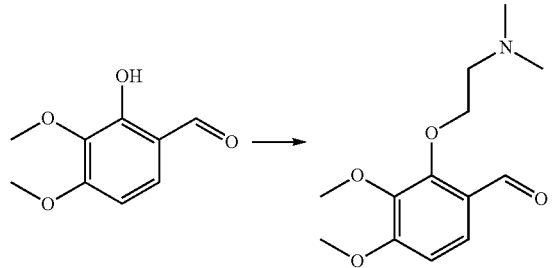 [SMILES: COc1ccc(C=O)c(O)c1OC ; COc1ccc(C=O)c(OCCN(C)C)c1OC]

To a solution of 2-hydroxy-3,4-dimethoxybenzaldehyde (3.00 g, 16.5 mmol, 1.0 equiv.) and dimethylaminoethyl-chloride hydrochloride (2.38 g, 16.5 mmol, 1.0 equiv.) in acetonitrile (50 mL) was added potassium carbonate (6.83 g, 49.4 mmol, 3.0 equiv.) and sodium iodide (0.247 g, 1.65 mmol, 0.1 equiv.) and the mixture stirred at 80° C. for 12 hours. The reaction mixture was filtered and the filtrate concentrated under reduced pressure. The residue was purified by silica gel column chromatography (dichloromethane:methanol 1:0 to 10:1) to provide the desired product as brown oil, (3.20 g) which was used without further purification; $^1$H NMR (CDCl$_3$, 400 MHz) δ 10.30 (s, 1H), 7.61 (d, J=8.4 Hz, 1H), 6.76 (d, J=8.8 Hz, 1H), 4.27 (t, J=5.6 Hz, 2H), 3.93 (s, 3H), 3.89 (s, 3H), 2.69 (t, J=5.6 Hz, 2H), 2.31 (s, 6H).

b) (E)-3-(2-(2-(dimethylamino)ethoxy)-3,4-dimethoxyphenyl)acrylic acid

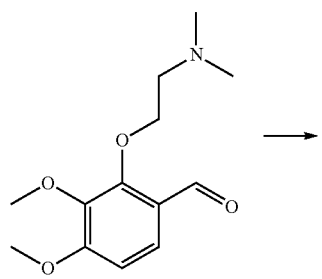

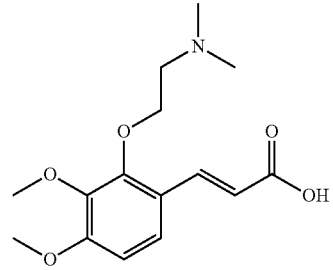

The title compound was prepared according to the procedure described for the synthesis of (E)-3-(3-ethyl-4-prop-2-ynoxyphenyl)prop-2-enoic acid starting from 2-(2-(dimethylamino)ethoxy)-3,4-dimethoxybenzaldehyde and malonic acid; $^1$H NMR (CD$_3$OD, 400 MHz) δ 7.75 (d, J=16.0 Hz, 1H), 7.42 (d, J=8.8 Hz, 1H), 6.92 (d, J=8.8 Hz, 1H), 6.44 (d, J=16.0 Hz, 1H), 4.28 (t, J=4.8 Hz, 2H), 3.90 (s, 3H), 3.89 (s, 3H), 3.62 (t, J=4.8 Hz, 2H), 3.07 (s, 6H).

c) (E)-1-(2H-benzo[b][1,4]oxazin-4(3H)-yl)-3-(2-(2-(dimethylamino)ethoxy)-3,4-dimethoxyphenyl)prop-2-en-1-one

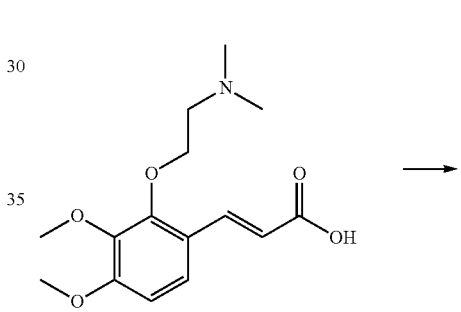

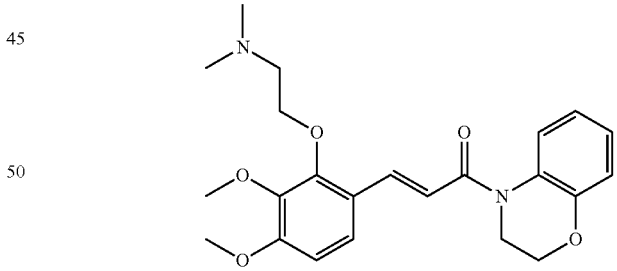

The title compound was prepared according to the procedure described for the synthesis of (E)-1-(2H-benzo[b][1,4]oxazin-4(3H)-yl)-3-(3-ethyl-4-(prop-2-yn-1-yloxy)phenyl)prop-2-en-1-one (113) starting from (E)-3-(2-(2-(dimethylamino)ethoxy)-3,4-dimethoxyphenyl)acrylic acid and 3,4-dihydro-2H-benzo[b][1,4]oxazine (11%); $^1$H NMR (CD$_3$OD, 400 MHz) δ 7.91 (d, J=15.6 Hz, 1H), 7.29 (d, J=8.8 Hz, 2H), 7.15-7.12 (m, 2H), 6.95-6.93 (m, 2H), 6.83 (d, J=8.8 Hz, 1H), 4.35 (t, J=4.8 Hz, 2H), 4.13 (t, J=5.6 Hz, 2H), 4.04 (t, J=4.8 Hz, 2H), 3.88 (s, 3H), 3.83 (s, 3H), 2.68 (t, J=5.6 Hz, 2H), 2.32 (s, 6H). MS (ESI+) m/z 413.2 (M+H)+; 100% purity, RT 1.58 min (Method 10).

(E)-2-(3-(2-(2-(dimethylamino)ethoxy)-3,4-dimethoxyphenyl)acrylamido)benzoic acid (116)

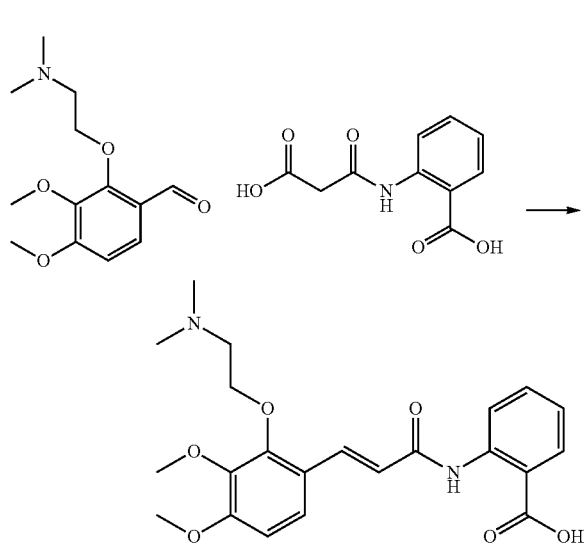

A mixture of 2-(2-(dimethylamino)ethoxy)-3,4-dimethoxybenzaldehyde (4.17 g, 16.4 mmol, 1.0 equiv.), 2-(2-carboxyacetamido)benzoic acid (3.99 g, 18.0 mmol, 1.1 equiv.) and piperidine (1.78 mL, 18.0 mmol, 1.1 equiv.) in toluene (100 mL) was heated at 115° C. for 4 hours. The mixture was cooled to room temperature and the solvent removed in vacuo. The residue was dissolved in a minimal amount of methanol, allowed to stand overnight and the resulting solid collected. The solid was washed with methanol, the washings concentrated in vacuo and the residue was purified by silica gel column chromatography (methanol/DCM 2% to 10%). The product from the column was then combined with the solid and recrystallized from methanol to afford the title compound as a white solid (4.07 g, 60%). $^1$H NMR (400 MHz, DMSO) δ 14.27 (s, 1H), 8.62-8.60 (m, 1H), 8.10 (dd, J=7.8 Hz, J=1.5 Hz, 1H), 7.97 (d, J=16.6 Hz, 1H), 7.67 (d, J=8.8 Hz, 1H), 7.45-7.39 (m, 1H), 7.09-7.04 (m, 1H), 6.99 (d, J=9.1 Hz, 1H), 6.56 (d, J=17.0 Hz, 1H), 4.42-4.37 (m, 2H), 3.91 (s, 3H), 3.85 (s, 3H), 3.66 (dd, J=4.4 Hz, J=4.4 Hz, 2H), 3.01 (s, 6H). MS (ESI) m/z 415.4 (M+H)+: 99.0% purity, RT 2.60 min (Method 2).

(E)-4-chloro-2-(3-(2-(2-(dimethylamino)ethoxy)-3,4-dimethoxyphenyl)acrylamido)benzoic acid (117)

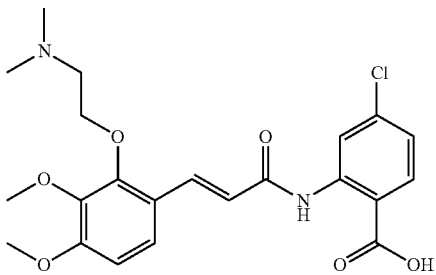 [SMILES: COc1ccc(/C=C/C(=O)Nc2cc(Cl)ccc2C(=O)O)c(OCCN(C)C)c1OC]

a) 2-(2-Carboxyacetamido)-4-chlorobenzoic acid

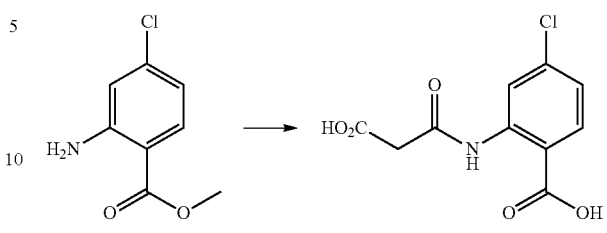

A mixture of methyl 2-amino-4-chlorobenzoate (0.50 g, 2.69 mmol, 1.0 equiv.) and NaOH (0.14 g, 3.58 mmol, 1.3 equiv.) in ethanol (5 mL) and water (5 mL) was heated at reflux for 1.5 hours and then cooled to room temperature. The pH was adjusted to pH 1 with 2N hydrochloric acid and the resulting precipitate was isolated by filtration, washed with water then dried under suction and used without further purification.

The solid (0.37 g, 2.16 mmol, 1.05 equiv.) was suspended in toluene (5 mL) and 2,2-dimethyl-1,3-dioxane-4,6-dione (0.295 g, 2.05 mmol, 1.0 equiv.) was added. The mixture was heated at reflux for 6 hours at which point a further portion of 2,2-dimethyl-1,3-dioxane-4,6-dione (0.016 g, 0.11 mmol) was added. After a further 30 minutes at reflux the mixture was cooled and the resulting precipitate was isolated by filtration, washed with toluene and dried under suction to give the title compound as a cream solid (0.49 g, 89%). $^1$H NMR (400 MHz, DMSO): δ, ppm 12.95-12.95 (m, 1H), 11.47 (s, 1H), 8.64 (d, J=2.3 Hz, 1H), 8.05 (d, J=8.6 Hz, 1H), 7.33-7.29 (m, 1H), 3.57 (s, 2H). MS (ESI+) m/z 258 (M+H)+.

b) (E)-4-chloro-2-(3-(2-(2-(dimethylamino)ethoxy)-3,4-dimethoxyphenyl)acrylamido)benzoic acid

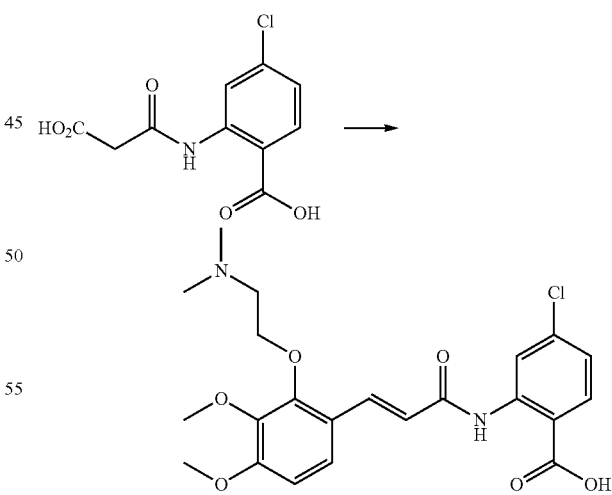

The title compound was prepared according to the procedure for (E)-2-(3-(2-(2-(dimethylamino)ethoxy)-3-methoxy-4-(prop-2-yn-1-yloxy)phenyl)acrylamido)-benzoic acid (78) starting from 2-(2-carboxyacetamido)-4-chlorobenzoic acid and 2-(2-(dimethylamino)ethoxy)-3,4-dimethoxybenzaldehyde (50%); $^1$H NMR (400 MHz, CDCl$_3$): δ ppm 7.51 (1H, d, J=15.4 Hz), 7.10-7.07 (1H, m), 7.06-7.02 (1H, m), 6.97 (1H, d, J=8.3 Hz), 6.41 (1H, d, J=14.9 Hz), 6.00-5.93 (1H, m), 4.78 (2H, d, J=2.5 Hz), 3.89 (3H, s), 3.77-3.66 (1H, m), 2.68-2.59 (1H, m), 2.54-2.51 (1H, m), 2.01-1.96 (2H, m), 1.77-1.66 (2H, m), 1.33-1.19 (4H, m); MS: (ESI+) m/z 329.2 (M+H)+99.01% purity, RT=2.87 min., (Method 3).

(E)-1-(2H-benzo[b][1,4]oxazin-4(3H)-yl)-3-(3-methoxy-4-((1-methylpyrrolidin-3-yl)oxy)phenyl) prop-2-en-1-one (118)

a) (E)-methyl 3-(3-methoxy-4-((1-methylpyrrolidin-3-yl)oxy)phenyl)acrylate

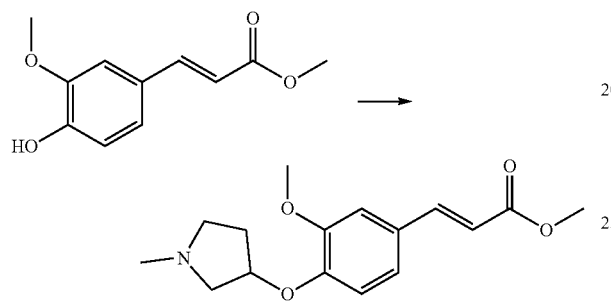

To a solution of methyl (E)-3-(4-hydroxy-3-methoxyphenyl)prop-2-enoate (2.00 g, 9.61 mmol, 1.0 equiv.), 1-methylpyrrolidin-3-ol (1.17 g, 11.5 mmol, 1.2 equiv.) and triphenylphosphine (3.02 g, 11.53 mmol, 1.20 equiv.) in tetrahydrofuran (10 mL) at 0° C. was added diisopropylazodicarboxylate (2.33 g, 11.5 mmol, 1.2 equiv.) over 30 minutes. The reaction mixture was diluted with 1N hydrochloric acid (50 mL) and extracted with ethyl acetate (3×50 mL), the aqueous layer was adjusted to pH=8 with 1N sodium hydroxide solution and extracted with ethyl acetate (3×50 mL). The combined organic layer was washed with brine (50 mL), dried over sodium sulfate and concentrated in vacuo to give the desired product as a yellow oil (2.50 g, 89%) which was used without further purification; $^1$H NMR (CDCl$_3$, 400 MHz) δ 7.62 (d, J=16.0 Hz, 1H), 7.05 (d, J=8.0 Hz, 1H), 7.04 (s, 1H), 7.76 (d, J=8.0 Hz, 1H), 6.30 (d, J=16.0 Hz, 1H), 4.89-4.85 (m, 1H), 3.87 (s, 3H), 3.79 (s, 3H), 2.95-2.92 (m, 1H), 2.80-2.76 (m, 2H), 2.55-2.53 (m, 1H), 2.39 (s, 3H), 2.38-2.35 (m, 1H), 2.05-2.01 (m, 1H).

b) (E)-3-(3-methoxy-4-((1-methylpyrrolidin-3-yl)oxy)phenyl)acrylic acid

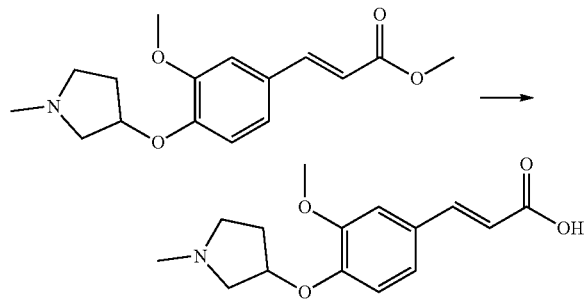

To a mixture of (E)-methyl 3-(3-methoxy-4-((1-methylpyrrolidin-3-yl)oxy)phenyl)acrylate (1.50 g, 5.15 mmol, 1.0 equiv.) in methanol (15 mL) and water (2 mL) was added lithium hydroxide (0.247 g, 10.3 mmol, 2.0 equiv.) and the mixture stirred at 25° C. for 12 hours. The reaction mixture was concentrated under reduced pressure. The residue was diluted with water (100 mL) and the mixture extracted with dichloromethane (30 mL×3). The aqueous phase was adjusted to pH=5 with 1N hydrochloric acid and concentrated under reduced pressure to get the desired product as a brown oil, which was used directly without further purification (1.50 g); $^1$H NMR (CD$_3$OD, 400 MHz) δ 7.39 (d, J=16.0 Hz, 1H), 7.19 (d, J=2.0 Hz, 1H), 7.09 (dd, J=8.0 Hz, J=2.0 Hz, 1H), 6.97 (d, J=8.0 Hz, 1H), 6.40 (d, J=16.0 Hz, 1H), 5.14-5.12 (m, 1H), 3.88 (s, 3H), 3.53-3.49 (m, 3H), 3.31-3.30 (m, 1H), 2.90 (s, 3H), 2.47-2.43 (m, 1H), 2.54-2.27 (m, 1H).

c) (E)-1-(2H-benzo[b][1,4]oxazin-4(3H)-yl)-3-(3-methoxy-4-((1-methylpyrrolidin-3-yl)oxy)phenyl)-prop-2-en-1-one

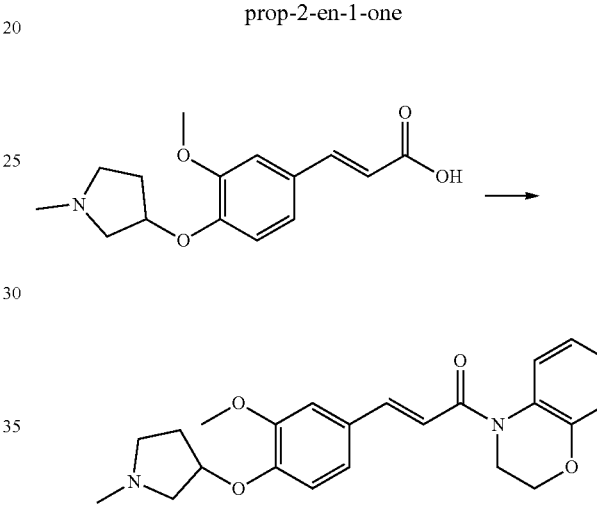

The title compound was prepared according to the procedure described for the synthesis of (E)-1-(2H-benzo[b][1,4]oxazin-4(3H)-yl)-3-(3-ethyl-4-(prop-2-yn-1-yloxy)phenyl)prop-2-en-1-one (113) starting from (E)-3-(3-methoxy-4-((1-methylpyrrolidin-3-yl)oxy)phenyl)acrylic acid and 3,4-dihydro-2H-benzo[b][1,4]oxazine (9%); $^1$H NMR (CDCl$_3$, 400 MHz) δ 7.64 (d, J=15.2 Hz, 1H), 7.13 (d, J=2.0 Hz, 1H), 7.09-7.05 (m, 1H), 7.04-6.98 (m, 1H), 6.91 (d, J=1.6 Hz, 1H), 6.88 (t, J=6.8 Hz, 1H), 6.83-6.81 (m, 2H), 6.71 (d, J=8.0 Hz, 1H), 4.80-4.80 (m, 1H), 4.29 (t, J=4.8 Hz, 2H), 4.00 (t, J=4.8 Hz, 2H), 3.78 (s, 3H), 2.89-2.87 (m, 1H), 2.77-2.74 (m, 2H), 2.52-2.47 (m, 1H), 2.35 (s, 3H), 2.27-2.23 (m, 1H), 1.99-1.96 (m, 1H); MS (ESI+) m/z 395.2 (M+H)+; 92.8% purity, RT 2.59 min (Method 8).

(2H-benzo[b][1,4]oxazin-4(3H)-yl)(2-(3-methoxy-4-(prop-2-yn-1-yloxy) phenyl) cyclopropyl) methanone (119)

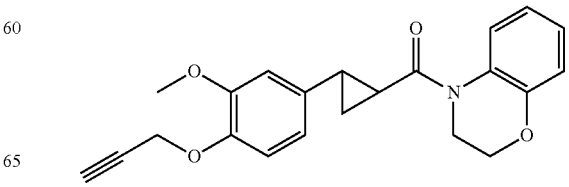

a) methyl 2-(3-methoxy-4-(prop-2-yn-1-yloxy)phenyl)cyclopropanecarboxylate

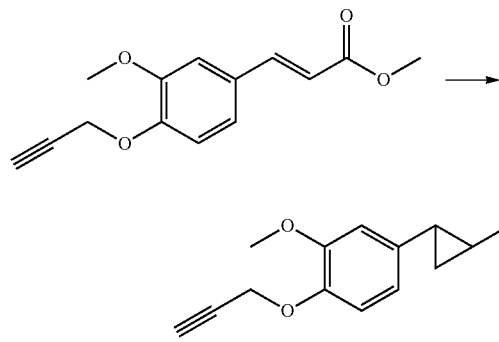

To a solution of trimethylsulfoxonium iodide (1.34 g, 6.09 mmol, 1.5 equiv.) in dimethylsulfoxide (10 ml) at 0° C. was added sodium hydride (0.107 g, 4.47 mmol, 1.1 equiv.) and the mixture stirred at 25° C. for 30 minutes. Methyl (E)-3-(3-methoxy-4-prop-2-ynoxy-phenyl)prop-2-enoate (1.00 g, 4.06 mmol, 1.0 equiv.) was then added and the reaction stirred at 25° C. for 12 hours. The reaction mixture was diluted with water (30 mL) and extracted with ethyl acetate (5×10 mL). The combined organic phase was washed with water (5×30 ml), dried over sodium sulfate and concentrated under reduced pressure to give the desired product as a yellow oil (1.00 g) which was used without further purification; $^1$H NMR (CDCl$_3$, 400 MHz) δ 6.95 (d, J=8.1 Hz, 1H), 6.66-6.63 (m, 2H), 4.75 (d, J=2.4 Hz, 2H), 3.87 (s, 3H), 3.73 (s, 3H), 2.52 (d, J=2.4 Hz, 1H), 2.51-2.49 (m, 1H), 1.65-1.59 (m, 1H), 1.58-1.56 (m, 1H), 1.30-1.27 (m, 1H).

b) 2-(3-methoxy-4-(prop-2-yn-1-yloxy)phenyl)cyclopropanecarboxylic acid

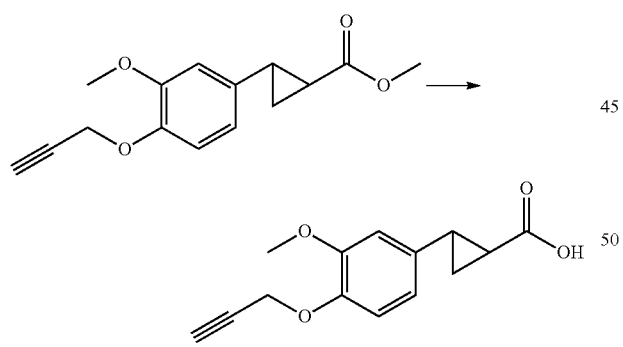

To a mixture of methyl 2-(3-methoxy-4-(prop-2-yn-1-yloxy)phenyl)cyclopropanecarboxylate (1.00 g, 3.86 mmol, 1.0 equiv.) in methanol (15 mL) and water (2 mL) was added lithium hydroxide (0.185 g, 7.72 mmol, 2.0 equiv.) and the reaction was stirred at 25° C. for 12 hours. The reaction was concentrated under reduced pressure to give a residue which was diluted with water (100 mL) and the aqueous mixture extracted with dichloromethane (3×30 mL). The aqueous phase was adjusted to pH 5 with 1N hydrochloric acid and concentrated under reduced pressure to get the desired product as brown oil, which was used directly without further purification (0.4 g, 42%); $^1$H NMR (CDCl$_3$, 400 MHz) δ 6.96 (d, J=8.4 Hz, 1H), 6.69 (d, J=2.4 Hz, 1H), 6.65 (dd, J=8.4 Hz, J=2.0 Hz, 1H), 4.74 (d, J=2.4 Hz, 2H), 3.90 (s, 3H), 2.58-2.51 (m, 1H), 2.50 (t, J=2.4 Hz, 1H), 1.88-1.86 (m, 1H), 1.65-1.62 (m, 1H), 1.29-1.25 (m, 1H).

c) (2H-benzo[b][1,4]oxazin-4(3H)-yl)(2-(3-methoxy-4-(prop-2-yn-1-yloxy) phenyl) cyclopropyl) methanone

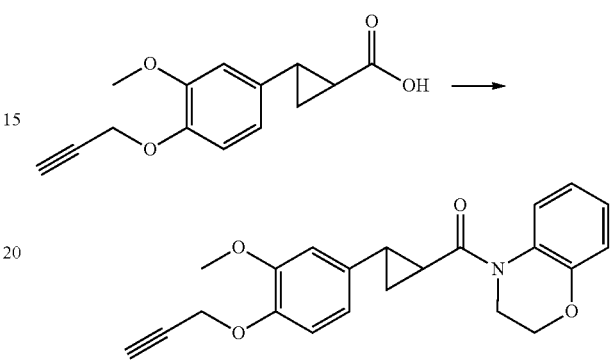

The title compound was prepared according to the procedure described for the synthesis of (E)-1-(2H-benzo[b][1,4]oxazin-4(3H)-yl)-3-(3-ethyl-4-(prop-2-yn-1-yloxy)phenyl)prop-2-en-1-one (113) starting from 2-(3-methoxy-4-(prop-2-yn-1-yloxy)phenyl)cyclopropanecarboxylic acid and 3,4-dihydro-2H-benzo[b][1,4]oxazine (9%); $^1$H NMR (CDCl$_3$, 400 MHz) δ 7.27-7.26 (m, 1H), 7.04-7.02 (m, 1H), 6.96-6.91 (m, 2H), 6.75-6.70 (m, 1H), 6.64-6.63 (m, 1H), 6.62-6.61 (m, 1H), 4.74 (d, J=2.4 Hz, 2H), 4.36-4.30 (m, 2H), 4.22-4.21 (m, 1H), 3.85-3.84 (m, 4H), 2.63-2.59 (m, 1H), 2.51 (t, J=2.0 Hz, 1H), 2.40-2.39 (m, 1H), 1.83-1.79 (m, 1H), 1.33-1.30 (m, 1H); MS (ESI+) m/z 364.1 (M+H)+; 99.7% purity, RT 2.12 min (Method 9).

(E)-N-(4-fluorophenyl)-3-(3-methoxy-4-(1,2,3,6-tetrahydropyridin-4-yl)phenyl)acrylamide (120)

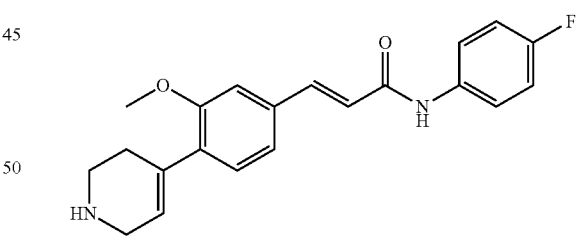

a) (E)-tert-butyl 4-(2-methoxy-4-(3-methoxy-3-oxoprop-1-en-1-yl)phenyl)-5,6-dihydropyridine-1(2H)-carboxylate

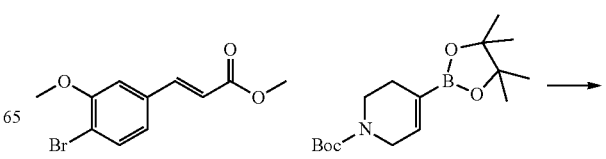

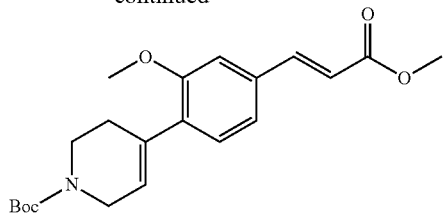

A mixture of methyl (E)-3-(4-bromo-3-methoxyphenyl)prop-2-enoate (0.5 g, 1.84 mmol, 1.0 equiv.), tert-butyl 4-(4,4,5,5-tetramethyl-1,3,2-dioxaborolan-2-yl)-3,6-dihydro-2H-pyridine-1-carboxylate (0.683 g, 2.21 mmol, 1.2 equiv.), Pd(dppf)Cl$_2$ (0.135 g, 0.184 mmol, 0.1 equiv.) and potassium carbonate (0.509 g, 3.68 mmol, 2.0 equiv.) in water (2 mL) and N,N-dimethylformamide (10 mL) was degassed and then stirred at 100° C. for 2 hours under a nitrogen atmosphere. The reaction mixture was concentrated under reduced pressure to give a residue which was purified by silica gel column chromatography (petroleum ether:ethyl acetate 30:1 to 10:1) to give the desired product as a yellow oil (0.65 g, 93%); $^1$H NMR (CDCl$_3$, 400 MHz) δ 7.68 (d, J=16.0 Hz, 1H), 7.17 (d, J=7.6 Hz, 1H), 7.11-7.10 (m, 1H), 7.01-7.00 (m, 1H), 6.43 (d, J=16.0 Hz, 1H), 5.83-5.82 (m, 1H), 4.08-4.05 (m, 2H), 3.86 (s, 3H), 3.82 (s, 3H), 3.64-3.61 (m, 2H), 2.50-2.45 (m, 2H), 1.48 (s, 9H); MS (ESI+) m/z 396.2 (M+Na)$^+$.

b) (E)-3-(4-(1-(tert-butoxycarbonyl)-1,2,3,6-tetrahydropyridin-4-yl)-3-methoxyphenyl)acrylic acid

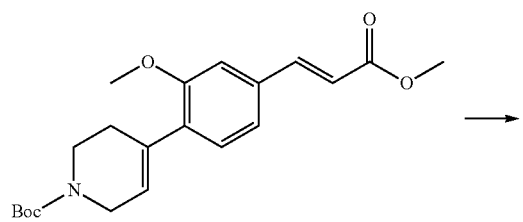

The title compound was prepared according to the procedure described for the synthesis of 2-(3-methoxy-4-(prop-2-yn-1-yloxy)phenyl)cyclopropanecarboxylic acid starting from (E)-tert-butyl 4-(2-methoxy-4-(3-methoxy-3-oxoprop-1-en-1-yl)phenyl)-5,6-dihydropyridine-1(2H)-carboxylate; $^1$H NMR (CD$_3$OD, 400 MHz) δ 7.36 (d, J=15.6 Hz, 1H), 7.13-7.06 (m, 3H), 6.49 (d, J=16.0 Hz, 1H), 5.77-5.76 (m, 1H), 4.04-4.01 (m, 2H), 3.84 (s, 3H), 3.62-3.58 (m, 2H), 2.49-2.45 (m, 2H), 1.47 (s, 9H); MS (ESI+) m/z 382.1 (M+Na)$^+$.

c) (E)-N-(4-fluorophenyl)-3-(3-methoxy-4-(1,2,3,6-tetrahydropyridin-4-yl)phenyl)acrylamide

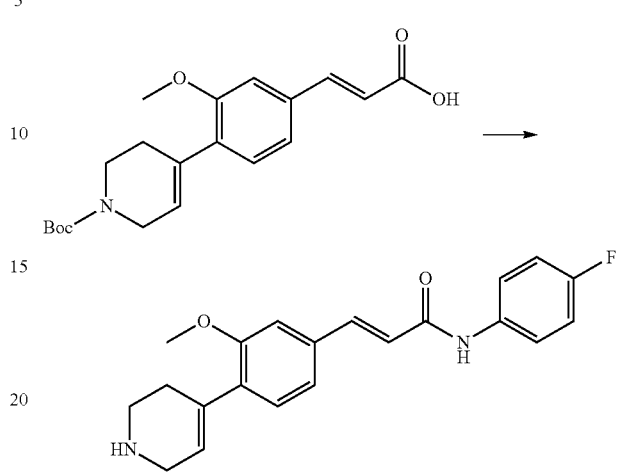

To a solution of (E)-3-[4-(1-tert-butoxycarbonyl-3,6-dihydro-2H-pyridin-4-yl)-3-methoxy-phenyl]prop-2-enoic acid (0.1 g, 0.278 mmol, 1.0 equiv.) in N,N-dimethylformamide (5 mL) was added HATU (0.159 g, 0.417 mmol, 1.5 equiv.) and diisopropylethylamine (0.108 g, 0.835 mmol, 3.0 equiv.) and the resultant mixture was stirred at 20° C. for 1 hour. Then 4-fluoroaniline (0.037 g, 0.334 mmol, 1.2 equiv.) was added and the mixture was stirred for 3 hours at 20° C. The reaction mixture was diluted with ethyl acetate (15 mL) and washed with water (3×10 mL). The organic layer was dried over sodium sulfate and concentrated under reduced pressure. The resulting yellow oil was dissolved in dichloromethane (5 mL) and treated with trifluoroacetic acid (0.378 g, 3.31 mmol, 10.0 equiv.) and the resulting solution was stirred at 20° C. for 2 hours. The mixture was concentrated under reduced pressure to give a residue which was purified by preparative HPLC to give the desired product as a yellow solid (0.042 g, 27%); 1H NMR (CD$_3$OD, 400 MHz) δ 7.69-7.65 (m, 2H), 7.62 (s, 1H), 7.23-7.21 (m, 3H), 7.10-7.06 (m, 2H), 6.80 (d, J=16.0 Hz, 1H), 5.88-5.87 (m, 1H), 3.89 (s, 3H), 3.83 (d, J=2.4 Hz, 2H), 3.43-3.40 (m, 2H), 2.98-2.78 (m, 2H); MS (ESI+) m/z 353.1 (M+H)+; 98.3% purity, RT 2.47 min (Method 11).

N-(4-cyanophenyl)-2-(3-methoxy-4-(1,2,3,6-tetrahydropyridin-4-yl)phenyl)cyclopropane carboxamide (121)

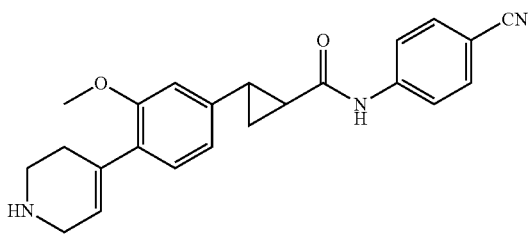 [SMILES: COc1cc(C2CC2C(=O)Nc2ccc(C#N)cc2)ccc1C1=CCNCC1]

a) methyl 2-(4-bromo-3-methoxyphenyl)cyclopropanecarboxylate

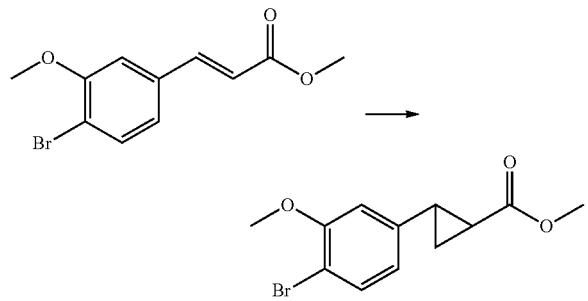

The title compound was prepared according to the procedure described for the synthesis of methyl 2-(3-methoxy-4-(prop-2-yn-1-yloxy)phenyl)cyclopropanecarboxylate starting from (E)-methyl 3-(4-bromo-3-methoxyphenyl)acrylate; $^1$H NMR (CDCl$_3$, 400 MHz) δ 7.42 (d, J=8.4 Hz, 1H), 6.67 (d, J=8.4 Hz, 1H), 6.55 (dd, J=8.4 Hz, J=2.0 Hz, 1H), 3.89 (s, 3H), 3.73 (s, 3H), 2.52-2.48 (m, 1H), 1.91-1.89 (m, 1H), 1.63-1.59 (m, 1H), 1.33-1.31 (m, 1H).

b) tert-butyl 4-(2-methoxy-4-(2-(methoxycarbonyl)cyclopropyl)phenyl)-5,6-dihydropyridine-1(2H)-carboxylate

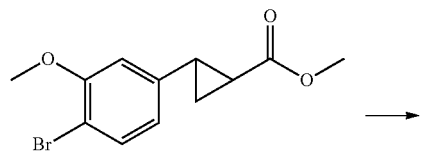

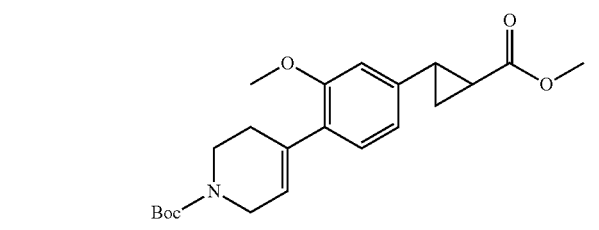

The title compound was prepared according to the procedure described for the synthesis of (E)-tert-butyl 4-(2-methoxy-4-(3-methoxy-3-oxoprop-1-en-1-yl)phenyl)-5,6-dihydropyridine-1(2H)-carboxylate starting from methyl 2-(4-bromo-3-methoxyphenyl)cyclopropanecarboxylate and tert-butyl 4-(4,4,5,5-tetramethyl-1,3,2-dioxaborolan-2-yl)-5,6-dihydropyridine-1(2H)-carboxylate; $^1$H NMR (CDCl$_3$, 400 MHz) δ 7.05 (d, J=7.6 Hz, 1H), 6.66-6.61 (m, 2H), 5.75-5.72 (m, 1H), 4.04 (s, 2H), 3.81 (s, 3H), 3.73 (s, 3H), 3.59 (t, J=4.8 Hz, 2H), 2.53 (m, 3H), 1.93-1.92 (m, 1H), 1.62-1.60 (m, 1H), 1.48 (s, 9H), 1.35-1.33 (m, 1H).

c) 2-(4-(1-(tert-butoxycarbonyl)-1,2,3,6-tetrahydropyridin-4-yl)-3-methoxyphenyl)cyclopropane carboxylic acid

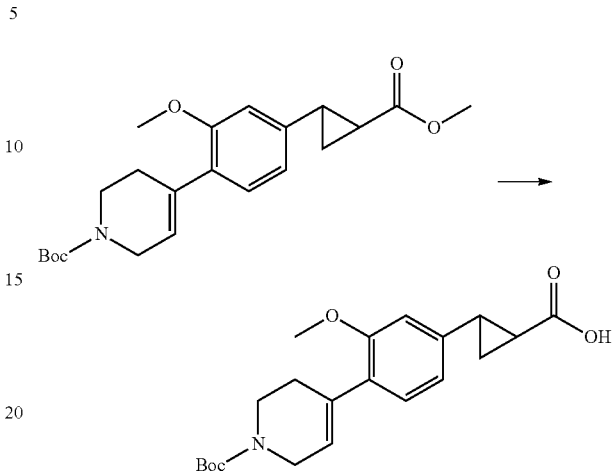

The title compound was prepared according to the procedure described for the synthesis of (E)-3-[4-(1-tert-butoxycarbonyl-3,6-dihydro-2H-pyridin-4-yl)-3-methoxyphenyl]prop-2-enoic acid starting from tert-butyl 4-(2-methoxy-4-(2-(methoxycarbonyl)cyclopropyl)phenyl)-5,6-dihydropyridine-1(2H)-carboxylate (75%); MS (ESI+) m/z 396.2 (M+Na)$^+$.

d) N-(4-cyanophenyl)-2-(3-methoxy-4-(1,2,3,6-tetrahydropyridin-4-yl)phenyl)cyclopropane carboxamide

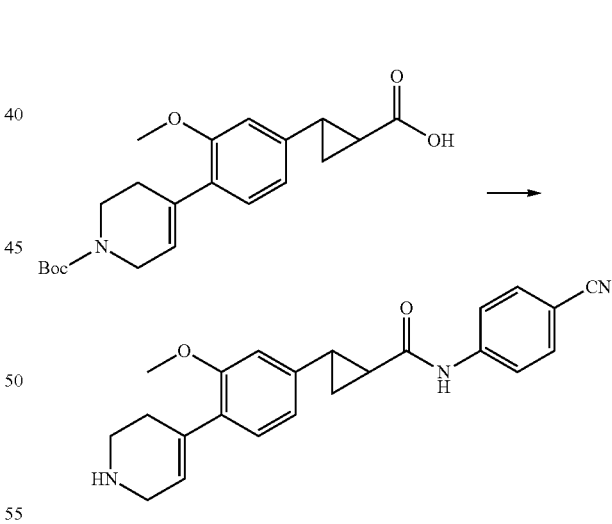

The title compound was prepared as the trifluoroacetic acid salt according to the procedure described for the synthesis of (E)-N-(4-fluorophenyl)-3-(3-methoxy-4-(1,2,3,6-tetrahydropyridin-4-yl)phenyl)acrylamide (120) starting from 2-(4-(1-(tert-butoxycarbonyl)-1,2,3,6-tetrahydropyridin-4-yl)-3-methoxyphenyl)cyclopropane carboxylic acid and 4-fluorobenzonitrile (17%); $^1$H NMR (CD$_3$OD, 400 MHz) δ 7.78 (d, J=8.4 Hz, 2H), 7.67 (d, J=8.4 Hz, 2H), 7.10 (d, J=7.6 Hz, 1H), 6.83 (s, 1H), 6.75 (d, J=7.6 Hz, 1H), 5.79-5.78 (m, 1H), 3.83 (s, 3H), 3.81 (d, J=2.8 Hz, 2H), 3.40 (t, J=6.0 Hz, 2H), 2.76 (d, J=2.0 Hz, 2H), 2.53-2.51 (m, 1H), 2.11-2.09 (m, 1H), 1.65-1.62 (m, 1H), 1.43-1.42 (m, 1H); MS (ESI+) m/z 374.1 (M+H)+; 97.5% purity, RT 2.48 min (Method 11).

2-(2-(2-(dimethylamino)ethoxy)-3,4-dimethoxyphenyl)-N-(4-fluorophenyl)cyclopropane-1-carboxamide (122)

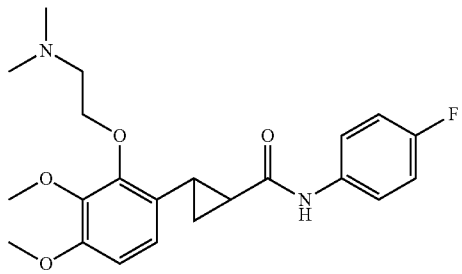 [SMILES: COc1ccc(C2CC2C(=O)Nc2ccc(F)cc2)c(OCCN(C)C)c1OC]

a) (E)-methyl 3-(2-(2-(dimethylamino)ethoxy)-3,4-dimethoxyphenyl)acrylate

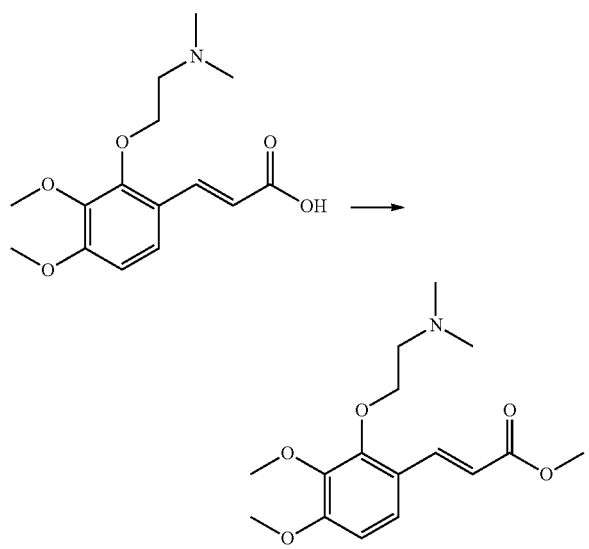

To a solution of (E)-3-(2-(2-(dimethylamino)ethoxy)-3,4-dimethoxyphenyl)acrylic acid (1.50 g, 5.08 mmol, 1.0 equiv.) in methanol (20 mL) was added copper sulfate (1.49 g, 15.2 mmol, 3.0 equiv.) at 0° C. and the resultant mixture stirred at 20° C. for 3 hours. The reaction mixture was adjusted to pH 7 with 1N hydrochloric acid and concentrated under reduced pressure. The residue was diluted with ethyl acetate (20 mL) and washed with water (20 mL×3). The organic layer was dried over anhydrous sodium sulfate and concentrated under reduced pressure to give the desired product as yellow oil (1.35 g) which was used without further purification; 1H NMR (CDCl$_3$, 400 MHz) δ 7.96 (d, J=16.4 Hz, 1H), 7.26 (d, J=8.4 Hz, 1H), 6.68 (d J=8.4 Hz, 1H), 6.40 (d, J=16.4 Hz, 1H), 4.13 (t, J=6.0 Hz, 2H), 3.90 (s, 3H), 3.88 (s, 3H), 3.33 (s, 3H), 2.73 (t, J=5.6 Hz, 2H), 2.35 (s, 6H).

b) 2-(2-(2-(dimethylamino)ethoxy)-3,4-dimethoxyphenyl)-N-(4-fluorophenyl)cyclopropane-1-carboxamide

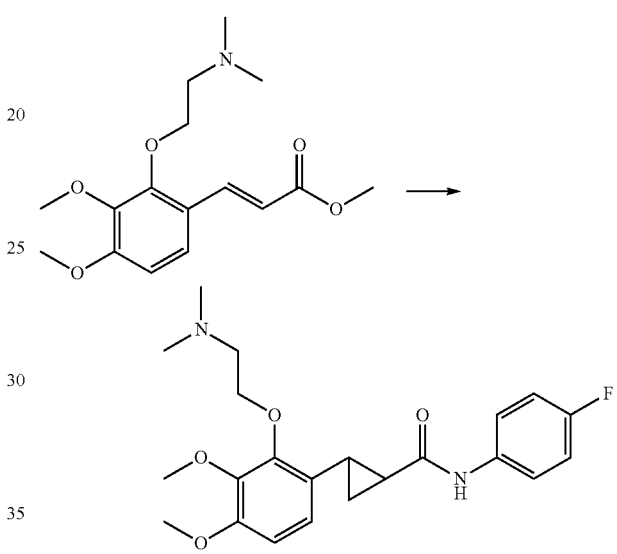

The title compound was prepared as the trifluoroacetic acid salt according to the procedure described for the synthesis of (2H-benzo[b][1,4]oxazin-4(3H)-yl)(2-(3-methoxy-4-(prop-2-yn-1-yloxy)phenyl) cyclopropyl)methanone (119) starting from (E)-methyl 3-(2-(2-(dimethylamino)ethoxy)-3,4-dimethoxyphenyl)acrylate and 4-fluoroaniline; $^1$H NMR (CD$_3$OD, 400 MHz) δ 7.59-7.56 (m, 2H), 7.06 (t, J=8.8 Hz, 2H), 6.81 (d, J=8.8 Hz, 1H), 6.73 (d, J=8.4 Hz, 1H), 4.31-4.26 (m, 2H), 3.88 (s, 3H), 3.85 (s, 3H), 3.53 (t, J=2.4 Hz, 2H), 3.00 (s, 6H), 2.67-2.65 (m, 1H), 1.90-1.88 (m, 1H), 1.55-1.53 (m, 1H), 1.40-1.38 (m, 1H); MS (ESI+) m/z 403.2 (M+H)+; 96.7% purity, RT 2.48 min (Method 11).

| Ex | Structure | Data | Method |
|---|---|---|---|
| 123 | (E)-3-(3-ethyl-4-(prop-2-yn-1-yloxy)phenyl)-N-(2-fluorophenyl)acrylamide | $^1$H NMR (CDCl$_3$, 400 MHz) δ 8.49 (t, J = 3.2 Hz, 1H), 7.73 (d, J = 15.6 Hz, 1H), 7.48 (s, 1H), 7.42-7.38 (m, 2H), 7.17-7.15 (m, 1H), 7.12-7.10 (m, 1H), 7.10-7.09 (m, 1H), 6.98 (d, J = 8.4 Hz, 1H), 6.47 (d, J = 15.2 Hz, 1H), 4.77 (d, J = 2.4 Hz, 2H), 2.68 (q, J = 7.2 Hz, 2H), 2.53 (t, J = 2.4 Hz, 1H), 1.24 (t, J = 7.2 Hz, 3H); MS (ESI+) m/z 324.1 (M + H)+; 100% purity, RT 2.33 min (Method 10) | Prepared according to the method for 113 starting from 2-fluoroaniline |

| Ex | Structure | Data | Method |
|---|---|---|---|
| 124 | 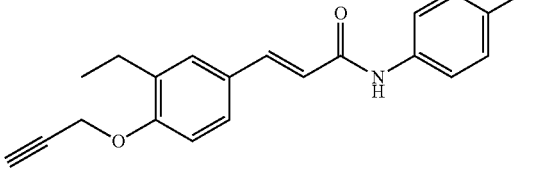<br>(E)-N-(4-cyanophenyl)-3-(3-ethyl-4-(prop-2-yn-1-yloxy)phenyl)acrylamide | 1H NMR (CDCl$_3$, 400 MHz) δ 7.77-7.73 (m, 3H), 7.64 (d, J = 8.8 Hz, 2H), 7.44-7.38 (m, 3H), 6.98 (d, J = 8.0 Hz, 1H), 6.43 (d, J = 15.6 Hz, 1H), 4.77 (d, J = 2.4 Hz, 2H), 2.68 (q, J = 6.8 Hz, 2H), 2.54 (t, J = 2.4 Hz, 1H), 1.23 (t, J = 6.8 Hz, 3H); MS (ESI+) m/z 331.2 (M + H)+; 92% purity, RT 2.33 min (Method 10) | Prepared according to the method for 113 starting from 4-aminobenzonitrile |
| 125 | 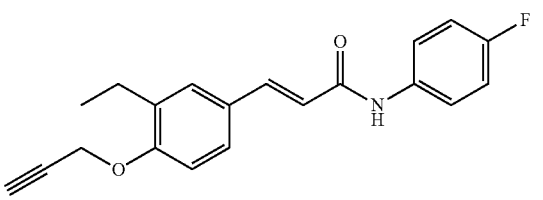<br>(E)-3-(3-ethyl-4-(prop-2-yn-1-yloxy)phenyl)-N-(4-fluorophenyl)acrylamide | 1H NMR (CDCl$_3$, 400 MHz) δ 7.71 (d, J = 15.2 Hz, 1H), 7.58 (s, 2H), 7.38-7.35 (m, 3H), 7.05 (t, J = 8.4 Hz, 2H), 6.95 (d, J = 8.4 Hz, 1H), 6.43 (d, J = 15.6 Hz, 1H), 4.76 (d, J = 2.4 Hz, 2H), 2.66 (q, J = 7.6 Hz, 2H), 2.53 (t, J = 2.4 Hz, 1H), 1.22 (t, J = 7.6 Hz, 3H); MS (ESI+) m/z 324.1 (M + H)+; 96.5% purity, RT 2.32 min (Method 9) | Prepared according to the method for 113 starting from 4-fluoroaniline |
| 126 | 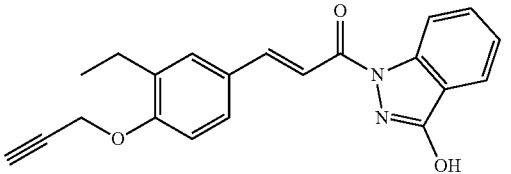<br>(E)-3-(3-ethyl-4-(prop-2-yn-1-yloxy)phenyl)-1-(3-hydroxy-1H-indazol-1-yl)prop-2-en-1-one | $^1$H NMR (CDCl$_3$, 400 MHz) δ 7.96 (d, J = 16.0 Hz, 1H), 7.62 (d, J = 8.0 Hz, 1H), 7.48-7.46 (m, 3H), 7.41 (t, J = 8.0 Hz, 1H), 7.24 (d, J = 7.6 Hz, 1H), 7.01 (d, J = 8.0 Hz, 1H), 6.65 (d, J = 13.2 Hz, 1H), 4.79 (d, J = 2.4 Hz, 2H), 2.70 (q, J = 7.6 Hz, 2.4 Hz, 2H), 2.55 (t, J = 2.4 Hz, 1H), 1.25 (t, J = 7.6 Hz, 3H); MS (ESI+) m/z 347.1 (M + H)+; 96.8% purity, RT 2.97 min (Method 12) | Prepared according to the method for 113 starting from 1H-indazol-3-ol |
| 127 | 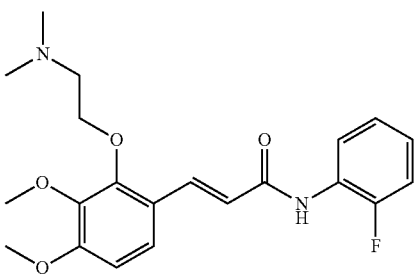<br>(E)-3-(2-(2-(dimethylamino)ethoxy)-3,4-dimethoxyphenyl)-N-(2-fluorophenyl)acrylamide | $^1$H NMR (CD$_3$OD, 400 MHz) δ 8.04-8.03 (m, 1H), 7.94 (d, J = 15.6 Hz, 1H), 7.42 (d, J = 8.8 Hz, 1H), 7.24-7.13 (m, 3H), 6.89 (s, 1H), 6.85 (d, J = 8.0 Hz, 1H), 4.16 (d, J = 5.6 Hz, 2H), 3.90 (s, 3H), 3.85 (s, 3H), 2.83 (t, J = 5.6 Hz, 2H), 2.38 (s, 6H); MS (ESI+) m/z 389.2 (M + H)+; 100% purity, RT 1.44 min (Method 10) | Prepared according to the method for 118 starting from 2-fluoroaniline |

| Ex | Structure | Data | Method |
|---|---|---|---|
| 128 | 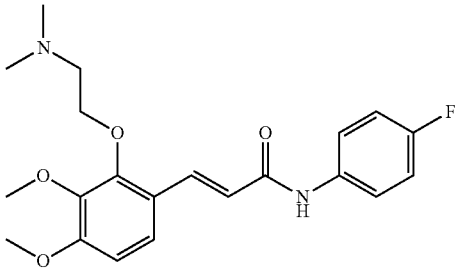<br>(E)-3-(2-(2-(dimethylamino)ethoxy)-3,4-dimethoxyphenyl)-N-(4-fluorophenyl)acrylamide trifluoroacetic acid salt | $^1$H NMR (CD$_3$OD, 400 MHz) δ 7.90 (d, J = 15.6 Hz, 1H), 7.68-7.66 (m, 2H), 7.48 (d, J = 8.8 Hz, 1H), 7.08 (t, J = 8.4 Hz, 2H), 6.95 (d, J = 8.8 Hz, 1H), 6.72 (d, J = 15.6 Hz, 1H), 4.30 (t, J = 4.8 Hz, 2H), 3.92 (s, 3H), 3.91 (s, 3H), 3.65 (t, J = 5.2 Hz, 2H), 3.10 (s, 6H); MS (ESI+) m/z 389.2 (M + H)$^+$; 100% purity, RT 1.46 min (Method 10) | Prepared according to the method for 115 starting from 4-fluoroaniline |
| 129 | 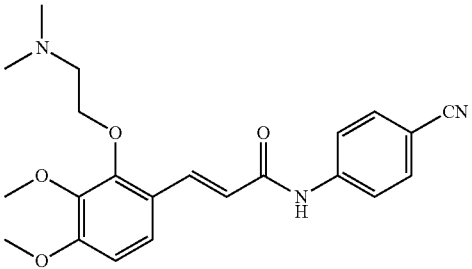<br>(E)-N-(4-cyanophenyl-3-(2-(2-(dimethylamino)ethoxy)-3,4-dimethoxyphenyl)acrylamide trifluoroacetic acid salt | $^1$H NMR (CD$_3$OD, 400 MHz) δ 7.96 (d, J = 16.0 Hz, 1H), 7.88 (d, J = 8.8 Hz, 2H), 7.70 (d, J = 8.8 Hz, 2H), 7.50 (d, J = 8.8 Hz, 1H), 6.97 (d, J = 8.8 Hz, 1H), 6.74 (d, J = 16.0 Hz, 1H), 4.31 (t, J = 4.8 Hz, 2H), 3.93 (s, 3H), 3.91 (s, 3H), 3.66 (t, J = 4.8 Hz, 2H), 3.10 (s, 6H); MS (ESI+) m/z 396.2 (M + H)$^+$; 97.5% purity, RT 1.44 min (Method 10) | Prepared according to the method for 115 starting from 4-aminobenzonitrile |
| 130 | 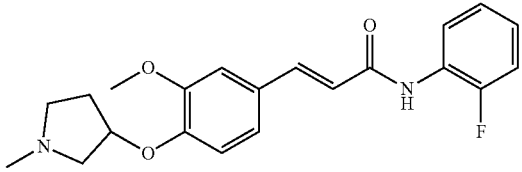<br>(E)-N-(2-fluorophenyl)-3-(3-methoxy-4-((1-methylpyrrolidin-3-yl)oxy)phenyl)acrylamide | $^1$H NMR (CD$_3$OD, 400 MHz) δ 8.11-8.09 (m, 1H), 7.64 (d, J = 15.6 Hz, 1H), 7.26-7.25 (m, 1H), 7.26-7.17 (m, 4H), 6.96 (d, J = 7.6 Hz, 1H), 6.94 (d, J = 15.6 Hz, 1H), 5.03-5.02 (m, 1H), 3.90 (s, 3H), 3.09-3.04 (m, 3H), 2.77-2.75 (m, 1H), 2.56 (s, 3H), 2.44-2.37 (m, 1H), 2.13-2.11 (m, 1H); MS (ESI+) m/z 371.2 (M + H)+; 98.1% purity, RT 2.48 min (Method 8) | Prepared according to the method for 118 starting from 2-fluoroaniline |
| 131 | 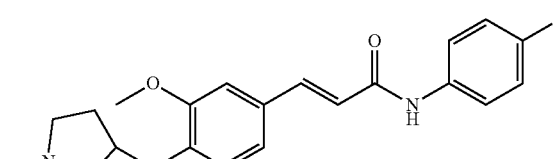<br>(E)-N-(4-cyanophenyl)-3-(3-methoxy-4-((1-methylpyrrolidin-3-yl)oxy)phenyl)acrylamide trifluoroacetic acid salt | $^1$H NMR (CD$_3$OD, 400 MHz) δ 7.96-7.60 (m, 2H), 7.72-7.58 (m, 3H), 7.28 (s, 1H), 7.21 (d, J = 8.0 Hz, 1H), 7.04 (d, J = 7.2 Hz, 1H), 6.71 (d, J = 15.6 Hz, 1H), 5.30-5.16 (m, 1H), 3.95-3.70 (m, 5H), 3.48-3.31 (m, 1H), 3.30-3.17 (m, 1H), 3.01 (s, 3H), 2.65-2.21 (m, 2H); MS (ESI+) m/z 378.2 (M + H)+; 100% purity, RT 1.44 min (Method 10) | Prepared according to the method for 118 starting from 4-aminobenzonitrile |

-continued

| Ex | Structure | Data | Method |
|---|---|---|---|
| 132 | 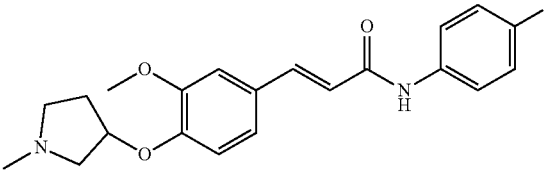<br>(E)-N-(4-fluorophenyl)-3-(3-methoxy-4-((1-methylpyrrolidin-3-yl)oxy)phenyl)acrylamide trifluoroacetic acid salt | $^1$H NMR (CD$_3$OD, 400 MHz) δ 7.70-7.65 (m, 2H), 7.59 (d, J = 15.6 Hz, 1H), 7.26-7.25 (m, 1H), 7.10-7.09 (m, 1H), 7.07-7.04 (m, 3H), 6.72 (d, J = 15.6 Hz, 1H), 5.25-5.23 (m, 1H), 3.93-3.88 (m, 5H), 3.45-3.10 (m, 1H), 3.33-3.32 (m, 1H), 3.24-3.03 (m, 3H), 2.33-2.26 (m, 2H); MS (ESI+) m/z 371.2 (M + H)+; 100% purity, RT 1.45 min (Method 10) | Prepared according to the method for 118 starting from 4-fluoroaniline |
| 133 | 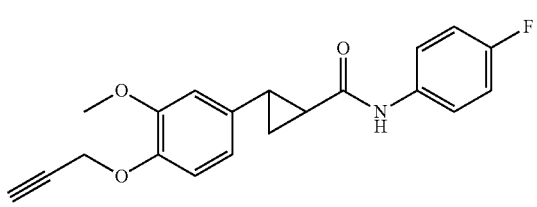<br>N-(4-fluorophenyl)-2-(3-methoxy-4-(prop-2-yn-1-yloxy)phenyl)cyclo-propanecarboxamide | $^1$H NMR (CDCl$_3$, 400 MHz) δ 7.58 (s, 1H), 7.52-7.48 (m, 2H), 7.01 (d, J = 8.4 Hz, 2H), 6.94 (d, J = 8.0 Hz, 1H), 6.65 (d, J = 8.4 Hz, 2H), 4.74 (d, J = 2.4 Hz, 2H), 3.82 (s, 3H), 2.55-2.53 (m, 1H), 2.50 (t, J = 2.4 Hz, 1H), 1.73-1.68 (m, 2H), 1.34-1.31 (m, 1H); MS (ESI+) m/z 340.3 (M + H)$^+$; 100% purity, RT 2.11 min (Method 10) | Prepared according to the method for 119 starting from 4-fluoroaniline |
| 134 | 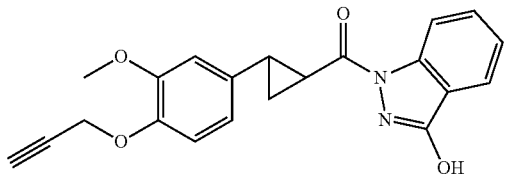<br>(3-hydroxy-1H-indazol-1-yl)(2-(3-methoxy-4-(prop-2-yn-1-yloxy)phenyl)cyclopropyl)methanone | $^1$H NMR (CDCl$_3$, 400 MHz) δ 8.43 (br. s, 1H), 7.70 (d, J = 6.8 Hz, 1H), 7.62 (d, J = 8.0 Hz, 1H), 7.39 (d, J = 7.2 Hz, 1H), 6.97 (d, J = 8.0 Hz, 1H), 6.79-6.77 (m, 2H), 4.74 (d, J = 2.4 Hz, 2H), 3.84 (s, 3H), 3.04 (s, 1H), 2.82-2.77 (m, 1H), 2.48 (t, J = 2.4 H, 1H), 1.91-1.89 (m, 1H), 1.58-1.55 (m, 1H); MS (ESI+) m/z 363.1 (M + H)$^+$; 385.1 (M + Na)$^+$; 97.9% purity, RT 2.94 min (Method 7) | Prepared according to the method for 119 starting from 1H-indazol-3-ol |
| 135 | 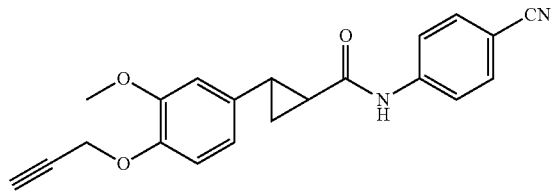<br>N-(4-cyanophenyl)-2-(3-methoxy-4-(prop-2-yn-1-yloxy)phenyl)cyclo-propanecarboxamide | $^1$H NMR (CDCl$_3$, 400 MHz) δ 7.78 (s, 1H), 7.68 (d, J = 8.8 Hz, 2H), 7.61 (d, J = 8.8 Hz, 2H), 6.97 (d, J = 8.4 Hz, 1H), 6.65-6.64 (m, 2H), 4.75 (d, J = 2.4 Hz, 2H), 3.82 (s, 3H), 2.63-2.50 (m, 1H), 2.49 (t, J = 2.4 Hz, 1H), 1.61-1.40 (m, 2H), 1.45-1.34 (m, 1H); MS (ESI+) m/z 347.1 (M + H)$^+$; 98.6% purity, RT 2.04 min (Method 9) | Prepared according to the method for 119 starting from 4-aminobenzonitrile |
| 136 | 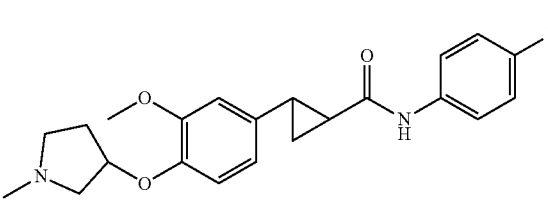<br>N-(4-fluorophenyl)-2-(3-methoxy-4-((1-methylpyrrolidin-3-yl-oxy)phenyl)cyclopropane-1-carboxamide | $^1$H NMR (CDCl$_3$, 400 MHz) δ 7.59-7.51 (m, 3H), 7.02 (d, J = 8.8 Hz, 2H), 6.76 (d, J = 8.4 Hz, 1H), 6.70 (s, 1H), 6.63 (d, J = 1.6 Hz, 1H), 4.89-4.85 (m, 1H), 3.84 (s, 3H), 3.30-3.25 (m, 1H), 2.94-2.90 (m, 3H), 2.60-2.53 (m, 4H), 2.31-2.28 (m, 1H), 2.20-2.15 (m, 1H), 1.71-1.60 (m, 2H), 1.34-1.32 (m, 1H); MS (ESI+) m/z 385.1 (M + H)$^+$; 96.4% purity, RT 1.56 min (Method 9) | Prepared according to the method for 119 starting from (E)-methyl 3-(3-methoxy-4-((1-methylpyrrolidin-3-yl)oxy)phenyl) acrylate and 4-fluoroaniline |

| Ex | Structure | Data | Method |
|---|---|---|---|
| 137 | 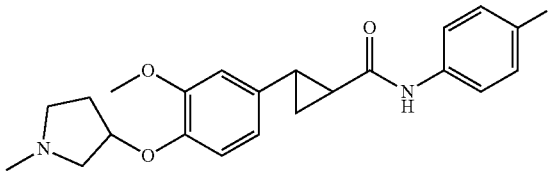<br>N-(4-cyanophenyl)-2-(3-methoxy-4-((1-methylpyrrolidin-3-yl-oxy)phenyl)cyclopropane-1-carboxamide | $^1$H NMR (CD$_3$OD, 400 MHz) δ 7.78 (d, J = 8.8 Hz, 2H), 7.70-7.65 (m, 2H), 6.94 (d, J = 8.0 Hz, 1H), 6.87 (s, 1H), 6.75-6.73 (m, 1H), 5.08 (s, 1H), 3.91 (d, J = 8.4 Hz 1H), 3.86 (s, 3H), 3.43-3.40 (m, 1H), 3.25-3.18 (m, 1H), 3.10-3.00 (m, 4H), 2.50-2.48 (m, 1H), 2.35-2.15 (m, 2H), 2.05-2.03 (m, 1H), 1.61-1.59 (m, 1H), 1.39-1.30 (m, 1H); MS (ESI+) m/z 392.2 (M + H)+; 94.5% purity, RT 2.72 min (Method 12) | Prepared according to the method for 119 starting from (E)-methyl 3-(3-methoxy-4-((1-methylpyrrolidin-3-yl)oxy)phenyl) acrylate and 4-aminobenzonitrile |
| 138 | 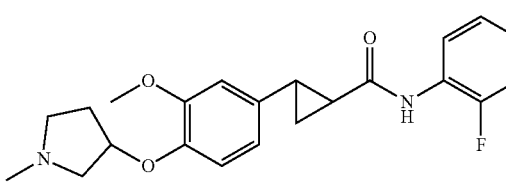<br>N-(2-fluorophenyl)-2-(3-methoxy-4-((1-methylpyrrolidin-3-yl)oxy)phenyl)cyclopropane carboxamide | $^1$H NMR (CD$_3$OD, 400 MHz) δ 7.94-7.92 (m, 1H), 7.17-7.14 (m, 3H), 6.94 (d, J = 7.2 Hz, 1H), 6.88 (s, 1H), 6.75 (d, J = 8.0 Hz, 1H), 5.10-5.09 (m, 1H), 3.93-3.87 (m, 5H), 3.41-3.42 (m, 1H), 3.27-3.17 (m, 1H), 3.10-3.00 (m, 3H), 2.50-2.47 (m, 2H), 2.30-2.19 (m, 2H), 1.60-1.57 (m, 1H), 1.37-1.33 (m, 1H); MS (ESI+) m/z 385.2 (M + H)+; 96.5% purity, RT 2.4 min (Method 11) | Prepared according to the method for 119 starting from (E)-methyl 3-(3-methoxy-4-((1-methylpyrrolidin-3-yl)oxy)phenyl) acrylate and 2-fluoroaniline |
| 139 | 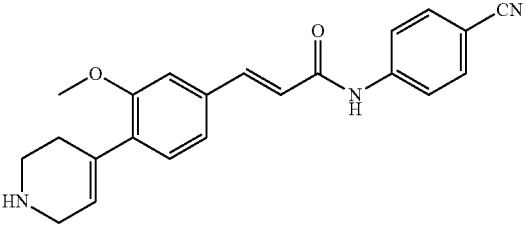<br>(E)-N-(4-cyanophenyl)-3-(3-methoxy-4-((1,2,3,6-tetrahydropyridin-4-yl)phenyl)acrylamide trifluoroacetic acid salt | 1H NMR (CD$_3$OD, 400 MHz) δ 7.88-7.86 (m, 2H), 7.71-7.67 (m, 3H), 7.26-7.22 (m, 3H), 6.82 (d, J = 15.6 Hz, 1H), 5.89 (s, 1H), 3.90 (s, 3H), 3.83 (d, J = 2.8 Hz, 2H), 3.42 (t, J = 6.0 Hz, 2H), 2.86-2.79 (m, 2H); MS (ESI+) m/z 360.3 (M + H)+; 98.2% purity, RT 1.61 min (Method 9) | Prepared according to the method for 120 starting from 4-aminobenzonitrile. |
| 140 | 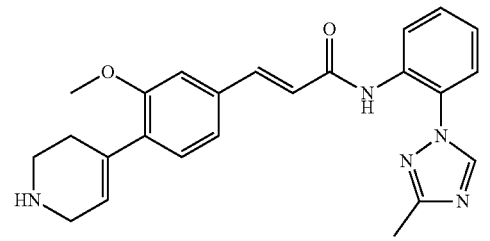<br>(E)-3-(3-methoxy-4-(1,2,3,6-tetrahydropyridin-4-yl)phenyl)-N-(2-(3-methyl-1H-1,2,4-triazol-1-yl)phenyl)acrylamide trifluoroacetic acid salt | 1H NMR (CD$_3$OD, 400 MHz) δ 8.69 (s, 1H), 7.97 (d, J = 7.6 Hz, 1H), 7.61-7.53 (m, 3H), 7.39-7.38 (m, 1H), 7.22-7.18 (m, 3H), 6.75 (d, J = 15.6 Hz, 1H), 5.87 (t, J = 1.6 Hz, 1H), 3.87 (s, 3H), 3.83 (d, J = 2.8 Hz, 2H), 3.42 (t, J = 6.0 Hz, 2H), 2.78-2.76 (m, 2H), 2.46 (s, 3H); MS (ESI+) m/z 416.3 (M + H)+; 100% purity, RT 2.26 min (Method 8) | Prepared according to the method for 120 starting from 2-(3-methyl-1H-1,2,4-triazol-1-yl)aniline. |

| Ex | Structure | Data | Method |
|---|---|---|---|
| 141 | (E)-N-(2-fluorophenyl)-3-(3-methoxy-4-((1,2,3,6-tetrahydropyridin-4-yl)phenyl)acrylamide | 1H NMR (CD$_3$OD, 400 MHz) δ 8.09 (t, J = 1.2 Hz, 1H), 7.68 (d, J = 15.6 Hz, 1H), 7.24-7.17 (m, 6H), 6.67 (d, J = 15.6 Hz, 1H), 5.89 (s, 1H), 3.90 (s, 3H), 3.84 (d, J = 2.0 Hz, 2H), 3.43 (t, J = 6.0 Hz, 2H), 2.80-2.78 (m, 2H); MS (ESI+) m/z 353.2 (M + H)+; 100% purity, RT 2.52 min (Method 8) | Prepared according to the method for 120 starting from 2-fluoroaniline |
| 142 | (E)-1-(3-hydroxy-1H-indazol-1-yl)(3-(3-methoxy-4-(1,2,3,6-tetrahydropyridin-4-yl)phenyl)prop-2-en-1-one | 1H NMR (CD$_3$OD, 400 MHz) δ 8.44 (d, J = 8.4 Hz, 1H), 7.90-7.78 (m, 2H), 7.78 (d, J = 7.6 Hz, 1H), 7.63-7.59 (m, 1H), 7.43-7.40 (m, 1H), 7.35-7.32 (m, 1H), 7.31-7.29 (m, 1H), 7.29-7.27 (m, 1H), 5.91 (t, J = 2.0 Hz, 1H), 3.93 (s, 3H), 3.84 (d, J = 2.8 Hz, 2H), 3.43 (t, J = 6.0 Hz, 2H), 2.82-2.80 (m, 2H); MS (ESI+) m/z 376.2 (M + H)+; 91.6% purity, RT 1.6 min (Method 10) | Prepared according to the method for 120 starting from 1H-indazol-3-ol |
| 143 | N-(4-fluorophenyl)-2-(3-methoxy-4-(1,2,3,6-tetrahydropyridin-4-yl)phenyl)cyclopropane carboxamide trifluoroacetic acid salt | $^1$H NMR (CD$_3$OD, 400 MHz) δ 7.57-7.54 (m, 2H), 7.09 (d, J = 8.0 Hz, 1H), 7.06-7.02 (m, 2H), 6.82 (s, 1H), 6.74 (d, J = 6.8 Hz, 1H), 5.79-5.78 (m, 1H), 3.83 (s, 3H), 3.80 (t, J = 2.4 Hz, 2H), 3.40 (t, J = 6.0 Hz, 2H), 2.77-2.73 (m, 2H), 2.49-2.47 (m, 1H), 2.07-2.05 (m, 1H), 1.62-1.59 (m, 1H), 1.39-1.38(m, 1H); MS (ESI+) m/z 367.1 (M + H)+; 97.6% purity, RT 2.47 min (Method 11) | Prepared according to the method for 121 starting from 4-fluoroaniline. |
| 144 | 2-(3-methoxy-4-(1,2,3,6-tetrahydropyridin-4-yl-phenyl)-N-(2-(3-methyl-1H-1,2,4-triazol-1-yl)phenyl) cyclopropanecarboxamide trifluoroacetic acid salt | $^1$H NMR (CD$_3$OD, 400 MHz) δ 8.66 (s, 1H), 7.79 (d, J = 8.0 Hz, 1H), 7.52-7.49 (m, 2H), 7.39 (t, J = 7.6 Hz, 1H), 7.09 (d, J = 7.6 Hz, 1H), 6.79 (s, 1H), 6.72 (d, J = 8.0 Hz, 1H), 5.78-5.77 (m, 1H), 3.82 (s, 3H), 3.80 (d, J = 2.0 Hz, 2H), 3.40 (t, J = 6.0 Hz, 2H), 2.75 (d, J = 2.0 Hz, 2H), 2.40 (s, 3H), 2.37-2.35 (m, 1H), 2.02-2.00 (m, 1H), 1.53-1.50 (m, 1H), 1.36-1.29 (m, 1H); MS (ESI+) m/z 430.2 (M + H)+; 98.1% purity, RT 2.33 min (Method 11) | Prepared according to the method for 121 starting from 2-(3-methyl-1H-1,2,4-triazol-1-yl)aniline |

| Ex | Structure | Data | Method |
|---|---|---|---|
| 145 | N-(2-fluorophenyl)-2-(3-methoxy-4-(1,2,3,6-tetrahydropyridin-4-yl)phenyl)cyclopropane carboxamide trifluoroacetic acid salt | $^1$H NMR (CD$_3$OD, 400 MHz) δ 7.93 (d, J = 8.4 Hz, 1H), 7.16-7.10 (m, 4H), 6.83 (s, 1H), 6.76 (d, J = 7.6 Hz, 1H), 5.80 (s, 1H), 3.84 (s, 3H), 3.81 (d, J = 2.4 Hz, 2H), 3.40 (t, J = 6.0 Hz, 2H), 2.76 (d, J = 2.0 Hz, 2H), 2.53-2.51 (m, 1H), 2.62-2.25 (m, 1H), 1.63-1.60 (m, 1H), 1.40-1.38 (m, 1H); MS (ESI+) m/z 367.2 (M + H)+; 97.8% purity, RT 2.44 min (Method 11) | Prepared according to the method for 121 starting from 2-fluoroaniline |
| 146 | (3-hydroxy-1H-indazol-1-yl)(2-(3-methoxy-4-(1,2,3,6-tetrahydropyridin-4-yl)phenyl)cyclopropyl)methanone trifluoroacetic acid salt | $^1$H NMR (CD$_3$OD, 400 MHz) δ 8.33 (d, J = 8.4 Hz, 1H), 7.73 (d, J = 7.6 Hz, 1H), 7.58 (d, J = 8.0 Hz, 1H), 7.36 (d, J = 7.6 Hz, 1H), 7.10 (d, J = 8.0 Hz, 1H), 6.87 (s, 1H), 6.79 (d, J = 7.6 Hz, 1H), 5.80-5.79 (m, 1H), 3.92 (s, 3H), 3.83-3.81 (m, 2H), 3.40 (t, J = 6.0 Hz, 2H), 3.31 (s, 1H), 2.85-2.70 (m 2H), 2.68-2.66 (m, 1H), 1.82-1.80 (m, 1H), 1.59-1.58 (m, 1H); MS (ESI+) m/z 390.1 (M + H)+; 96.8% purity, RT 2.52 min (Method 11) | Prepared according to the method for 121 starting from 1H-indazol-3-ol |

(E)-N-(3-chlorophenyl)-3-(3-methoxy-4-(oxetan-3-ylmethoxy)phenyl)acrylamide (147)

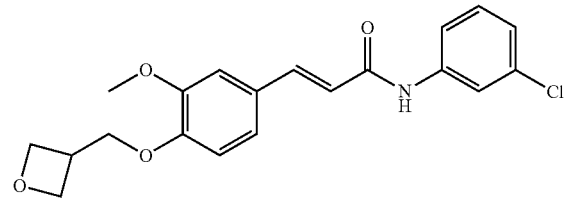 [SMILES: COc1cc(/C=C/C(=O)Nc2cccc(Cl)c2)ccc1OCC1COC1]

a) ethyl (E)-3-(3-methoxy-4-(oxetan-3-ylmethoxy)phenyl)acrylate

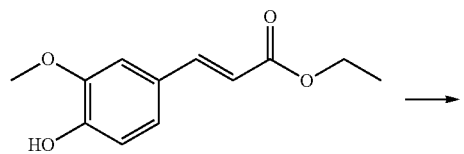

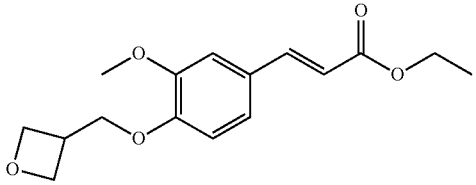

To a stirred solution of ethyl (E)-3-(4-hydroxy-3-methoxyphenyl)acrylate (1.0 g, 4.5 mmol, 1.0 equiv.) in dry N,N-dimethylformamide (10 mL) under a nitrogen atmosphere at 0° C. was added portion-wise sodium hydride (24 mg, 6.76 mmol, 60% in mineral oil. 1.5 equiv.). After stirring for 15 minutes in the cold the mixture was treated with a solution of oxetan-3-ylmethyl methanesulfonate (0.90 g, 5.41 mmol, 1.2 equiv.) in N,N-dimethylformamide (5 mL). The mixture was allowed to warm to room temperature and after 1 hour the reaction was quenched by addition of water (30 mL) and was then extracted with ethyl acetate (150 mL). The organic layer was washed with water (7×30 mL) and brine (30 mL) and concentrated to dryness under vacuum to give a yellow oil. The crude product was purified by chromatography on silica gel (Interchim 80 g column, eluting with 30-60% ethyl acetate/isohexane) to afford the title compound as a colourless solid (0.93 g, 73%); $^1$H NMR (400 MHz, CDCl$_3$): δ 7.64 (s, 1H), 7.60 (s, 1H), 7.11-7.05 (m, 1H), 6.90 (d, J=8.1 Hz, 1H), 6.34 (d, J=8.1 Hz, 1H), 4.90 (dd, J=6.3, J=7.6 Hz, 2H), 4.55 (q, J=6.1 Hz, 2H), 4.31-4.23 (m, 4H), 3.88 (s, 3H), 3.55-3.45 (m, 1H), 1.34 (t, J=7.2 Hz, 3H).

b) (E)-3-(3-methoxy-4-(oxetan-3-ylmethoxy)phenyl)acrylic acid

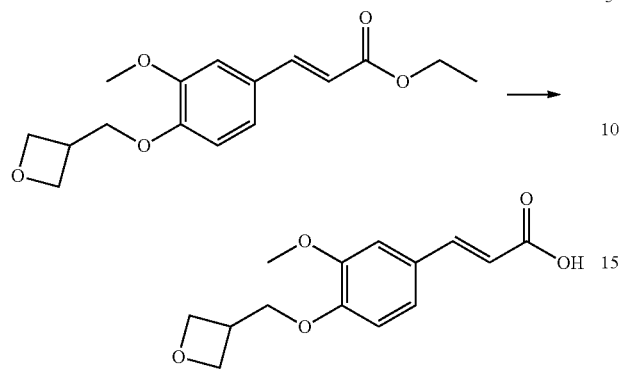

A stirred mixture of ethyl (E)-3-(3-methoxy-4-(oxetan-3-ylmethoxy)phenyl)acrylate (250 mg, 0.88 mmol, 1.0 equiv.) and lithium hydroxide monohydrate (74 mg, 1.77 mmol, 2.0 equiv.) in 30% aqueous dioxane (13 mL) was heated to 50° C. for 2 hours. The mixture was concentrated in vacuo and then diluted with water (5 mL) and acidified with 2N hydrochloric acid. The precipitate was filtered, washed with water and dried under vacuum to afford the title compound as a colourless solid (190 mg, 81%); $^1$H NMR (400 MHz, DMSO): δ 7.56 (d, J=16.2 Hz, 1H), 7.37 (d, J=1.8 Hz, 1H), 7.26 (dd, J=8.3 Hz, J=1.8 Hz, 1H), 7.08 (d, J=8.3 Hz, 1H), 6.52 (d, J=16.2 Hz, 1H), 4.76 (dd, J=7.8 Hz, J=6.1, Hz, 2H), 4.46 (dd, J=6.1 Hz, J=6.1 Hz, 2H), 4.29 (d, J=6.8 Hz, 2H), 3.86 (3H, s), 3.49-3.43 (1H, m).

c) (E)-N-(3-chlorophenyl)-3-(3-methoxy-4-(oxetan-3-ylmethoxy)phenyl)acrylamide

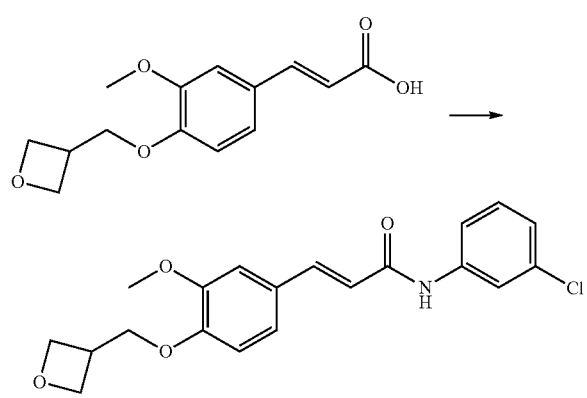

To a solution of (E)-3-(3-methoxy-4-(oxetan-3-ylmethoxy)phenyl)acrylic acid (60 mg, 0.227 mmol, 1 equiv.) in N,N-dimethylformamide (2 mL) was added diisopropylethylamine (0.12 mL, 0.682 mmol 3 equiv.) followed by HATU (104 mg, 0.273 mmol, 1.2 equiv.) and 3-chloroaniline (29 mg, 0.227 mmol, 1 equiv.) and the mixture stirred overnight at room temperature. The product was purified by preparative HPLC and was obtained as an off-white solid (72 mg, 85%); $^1$H NMR (400 MHz, CDCl$_3$): δ 7.73 (m, 2H), 7.67 (s, 1H), 7.46 (dd, J=8.1 Hz, J=1.3 Hz, 1H), 7.37 (s, 1H), 7.14-7.09 (m, 2H), 7.05 (d, J=1.8 Hz, 1H), 6.91 (d, J=8.3 Hz, 1H), 6.43 (d, J=16.2 Hz, 1H), 4.91 (dd, J=7.7 Hz, J=6.4 Hz, 2H), 4.56 (dd, J=5.9 Hz, J=5.9 Hz, 2H), 4.30 (d, J=7.1 Hz, 2H), 3.88 (s, 3H), 3.54-3.47 (m, 1H); MS (ESI+) m/z 374/376 (M+H)+; 99.3% purity, RT 3.32 min (Method 2).

N-(3-chlorophenyl)-2-(3-methoxy-4-(oxetan-3-ylmethoxy)phenyl)cyclopropane-1-carboxamide (148)

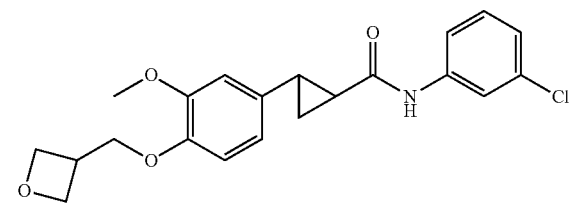 [SMILES: COc1cc(C2CC2C(=O)Nc2cccc(Cl)c2)ccc1OCC1COC1]

a) ethyl 2-(3-methoxy-4-(oxetan-3-ylmethoxy)phenyl)cyclopropane-1-carboxylate

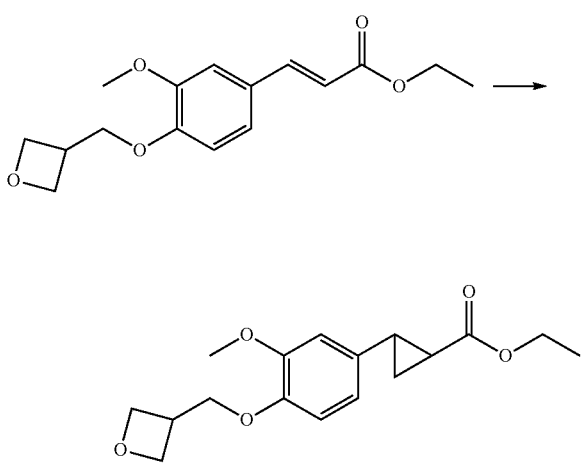

A stirred solution of trimethylsulfoxonium iodide (904 mg, 4.11 mmol, 3.0 equiv.) in dimethylsulfoxide (7 mL) was treated with sodium hydride (192 mg, 4.79 mmol, 60% in mineral oil, 3.5 equiv.). After 1 hour the resultant solution was added drop-wise to a solution of ethyl (E)-3-(3-methoxy-4-(oxetan-3-ylmethoxy)phenyl)acrylate (292 mg, 1.36 mmol, 1 equiv.) in dimethylsulfoxide (7 mL). The mixture was then heated to 80° C. for 18 hours. The cooled mixture was poured into saturated ammonium chloride solution (50 mL) and extracted with ethyl acetate (3×30 mL). The combined extracts were washed with brine, dried and concentrated to dryness under vacuum. The crude product was purified by chromatography on silica gel (Interchim 40 g column, eluting with 30-60% ethyl acetate/isohexane) to afford the title compound as a colourless oil (203 mg, 48%). $^1$H NMR (400 MHz, CDCl$_3$) δ 6.83 (d, J=8.1 Hz, 1H), 6.67-6.61 (m, 2H), 4.88 (dd, J=7.6 Hz, J=6.3 Hz, 2H), 4.54 (dd, J=6.1 Hz, J=6.1 Hz, 2H), 4.24 (d, J=7.1 Hz, 2H), 4.21-4.14 (m, 2H), 3.84 (s, 3H), 3.50-3.41 (m, 1H), 2.48 (ddd, J=9.1 Hz, J=6.6 Hz, J=4.0 Hz, 1H), 1.87-1.82 (m, 1H), 1.59-1.50 (m, 1H), 1.30-1.25 (m, 4H).

201 b) 2-(3-methoxy-4-(oxetan-3-ylmethoxy)phenyl)cyclopropane-1-carboxylic acid

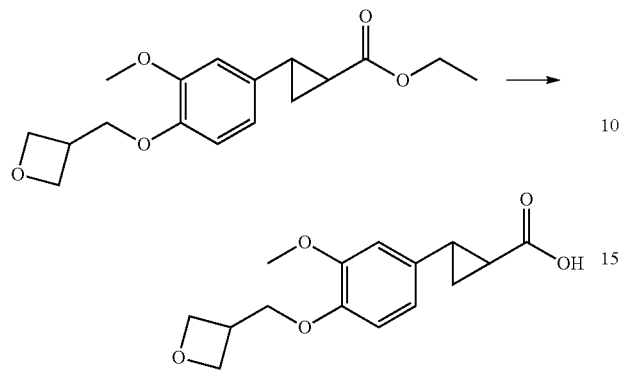

The title compound was prepared in a similar manner to (E)-3-(3-methoxy-4-(oxetan-3-ylmethoxy)phenyl)acrylic acid from ethyl 2-(3-methoxy-4-(oxetan-3-ylmethoxy)phenyl)cyclopropane-1-carboxylate and lithium hydroxide monohydrate and was isolated as a colourless solid (171 mg, 79%); $^1$H NMR (400 MHz, CDCl$_3$): δ 6.83 (d, J=8.1 Hz, 1H), 6.68-6.62 (m, 2H), 4.88 (dd, J=7.6 Hz, J=6.3 Hz, 2H), 4.54 (dd, J=6.1 Hz, J=6.1 Hz, 2H), 4.24 (d, J=7.1 Hz, 2H), 3.84 (s, 3H), 3.51-3.42 (m, 1H), 2.57 (ddd, J=9.2 Hz, J=6.6 Hz, J=4.0 Hz, 1H), 1.88-1.82 (m, 1H), 1.66-1.59 (m, 1H), 1.36 (ddd, J=8.3 Hz J=6.7 Hz, J=4.7 Hz, 1H).

c) N-(3-chlorophenyl)-2-(3-methoxy-4-(oxetan-3-ylmethoxy)phenyl)cyclopropane-1-carboxamide

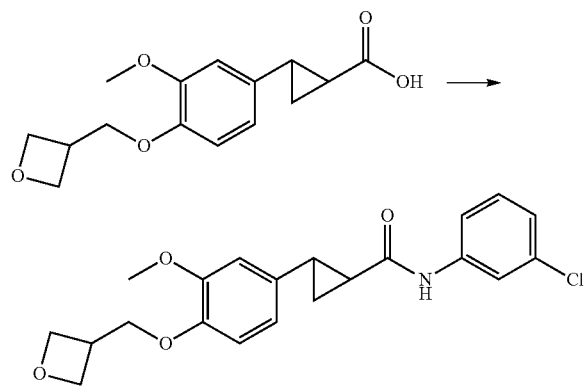

The title compound was prepared using a similar method to (E)-N-(3-chlorophenyl)-3-(3-methoxy-4-(oxetan-3-ylmethoxy)phenyl)acrylamide (147) using 2-(3-methoxy-4-(oxetan-3-ylmethoxy)phenyl) cyclopropane-1-carboxylic acid and 3-chloroaniline and was obtained as an off-white solid (70%); $^1$H NMR (400 MHz, CDCl$_3$) δ 7.67 (s, 1H), 7.52-7.49 (m, 1H), 7.35 (d, J=7.8 Hz, 1H), 7.23 (dd, J=8.1 Hz, J=8.1 Hz, 1H), 7.08 (d, J=7.8 Hz, 1H), 6.86-6.82 (m, 1H), 6.67-6.63 (m, 2H), 4.90-4.84 (m, 2H), 4.55-4.50 (m, 2H), 4.25 (d, J=7.1 Hz, 2H), 3.80 (s, 3H), 3.49-3.40 (m, 1H), 2.55 (ddd, J=9.1 Hz, J=6.4 Hz, J=4.0 Hz, 1H), 1.74-1.64 (m, 2H), 1.34 (ddd, J=7.8 Hz, J=6.6. Hz, J=4.4 Hz, 1H). MS (ESI+) m/z 388/390 (M+H)+; 97.2% purity, RT 3.39 min (Method 2).

202

N-(4-chlorophenyl)-2-(4-methoxy-3-((1-methyl-1H-pyrazol-4-yl)methoxy)phenyl)cyclopropane-1-carboxamide (149)

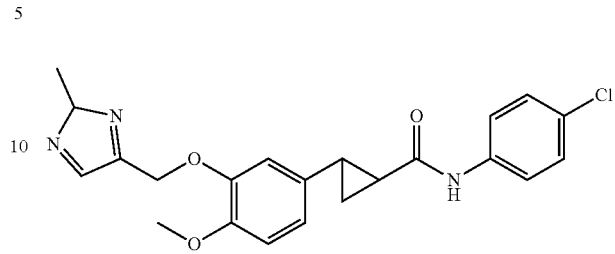

a) 4-methoxy-3-((1-methyl-1H-pyrazol-4-yl)methoxy)benzaldehyde

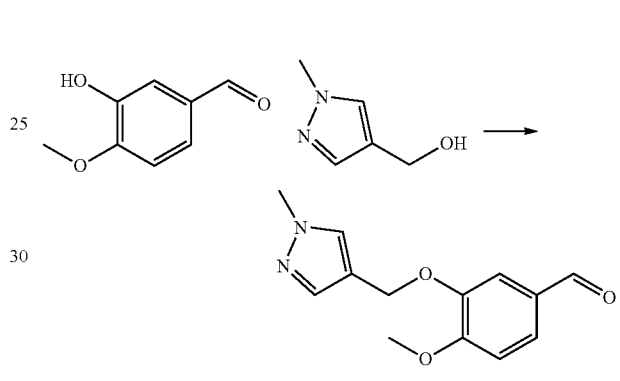

A stirred solution of (1-methyl-1H-pyrazol-4-yl)methanol (0.74 g, 6.58 mmol, 1 equiv.) in tetrahydrofuran (30 mL) was treated with isovanillin (1.00 g, 6.58 mmol, 1 equiv.) and triphenylphosphine (2.10 g, 7.89 mmol, 1.2 equiv.). The mixture was cooled to 0° C. and diisopropyl azodicarboxylate (1.55 mL, 7.89 mmol, 1.2 equiv.) was added drop-wise. The mixture was then allowed to warm to room temperature and was stirred overnight. The mixture was concentrated to dryness under vacuum and the residue purified by chromatography on silica gel (Interchim 80 g column, eluting with 50-80% ethyl acetate/isohexane) to afford the title compound as a pale yellow oil (1.37 g, 85%) which was used without further purification; $^1$H NMR (400 MHz, CDCl$_3$): δ 9.85 (s, 1H), 7.70-7.64 (m, 2H), 7.58-7.44 (m, 3H), 5.08 (s, 2H), 3.94 (s, 3H), 3.89 (s, 3H).

b) ethyl (E)-3-(4-methoxy-3-((1-methyl-1H-pyrazol-4-yl)methoxy)phenyl)acrylate

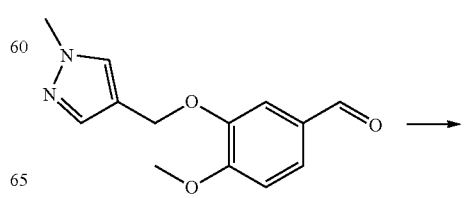

-continued

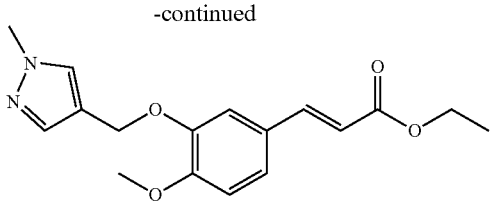

To a stirred suspension of sodium hydride (205 mg, 5.12 mmol, 60% in mineral oil, 1.5 equiv.) in tetrahydrofuran (10 mL) under a nitrogen atmosphere was added drop-wise a solution of triethyl phosphonoacetate (840 mg, 3.76 mmol, 1.1 equiv.) in tetrahydrofuran (5 mL). After 15 minutes a solution of 4-methoxy-3-((1-methyl-1H-pyrazol-4-yl)methoxy)benzaldehyde (840 mg, 3.41 mmol, 1.0 equiv.) in tetrahydrofuran (15 mL) was slowly added and the mixture stirred for a further 4 hours. Water (30 mL) was added and the mixture extracted with ethyl acetate (150 mL). The organic phase was washed the brine, dried and concentrated to dryness under vacuum. The residue was purified by chromatography on silica gel (Interchim 80 g column, eluting with 50-80% ethyl acetate/isohexane) to afford the title compound as an off-white solid (786 mg, 85%) which was used without further purification; $^1$H NMR (400 MHz, CDCl$_3$) δ 7.61 (d, J=16.3 Hz, 1H), 7.56 (s, 1H), 7.45 (s, 1H), 7.14-7.10 (m, 2H), 6.87 (d, J=8.4 Hz, 1H), 6.28 (d, J=16.3 Hz, 1H), 5.05 (s, 2H), 4.26 (q, J=6.9 Hz, 2H), 3.89 (s, 3H), 3.88 (s, 3H), 1.34 (t, J=7.0 Hz, 3H).

c) ethyl 2-(4-methoxy-3-((1-methyl-1H-pyrazol-4-yl)methoxy)phenyl)cyclopropane-1-carboxylate

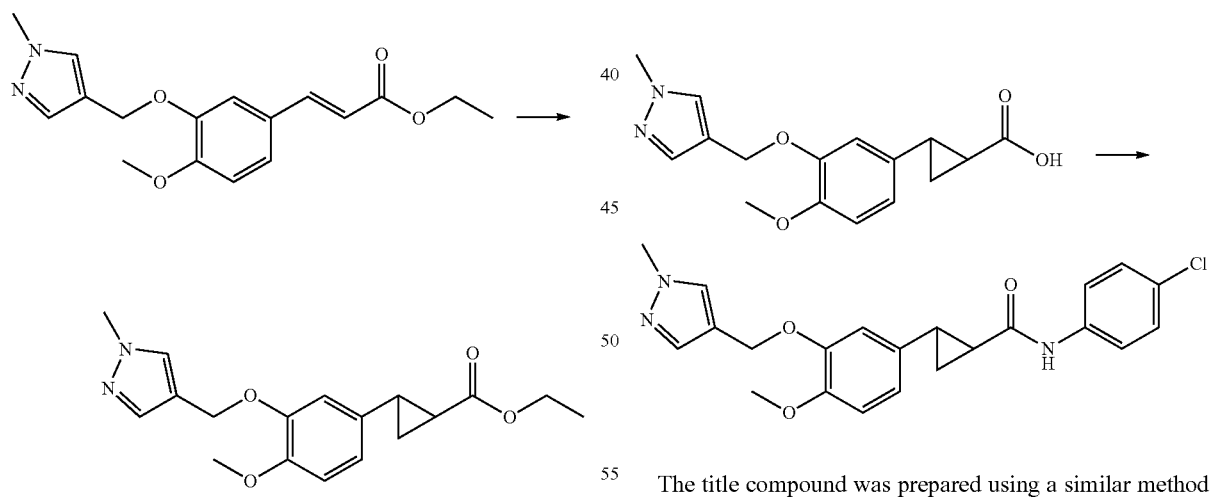

The title compound was prepared in a similar manner to ethyl 2-(3-methoxy-4-(oxetan-3-ylmethoxy)phenyl)cyclopropane-1-carboxylate from ethyl (E)-3-(4-methoxy-3-((1-methyl-1H-pyrazol-4-yl)methoxy)phenyl)acrylate to afford the product as a cream solid (31%); $^1$H NMR (400 MHz, CDCl$_3$): δ 7.53 (s, 1H), 7.44 (s, 1H), 6.79 (d, J=8.3 Hz, 1H), 6.71 (d, J=2.0 Hz, 1H), 6.67 (dd, J=8.2 Hz, J=1.9 Hz, 1H), 4.99 (s, 2H), 4.17 (q, J=7.2 Hz, 2H), 3.89 (s, 3H), 3.82 (s, 3H), 2.49-2.42 (m, 1H), 1.84-1.78 (m, 1H), 1.58-1.52 (m, 1H), 1.31-1.21 (m, 4H).

d) 2-(4-methoxy-3-((1-methyl-1H-pyrazol-4-yl)methoxy)phenyl)cyclopropane-1-carboxylic acid

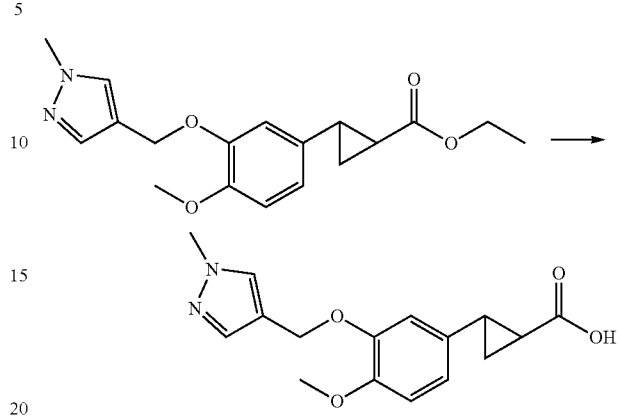

The title compound was prepared in a similar manner to (E)-3-(3-methoxy-4-(oxetan-3-ylmethoxy)phenyl)acrylic acid from ethyl 2-(4-methoxy-3-((1-methyl-1H-pyrazol-4-yl)methoxy)phenyl)cyclopropane-1-carboxylate and lithium hydroxide monohydrate and was isolated as a pale yellow gum (94%); $^1$H NMR (400 MHz, DMSO): δ 7.81 (s, 1H), 7.52 (s, 1H), 6.91-6.87 (m, 2H), 6.73 (dd, J=8.3 Hz, J=2.0 Hz, 1H), 4.96 (s, 2H), 3.87 (s, 3H), 3.74 (s, 3H), 2.41-2.34 (m, 1H), 1.83-1.77 (m, 1H), 1.45-1.29 (m, 2H).

e) N-(4-chlorophenyl)-2-(4-methoxy-3-((1-methyl-1H-pyrazol-4-yl)methoxy)phenyl)-cyclopropane-1-carboxamide The title compound was prepared using a similar method to (E)-N-(3-chlorophenyl)-3-(3-methoxy-4-(oxetan-3-ylmethoxy)phenyl)acrylamide (147) using 2-(4-methoxy-3-((1-methyl-1H-pyrazol-4-yl)methoxy)phenyl)cyclopropane-1-carboxylic acid and 4-chloroaniline and was obtained as an off-white solid (63%); $^1$H NMR (400 MHz, CDCl$_3$) δ 7.55 (s, 1H), 7.52-7.46 (m, 3H), 7.42 (s, 1H), 7.29 (m, 2H), 6.80 (d, J=8.1 Hz, 1H), 6.72-6.65 (m, 2H), 4.97 (s, 2H), 3.86 (s, 3H), 3.84 (s, 3H), 2.55-2.48 (m, 1H), 1.72-1.65 (m, 1H), 1.60 (m, 1H), 1.28 (dd, J=11.5 Hz, J=7.5 Hz, 1H). MS (ESI+) m/z 412/414 (M+H)+; 98.7% purity. RT 3.41 min. (Method 2)

(E)-3-(4-methoxy-3-((1-methyl-1H-pyrazol-4-yl)methoxy)phenyl)-N-(pyridin-3-yl)acrylamide (150)

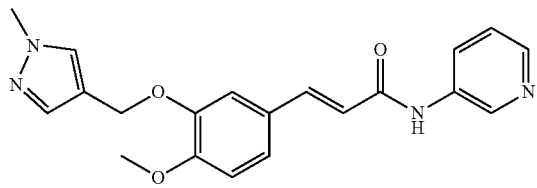 [SMILES: COc1ccc(/C=C/C(=O)Nc2cccnc2)cc1OCc1cnn(C)c1]

a) (E)-3-(4-methoxy-3-((1-methyl-1H-pyrazol-4-yl)methoxy)phenyl)acrylic acid

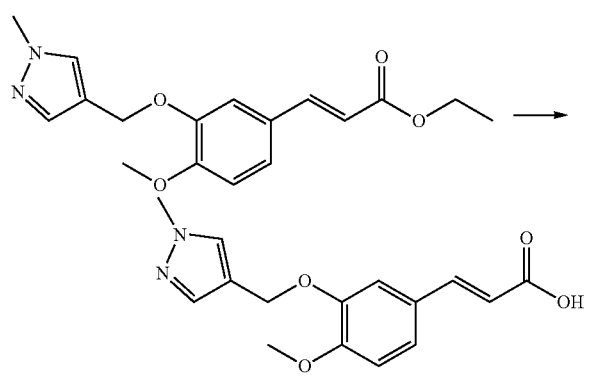

The title compound was prepared in a similar manner to (E)-3-(3-methoxy-4-(oxetan-3-ylmethoxy)phenyl)acrylic acid from ethyl (E)-3-(4-methoxy-3-((1-methyl-1H-pyrazol-4-yl)methoxy)phenyl)acrylate and lithium hydroxide monohydrate and was obtained as an off-white solid (92%); $^1$H NMR (400 MHz, DMSO) δ 12.25 (s, 1H), 7.84 (s, 1H), 7.61-7.47 (m, 3H), 7.26 (d, J=7.6 Hz, 1H), 7.03 (d, J=8.1 Hz, 1H), 6.50 (d, J=15.6 Hz, 1H), 5.04 (s, 2H), 3.88 (s, 3H), 3.82 (s, 3H).

b) (E)-3-(4-methoxy-3-((1-methyl-1H-pyrazol-4-yl)methoxy)phenyl)-N-(pyridin-3-yl)acrylamide

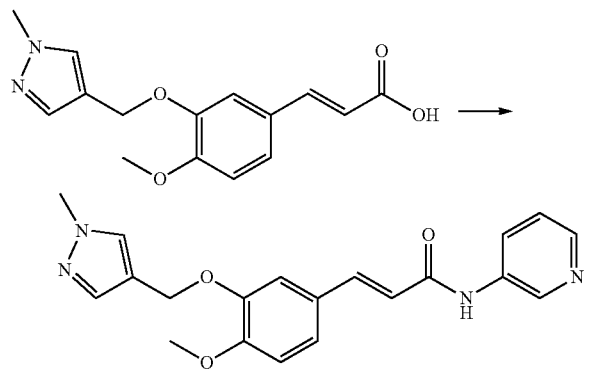

The title compound was prepared using a similar method to (E)-N-(3-chlorophenyl)-3-(3-methoxy-4-(oxetan-3-yl-methoxy)phenyl)acrylamide (147) using (E)-3-(4-methoxy-3-((1-methyl-1H-pyrazol-4-yl)methoxy)phenyl)acrylic acid and 3-aminopyridine and was obtained as an off-white solid (63%); $^1$H NMR (400 MHz, CDCl$_3$) δ 8.64 (d, J=2.5 Hz, 1H), 8.36 (d, J=4.8 Hz, 1H), 8.31 (d, J=8.3 Hz, 1H), 7.70 (d, J=15.3 Hz, 1H), 7.64 (s, 1H), 7.57 (s, 1H), 7.45 (s, 1H), 7.31 (dd, J=8.3 Hz, J=4.8 Hz, 1H), 7.17-7.12 (m, 2H), 6.89 (d, J=8.3 Hz, 1H), 6.40 (d, J=15.3 Hz, 1H), 5.04 (s, 2H), 3.90 (s, 3H), 3.89 (s, 3H); MS (ESI+) m/z 365 (M+H)+; 94.7% purity, RT 2.88 min (Method 3).

(E)-N-(3-chlorophenyl)-3-(4-methoxy-3-morpholinophenyl)acrylamide (151)

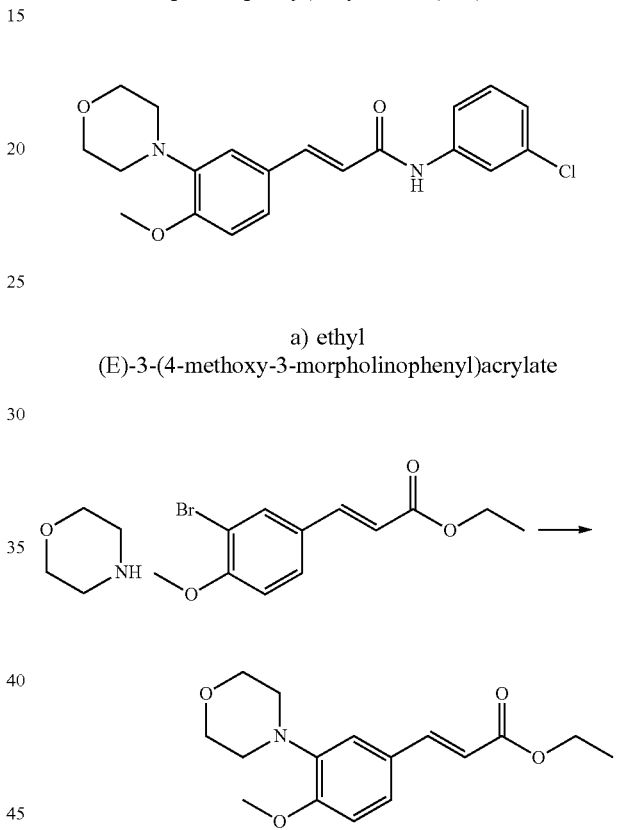

a) ethyl (E)-3-(4-methoxy-3-morpholinophenyl)acrylate

To a stirred mixture of ethyl (E)-3-(3-bromo-4-methoxyphenyl)acrylate (0.150 g, 0.53 mmol, 1.0 equiv.), morpholine (0.06 mL, 0.63 mmol, 1.2 equiv.), RuPhos (0.025 g, 0.05 mmol, 0.1 equiv.) and sodium tert-butoxide (0.111 g, 1.16 mmol, 2.2 equiv.) in dry, degassed toluene was added palladium acetate (0.006 g, 0.03 mmol, 0.05 equiv.) and the mixture stirred under a nitrogen atmosphere under reflux overnight. The reaction was cooled to room temperature and filtered through a plug of celite which was washed with ethyl acetate. The filtrate was concentrated in vacuo and the residue partitioned between ethyl acetate and water. The organic phase was washed with water and brine and the solvent removed in vacuo. The residue was purified by silica gel column chromatography (20-40% ethyl acetate in hexane as gradient) to afford the title compound as an amber oil (0.081 g, 52%); $^1$H NMR (400 MHz, CDCl$_3$) δ 7.63 (d, J=16.7 Hz, 1H), 7.20 (dd, J=8.3 Hz, J=2.3 Hz, 1H), 7.10-7.09 (m, 1H), 6.86 (d, J=8.6 Hz, 1H), 6.31 (d, J=16.2 Hz, 1H), 4.26 (q, J=7.1 Hz, 2H), 3.92-3.88 (m, 7H), 3.10-3.07 (m, 4H), 1.34 (t, J=6.5 Hz, 3H).

b) (E)-N-(3-chlorophenyl)-3-(4-methoxy-3-morpholinophenyl)acrylamide

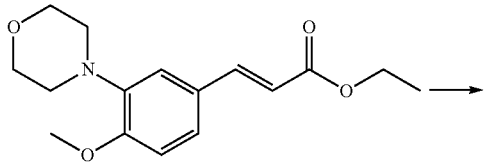

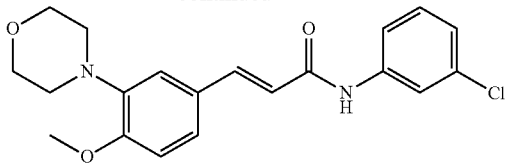 [SMILES: COc1ccc(/C=C/C(=O)Nc2cccc(Cl)c2)cc1N1CCOCC1]

The title compound was prepared according to the method described for the synthesis of (E)-N-(3-chlorophenyl)-3-(3-methoxy-4-(oxetan-3-ylmethoxy)phenyl)acrylamide (147) starting from ethyl (E)-3-(4-methoxy-3-morpholinophenyl)acrylate and 3-chloroaniline and was obtained as a beige solid (17%). $^1$H NMR (400 MHz, CDCl$_3$) δ 7.74-7.68 (m, 2H), 7.45 (dd, J=8.2 Hz, J=1.1 Hz, 1H), 7.29-7.24 (m, 2H), 7.22 (dd, J=8.5 Hz, J=2.6 Hz, 1H), 7.12-7.08 (m, 2H), 6.88 (d, J=8.6 Hz, 1H), 6.39 (d, J=15.1 Hz, 1H), 3.92-3.89 (m, 7H), 3.11-3.07 (m, 4H); MS (ESI+) m/z 373/375 (M+H)+; 99.4% purity. RT 3.42 min (Method 2).

| Ex | Structure | Data | Method |
|---|---|---|---|
| 152 | (E)-N-(2-chlorophenyl)-3-(3-methoxy-4-(oxetan-3-ylmethoxy)phenyl)acrylamide | $^1$H NMR (400 MHz, CDCl$_3$): δ 8.54 (d, J = 7.8 Hz, 1H), 7.77 (s, 1H), 7.71 (d, J = 15.6 Hz, 1H), 7.40 (dd, J = 8.1 Hz, J = 1.5 Hz, 1H), 7.34-7.28 (m, 1H), 7.15 (dd, J = 8.3 Hz, J = 2.0 Hz, 1H), 7.11-7.03 (m, 2H), 6.92 (d, J = 8.3 Hz, 1H), 6.49 (d, J = 16.2 Hz, 1H), 4.91 (dd, J = 7.8 Hz, J = 6.3 Hz, 2H), 4.56 (dd, J = 6.1 Hz, J = 6.1 Hz, 2H), 4.32 (d, J = 7.1 Hz, 2H), 3.92 (s, 3H), 3.55-3.47 (m, 1H); MS (ESI+) m/z 374/376 (M + H)+; 97.9 % purity RT 3.28 min (Method 2) | Prepared according to the method for 147 stalling from 2-chloroaniline |
| 153 | (E)-N-(4-chlorophenyl)-3-(3-methoxy-4-(oxetan-3-ylmethoxy)phenyl)acrylamide | $^1$H NMR (400 MHz, CDCl$_3$) δ 7.69 (d, J = 15.4 Hz, 1H), 7.57 (d, J = 8.8 Hz, 2H), 7.33-7.29 (m, 3H), 7.12 (dd, J = 8.2 Hz, J = 1.9 Hz, 1H), 7.06 (d, J = 2.0 Hz, 1H), 6.91 (d, J = 8.3 Hz, 1H), 6.40 (d, J = 15.4 Hz, 1H), 4.91 (dd, J = 7.6 Hz, J = 6.3 Hz, 2H), 4.56 (dd, J = 6.1 Hz, 6.1 Hz, 2H), 4.30 (d, J = 7.1 Hz, 2H), 3.88 (s, 3H), 3.54-3.46 (m, 1H); MS (ESI+) m/z 374/376 (M + H)+ 99.5 % purity RT 3.31 min (Method 2) | Prepared according to the method for 147 stalling from 4-chloroaniline |
| 154 | N-(4-chlorophenyl)-2-(3-methoxy-4-(oxetan-3-ylmethoxy)phenyl)cyclopropane-1-carboxamide | $^1$H NMR (400 MHz, CDCl$_3$) δ 7.48 (d, J = 8.1 Hz, 2H), 7.42 (s, 1H), 7.28 (d, J = 8.8 Hz, 2H), 6.84 (d, J = 8.1 Hz, 1H), 6.66-6.63 (m, 2H), 4.90-4.85 (m, 2H), 4.56-4.50 (m, 2H), 4.24 (d, J = 7.1 Hz, 2H), 3.82 (s, 3H), 3.49-3.42 (m, 1H), 2.59-2.52 (m, 1H), 1.74-1.64 (m, 2H), 1.37-1.31 (m, 1H); MS (ESI+) m/z 388/390 (M + H)+ 97.8% purity, RT 3.37 min (Method 2) | Prepared according to the method for 148 starting from 4-chloroaniline |

| Ex | Structure | Data | Method |
|---|---|---|---|
| 155 | 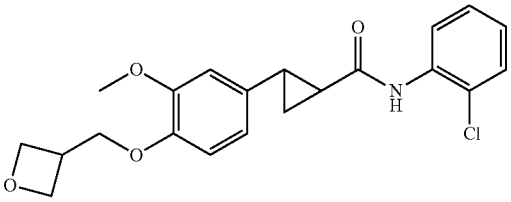<br>N-(2-chlorophenyl)-2-(3-methoxy-4-(oxetan-3-ylmethoxy)phenyl)cyclopropane-1-carboxamide | $^1$H NMR (400 MHz, CDCl$_3$) δ 8.42 (d, J = 7.3 Hz, 1H), 7.87-7.85 (m, 1H), 7.37 (dd, J = 8.1 Hz, J = 1.3 Hz, 1H), 7.30-7.27 (m, 1H), 7.06-7.01 (m, 1H), 6.86 (d, J = 8.3 Hz, 1H), 6.72 (d, J = 2.0 Hz, 1H), 6.66 (dd, J = 8.1 Hz, J = 2.0 Hz, 1H), 4.89 (dd, J = 7.6 Hz, J = 6.3 Hz, 2H), 4.54 (dd, J = 6.1 Hz, J = 6.1 Hz, 2H), 4.25 (d, J = 7.1 Hz, 2H), 3.86 (s, 3H), 3.51-3.43 (m, 1H), 2.60 (ddd, J = 9.0 Hz, J = 6.5 Hz, J = 4.0 Hz, 1H), 1.79-1.68 (m, 2H), 1.42-1.36 (m, 1H); MS (ESI+) m/z 388/390 (M + H)$^+$ 98.3% purity, RT 3.31 min (Method 2) | Prepared according to the method for 148 starting from 2-chloroaniline |
| 156 | 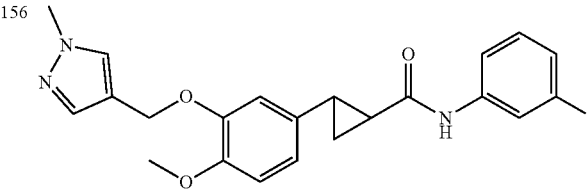<br>N-(3-chlorophenyl)-2-(4-methoxy-3-((1-methyl-1H-pyrazol-4-yl)methoxy)phenyl)cyclopropane-1-carboxamide | $^1$H NMR (400 MHz, CDCl$_3$) δ 8.43-8.39 (m, 1H), 7.85 (s, 1H), 7.53 (s, 1H), 7.45 (s, 1H), 7.37 (dd, J = 8.1 Hz, J = 1.3 Hz, 1H), 7.30-7.23 (m, 1H), 7.07-7.00 (m, 1H), 6.82 (d, J = 8.3 Hz, 1H), 6.77 (d, J = 1.8 Hz, 1H), 6.70 (dd, J = 8.2 Hz, J = 1.6 Hz, 1H), 5.01 (s, 2H), 3.88 (s, 3H), 3.84 (s, 3H), 2.61-2.54 (m, 1H), 1.76-1.67 (m, 2H), 1.38-1.32 (m, 1H); MS (ESI+) m/z 412/414 (M + H)+; 99.6% purity, RT 3.43 min (Method 2). | Prepared according to the method for 149 starting from 3-chloroaniline |
| 157 | 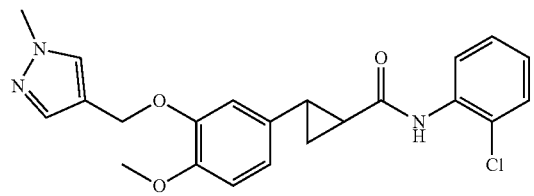<br>N-(2-chlorophenyl)-2-(4-methoxy-3-((1-methyl-1H-pyrazol-4-yl)methoxy)phenyl)cyclopropane-1-carboxamide | $^1$H NMR (400 MHz, CDCl3): δ 8.43-8.39 (m, 1H), 7.85 (s, 1H), 7.53 (s, 1H), 7.45 (s, 1H), 7.37 (dd, J = 8.1 Hz, J = 1.3 Hz, 1H), 7.29 (m, 1H), 7.07-7.00 (m, 1H), 6.82 (d, J = 8.3 Hz, 1H), 6.77 (d, J = 1.8 Hz, 1H), 6.70 (dd, J = 8.2 Hz, J = 1.6 Hz, 1H), 5.01 (s, 2H), 3.88 (s, 3H), 3.84 (s, 3H), 2.61-2.54 (m, 1H), 1.76-1.67 (m, 2H), 1.38-1.32 (m, 1H). MS (ESI+) m/z 412/414 (M + H)+; 98.5% purity. RT 3.29 min (Method 2) | Prepared according to the method for 149 starting from 2-chloroaniline |
| 158 | 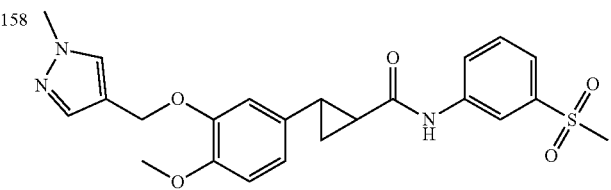<br>2-(4-methoxy-3-((1-methyl-1H-pyrazol-4-yl)methoxy)phenyl)-N-(3-(methylsulfonyl)phenyl)cyclopropane-1-carboxamide | $^1$H NMR (400 MHz, DMSO): δ 10.70 (s, 1H), 8.34 (s, 1H), 7.91-7.87 (m, 1H), 7.82 (s, 1H), 7.66-7.62 (m, 2H), 7.53 (s, 1H), 6.96 (d, J = 2.0 Hz, 1H), 6.92 (d, J = 8.3 Hz, 1H), 6.76 (dd, J = 8.5 Hz, J = 1.9 Hz, 1H), 4.97 (d, J = 3.3 Hz, 2H), 3.88 (s, 3H), 3.75 (s, 3H), 3.24 (s, 3H), 2.45-2.38 (m, 1H), 2.13-2.05 (m, 1H), 1.56-1.42 (m, 2H). MS (ESI+) m/z 456 (M + H)+; 98.3% purity. RT 3.03 min (Method 2). | Prepared according to the method for 149 starting from 3-(methylsulfonyl)aniline |
| 159 | 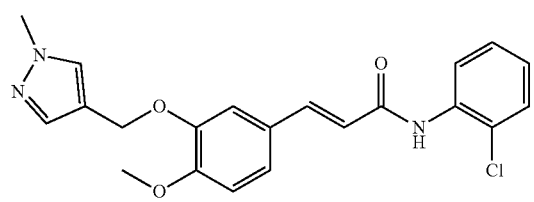<br>(E)-N-(2-chlorophenyl)-3-(4-methoxy-3-((1-methyl-1H-pyrazol-4-yl)methoxy)phenyl)acrylamide | $^1$H NMR (400 MHz, CDCl$_3$) δ 8.53 (d, J = 7.8 Hz, 1H), 7.76 (s, 1H), 7.70 (d, J = 15.8 Hz, 1H), 7.57 (s, 1H), 7.47 (s, 1H), 7.39 (dd, J = 8.1 Hz, J = 1.5 Hz, 1H), 7.34-7.28 (m, 1H), 7.20-7.16 (m, 2H), 7.08-7.03 (m, 1H), 6.90 (d, J = 8.1 Hz, 1H), 6.43 (d, J = 15.8 Hz, 1H), 5.07 (s, 2H), 3.90 (s, 3H), 3.90 (s, 3H); MS (ESI+) m/z 398/400 (M + H)+; 99.1% purity, RT 3.33 min (Method 2) | Prepared according to the method for 150 starting from 2-chloroaniline |

| Ex | Structure | Data | Method |
|---|---|---|---|
| 160 | 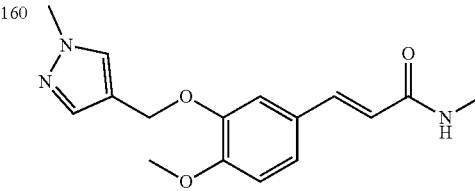<br>(E)-N-(3-chlorophenyl)-3-(4-methoxy-3-((1-methyl-1H-pyrazol-4-yl)methoxy)phenyl)acrylamide | $^1$H NMR (400 MHz, CDCl$_3$) δ 7.74 (dd, J = 2.1 Hz, J = 2.1 Hz, 1H), 7.68 (d, J = 14.9 Hz, 1H), 7.57 (s, 1H), 7.49-7.44 (m, 3H), 7.29-7.23 (m, 1H), 7.16-7.08 (m, 3H), 6.88 (d, J = 8.3 Hz, 1H), 6.35 (d, J = 15.4 Hz, 1H), 5.03 (s, 2H), 3.89 (s, 3H), 3.88 (s, 3H); MS (ESI+) m/z 398/400 (M + H)+; 99.5% purity, RT 3.35 min (Method 3) | Prepared according to the method for 150 starting from 3-chloroaniline |

Biological Activity

[$^{14}$C]-Proline Incorporation Plus MTS Viability Assay

The compounds of the disclosure were evaluated to determine the effect of inhibitors on collagen biosynthesis in a [$^{14}$C]-proline incorporation assay and cell viability using a MTS tetrazolium reduction assay. In particular, the assay evaluated inhibition of TGF-β induced [$^{14}$C]-proline incorporation in rat mesangial cells.

TABLE 1

Reagents and consumables

| Reagent/Consumable | Supplier | Cat No. |
|---|---|---|
| 1097/IRMC cells | FibroTech (Shire) | |
| DMEM + Glutamax | Invitrogen | 31966-021 |
| Foetal Bovine Serum (FBS) | Invitrogen | 10082-147 |
| Pen-Strep | Invitrogen | 15140-122 |
| Ascorbic acid phosphate magnesium salt (APM) | Sigma | A8960-5G |
| Chlorpromazine hydrochloride | Sigma | C8138-5G |
| TGF-β1 | PreproTech | 100-21 |
| 1M hydrochloric acid (HCl) | Fluka | 35328-1L |
| Bovine serum albumin (BSA) | Sigma | A7906 |
| [$^{14}$C]-proline | Perkin Elmer | NEC851250UC |
| MTS | Promega | G5430 |
| 96 well CytoStar-T plates | Perkin Elmer | RPNQ0163 |
| Adhesive Topseal A-Plus | Perkin Elmer | 6050185 |

Day 1—Plating Cells:

Seed IRMC cells at 10,000 cells/200 µl (=50,000 cells/ml) in DMEM supplemented with 5% FBS in 96 well CytoStar-T plates; Leave plates 1 hour at room temperature before transferring to 37° C./5% CO$_2$ incubator and incubate overnight.

Day 2—Serum Starvation:

Aspirate off media; Replace with 150 µl of 150 µM APM made up in DMEM supplemented with 0.1% FBS and 1% Pen-Strep (Starvation media); Return plates to the 37° C./5% CO$_2$ incubator overnight.

Day 3:

Compound addition: Add 20 µl of: 10× compound in starvation media, 10% DMSO in starvation media to controls and no TGF-β1 blanks, 100 µM Chlorpromazine hydrochloride to dead cell blanks, and Reference compound tranilast (ADS 143566) tested from 1 µM-300 µM; Return plates to 37° C./5% CO$_2$ incubator and incubate for 4 hours; Add 10 µl of: 20 ng/ml TGF-β1 (final concentration=1 ng/ml) to all wells except no TGF-β1 blanks, and Starvation media to TGF-β1 blanks; Add 20 µl of 1 µCi/ml [$^{14}$C]-proline (final concentration=0.1 µCi/ml) and 1.5 mM APM (final concentration=150 µM) made up in starvation media; Return plates to the 37° C./5% CO$_2$ incubator and incubate for 44 hours.

Day 5: [$^{14}$C]—Proline and MTS Assay:

Remove plates from incubator and transfer to radioactive work area in AD1 in appropriate container; Seal plates with adhesive seals; Place plates in counting cassettes and Count on Microbeta using n_14C protocol; Once plates have finished counting, remove seals and aspirate off media; Add 200 µl of 1:21 dilution of MTS reagent; Return plates to the 37° C./5% CO$_2$ incubator and incubate for further 2 hours; Remove plates from incubator and transfer to radioactive work area in AD1 in appropriate container; Seal plates with adhesive seals; Read absorbance at 490 nm on Spectramax M5$^e$.

Final Assay Volumes/Concentrations (Day 3):

150 µl cells in 150 µM APM made up in starvation media; 20 µl Compound/Controls/Blanks/Dead Cell Blanks in 1% DMSO; 10 al 1 ng/ml or 0 ng/ml TGF-β1 (Blanks); 20 µl 0.1 µCi/ml [$^{14}$C]-proline/150 µM APM.

IC$_{50}$ generation—[14C]-proline incorporation. TGF-β1-induced proline incorporation was determined by subtraction of basal (non-TGF-β1 treated cells) CPM from the TGF-β1 stimulated cell CPM. % inhibition of the 1% DMSO vehicle stimulated TGF-β1 response at each concentration of compound was calculated by the formula: (100−(((test data−blank data)/(control data−blank data))*100)). IC$_{50}$ values were generated from the associated log dose-response curve fits using ActivityBase (IDBS).

CC$_{50}$ generation—cell viability. The effects of compound on cell viability were quantified by comparison to the 1% DMSO vehicle-treated TGF-β1 stimulated cells, which were used as the 100% viability reference. % cell viability at each concentration of compound was calculated by the formula: (((test data−blank data)/(control data−blank data))*100). CC$_{50}$ values were generated from the associated log dose-response curve fits using ActivityBase (IDBS).

Table 2 provides the assay results of the example compounds of the present disclosure.

TABLE 2

| | IC$_{50}$ (µM) | CC$_{50}$ (µM) |
|---|---|---|
| 106 | 1.579 | 25.096 |
| 9 | 1.94 | 25.478 |
| 7 | 1.97 | 62.54 |
| 159 | 2.427 | >10 |

TABLE 2-continued

| | IC$_{50}$ (μM) | CC$_{50}$ (μM) |
|---|---|---|
| 143 | 2.814 | 7.2 |
| 120 | 3.218 | 10.799 |
| 82 | 3.419 | 13.516 |
| 87 | 3.688 | 12.102 |
| 145 | 3.705 | 11.741 |
| 121 | 3.792 | 8.473 |
| 126 | 3.812 | >27.546 |
| 102 | 3.871 | 11.411 |
| 3 | 3.936 | 71.142 |
| 150 | 4.075 | >31.623 |
| 136 | 4.134 | 16.263 |
| 4 | 4.317 | 323.001 |
| 88 | 4.449 | 12.372 |
| 89 | 4.662 | 19.784 |
| 77 | 4.689 | 26.47 |
| 141 | 4.851 | 13.502 |
| 93 | 5.227 | 17.24 |
| 8 | 5.335 | 109.497 |
| 139 | 5.363 | 9.028 |
| 10 | 6.038 | 66.438 |
| 40 | 6.764 | >300 |
| 115 | 7.028 | 45.398 |
| 11 | 7.073 | 104.152 |
| 81 | 7.146 | 24.877 |
| 113 | 7.747 | 32.642 |
| 149 | 8.353 | >54.772 |
| 91 | 8.376 | 18.074 |
| 105 | 8.439 | 79.717 |
| 140 | 8.469 | 36.121 |
| 148 | 8.475 | 77.555 |
| 85 | 8.92 | 108.723 |
| 154 | 8.972 | >300 |
| 100 | 9.293 | 36.959 |
| 57 | 9.366 | >76.621 |
| 79 | 9.52 | 23.378 |
| 12 | 10.203 | 334.782 |
| 14 | 10.367 | 48.916 |
| 2 | 10.43 | >300 |
| 5 | 10.55 | 368.548 |
| 1 | 10.945 | >300 |
| 138 | 10.976 | 50.896 |
| 52 | 11.341 | 140.287 |
| 6 | 11.381 | >300 |
| 128 | 11.494 | 24.402 |
| 28 | 11.555 | 146.496 |
| 30 | 11.804 | 37.171 |
| 132 | 11.965 | 16.564 |
| 59 | 12.121 | 147.593 |
| 71 | 12.195 | 116.353 |
| 129 | 12.329 | 28.878 |
| 157 | 12.644 | 45.334 |
| 45 | 12.949 | 307.408 |
| 24 | 12.974 | 41.361 |
| 112 | 12.984 | >300 |
| 44 | 13.224 | 11.074 |
| 26 | 13.454 | 189.712 |
| 98 | 13.549 | 288.628 |
| 31 | 13.855 | >300 |
| 110 | 13.871 | >300 |
| 64 | 14.211 | 141.569 |
| 114 | 14.277 | 82.035 |
| 118 | 14.309 | 25.477 |
| 74 | 14.679 | 318.544 |
| 84 | 14.749 | >300 |
| 107 | 14.877 | >100 |
| 76 | 14.886 | 18.084 |
| 53 | 14.962 | 225.798 |
| 72 | 14.967 | >300 |
| 137 | 15.354 | 30.79 |
| 51 | 15.489 | >300 |
| 130 | 15.589 | 51.799 |
| 36 | 15.84 | 15.168 |
| 22 | 16.353 | 240.422 |
| 101 | 16.956 | 119.375 |
| 42 | 16.965 | 51.963 |
| 66 | 16.98 | >300 |
| 122 | 17.15 | 234.488 |
| 18 | 17.196 | 150.629 |
| 134 | 17.475 | >300 |
| 125 | 17.633 | >300 |
| 95 | 17.637 | 110.748 |
| 156 | 17.822 | >100 |
| 37 | 18.027 | 29.157 |
| 63 | 18.184 | 79.385 |
| 65 | 18.279 | 151.764 |
| 155 | 18.722 | 196.232 |
| 123 | 19.333 | >300 |
| 146 | 19.577 | >300 |
| 19 | 19.665 | 122.039 |
| 60 | 20.321 | 100.172 |
| 144 | 20.928 | 81.022 |
| 117 | 21.354 | >300 |
| 27 | 21.443 | 119.603 |
| 131 | 21.553 | 17.713 |
| 94 | 21.653 | 35.043 |
| 90 | 21.9 | >300 |
| 16 | 22.338 | 107.391 |
| 133 | 23.44 | >300 |
| 67 | 23.469 | 144.286 |
| 48 | 23.861 | 309.178 |
| 54 | 24.004 | >300 |
| 109 | 24.26 | >300 |
| 80 | 24.46 | >100 |
| 119 | 24.717 | 74.751 |
| 41 | 24.845 | 341.082 |
| 86 | 24.928 | >300 |
| 21 | 24.975 | >300 |
| 15 | 25.24 | 303.574 |
| 49 | 25.264 | 30.57 |
| 29 | 25.632 | >300 |
| 158 | 25.888 | 68.838 |
| 23 | 26.313 | 103.647 |
| 32 | 27.356 | 32.019 |
| 75 | 27.608 | >300 |
| 103 | 27.994 | 264.891 |
| 34 | 28.437 | 37.258 |
| 47 | 29.103 | >300 |
| 33 | 29.249 | 199.079 |
| 111 | 29.977 | >300 |
| 160 | 30.356 | >300 |
| 78 | 30.45 | 404.427 |
| 151 | 31.551 | >300 |
| 17 | 31.645 | >300 |
| 142 | 31.687 | >300 |
| 56 | 32.238 | 150.03 |
| 83 | 32.469 | >300 |
| 73 | 33.076 | >300 |
| 96 | 33.626 | >300 |
| 99 | 34.747 | >300 |
| 124 | 34.752 | >300 |
| 153 | 35.395 | >300 |
| 127 | 35.415 | 82.939 |
| 13 | 36.042 | 96.448 |
| 35 | 37.416 | 301.223 |
| 152 | 38.173 | >300 |
| 38 | 38.23 | 236.349 |
| 147 | 39.084 | >300 |
| 58 | 39.221 | 265.689 |
| 20 | 39.506 | >300 |
| 108 | 40.398 | >300 |
| 104 | 41.364 | 280.87 |
| 55 | 44.339 | 86.083 |
| 43 | 44.556 | >300 |
| 68 | 44.861 | >300 |
| 135 | 45.273 | >300 |
| 25 | 45.547 | >300 |
| 97 | 46.208 | >300 |
| 46 | 46.579 | 186.19 |
| 50 | 47.422 | 107.475 |
| 39 | 48.256 | 85.832 |
| 69 | 48.351 | 691.029 |
| 61 | 48.932 | 276.157 |
| 62 | 49.012 | 320.758 |
| 92 | 49.215 | 108.846 |
| 70 | 49.759 | >300 |
| 116 | 60.453 | 294.25 |

TABLE 2-continued

| | IC$_{50}$ (μM) | CC$_{50}$ (μM) |
|---|---|---|
| 116 | 192.65 | >300 |
| FT011 | 16 | 119 |

Pharmacokinetic Studies

Discrete oral pharmacokinetic studies were performed for example compounds 116, 107, and 102.

Figure 2:
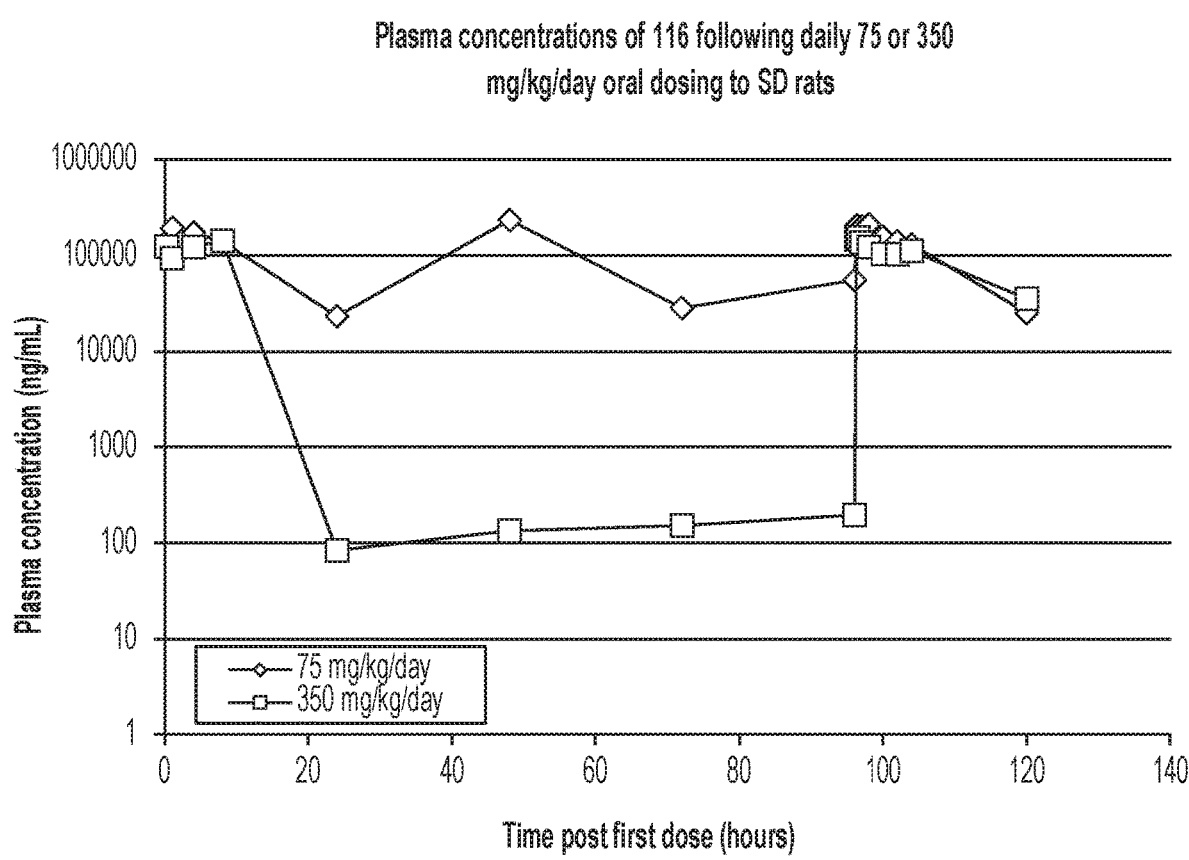
FIG. 2 shows a pharmacokinetic profile plot (plasma concentration vs. time) after daily administration (5 days) of 75 mg/kg, and 350 mg/kg of 116 to male SD rats.

116:

2 mg/kg and 20 mg/kg of 116 were administered as single doses to male Sprague Dawley (SD) rats. 75 mg/kg and 350 mg/kg of 116 were administered daily (5 days) to male Sprague Dawley (SD) rats. FIG. 1 shows the time versus concentration profile after administration of the initial dose of all dosing groups. No adverse compound related effects were observed at any dose level, and little to no increase in plasma concentrations were observed between the 75 and 350 mg/kg/day dosing groups. However, trough concentrations for the 350 mg/kg/day dosing group were lower than expected throughout the 5-day study (FIG. 2).

Figure 3:
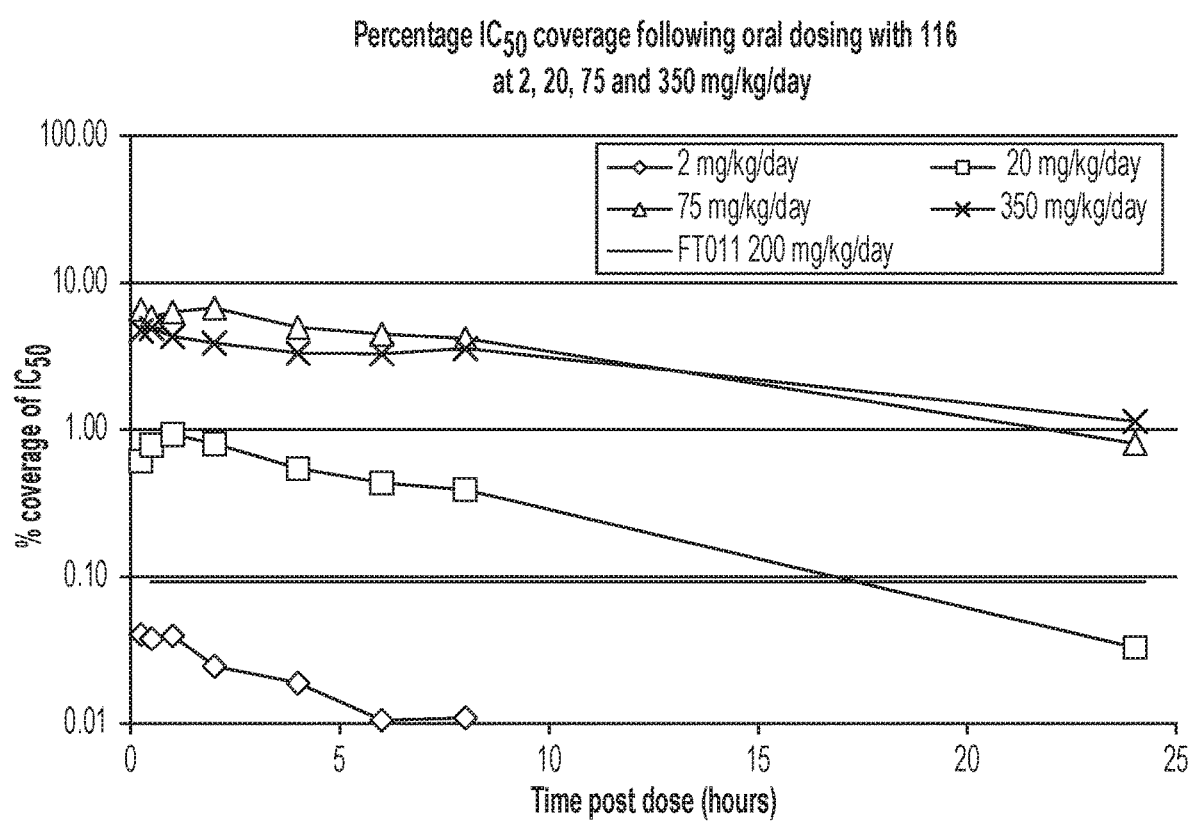
FIG. 3 shows a pharmacokinetic profile plot (% $IC_{50}$ coverage vs. time) after administration of 2 mg/kg, 20 mg/kg, 75 mg/kg, and 350 mg/kg of 116 to male SD rats in comparison to known values of a known compound, (E)-2-(3-(3-methoxy-4-(prop-2-yn-1-yloxy)phenyl)acrylamido)benzoic acid.

The pharmacokinetic results were compared to the known compound (E)-2-(3-(3-methoxy-4-(prop-2-yn-1-yloxy)phenyl)acrylamido)benzoic acid (FT011), which has an IC$_{50}$ of 17 μM and a CC$_{50}$ of 119 μM in the assays described above. FIG. 3 shows that coverage of IC$_{50}$ relative to a 200 mg/kg/day regime of (E)-2-(3-(3-methoxy-4-(prop-2-yn-1-yloxy)phenyl)acrylamido)benzoic acid (shown as a straight line at 0.10 of the y-axis in FIG. 3) was superior for 116 at 75 mg/kg and 350 mg/kg even though it possesses a less potent IC$_{50}$.

Figure 4:
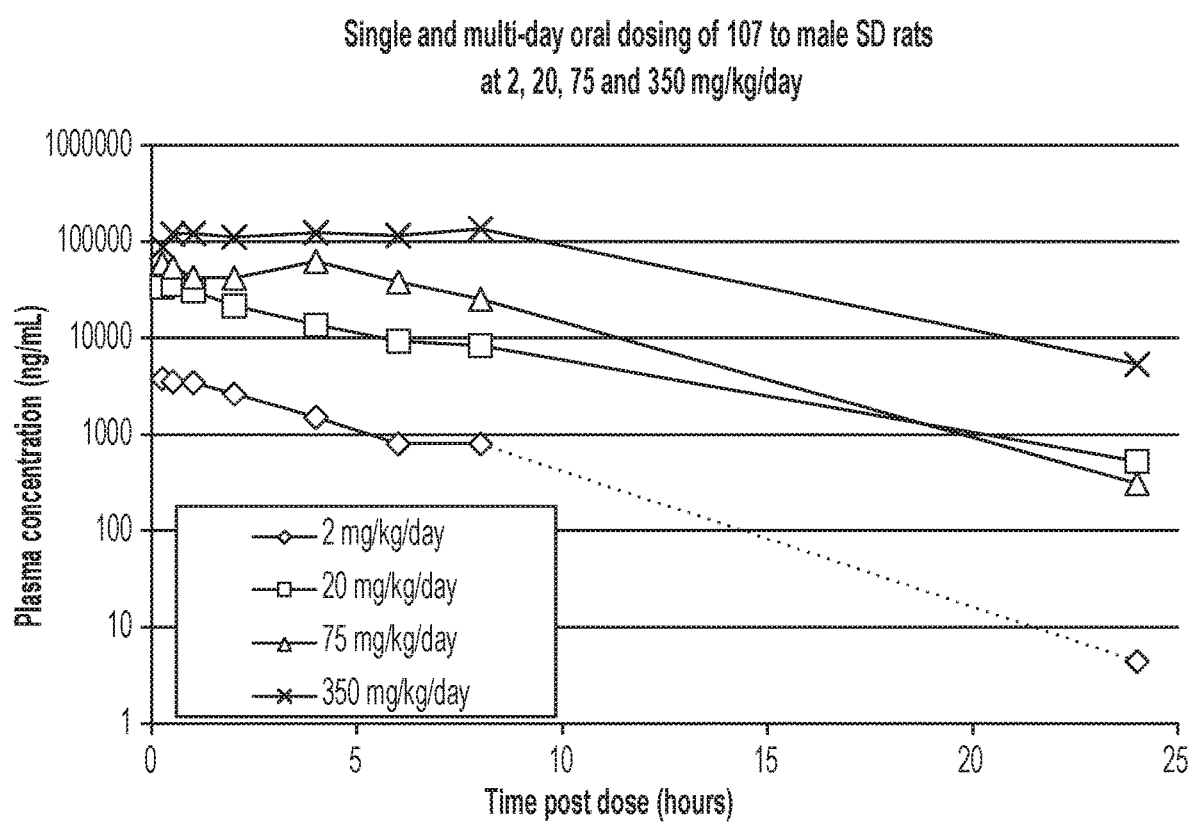
FIG. 4 shows a pharmacokinetic profile plot (plasma concentration vs. time) after administration of 2 mg/kg, 20 mg/kg, 75 mg/kg, and 350 mg/kg of 107 to male SD rats.
Figure 5:
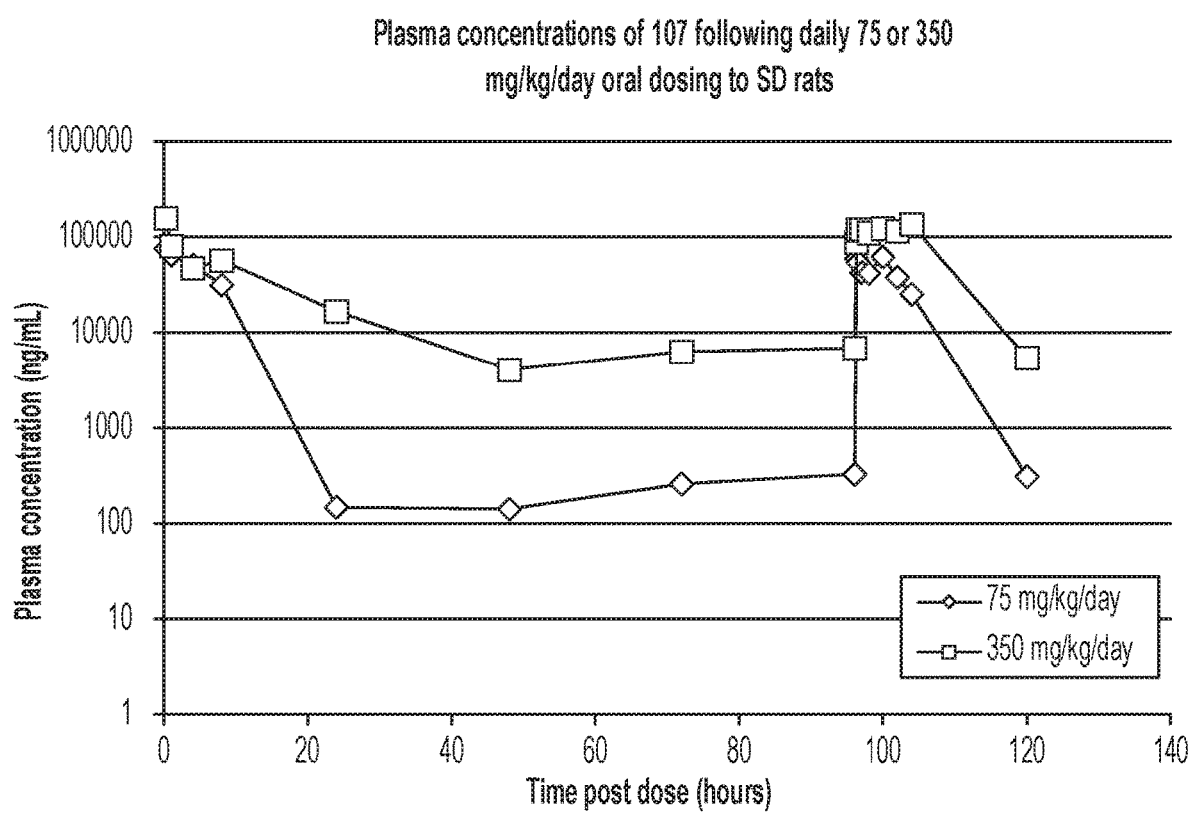
FIG. 5 shows a pharmacokinetic profile plot (plasma concentration vs. time) after daily administration (5 days) of 75 mg/kg, and 350 mg/kg of 107 to male SD rats.

107:

2 mg/kg and 20 mg/kg of 107 were administered as single doses to male Sprague Dawley (SD) rats. 75 mg/kg and 350 mg/kg of 107 were administered daily (5 days) to male Sprague Dawley (SD) rats. FIG. 4 shows the time versus concentration profile after administration of the initial dose of all dosing groups. No adverse compound related effects were observed at any dose level, and an increase in plasma concentrations were observed between the 75 and 350 mg/kg/day dosing groups. In addition, trough concentrations for the 75 and 350 mg/kg/day dosing group were consistent with dosing amounts throughout the 5-day study (FIG. 5).

Figure 6:
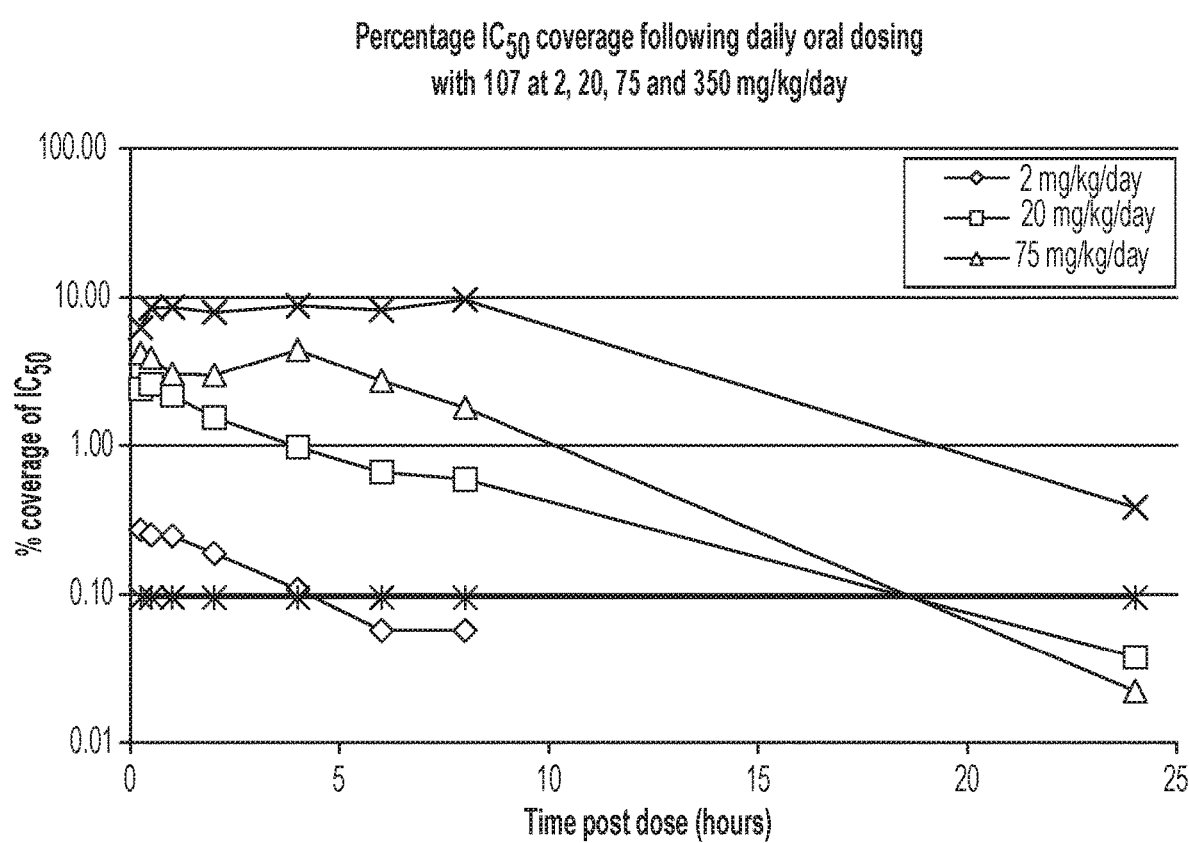
FIG. 6 shows a pharmacokinetic profile plot (% $IC_{50}$ coverage vs. time) after administration of 2 mg/kg, 20 mg/kg, 75 mg/kg, and 350 mg/kg of 107 to male SD rats in comparison to known values of a known compound, (E)-2-(3-(3-methoxy-4-(prop-2-yn-1-yloxy)phenyl)acrylamido)benzoic acid.

The pharmacokinetic results were also compared to the known compound (E)-2-(3-(3-methoxy-4-(prop-2-yn-1-yloxy)phenyl)acrylamido)benzoic acid (FT011). FIG. 6 shows that coverage of IC$_{50}$ relative to a 200 mg/kg/day regime of (E)-2-(3-(3-methoxy-4-(prop-2-yn-1-yloxy)phenyl)acrylamido)benzoic acid (shown as a straight line at 0.10 of the y-axis in FIG. 6) was superior for 107 at 350 mg/kg.

Figure 7:
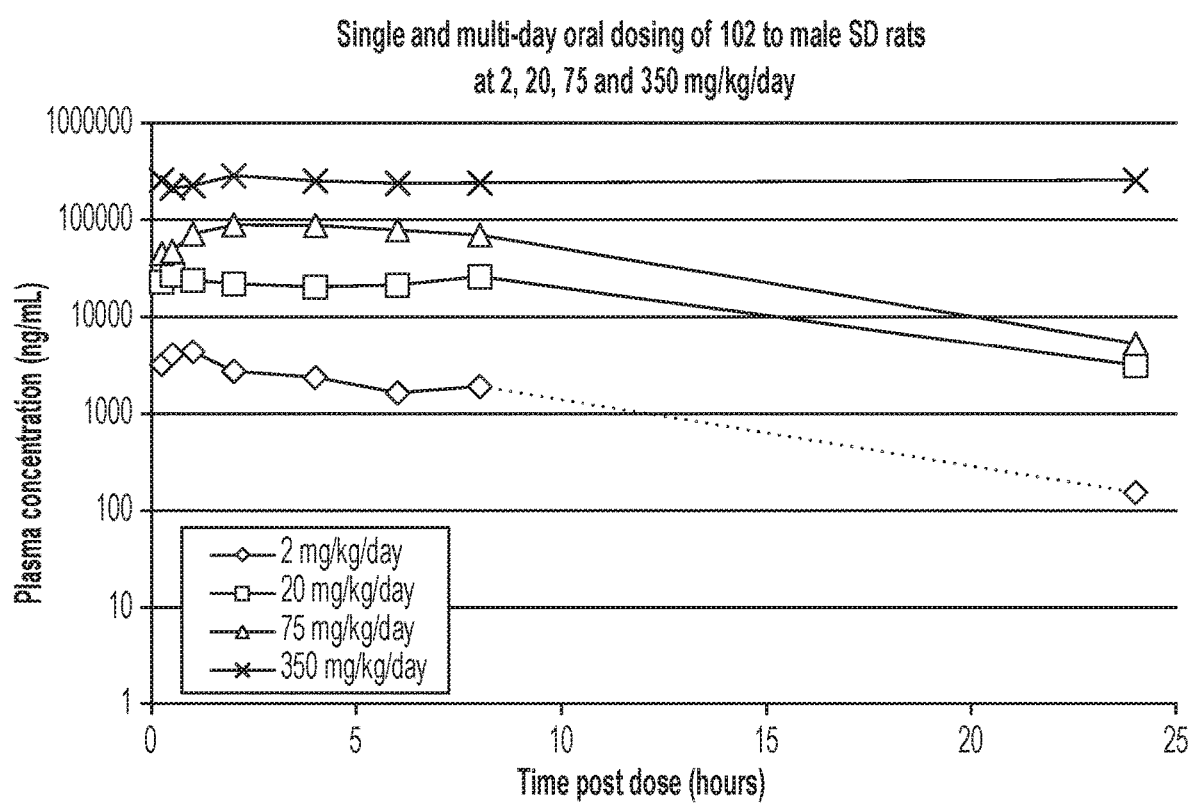
FIG. 7 shows a pharmacokinetic profile plot (plasma concentration vs. time) after administration of 2 mg/kg, 20 mg/kg, 75 mg/kg, and 350 mg/kg of 102 to male SD rats.
Figure 8:
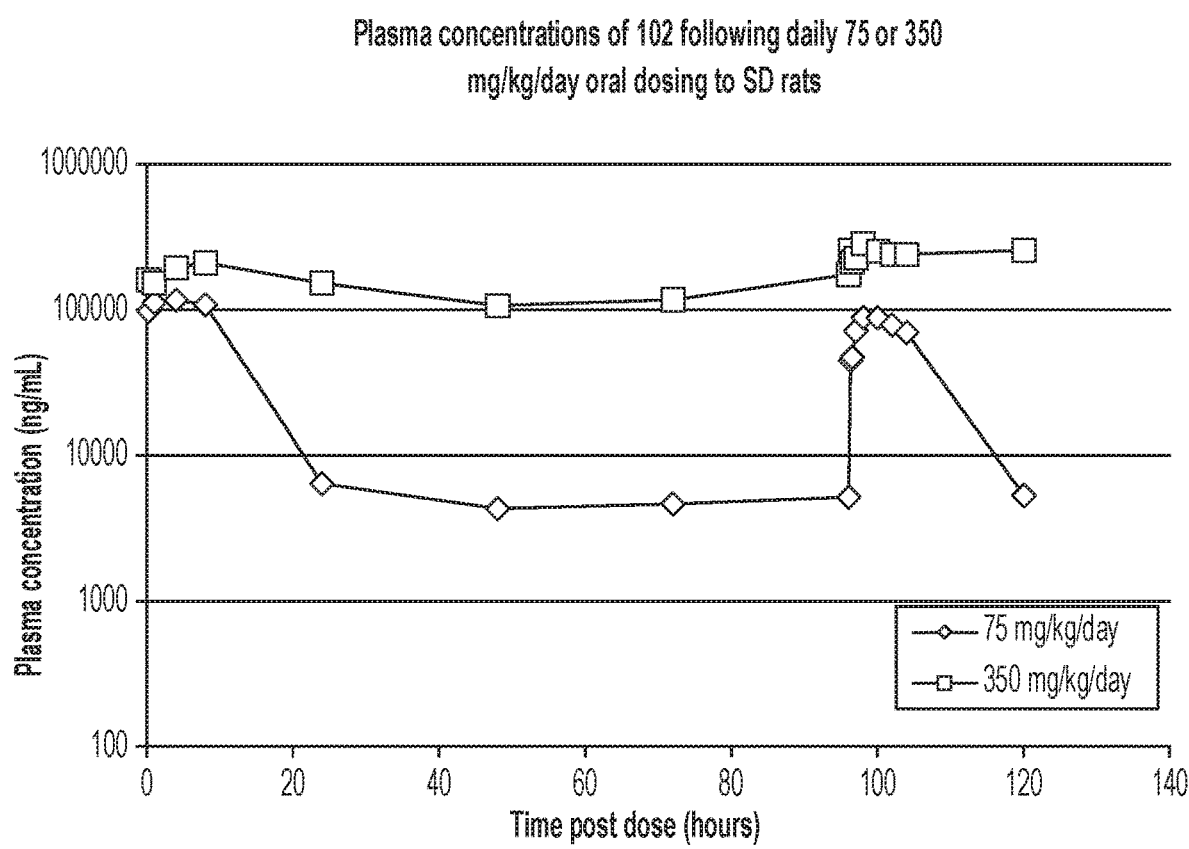
FIG. 8 shows a pharmacokinetic profile plot (plasma concentration vs. time) after daily administration (5 days) of 75 mg/kg, and 350 mg/kg of 102 to male SD rats.

102:

2 mg/kg and 20 mg/kg of 102 were administered as single doses to male Sprague Dawley (SD) rats. 75 mg/kg and 350 mg/kg of 102 were administered daily (5 days) to male Sprague Dawley (SD) rats. FIG. 7 shows the time versus concentration profile after administration of the initial dose of all dosing groups. An increase in plasma concentrations were observed between the 75 and 350 mg/kg/day dosing groups. In addition, trough concentrations for the 75 and 350 mg/kg/day dosing group were consistent with dosing amounts throughout the 5-day study (FIG. 8).

Figure 9:
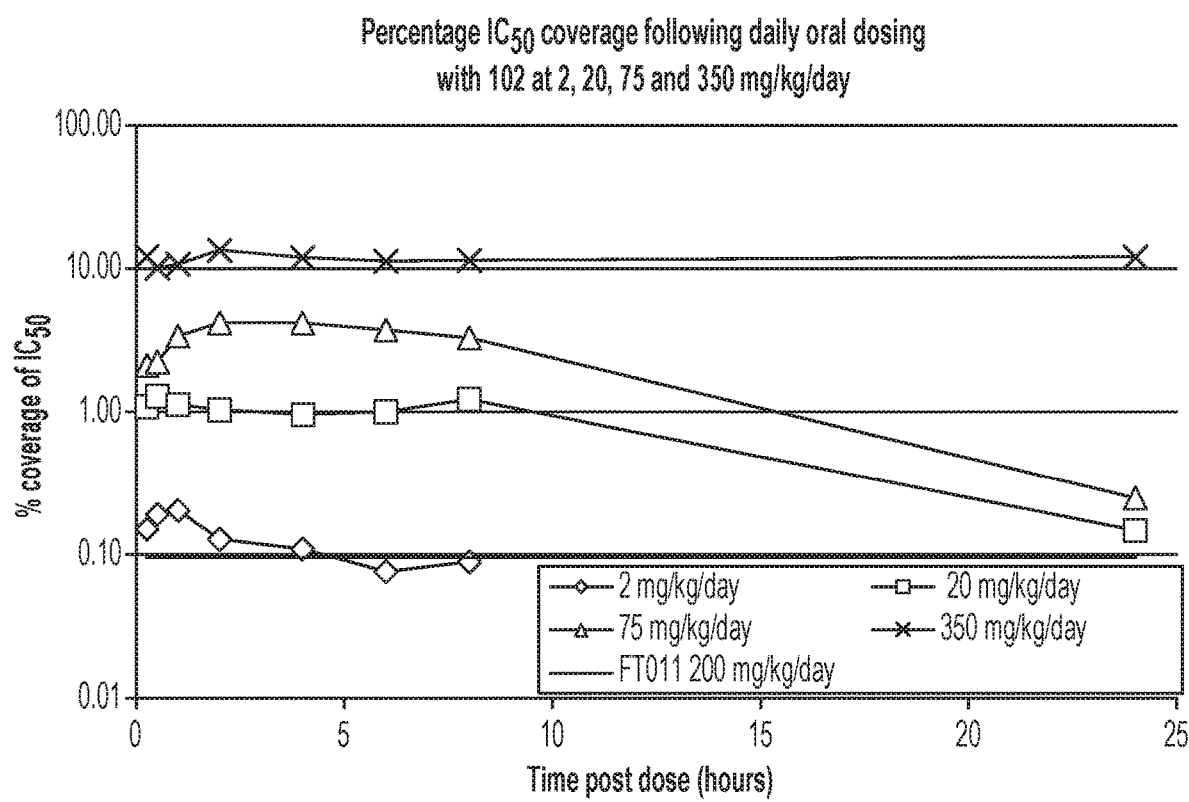
FIG. 9 shows a pharmacokinetic profile plot (% $IC_{50}$ coverage vs. time) after administration of 2 mg/kg, 20 mg/kg, 75 mg/kg, and 350 mg/kg of 102 to male SD rats in comparison to known values of a known compound, (E)-2-(3-(3-methoxy-4-(prop-2-yn-1-yloxy)phenyl)acrylamido)benzoic acid.

The pharmacokinetic results were also compared to the known compound (E)-2-(3-(3-methoxy-4-(prop-2-yn-1-yloxy)phenyl)acrylamido)benzoic acid (FT011). FIG. 9 shows that coverage of IC$_{50}$ relative to a 200 mg/kg/day regime of (E)-2-(3-(3-methoxy-4-(prop-2-yn-1-yloxy)phenyl)acrylamido)benzoic acid (shown as a straight line at 0.10 of the y-axis in FIG. 9) was superior for 102 at 20 mg/kg, 75 mg/kg and 350 mg/kg.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula I-i:

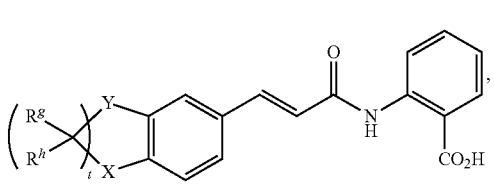

I-i or a pharmaceutically acceptable salt thereof; wherein
X is O or NR$^{10}$;
Y is O or NR$^{10}$; provided that at least one of X and Y is NR$^{10}$;
each occurrence of R$^g$ and R$^h$ is, independently, hydrogen or alkyl, or R$^g$ and R$^h$ together with the carbon atom to which they are attached form a carbonyl;
t is 1 or 2;
each occurrence of R$^{10}$ is, independently, hydrogen or C$_{1-4}$ alkyl optionally substituted with oxo.

2. The compound of claim 1, or a pharmaceutically acceptable salt thereof, wherein each occurrence of R$^{10}$ is, independently, hydrogen or C$_{1-4}$ alkyl.

3. The compound of claim 2, wherein R$^{10}$ is methyl.

4. The compound of claim 2, wherein R$^{10}$ is hydrogen.

5. The compound of claim 2, or a pharmaceutically acceptable salt thereof, wherein
X is O;
Y is NR$^{10}$; and
R$^{10}$ is C$_{1-4}$ alkyl.

6. The compound of claim 2, or a pharmaceutically acceptable salt thereof, wherein
X is NR$^{10}$;
Y is O; and
R$^{10}$ is C$_{1-4}$ alkyl.

7. The compound of claim 2, or a pharmaceutically acceptable salt thereof, wherein t is 2.

8. The compound of claim 7, wherein each occurrence of R$^g$ and R$^h$ is hydrogen.

9. The compound of claim 7, wherein one occurrence of R$^g$ and R$^h$ is hydrogen, and the other occurrence of R$^g$ and R$^h$ is that R$^g$ and R$^h$ together with the carbon atom to which they are attached form a carbonyl.

10. The compound of claim 2, wherein the compound is of Formula I-j:

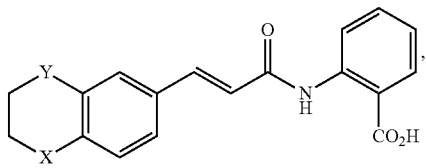

I-j or a pharmaceutically acceptable salt thereof, wherein:
X is O;
Y is NR$^{10}$; and
R$^{10}$ is C$_{1-4}$ alkyl.

11. The compound of claim 2, wherein the compound is of Formula I-j:

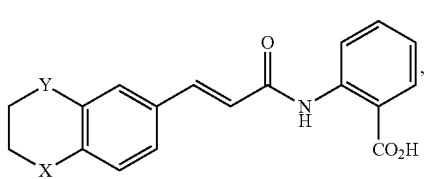

I-j or a pharmaceutically acceptable salt thereof, wherein:
X is NR$^{10}$;
Y is O; and
R$^{10}$ is C$_{1-4}$ alkyl.

12. A compound selected from the group consisting of:
2-[[(E)-3-(4-methyl-2,3-dihydro-1,4-benzoxazin-6-yl) prop-2-enoyl]amino]benzoic acid (107);
(E)-2-(3-(4-methyl-3-oxo-3,4-dihydro-2H-benzo[b][1,4] oxazin-7-yl)acrylamido)benzoic acid (109);
(E)-2-(3-(4-methyl-3,4-dihydro-2H-benzo[b][1,4]oxazin-7-yl)acrylamido)benzoic acid (110);
(E)-2-(3-(3-oxo-3,4-dihydro-2H-benzo[b][1,4]oxazin-6-yl)acrylamido)benzoic acid (111);
(E)-2-(3-(4-methyl-3-oxo-3,4-dihydro-2H-benzo[b][1,4] oxazin-6-yl)acrylamido)benzoic acid (112);
and pharmaceutically acceptable salts thereof.

13. The compound of claim 12, wherein the compound is:
2-[[(E)-3-(4-methyl-2,3-dihydro-1,4-benzoxazin-6-yl) prop-2-enoyl]amino]benzoic acid (107);
(E)-2-(3-(4-methyl-3,4-dihydro-2H-benzo[b][1,4]oxazin-7-yl)acrylamido)benzoic acid (110); or
(E)-2-(3-(4-methyl-3-oxo-3,4-dihydro-2H-benzo[b][1,4] oxazin-6-yl)acrylamido)benzoic acid (112);
or a pharmaceutically acceptable salt thereof.

14. The compound of claim 13, wherein the compound is:

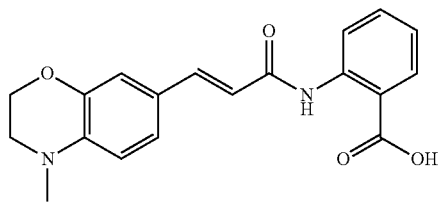 [SMILES: CN1CCOc2cc(/C=C/C(=O)Nc3ccccc3C(=O)O)ccc21]

(E)-2-(3-(4-methyl-3,4-dihydro-2H-benzo[b][1,4]oxazin-7-yl)acrylamido)benzoic acid (110); or a pharmaceutically acceptable salt thereof.

15. A pharmaceutical composition comprising the compound of claim 1, or a pharmaceutically acceptable salt thereof, and a pharmaceutically acceptable carrier.

16. A pharmaceutical composition comprising the compound of claim 12, or a pharmaceutically acceptable salt thereof, and a pharmaceutically acceptable carrier.

* * * * *